United States Patent
Whitney et al.

(10) Patent No.: US 9,845,489 B2
(45) Date of Patent: *Dec. 19, 2017

(54) COMPOSITIONS FOR STABILIZING DNA, RNA AND PROTEINS IN SALIVA AND OTHER BIOLOGICAL SAMPLES DURING SHIPPING AND STORAGE AT AMBIENT TEMPERATURES

(75) Inventors: Scott E. Whitney, San Diego, CA (US); Senait Ghirmai, San Diego, CA (US); Rolf Muller, Del Mar, CA (US)

(73) Assignee: BIOMATRICA, INC., San Diego, CA (US)

( * ) Notice: Subject to any disclaimer, the term of this patent is extended or adjusted under 35 U.S.C. 154(b) by 305 days.

This patent is subject to a terminal disclaimer.

(21) Appl. No.: 13/812,288

(22) PCT Filed: Jul. 26, 2011

(86) PCT No.: PCT/US2011/045405
§ 371 (c)(1),
(2), (4) Date: May 2, 2013

(87) PCT Pub. No.: WO2012/018639
PCT Pub. Date: Feb. 9, 2012

(65) Prior Publication Data
US 2013/0209997 A1    Aug. 15, 2013

Related U.S. Application Data

(60) Provisional application No. 61/367,789, filed on Jul. 26, 2010.

(51) Int. Cl.
*C12Q 1/68* (2006.01)
*A01N 1/02* (2006.01)

(52) U.S. Cl.
CPC .......... *C12Q 1/6806* (2013.01); *A01N 1/021* (2013.01)

(58) Field of Classification Search
CPC . C12Q 1/3803; C12Q 2527/137; A01N 1/021
See application file for complete search history.

(56) References Cited

U.S. PATENT DOCUMENTS

| | | |
|---|---|---|
| 3,673,158 A | 6/1972 | Reader et al. |
| 4,024,548 A | 5/1977 | Alonso et al. |
| 4,040,785 A | 8/1977 | Kim et al. |
| 4,127,502 A | 11/1978 | Li Mutti et al. |
| 4,185,964 A | 1/1980 | Lancaster |
| 4,257,958 A | 3/1981 | Powell |
| 4,264,560 A | 4/1981 | Natelson |
| 4,342,740 A | 8/1982 | Narra et al. |
| 4,451,569 A | 5/1984 | Kobayashi et al. |
| 4,473,552 A | 9/1984 | Jost |
| 4,683,195 A | 7/1987 | Mullis et al. |
| 4,683,202 A | 7/1987 | Mullis |
| 4,800,159 A | 1/1989 | Mullis et al. |
| 4,801,428 A | 1/1989 | Homolko et al. |
| 4,806,343 A | 2/1989 | Carpenter et al. |
| 4,842,758 A | 6/1989 | Crutzen |
| 4,889,818 A | 12/1989 | Gelfand et al. |
| 4,891,319 A | 1/1990 | Roser |
| 4,898,813 A | 2/1990 | Albarella et al. |
| 4,933,145 A | 6/1990 | Uchida et al. |
| 4,962,020 A | 10/1990 | Tabor et al. |
| 4,962,022 A | 10/1990 | Fleming et al. |
| 4,965,188 A | 10/1990 | Mullis et al. |
| 4,978,688 A | 12/1990 | Louderback |
| 5,039,704 A | 8/1991 | Smith et al. |
| 5,047,342 A | 9/1991 | Chatterjee |
| 5,071,648 A | 12/1991 | Rosenblatt |
| 5,078,997 A | 1/1992 | Hora et al. |
| 5,079,352 A | 1/1992 | Gelfand et al. |
| 5,089,407 A | 2/1992 | Baker et al. |
| 5,096,670 A | 3/1992 | Harris et al. |
| 5,096,744 A | 3/1992 | Takei et al. |
| 5,098,893 A | 3/1992 | Franks et al. |
| 5,198,353 A | 3/1993 | Hawkins et al. |
| 5,200,399 A | 4/1993 | Wettlaufer et al. |

(Continued)

FOREIGN PATENT DOCUMENTS

| | | |
|---|---|---|
| CA | 1022441 | 12/1977 |
| CA | 2467563 | 5/2003 |
| CN | 102947082 A | 2/2013 |
| DE | 19834816 | 2/2000 |
| DE | 102008029734 A1 | 12/2009 |
| EP | 0448146 | 9/1991 |
| EP | 0451924 | 10/1991 |
| EP | 0329822 B1 | 6/1994 |
| EP | 0236069 B1 | 5/1997 |
| EP | 0774464 | 5/1997 |

(Continued)

OTHER PUBLICATIONS

US 8,785,182, 07/2014, Muller-Cohn et al. (withdrawn)
Branco et al. Chem. Eur. J. (2002) 8(16) 3671-3677.*
Sigma Catalog (1998)(Sigma-Aldrich: St. Louis, MO) p. 1874.*
Stock et al. Green Chemistry (2004) 6: 266-290.*
Defintion of aqueous http://www.merriam-webster.com/dictionary/aqueous downloaded Aug. 20, 2016.*
Jin et al. Biotechnol. Bioprocess Engineer. (2007) 12: 525-530.*
"Antibiotics from Prokaryotes." https://www.boundless.com/microbiology/antimicrobial-drugs/commonly-used-antimicrobial-drugs/antibiotics-from-prokaryotes/, downloaded Aug. 1, 2014.

(Continued)

*Primary Examiner* — Susan Hanley
(74) *Attorney, Agent, or Firm* — Wilson Sonsini Goodrich & Rosati

(57) ABSTRACT

Compositions and methods are disclosed for substantially liquid, gel, suspension, slurry, semisolid and/or colloid storage of biological samples following admixture with the herein disclosed storage composition, permitting substantial recovery of biological activity following storage without refrigeration. In certain embodiments, unfractionated saliva samples may be stored without refrigeration for weeks, months or years in a form that permits recovery of intact DNA following the storage period.

24 Claims, 3 Drawing Sheets

(56) References Cited

U.S. PATENT DOCUMENTS

| | | |
|---|---|---|
| 5,240,843 A | 8/1993 | Gibson et al. |
| 5,242,792 A | 9/1993 | Rudolph et al. |
| 5,270,179 A | 12/1993 | Chatterjee |
| 5,290,765 A | 3/1994 | Wettlaufer et al. |
| 5,315,505 A | 5/1994 | Pratt et al. |
| 5,351,801 A | 10/1994 | Markin et al. |
| 5,374,553 A | 12/1994 | Gelfand et al. |
| 5,397,711 A | 3/1995 | Finckh |
| 5,403,706 A | 4/1995 | Wilk et al. |
| 5,409,818 A | 4/1995 | Davey et al. |
| 5,418,141 A | 5/1995 | Zweig et al. |
| 5,428,063 A | 6/1995 | Barak et al. |
| 5,436,149 A | 7/1995 | Barnes |
| 5,455,166 A | 10/1995 | Walker |
| 5,496,562 A | 3/1996 | Burgoyne |
| 5,498,523 A | 3/1996 | Tabor et al. |
| 5,512,462 A | 4/1996 | Cheng |
| 5,516,644 A | 5/1996 | Yamauchi et al. |
| 5,529,166 A | 6/1996 | Markin et al. |
| 5,541,290 A | 7/1996 | Harbeson et al. |
| 5,556,771 A | 9/1996 | Shen et al. |
| 5,593,824 A | 1/1997 | Treml et al. |
| 5,614,365 A | 3/1997 | Tabor et al. |
| 5,614,387 A | 3/1997 | Shen et al. |
| 5,684,045 A | 11/1997 | Smith et al. |
| 5,705,366 A | 1/1998 | Backus |
| 5,728,822 A | 3/1998 | MacFarlane |
| 5,741,462 A | 4/1998 | Nova et al. |
| 5,751,629 A | 5/1998 | Nova et al. |
| 5,763,157 A | 6/1998 | Treml et al. |
| 5,777,099 A | 7/1998 | Mehra |
| 5,777,303 A | 7/1998 | Berney |
| 5,779,983 A | 7/1998 | Dufresne et al. |
| 5,789,172 A | 8/1998 | Still et al. |
| 5,789,414 A | 8/1998 | Lapidot et al. |
| 5,798,035 A | 8/1998 | Kirk et al. |
| 5,814,502 A | 9/1998 | Hoeltke et al. |
| 5,827,874 A | 10/1998 | Meyer et al. |
| 5,834,254 A | 11/1998 | Shen et al. |
| 5,837,546 A | 11/1998 | Allen et al. |
| 5,856,102 A | 1/1999 | Bierke-Nelson et al. |
| 5,861,251 A | 1/1999 | Park et al. |
| 5,863,799 A | 1/1999 | Hengstenberg |
| 5,874,214 A | 2/1999 | Nova et al. |
| 5,876,992 A | 3/1999 | De Rosier et al. |
| 5,914,272 A | 6/1999 | Dufresne et al. |
| 5,918,273 A | 6/1999 | Horn |
| 5,939,259 A | 8/1999 | Harvey et al. |
| 5,945,515 A | 8/1999 | Chomczynski |
| 5,948,614 A | 9/1999 | Chatterjee |
| 5,955,448 A | 9/1999 | Colaco et al. |
| 5,985,214 A | 11/1999 | Stylli et al. |
| 5,991,729 A | 11/1999 | Barry et al. |
| 6,013,488 A | 1/2000 | Hayashizaki |
| 6,015,668 A | 1/2000 | Hughes et al. |
| 6,017,496 A | 1/2000 | Nova et al. |
| 6,025,129 A | 2/2000 | Nova et al. |
| 6,037,168 A | 3/2000 | Brown |
| 6,050,956 A | 4/2000 | Ikegami et al. |
| 6,057,117 A | 5/2000 | Harrison et al. |
| 6,057,159 A | 5/2000 | Lepre |
| 6,071,428 A | 6/2000 | Franks et al. |
| 6,090,925 A | 7/2000 | Woiszwillo et al. |
| 6,124,089 A | 9/2000 | Ryan |
| 6,127,155 A | 10/2000 | Gelfand et al. |
| 6,143,817 A | 11/2000 | Hallam et al. |
| 6,153,412 A | 11/2000 | Park et al. |
| 6,153,618 A | 11/2000 | Schultz et al. |
| 6,156,345 A | 12/2000 | Chudzik et al. |
| 6,166,117 A | 12/2000 | Miyazaki |
| 6,168,922 B1 | 1/2001 | Harvey et al. |
| 6,197,229 B1 | 3/2001 | Ando et al. |
| 6,204,375 B1 | 3/2001 | Lader |
| 6,221,599 B1 | 4/2001 | Hayashizaki |
| 6,242,235 B1 | 6/2001 | Shultz et al. |
| 6,251,599 B1 | 6/2001 | Chen et al. |
| 6,258,930 B1 | 7/2001 | Gauch et al. |
| 6,284,459 B1 | 9/2001 | Nova et al. |
| 6,294,203 B1 | 9/2001 | Burgoyne |
| 6,294,338 B1 | 9/2001 | Nunomura |
| 6,310,060 B1 | 10/2001 | Barrett et al. |
| 6,313,102 B1 | 11/2001 | Colaco et al. |
| 6,322,983 B1 | 11/2001 | Burgoyne |
| 6,323,039 B1 | 11/2001 | Dykens et al. |
| 6,329,139 B1 | 12/2001 | Nova et al. |
| 6,331,273 B1 | 12/2001 | Nova et al. |
| 6,352,854 B1 | 3/2002 | Nova et al. |
| 6,366,440 B1 | 4/2002 | Kung |
| 6,372,428 B1 | 4/2002 | Nova et al. |
| 6,372,437 B2 | 4/2002 | Hayashizaki |
| 6,380,858 B1 | 4/2002 | Yarin et al. |
| 6,416,714 B1 | 7/2002 | Nova et al. |
| 6,417,185 B1 | 7/2002 | Goff et al. |
| 6,426,210 B1 | 7/2002 | Franks et al. |
| 6,440,966 B1 | 8/2002 | Barrett et al. |
| 6,447,726 B1 | 9/2002 | Delucas et al. |
| 6,447,804 B1 | 9/2002 | Burgoyne |
| 6,448,245 B1 | 9/2002 | DePetrillo et al. |
| RE37,872 E | 10/2002 | Franks et al. |
| 6,458,556 B1 | 10/2002 | Hayashizaki |
| 6,465,231 B2 | 10/2002 | Harrison et al. |
| 6,475,716 B1 | 11/2002 | Seki |
| 6,489,344 B1 | 12/2002 | Nuss et al. |
| 6,503,411 B1 | 1/2003 | Franks et al. |
| 6,503,702 B1 | 1/2003 | Stewart |
| 6,528,309 B2 | 3/2003 | Levine |
| 6,534,483 B1 | 3/2003 | Bruno et al. |
| 6,535,129 B1 | 3/2003 | Petrick |
| 6,602,718 B1 | 8/2003 | Augello et al. |
| 6,608,632 B2 | 8/2003 | Daly et al. |
| 6,610,531 B1 | 8/2003 | Mateczun et al. |
| 6,617,170 B2 | 9/2003 | Augello et al. |
| 6,627,226 B2 | 9/2003 | Burgoyne et al. |
| 6,627,398 B1 | 9/2003 | Wilusz et al. |
| 6,638,945 B1 | 10/2003 | Gibson |
| 6,645,717 B1 | 11/2003 | Smith et al. |
| 6,649,406 B1 | 11/2003 | Williams et al. |
| 6,653,062 B1 | 11/2003 | DePablo et al. |
| 6,664,099 B1 | 12/2003 | Worrall |
| 6,667,167 B1 | 12/2003 | Sorensen et al. |
| 6,682,730 B2 | 1/2004 | Mickle et al. |
| 6,689,353 B1 | 2/2004 | Wang et al. |
| 6,696,028 B2 | 2/2004 | Bara |
| 6,746,841 B1 | 6/2004 | Fomovskaia et al. |
| 6,746,851 B1 | 6/2004 | Tseung et al. |
| 6,750,059 B1 | 6/2004 | Blakesley et al. |
| 6,776,959 B1 | 8/2004 | Helftenbein |
| 6,787,305 B1 | 9/2004 | Li et al. |
| 6,800,632 B2 | 10/2004 | Nuss et al. |
| 6,803,200 B2 | 10/2004 | Xia et al. |
| 6,821,479 B1 | 11/2004 | Smith et al. |
| 6,821,789 B2 | 11/2004 | Augello et al. |
| 6,852,833 B1 | 2/2005 | Machida et al. |
| 6,858,634 B2 | 2/2005 | Asrar et al. |
| 6,861,213 B2 | 3/2005 | Oelmuller et al. |
| 6,862,789 B1 | 3/2005 | Hering et al. |
| 6,872,357 B1 | 3/2005 | Bronshtein et al. |
| 6,896,894 B2 | 5/2005 | Brody et al. |
| 6,919,172 B2 | 7/2005 | DePablo et al. |
| 6,942,964 B1 | 9/2005 | Ward et al. |
| 6,949,544 B2 | 9/2005 | Bethiel et al. |
| 6,949,547 B2 | 9/2005 | Nuss et al. |
| 7,001,770 B1 | 2/2006 | Atencio et al. |
| 7,001,905 B2 | 2/2006 | Biwersi et al. |
| 7,011,825 B2 | 3/2006 | Yamazaki et al. |
| 7,037,918 B2 | 5/2006 | Nuss et al. |
| 7,045,519 B2 | 5/2006 | Nuss et al. |
| 7,049,065 B2 | 5/2006 | Hayashizaki |
| 7,083,106 B2 | 8/2006 | Albany |
| 7,098,033 B2 | 8/2006 | Chen et al. |
| 7,101,693 B2 | 9/2006 | Cicerone et al. |
| 7,129,242 B2 | 10/2006 | Satoh et al. |
| 7,142,987 B2 | 11/2006 | Eggers |
| 7,150,980 B1 | 12/2006 | Lapidot et al. |

(56) References Cited

U.S. PATENT DOCUMENTS

| | | |
|---|---|---|
| 7,169,584 B2 | 1/2007 | Ward et al. |
| 7,169,816 B2 | 1/2007 | Barrett et al. |
| RE39,497 E | 2/2007 | Franks et al. |
| 7,172,999 B2 | 2/2007 | Mattern et al. |
| 7,258,873 B2 | 8/2007 | Truong-Le et al. |
| 7,270,953 B2 | 9/2007 | Hollander et al. |
| 7,282,371 B2 | 10/2007 | Helftenbein |
| 7,326,418 B2 | 2/2008 | Franzoso et al. |
| 7,384,603 B2 | 6/2008 | Klein et al. |
| 7,425,557 B2 | 9/2008 | Nuss et al. |
| 7,476,754 B2 | 1/2009 | Herradon Garcia et al. |
| 7,521,460 B2 | 4/2009 | Langham et al. |
| 7,592,455 B2 | 9/2009 | Brookings et al. |
| 7,728,013 B2 | 6/2010 | Blatt et al. |
| 7,745,663 B2 | 6/2010 | Isshiki et al. |
| 7,795,256 B2 | 9/2010 | Alexander et al. |
| 7,803,839 B2 | 9/2010 | Aay et al. |
| 7,846,703 B2 | 12/2010 | Kobayashi et al. |
| 7,897,624 B2 | 3/2011 | Yan et al. |
| 7,919,294 B2 | 4/2011 | Franco De Sarabia Rosado et al. |
| 7,932,266 B2 | 4/2011 | Garcia et al. |
| 7,972,828 B2 | 7/2011 | Ward et al. |
| 8,143,271 B2 | 3/2012 | Ibrahim et al. |
| RE43,389 E | 5/2012 | Helftenbein |
| 8,178,555 B2 | 5/2012 | Chang et al. |
| 8,378,108 B2 | 2/2013 | Corkey et al. |
| 8,394,822 B2 | 3/2013 | Hutchings et al. |
| 8,440,665 B2 | 5/2013 | Corkey et al. |
| 8,492,427 B2 | 7/2013 | Gancia et al. |
| 8,519,125 B2 | 8/2013 | Whitney et al. |
| 8,530,480 B2 | 9/2013 | Kamenecka et al. |
| 8,598,360 B2 | 12/2013 | Corkey et al. |
| 8,642,584 B2 | 2/2014 | Aftab et al. |
| 8,664,244 B2 | 3/2014 | Chen |
| 8,900,856 B2 | 12/2014 | Muller-Cohn et al. |
| 9,376,709 B2 | 6/2016 | Whitney et al. |
| 2001/0038858 A1 | 11/2001 | Roser et al. |
| 2002/0039771 A1 | 4/2002 | Peters et al. |
| 2002/0055118 A1 | 5/2002 | Eym |
| 2002/0076819 A1 | 6/2002 | Bowman et al. |
| 2002/0081565 A1 | 6/2002 | Barnea et al. |
| 2002/0094533 A1 | 7/2002 | Hess et al. |
| 2002/0103086 A1 | 8/2002 | Asrar et al. |
| 2002/0182258 A1 | 12/2002 | Lansford et al. |
| 2002/0197628 A1* | 12/2002 | Stewart .................. G01N 33/68 435/6.11 |
| 2003/0022148 A1 | 1/2003 | Seki |
| 2003/0031697 A1 | 2/2003 | Chudzik et al. |
| 2003/0059468 A1 | 3/2003 | Mattern et al. |
| 2003/0091971 A1 | 5/2003 | Xia et al. |
| 2003/0119042 A1 | 6/2003 | Franco De Sarabia Rosado et al. |
| 2003/0129755 A1 | 7/2003 | Sadler et al. |
| 2003/0138805 A1 | 7/2003 | Loffert et al. |
| 2003/0157088 A1 | 8/2003 | Elliott et al. |
| 2003/0162284 A1 | 8/2003 | Dordick et al. |
| 2003/0163608 A1 | 8/2003 | Tiwary et al. |
| 2003/0165482 A1 | 9/2003 | Rolland et al. |
| 2003/0175232 A1 | 9/2003 | Elliott et al. |
| 2003/0199446 A1 | 10/2003 | Bunger et al. |
| 2003/0215369 A1 | 11/2003 | Eggers et al. |
| 2004/0014068 A1 | 1/2004 | Burgoyne |
| 2004/0058349 A1* | 3/2004 | Van Ness et al. ................ 435/6 |
| 2004/0101966 A1 | 5/2004 | Davis et al. |
| 2004/0110267 A1 | 6/2004 | Sundar |
| 2004/0121420 A1* | 6/2004 | Smith ............................. 435/18 |
| 2004/0121432 A1 | 6/2004 | Klein et al. |
| 2004/0142475 A1 | 7/2004 | Barman et al. |
| 2004/0208792 A1 | 10/2004 | Linton et al. |
| 2004/0228794 A1 | 11/2004 | Weller et al. |
| 2004/0241713 A1 | 12/2004 | Mirzabekov et al. |
| 2005/0026181 A1 | 2/2005 | Davis et al. |
| 2005/0053911 A1 | 3/2005 | Greener et al. |
| 2005/0084481 A1 | 4/2005 | Hand et al. |
| 2005/0086822 A1 | 4/2005 | Frisner et al. |
| 2005/0090009 A1 | 4/2005 | Cormier et al. |
| 2005/0112610 A1 | 5/2005 | Lee et al. |
| 2005/0186254 A1 | 8/2005 | Roser et al. |
| 2005/0196824 A1 | 9/2005 | Fisher et al. |
| 2005/0227269 A1 | 10/2005 | Lloyd, Jr. et al. |
| 2005/0251501 A1 | 11/2005 | Phillips et al. |
| 2005/0276728 A1 | 12/2005 | Muller-Cohn et al. |
| 2006/0014177 A1 | 1/2006 | Hogan et al. |
| 2006/0099567 A1 | 5/2006 | Muller-Cohn et al. |
| 2006/0127415 A1 | 6/2006 | Mayeresse |
| 2006/0147944 A1* | 7/2006 | Chomczynski ...... C12Q 1/6806 435/6.18 |
| 2006/0177855 A1 | 8/2006 | Utermohlen et al. |
| 2006/0183687 A1 | 8/2006 | Cory et al. |
| 2006/0193968 A1 | 8/2006 | Keogh et al. |
| 2006/0198891 A1 | 9/2006 | Ravenelle et al. |
| 2006/0210429 A1 | 9/2006 | Hunsley et al. |
| 2006/0293212 A1 | 12/2006 | Griese et al. |
| 2007/0020289 A1 | 1/2007 | Mattern et al. |
| 2007/0043216 A1 | 2/2007 | Bair, Jr. et al. |
| 2007/0048726 A1 | 3/2007 | Baust et al. |
| 2007/0073039 A1 | 3/2007 | Chisari |
| 2007/0117173 A1 | 5/2007 | Levison et al. |
| 2007/0135528 A1 | 6/2007 | Butler et al. |
| 2007/0212760 A1 | 9/2007 | Lapidot et al. |
| 2007/0243178 A1 | 10/2007 | Ho et al. |
| 2008/0050737 A1 | 2/2008 | Arieli et al. |
| 2008/0064071 A1 | 3/2008 | Hogrefe et al. |
| 2008/0146790 A1 | 6/2008 | Grolz et al. |
| 2008/0176209 A1 | 7/2008 | Muller et al. |
| 2008/0187924 A1 | 8/2008 | Korfhage et al. |
| 2008/0227118 A1 | 9/2008 | Kohno et al. |
| 2008/0268514 A1 | 10/2008 | Muller et al. |
| 2008/0307117 A1 | 12/2008 | Muller-Cohn et al. |
| 2009/0010858 A1* | 1/2009 | Asano ..................... A61K 8/19 424/53 |
| 2009/0233283 A1 | 9/2009 | Rashtchian et al. |
| 2009/0239208 A1 | 9/2009 | Mayaudon et al. |
| 2009/0259023 A1 | 10/2009 | Su et al. |
| 2009/0291427 A1 | 11/2009 | Muller-Cohn et al. |
| 2009/0298172 A1 | 12/2009 | Muller-Cohn et al. |
| 2009/0312285 A1 | 12/2009 | Fischer et al. |
| 2010/0099150 A1 | 4/2010 | Fang et al. |
| 2010/0159528 A1 | 6/2010 | Liu et al. |
| 2010/0159529 A1 | 6/2010 | Metzler et al. |
| 2010/0178210 A1 | 7/2010 | Hogan et al. |
| 2010/0196904 A1 | 8/2010 | Arieli et al. |
| 2010/0261252 A1 | 10/2010 | Long et al. |
| 2010/0292447 A1 | 11/2010 | Pitner et al. |
| 2011/0014676 A1 | 1/2011 | Cowan et al. |
| 2011/0027862 A1 | 2/2011 | Bates et al. |
| 2011/0059490 A1 | 3/2011 | Lagunavicius et al. |
| 2011/0081363 A1 | 4/2011 | Whitney et al. |
| 2012/0028933 A1 | 2/2012 | Baust et al. |
| 2012/0052572 A1 | 3/2012 | Whitney et al. |
| 2012/0100522 A1 | 4/2012 | Saghbini et al. |
| 2012/0142070 A1 | 6/2012 | Battrell et al. |
| 2012/0282634 A1 | 11/2012 | Hughes et al. |
| 2013/0209997 A1 | 8/2013 | Whitney et al. |
| 2014/0017712 A1 | 1/2014 | Shoji et al. |
| 2014/0065627 A1 | 3/2014 | Whitney et al. |
| 2014/0261474 A1 | 9/2014 | Gonda |
| 2015/0329849 A1 | 11/2015 | Whitney et al. |
| 2016/0135446 A1 | 5/2016 | Judy et al. |
| 2016/0338342 A1 | 11/2016 | Whitney et al. |

FOREIGN PATENT DOCUMENTS

| | | |
|---|---|---|
| EP | 0875292 | 11/1998 |
| EP | 0915167 | 5/1999 |
| EP | 1088060 A1 | 4/2001 |
| EP | 0833611 | 8/2001 |
| EP | 0684315 B1 | 6/2002 |
| EP | 0822861 | 11/2003 |
| EP | 1555033 | 7/2005 |
| EP | 1082006 | 2/2006 |
| EP | 0395736 B2 | 8/2006 |
| EP | 1736542 | 12/2006 |
| EP | 1736542 A1 * | 12/2006 |
| EP | 1758932 | 3/2007 |

(56) References Cited

FOREIGN PATENT DOCUMENTS

| | | |
|---|---|---|
| EP | 1651712 | 10/2007 |
| EP | 2934572 A2 | 10/2015 |
| EP | 3154338 A1 | 4/2017 |
| EP | 3155091 A1 | 4/2017 |
| EP | 3155395 A1 | 4/2017 |
| GB | 2129551 | 5/1984 |
| JP | 62-502633 | 10/1987 |
| JP | 8-211065 | 8/1996 |
| JP | 09-127106 | 5/1997 |
| JP | 2001-50872 | 2/2001 |
| JP | 2009096766 A | 5/2009 |
| WO | WO86/07462 | 12/1986 |
| WO | WO87/00196 | 1/1987 |
| WO | WO87/01206 | 2/1987 |
| WO | WO89/00012 | 1/1989 |
| WO | WO89/06542 | 7/1989 |
| WO | WO90/05182 | 5/1990 |
| WO | WO91/14773 | 10/1991 |
| WO | WO92/00091 | 1/1992 |
| WO | WO92/06188 | 4/1992 |
| WO | WO92/06200 | 4/1992 |
| WO | WO92/09300 | 6/1992 |
| WO | WO-9211864 A1 | 7/1992 |
| WO | WO95/01559 | 1/1995 |
| WO | WO95/02046 | 1/1995 |
| WO | WO95/10605 | 4/1995 |
| WO | WO95/16198 | 6/1995 |
| WO | WO96/10640 | 4/1996 |
| WO | WO-9705248 A2 | 2/1997 |
| WO | WO97/15394 | 5/1997 |
| WO | WO98/15355 | 4/1998 |
| WO | WO98/24543 | 6/1998 |
| WO | WO99/67371 | 12/1999 |
| WO | WO-9967371 | 12/1999 |
| WO | WO-0009746 A1 | 2/2000 |
| WO | WO00/14505 | 3/2000 |
| WO | WO00/20117 | 4/2000 |
| WO | WO00/62023 | 10/2000 |
| WO | WO00/76664 | 12/2000 |
| WO | WO-0137656 A2 | 5/2001 |
| WO | WO01/94016 | 12/2001 |
| WO | WO03/020924 | 3/2003 |
| WO | WO-03020874 A2 | 3/2003 |
| WO | WO03/056293 | 7/2003 |
| WO | WO-03087335 A2 | 10/2003 |
| WO | WO-2004031363 A2 | 4/2004 |
| WO | WP2004/112476 | 12/2004 |
| WO | WO2005/059178 | 6/2005 |
| WO | WO2005/113147 | 12/2005 |
| WO | WO2006/001499 | 1/2006 |
| WO | WO2007/075253 | 7/2007 |
| WO | WO2007/094581 | 8/2007 |
| WO | WO-2008007463 A1 | 1/2008 |
| WO | WO2008/040126 | 4/2008 |
| WO | WO-2008048228 A2 | 4/2008 |
| WO | WO-2008108549 A1 | 9/2008 |
| WO | WO2005/116081 | 12/2008 |
| WO | WO2009/002568 | 12/2008 |
| WO | WO2009/009210 | 1/2009 |
| WO | WO2009/038853 | 3/2009 |
| WO | WO-2010047592 A2 | 4/2010 |
| WO | WO-2010065924 A1 | 6/2010 |
| WO | WO-2010132508 A2 | 11/2010 |
| WO | WO-2010138522 A2 | 12/2010 |
| WO | WO2012/018639 | 2/2012 |
| WO | WO-2012018638 A2 | 2/2012 |
| WO | WO-2012170907 A2 | 12/2012 |
| WO | WO2013/077290 | 6/2014 |
| WO | WO-2014100755 A2 | 6/2014 |
| WO | WO-2015002729 A2 | 1/2015 |
| WO | WO-2015191632 A1 | 12/2015 |
| WO | WO-2015191633 A1 | 12/2015 |
| WO | WO-2015191634 A1 | 12/2015 |

OTHER PUBLICATIONS

"Are supplements with amino acid chelated minerals better than those with other forms of minerals?" https://www.consumerlab.com/answers/Are+supplements+with+amino+acid+chelated+minerals+better+than+those+with+other+forms+of+minerals%3F/amino_acid_mineral_chelates/, downloaded Jul. 31, 2014.
"Borax: Friend or foe?" Momsaware.org webpage, http://www.momsaware.org/household-general/139-borax-friend-or-foe.html, downloaded Jul. 31, 2014.
"Foods high in glycolic acid." http://www.ehow.com/list_5815634_foods-high-glycolic-acid.html , downloaded Jul. 31, 2014.
"The dose makes the poison." Yale chemsafe (http://learn.caim.yale.edu/chemsafe/references/dose.html, downloaded Aug. 1, 2014.
Balevicius et al., NMR and quantum chemistry study of mesoscopic effects in ionic liquids. J.Phys.Chem., 114:5365-5371 (2010).
Branco et al., Preparation and characterization of new room temperature ionic liquids. Chem.Eur.J., 8(16): 3671-3677 (2002).
DNA learning center, "Radiation can cause DNA mutations, 3D animation with narration." http://www.dnalc.org/view/15529-Radiation-can-cause-DNA-mutations-3D-animation-with-narration.html, downloaded Aug. 1, 2014.
Kravitz, "Lactate: Not guilty as charged." IDEA Fitness Journal 2(6), 23-25 (2005) http://www.unm.edu/lkravitz/Article/%20folder/lactate.html, 3d paragraph, downloaded Jul. 31, 2014.
Sadeghi et al., Effect of alkyl chain length and temperature on the thermodynamic properties of ionic liquids 1-alkyl-3-methylimidazolium bromide in aqueous and non-aqueous solutions at different temperatures. J.Chem.Thermodynamics, 41:273-289 (2009).
Sawicki, "Foods high in Glutathione." http://www.ehow.com/list_6900955_foods-high-glutathione.html, downloaded Jul. 31, 2014.
The Frontier energy solution, Inc.'s FAQ, http://www.frontierenergysolutionsinc.com/faq/, downloaded Jul. 31, 2014.
U.S. Appl. No. 11/102,588 Notice of Allowance dated Sep. 24, 2014.
U.S. Appl. No. 13/966,117 Final Office Action dated Feb. 26, 2015.
U.S. Appl. No. 13/966,117 Office action dated Sep. 25, 2014.
Allison et al., "Effects of Drying Methods and Additives on Structure and Function of Actin: Mechanisms of Dehydration-Induced Damage and Its Inhibition," Archives of Biochemistry and Biophysics 358(1):171-181, 1998.
Anchordoquy et al., "Frontiers in Clinical Research—Preservation of DNA," Cell Preservation Technology 5(4):180-188, 2007.
Ando et al., "PLGA Microspheres Containing Plasmid DNA: Preservation of Supercoiled DNA via Cryopreparatin and Carbohydrate Stabilization," Journ. Pharm. Sci., vol. 88, No. 1, pp. 126-130, 1999.
Anonymous, "Transmucosal polymeric molecular delivery systems," retrieved from http://www.antiagingresearch.com/hgh/transmucosal.php on Apr. 7, 2005, 2 pages.
Arakawa et al., "Small molecule pharmacological chaperones: From thermodynamic stabilization to pharmaceutical drugs," Biochimica et Biophysica Acta 1764:1677-1687, 2006.
Asano, "Glycosidase inhibitors: update and perspectives on practical use," Gycobiology /3(10):93R-104R, 2003.
Barnes, "The fidelity of Taq polymerase catalyzing PCR is improved by an N-terminal deletion," Gene 112:29-35, 1992.
Baskakov et al., "Forcing Thermodynamically Unfolded Proteins to Fold," The Journal of Biological Chemistry, 273(9):4831-4834, 1998.
Boyd et al., "Stabilization Effect of Polyvinyl Alcohol on Horseradish Peroxidase, Glucose Oxidase, 13-Galactosidase and Alkaline Phosphatase," Biotechnology Techniques 10(9):693-698, 1996.
Buhler et al., "Viral Evolution in Response to the Broad-Based Retroviral Protease Inhibitor TL-3," Journal of Virology, 75(19):9502-9508, 2001.
Calbiochem® Inhibitor SourceBook™ 2004 (1st Ed.)), EMD Biosciences, La Jolla, CA.
Calbiochem® Inhibitor SourceBook™ 2007 (2nd Ed.), EMD Biosciences, La Jolla, CA.

(56) References Cited

OTHER PUBLICATIONS

Carninci et al., "Thermostabilization and thermoactivation of thermolabile enzymes by trehalose and its application for the synthesis of full length cDNA," Proc. Natl. Acad. Sci. USA 95:520-524, 1998.
Carpenter et al., "Stabilization of phosphofructokinase during airdrying with sugars and sugar/transition metal mixtures," Cryobiology 24(5):455-464, 1987. (Abstract).
Catalan et al., "Progress towards a generalized solvent polarity scale: The solvatochromism of 2-(dimethylamino)-7-nitrofinorene and its homomorph 2-fluoro-7-nitrofluorene", Liebigs Ann. 1995(2):241-252, 1995.
Cavalieri et al., "Chaperone-like activity of nanoparticles or hydrophobized poly(vinyl alcohol)," Soft Matter 3:718-724, 2007.
Chen et al., "Stabilization of Recombinant Human Keratinocyte Growth Factor by Osmolytes and Salts," Journal of Pharmaceutical Sciences, 85(4):419-426, 1996.
Cheng et al., "Chip PCR. II. Investigation of different PCR amplification systems in microfabricated silicon-glass chips," Nucleic Acids Res. 24:380-385, 1996.
Cohen et al., "Diffusion NMR Spectroscopy in Supramolecular and Combinatorial Chemistry: An Old Parameter—New Insights," Angew. Chem. Int. Ed., 44: 520-554, 2005.
Dagani, "Stir, Heat—But No Need to Dissolve," Chemical & Engineering News 81(5): 3 pages, 2003.
Dankwardt et al., "Stabilization of enzyme immunoassays for atrazine," Analytica Chemica Acta 362:35-45, 1998.
Daugherty et al., "Formulation and delivery issues for monoclorial antibody therapeutics," Advanced Drug Delivery Reviews 58:686-706 2006.
De Sanctis et al., "Influence of Glycerol on the Structure and Redox Properties of Horse Heart Cytochrome c. A Circular Dichroism and Electrochemical Study," Journal of Protein Chemistry, 15(7):599-606, 1996.
Degim et al., "Controlled Delivery of Peptides and Proteins," Current Pharmaceutical Design 13:99-117, 2007.
DePaz et al., "Effects of drying methods and additives on the structure, function, and storage stability of subtillisin: role of protein conformation and molecular mobility," Enzyme and Microbial Technology 31:765-774, 2002.
Di Tullio et al., "Molecular recognition by mass spectrometry," J. Mass Spectrom, 40(7):845-865, 2005.
Dong et al., "Biosynthesis of the Validamycins: Identification of Intermediates in the Biosynthesis of Validamycin A by Streptomyces hygroscopicus var. limoneus," J. Am. Chem. Soc. 123:27332742, 2001.
Dowell et al. Otitis media—principles of judicious use of antimicrobial agents, Pedatrics; 101 Suppl. 1: 165-171, 1998.
Dowell et al. Principles of judicious use of antimicrobial agents for pediatric upper respiratory tract infections, Pedatrics. 101 Supl. 1: 163-165, 1998.
Dyke et al., "Solvent-Free Functionalization of Carbon Nanotubes," J. Am. Chem. Soc. 125:11561157, 2003
El-Bahiti, "Trehalose Metabolism in Wheat and Identification of Trehalose Metabolizing Enzymes Under Abiotic Stress Conditions," Thesis, The Graduate School of Natural and Applied Sciences of the Middle East Technical University, Jul. 2003, 140 pages.
Elzie et al., "The N-terminus of thrombospondin: the domain stands apart," The International Journal of Biochemistry & Cell Biology 36:1090-1101, 2004.
EP08826300.9 Supplementary Search Report dated Oct. 26, 2010.
EP10775442.6 Extended European Search Report dated Jan. 21, 2014.
EP11815081.2 Extended European Search Report dated Nov. 5, 2013.
EP11815082.0 Extended European Search Report dated Nov. 5, 2013.
Flaman et al., "A rapid PCR fidelity assay," Nucl. Acids Res., 22(15):3259-3260, 1994.
Frye et al., "The kinetic basis for the stabilization of *Staphylococcal* nuclease by xylose," Protein Science, 6:789-793, 1997.
Galinski et al., "1,4,5,6-Tetrahydro-2-methyl-4-pyrimidinecarboxylic acid. A novel cyclic amino acid from halophilic phototrophic bacteria of the genus Ectothiorhodospira," Eur. J. Biochem., 149:135-139, 1985.
Garcia de Castro et al., "Anhydrobiotic Engineering of Gram-Negative Bacteria," Applied and Environmental Microbiology 66(9):4142-4144, 2000.
Godfrey, "Solvent selection via miscibility number," Chem. Technol. 2(6):359-363, 1972.
Goller et al, Protection of a model enzyme (lcatate dehydrogenase) against heat, urea and freeze-thaw treatment by compatible solute additives, J. of Molecular Catalsys B: Enzymatic, 7(104):37-45, 1999.
Gombotz et al., "Biodegradable Polymers for Protein and Peptide Drug Delivery," Bioconjugate Chem. 6:332-351, 1995.
Gowrishankar, J. "Osmoregulation in enterobacteriaccae: Role of Proline/Betaine Transport Systems." Current Science, 57 (5): 225-234, 1988.
Green DR, "Apoptosis, Death deceiver," Nature, 396(6712):629-30, 1998.
Green DR, "Apoptotic pathways: the roads to ruin," Cell, 94(6):695-69, 1998.
Green et al., "Mitochondria and apoptosis," Science, 281(5381):1309-12, 1998.
Henke, et al., "Betaine Improves the PCR amplification of GC-rich DNA Sequences." Nucleic Acids Research. 25(19): 3957-3957, 1997.
Hoffman, "Hydrogels for biomedical applications," Advanced Drug Delivery Reviews 43:3-12, 2002.
Holland et al., "Biological sample collection and processing for molecular epidemiological studies," Mutation Research 543:217-234, 2003.
Holland et al., "Molecular epidemiology biomarkers—Sample collection and processing considerations," Toxicology and Applied Pharmacology 206:261-268, 2005.
Iyer et al, Enzyme stability and stabilization—Aqueous and non-aqueous environment, Process Biochemistry, 43:1019-1032, 2008.
Jones et al., "Long-term storage of DNA-free RNA for use in vaccine studies," BioTechniques 43(5):675-681, 2007.
Kaijalainen et al., "An alternative hot start technique for PCR in small volumes using beads of wax-embedded reaction components dried in trehalose," Nucleic Acids Research 21(12):29592960, 1993.
Kameda et al., "New Cyclitols, Degradation of Validamycin A by Flavobacterium Saaccharophilum," The Journal of Antibiotics 33(12):1573-1574, 1980.
Kirn-Safran et al., "Heparan Sulfate Proteoglycans: Coordinators of Multiple Signaling Pathways during Chondrogenesis," Birth Defects Research (Part C) 72:69-88, 2004.
Knapp et al., "Extrinsic protein stabilization by the naturally occurring osmolytes β-hydroxyectoine and betaine," Extremophiles, 3:191-198, 1999.
Knuesel et al., "Comparative studies of suidatrestin, a specific inhibitor of trehalases," Comparative Biochemistry and Physiology Part B 120:639-646 1998.
Komiyama et al., "Hydrolysis of DNA and RNA by lanthanide ions: mechanistic studies leading to new applications," Chem. Commun.:1443-1451, 1991.
Konishi et al., "Effects of Bay m 1099, an a-Glucosidase Inhibitor, on Starch Degradation in Germinating Mung Beans," Biosci. Biotechnol. Biochem. 62(1):142-144, 1998.
Kricka and Wilding, "Microchip PCR," Anal. Bioanal. Chem 377:820-825, 2003.
Kumar et al., "The role of proline in the prevention of aggregation during Protein folding in vitro," Biochemistry and Molecular Biology International, 46(3):509-517, 1998.
Langer, "New Methods of Drug Delivery," Science 249:1527-1533, 1990.
Langer, "Polymer-Controlled Drug Delivery Systems," Acc. Chem. Res. 26:537-542, 1993.

(56) References Cited

OTHER PUBLICATIONS

Lawyer et al., "High-level Expression, Purification, and Enzymatic Characterization of Full-length Thermus aquaticus DNA Polymerase and a Truncated Form Deficient in 5' to 3' Exonuclease Activity," PCR Meth. Appl. 2:275-287, 1993.

Lee et al., "Analysis of the S3 and S3' subsite specificities of feline immunodeficiency virus (FIV) protease: Development of a broad-based protease inhibitor efficacious against FIV, SW, and HIV in vitro and ex vivo," Proc. Natl. Acad. Sci. USA 95:939-944, 1998.

Lee et al., "Development of a New Type of Protease Inhibitors, Efficacious aganst FIV and HIV Variants," J. Am. Chem. Soc. 121:1145-1155, 1999.

Liao et al., "The effects of polyvinyl alcohol on the in vitro stability and delivery of spray-dried protein particles form surfactant-free HFA 134a-based pressurised metered dose inhalers," International Journal of Pharmaceutics 304:29-39, 2005.

Li et al., "Effect of Mobile Phase Additives on the Resolution of Four Bioactive Compounds by RP-HPLC" Int'l Journal of Molecular Sciences, 11(5):2229-2240 (Jan. 2010).

Loo et al., Peptide and Protein Analysis by Electrospray Ionization—MassSpectrometry and Capillary Electrophoresis—Mass Spectrometry, Anal. Biochem., 179(2):404-412, 1989.

Lou et al., "Increased amplification efficiency of microchip-based PCR by dynamic surface passivation," Biotechniques, vol. 36, No. 2, pp. 248-252, 2004.

Lozano et al., "Stabilization of a-Chymotrypsin by Ionic Liquids in Transesteri cation Reactions", Biotechnology and Bioengineering, 75(5):563-569 (Dec. 2001).

Luo et al., "Expression of a fusion protein of scFv-biotin mimetic peptide for immunoassay," J. Biotechnol. 65:225, 1998.

Malin et al., "Effect of Tetrahydropyrimidine Derivatives on Protein-Nucleic Acids Interaction," The Journal of Biological Chemistry, 274(11):6920-6929, 1999.

Manzanera et al., "Hydroxyectoine is Superior to Trehalose for Anhydrobiotic Engineering of Pseudomanas putida KT2440," Applied and Environmental Microbiology 68(9):4328-4333, 2002.

Manzanera et al., "Plastic Encapsulation of Stabilized *Escherichia coli* and Pseudomonas putida," Applied and Envrironmental Microbiology 70(5):3143-3145, 2004.

Marshall et al., "NXY-059, a Free Radical-Trapping Agent, Substantially Lessens the Functional Disability Resulting From Cerebral Ischemia in a Primate Species," Stroke, 32:190-198, 2001.

Mascellani et al., "Compatible solutes from hyperthermophiles improves the quality of DNA microarrays," BMC Biotechnology, 7(82):1-6, 2007.

Mitchell et al., "Dispersion of Functionalized Carbon Nanotubes in Polystyrene," Macromolecules 35:8825-8830, 2002.

Mohr, "Reversible chemical reactions as the basis for optical sensors used to detect amines, alcohols and humidity," J. Mater. Chem., 9:2259-2264, 1999.

Muller-Cohn et al., "Integration of Sample Storage and Sample Management for Life Science," Amendment filed in U.S. Appl. No. 11/102,588, filed Jan. 11, 2010, 21 pages.

Muller-Cohn et al., "Integration of Sample Storage and Sample Management for Life Science," Response filed in U.S. Appl. No. 11/102,588. filed Aug. 18, 2009, 31 pages.

Muller -Cohn et al., "Integration of Sample Storage and Sample Management for Life Science," Response filed in U.S. Appl. No. 11/102,588, filed Sep. 29, 2010, 28 pages.

Muller Cohn et al., U.S. Appl. No. 11/102,588, Amendment filed Apr. 1, 2011, 28 pages.

Natale et al., Sensitivity of Bovine Blastocyst Gene Expression Patterns to Culture Environments Assessed by Differential Display RT-PCR. Reproduction, 122 (5): 687-693, 2001.

O'Brien et al. Acute sinusitis—principles of judicious use of antimicrobial agents. Pedatrics. 101 Suppl. 1: 174-177, 1998.

O'Brien et al. Cough illness/bronchitis—principles of judicious use of antimicrobial agents. Pedatrics. 101 Suppl. 1: 178-181, 1998.

Ortega et al., "New functional roles for non-collagenous domains of basement membrane collagens," Journal of Cell Science 115:4201-4214, 2002.

Parsegian et al., "Macromolecules and Water: Probing with Osmotic Stress," Methods in Enzymology, 259:43-94, 1995.

Passot et al., "Physical characterization of formulations for the development of two stable freeze-dried proteins during both dried and liquid storage," European Journal of Pharmaceutics and Biopharmaceutics 60:335-348, 2005.

Pavlov et al., "The Role of ECM Molecules in Activity-Dependent Synaptic Development and Plasticity," Birth Defects Research (Part C) 72:12-24, 2004.

PCT/US2005/012084 International Preliminary Report on Patentability dated Oct. 11, 2006.

PCT/US2005/012084 International Search Report dated Feb. 7, 2006.

PCT/US2006/45661 International Preliminary Report on Patentability dated Jun. 30, 2008.

PCT/US2006/45661 International Search Report and Written Opinion dated Nov. 13, 2007.

PCT/US2008/061332 International Preliminary Report on Patentability dated Oct. 27, 2009.

PCT/US2008/061332 International Search Report and Written Opinion dated Jul. 29, 2009.

PCT/US2008/068628 International Preliminary Report on Patentability dated Jan. 5, 2010.

PCT/US2008/068628 International Search Report and Written Opinion dated Aug. 27, 2009.

PCT/US2010/34454 International Preliminary Report on Patentability dated Nov. 15, 2011.

PCT/US2010/34454 International Search Report and Written Opinon dated Jan. 20, 2011.

PCT/US2011/045404 International Preliminary Report on Patentability dated Jan. 29, 2013.

PCT/US2011/045404 International Search Report and Written Opinion dated Mar. 27, 2012.

PCT/US2011/045405 International Preliminary Report on Patentability dated Jan. 29, 2013.

PCT/US2011/045405 International Search Report and Written Opinion dated Mar. 26, 2012.

PCT/US2013/077290 International Search Report and Written Opinion dated Jun. 23, 2014.

Prestrelski et al., "Dehydration induced Conformational Transitions in Proteins and Their Inhibition by Stabilizers," Biophysical Journal 65:601-671, 1993.

Roberts, "Organic compatible solutes of halotolerant and halophilic microorganisms," Saline Systems,1(5):1-30, 2005.

Rosenstein et al. The common cold—principles of judicious use of antimicrobial agents. Pedatrics. 101 Suppl. 1: 181-184, 1998.

Sauer et al., "Bacterial Milking: A Novel Bioprocess for Production of Compatible Solutes," Biotechnology and Bioengineering, 57(3):306-313, 1998.

Schwartz et al. Pharyngitis—principles of judicious use of antimicrobial agents. Pedatrics. 101 Suppl. 1: 171-174, 1998.

Schyma et al., "DNA-PCR Analysis of Bloodstains Samples by the Polyvinyl-Alcohol Method," Journal of Forensic Sciences 44(1):95-99, 1999.

Schyma et al., "The Accelerated Polyvinyl-Alcohol Method for GSR Collection-PVAL 2.0" Journal of Forensic Sciences 45(6):1303-1306, 2000.

Schyma, "Erfahrungen mit der PVAL—Methode in der rechtsmedizinischen Praxis," Arch. Kriminol. /97(1-2):41-46, 1996.

Scouten, "A survey of enzyme coupling techniques," Methods in Enzymology, 135:30-65, 1987.

Sirieix-Plenet et al., "Behaviour of a binary solvent mixture constituted by an amphiphilic ionic liquid, 1-decyl-3-methylimidazolium bromide and water Potentiometric and conductimetric studies," Talanta 63(4):979-986, Jul. 8, 2004.

Slita et al., "DNA-polycation complexes Effect of polycation structure on physico-chemical and biological properties " Journal of Biotechnology, 127:679-693, 2007.

(56) References Cited

OTHER PUBLICATIONS

Smith et al., "Optimal Storage Conditions for Highly Dilute DNA Sampled: A Role for Trehalose as a Preserving Agent," Journal of Forensic Science 50(5): 1-8, 2005.

Sola-Penna et al., "Carbohydrate protection of enzyme structure and function against guanidinium chloride treatment depends on the nature of carbohydrate and enzyme," Eur. J. Biochem., 248:24-29, 1997.

Suslick. et al., "Colorimetric sensor arrays for molecular recognition," Tetrahedron 60:11133-11138, 2004.

Timasheff, "Water as Ligand: Preferential Binding and Exclusion of Denaturants in Protein Unfolding," Biochemistry, 3,40:9857-9864, 1992.

U.S. Appl. No. 12/509,303 Final Office action dated Jun. 9, 2014.
U.S. Appl. No. 11/291,267 Office action dated Jun. 13, 2014.
U.S. Appl. No. 12/182,926 Office action dated Apr. 30, 2014.
U.S. Appl. No. 13/191,346 Office action dated Jul. 22, 2014.

Vanin, "Iron diethyldithiocarbamate as spin trap for nitric oxide detection," Meth. Enzymol., 301:269-79, 1999.

Voziyan et al., "Chaperonin-assisted folding of glutamine synthetase under nonpermissive conditions: Off-pathway aggregation propensity does not determine the co-chaperonin requirement," Protein Science, 9:2405-2412, 2000.

Wang et al., "A Naturally Occuring Protective System in Urea-Rich Cells: Mechanism of Osmolyte Protection of Proteins against Urea Denaturation," Biochemistry, 36:9101-9108, 1997.

Wang et al., "Antibody Structure, Instability and Formulation," Journal of Pharmaceutical Sciences 96(1):1-26, 2007.

Wang et al., "Instability, stabilization, and formulation of liquid protein pharmaceuticals," International Journal of Pharmaceutics 185:129-188, 1999.

Wang, "Protein aggregation and its inhibition in biopharmaceutics," International Journal of Pharmaceutics 289:1-30, 2005.

Whitman et al., "Prokaryotes: the unseen majority," Proc. Natl. Acad. Sci. USA, 95:6578-83, 1998

Whittlesey et al., "Delivery systems for small molecule drug, proteins, and DNA: the neuroscience/biomaterial interface," Experimental Neurology 190:1-16, 2004.

Wierzbicka-Patynowski et al., "The ins and outs of fibronectin matrix assembly," Journal of Cell Science 116:3269-3276, 2003.

Yamamoto et al., "Molecular Design of Bioconjngated Cell Adhesion Peptide with a Water-Soluble Polymeric Modifier for Enhancement or Antimetastatic Effect," Current Drug Targets 3:123-130, 2002.

Yancey et al., "Living with Water Stress: Evolution of Osmolyte Systems," Science, 217;1214-1222, 1982.

Yang et al., Neuroprotection by 2-h postischemia administration of two free radical scavengers, alpha-phenyl-n-tert-butyl-nitrone (PBN) and N-tert-butyl-(2-sulfophenyl)-nitrone (S-PBN), in rats subjected to focal embolic cerebral ischemia., Exp. Neurol., 163(1):39-45, 2000.

Zhao et al., "NXY-059, a novel free radical trapping compound, reduces cortical infarction after permanent focal cerebral ischemia in the rat," Brain Res., 909(1-2):46-50, 2001.

Zhi et al., "Renaturation of citrate synthase: Influence of denaturant and folding assistants," Protein Science, 1:522-529, 1992.

Catalan, Solvent effects based on pure solvent scales. In: Handbook of Solvents. Wypych G., ed. Toronto: ChemTec Publishing and New York: William Andrew Publishing. 2001: 583-616.

Gerard et al., cDNA synthesis by moloney murine leukemia virus RNase H-minus reverse transcriptase possessing full DNA polymerase activity. Focus, 14(1): 91-93 (1992).

PCT Patent Application No. PCT/US2013/077290 International Preliminary Report on Patentability dated Jul. 2, 2015.

Pickering, LK, Ed. 2003 Red Book: Report of the Committee on Infectious Diseases, 26th edition. Elk Grove Village, IL, pp. 695-697.

Stock et al., Effects of ionic liquids on the acetylcholinesterase-a structure-activity relationship consideration. Green Chemistry, 6:286-290 (2004).

U.S. Appl. No. 11/291,267 Office Action dated Mar. 12, 2015.
U.S. Appl. No. 13/191,346 Office Action dated Mar. 20, 2015.
U.S. Appl. No. 13/191,346 Office Action dated Jul. 2, 2015.

Machine translation of DE 102008039734 downloaded from the EPO Jun. 3, 2015.

Machine translation of WO 00/09746 downloaded from the EPO Jun. 27, 2015.

Saiki et al., Primer-directed enzymatic amplification of DNA with a thermostable DNA polymerase. Science, New Series, 239(4839):487-491 (1988).

Braasch and Corey, Locked nucleic acid (LNA): fine-tuning the recognition of DNA and RNA. Chemistry and Biology, 8:1-7 (2001).

Calfon et al., IRE1 couples endoplasmic reticulum load to secretory capacity by processing the XBP-1 mRNA. (2002) Nature 415:92-96. doi: 10.1038/415092a (Abstract only).

Harding et al., Perk is Essential for Translational Regulation and Cell Survival during the Unfolded Protein Response. (2000) Mol Cell 5:897-904. doi: 10.1016/51097-2765(00)80330-5.

Haze et al., Mammalian Transcription Factor ATF6 is Synthesized as a Transmembrane Protein and Activated by Proteolysis in Response to Endoplasmic Reticulum Stress. (1999) Mol Biol Cell 10(11):3787-3799. doi: 10.1091/mbc.10.11.3787.

Henke et al., Betaine improves the PCR amplification of GC-rich DNA sequences. Nucleic Acids Research, 25(19): 3957-3958 (1997).

Houts et al., Reverse transcriptase from avian myeloblastosis virus. Journal of Virology, 29(2): 517-522 (1979).

Kaufman RJ, Orchestrating the unfolded protein response in health and disease. (2002) J Clin Invest 110:1389-1398. doi: 10.1172/jci0216886.

Kilger and Paabo, Direct DNA sequence determination from total genomic DNA. Nucleic Acids Research, 25(10): 2032-2034 (1997).

Kim et al., Chemical Biology Investigation of Cell Death Pathways Activated by Endoplasmic Reticulum Stress Reveals Cytoprotective Modulators of ASK1S. (2009) J. Biol. Chem. 284(3):1593-1603.

Kotewicz et al., Isolation of closed Moloney murine leukemia virus reverse transcriptase lacking ribonuclease H activity. Nucleic Acid Research, 16(1): 265 (1988).

Kudo et al., A molecular chaperone inducer protects neurons from ER stress. (2008) Cell Death and Differentiation, 15:364-375.

Mizuguchi et al., Characterization and application to hot start PCR of neutralizing momoclonal antibodies against KOD DNA polymerase J.Biochem., 126:762-768 (1999).

Mori K, Tripartite Management Mini review of Unfolded Proteins in the Endoplasmic Reticulum. (2000) Cell 101(5):451-454. doi: 10.1016/s0092-8674(00)80855-7.

Nielsen et al., Peptide nucleic acid (PNA). A DNA mimic with a peptide backbone. Bioconjugate Chemistry, 5:3-7 (1994).

Okada et al., Distinct roles of activating transcription factor 6 (ATF6) and double-stranded RNA-activated protein kinase-like endoplasmic reticulum kinase (PERK) in transcription during the mammalian unfolded protein response. (2002) Biochem J 366:585-594. doi: 10.1042/bj20020391.

Soltis and Skalka, The alpha and beta chains of avian retrovirus reverse transcriptase independently expressed in *Escherichia coli*: Characterization of enzymatic activities. Proc. Nat. Acad. Sci. USA, 85:3372-3376 (1968).

PCT Patent Application No. PCT/US2013/077290 International Search Report and Written Opinion dated Jun. 23, 2014.

PCT Patent Application No. PCT/US2014/041396 International Search Report dated Mar. 13, 2015.

PCT Patent Application No. PCT/US2014/042396 International Preliminary Report on Patentability dated Dec. 23, 2015.

PCT Patent Application No. PCT/US2014/042396 Written Opinion dated Mar. 13, 2015.

PCT Patent Application No. PCT/US2015/034967 International Search Report and Written Opinion dated Sep. 8, 2015.

PCT Patent Application No. PCT/US2015/034968 International Search Report and Written Opinion dated Sep. 16, 2015.

PCT Patent Application No. PCT/US2015/034969 International Search Report and Written Opinion dated Sep. 15, 2015.

(56) References Cited

OTHER PUBLICATIONS

Peters et al., Sensitivity of human, murine, and rat cells to 5-Fluorouracil and 5'-Deoxy-5-fluorouridine in relation to drug-metabolozing enzymes Cancer Research, 46:20-28 (1986).

Ron and Walter, Signal integration in the endoplasmic reticulum unfolded protein response. (2007) Nat Rev Mol Cell Biol 8:519-529 (Abstract only).

Yoshida et al., Identification of the cis-Acting Endoplasmic Reticulum Stress Response Element Responsible for Transcriptional Induction of Mammalian Glucose-regulated Proteins: Involvement of basic leucine zipper transcription factors. (1998) J Biol Chem 273:33741-33749. doi: 10.1074/jbc.273.50.33741.

Clement et al. Bioactive isomalabaricane triterpenoids from Rhabdastrella globostellata that stabile the binding of DNA polymerase beta to DNA. J. Nat. Prod., 2006, 69(3):373-6.

Clement et al., Following nature's lead: Generating compounds for stabilizing biomolecules. Biopreservation and Biobanking, 2012, 10(4):395-402.

Qu et al., Ambient stable quantitative PCR reagents for the detection of Yersinia pestis. PLoS Neglected Tropical Diseases, Mar. 2010, 4(3):e629.

Roche. "PCR Reaction Components." Downloaded from the internet (http://www.roche-appliedscience.com/sis/amplification/pcr_amplification_050300.html; Downloaded on Dec. 13, 2012, 4 pages.

Schnoor, et al. Characterization of the synthetic compatible solute homoectoine as a potent PCR enhancer. Biochem and Biophys. Res. Comm, 2004, 322:867-872.

Spiess et al., Trehalose is a potent PCR enhancer: Lowering of DNA melting temperature and thermal stabilization of Taq polymerase by the disaccharide trehalose. Clinical Chemistry, 2004, 50:1256-1259.

Del Vigna de Almeida et al., Saliva composition and functions: A comprehensive review. The Journal of Contemporary Dental Practice, 9(3):72-80, 2008.

European Patent Application No. 14819510.0 extended European Search Report dated Feb. 7, 2017.

PCT Patent Application No. PCT/US2015/034969 International Preliminary Report on Patentability dated Dec. 22, 2016.

PCT Patent Application No. PCT/US2016/065200 International Search Report and Written Opinion dated Feb. 16, 2017.

PCT Patent Application No. PCT/US2016/065198 International Search Report and Written Opinion dated Mar. 13, 2017.

U.S. Appl. No. 14/895,475 Office Action dated Jan. 10, 2017.

\* cited by examiner

COMPOSITIONS FOR STABILIZING DNA, RNA AND PROTEINS IN SALIVA AND OTHER BIOLOGICAL SAMPLES DURING SHIPPING AND STORAGE AT AMBIENT TEMPERATURES

BACKGROUND OF THE INVENTION

Technical Field

The present invention relates generally to compositions and methods for biological sample storage.

Description of the Related Art

Research in the life sciences field is based upon the analysis of biological materials and samples, such as DNA, RNA, saliva, sputum, blood, blood buffy coat cells, urine, buccal swabs, bacteria, archaebacteria, viruses, phage, plants, algae, yeast, microorganisms, PCR products, cloned DNA, proteins, enzymes, peptides, prions, eukaryotes (e.g., protoctisca, fungi, plantae and animalia), prokaryotes, cells and tissues, germ cells (e.g., sperm and oocytes), stem cells, sorted (e.g., following immunochemical labeling) or selected (e.g., positively selected or negatively selected) cells, and of minerals or chemicals. Such samples are typically collected or obtained from appropriate sources and placed into storage and inventory for further processing and analysis. Oftentimes, transportation of samples is required, and attention is given to preserve their integrity, sterility and stability. Biological samples can be transported in a refrigerated environment using ice, dry ice or other freezing facility. However, adequate low temperatures often cannot conveniently be maintained for extended time periods such as those required for transportation between countries or continents, particularly where an energy source for the refrigeration device is lacking.

Storage containers for such samples include bottles, tubes, vials, bags, boxes, racks, multi-well dishes and multi-well plates which are typically sealed by individual screw caps or snap caps, snap or seal closures, lids, adhesive strips or tape, or multi-cap strips. The standard container format for medium to high throughput of sample storage, processing and automation of biological processes is a 96-, 384-, or 1536-well plate or array. The containers and the samples contained therein are stored at various temperatures, for example at ambient temperature or at 4° C. or at temperatures below 0° C., typically at about −20° C. or at −70° C. to −80° C. The samples that are placed and stored in the devices are most frequently contained in liquid medium or a buffer solution, and they require storage at such subzero temperatures (e.g., −20° C. or −70 to −80° C.). In some cases, samples are first dried and then stored at ambient temperature (e.g., WO 2005/113147, US 2005/0276728, US 2006/0099567), or at 4° C., at −20° C. or at −70 to −80° C.

For example, presently, nucleic acids are stored in liquid form at low temperatures. For short term storage, nucleic acids can be stored at 4° C. For long-term storage the temperature is generally lowered to −20° C. to −70° C. to prevent degradation of the genetic material, particularly in the case of genomic DNA and RNA. Nucleic acids are also stored at room temperature on solid matrices such as cellulose membranes. Both storage systems are associated with disadvantages. Storage under low temperature requires costly equipment such as cold rooms, freezers, electric generator back-up systems; such equipment can be unreliable in cases of unexpected power outage or may be difficult to use in areas without a ready source of electricity or having unreliable electric systems. The storage of nucleic acids on cellulose fibers also results in a substantial loss of material during the rehydration process, since the nucleic acid remains trapped by, and hence associated with, the cellulose fibers instead of being quantitatively recoverable. Nucleic acid dry storage on cellulose also requires the subsequent separation of the cellulose from the biological material, since the cellulose fibers otherwise contaminate the biological samples. The separation of the nucleic acids from cellulose filters requires additional handling, including steps of pipetting, transferring of the samples into new tubes or containers, and centrifugation, all of which can result in reduced recovery yields and/or increased opportunity for the introduction of unwanted contaminants and/or exposure to conditions that promote sample degradation, and which are also cost- and labor-intensive.

Proteins are presently handled primarily in liquid form as solutions (e.g., in a compatible aqueous solution containing a salt and/or buffer) or suspensions (e.g., in a saturated ammonium sulfate slurry), in cooled or frozen environments typically ranging from −20° C. to storage in liquid nitrogen (Wang et al., 2007 *J. Pharm. Sci.* 96(1):1-26; Wang, 1999 *Inter. J. of Pharm.* 185: 129-188). In some exceptions proteins may be freeze-dried, or dried at room temperature in the presence of trehalose and applied directly to an untreated surface. (Garcia de Castro et al., 2000 *Appl. Environ. Microbiol.* 66:4142; Manzanera et al., 2002 *Appl. Environ. Microbiol.* 68:4328). Proteins often degrade and/or lose activity even when stored cooled (4° C.), or frozen (−20° C. or −80° C.). The freeze-thaw stress on proteins reduces bioactivity (e.g., enzymatic activity, specific binding to a cognate ligand, etc.) especially if repeated freeze-thawing of aliquots of a protein sample is required. The consequent loss of protein activity that may be needed for biological assays typically requires the readjustment of the protein concentration in order to obtain comparable assay results in successive assays, and oftentimes results in compromised reliability of experimental data generated from such samples.

Drying of proteins and nucleic acids has yet to be universally adopted by the research scientific, biomedical, biotechnology and other industrial business communities because of the lack of standard established and reliable processes, difficulties with recoveries of quantitative and functional properties, variable buffer and solvent compatibilities and tolerances, and other difficulties arising from the demands of handling nucleic acids and proteins. The same problems apply to the handling, storage, and use of other biological materials, such as viruses, phage, bacteria, cells and multicellular organisms. Dissacharides such as trehalose or lactitol, for example, have been described as additives for dry storage of protein-containing samples (e.g., U.S. Pat. No. 4,891,319; U.S. Pat. No. 5,834,254; U.S. Pat. No. 6,896,894; U.S. Pat. No. 5,876,992; U.S. Pat. No. 5,240,843; WO 90/05182; WO 91/14773), but usefulness of such compounds in the described contexts has been compromised by their serving as energy sources for undesirable microbial contaminants, by their limited stabilizing effects when used as described, by their lack of general applicability across a wide array of biological samples, and by other factors.

The highly labile nature of biological samples makes it extremely difficult to preserve their biological activity over extended time periods. While storing nucleic acids and proteins under freeze-dried conditions (e.g., as lyophilizates) can extend the storage life (shelf-life) of a sample, the subsequent loss of activity upon reconstitution in a liquid makes freeze-drying (e.g., lyophilization) a less than ideal storage technique. Moreover, drying methods cannot be used effectively for other biological materials such as those collected in large volumes, or as swabs of surfaces for biofilm collection, or for some viruses, bacteria, or multicellular organisms. For example, the ability to maintain liquid bacteria cultures under non-selective growth conditions would be particularly desirable during long term transportation, particularly in an environment that retards the growth rate and preserves the survival of the bacteria, but no such ability currently exists. Similarly, the ability to store samples stably and for extended periods in a liquid or semi-liquid environment at ambient or near-ambient temperatures (e.g., about 23° C. to 37° C.) thereby avoiding extreme temperatures (e.g., about 0° C. to –80° C.) would be highly advantageous in maintaining fully functional and intact biological samples, as these are native conditions for many biomolecules. Such capabilities are not, however, presently known.

The degradation of biological samples collected from distant places, be it a foreign country, continent, undersea or outer space, is also currently problematic, as proper analysis and testing of the samples are subsequently compromised and/or delayed. As such, presently available storage technologies for biological samples are not adequate, particularly with regard to preparation or collection of large quantities of proteins or other types of biomolecules that may not be amenable to dry storage, and/or to biological sample modalities for which it is desirable to have a storage capability for long time periods while retaining substantially constant biological activity. For example, in the case of disease outbreak or bioterrorism investigations, such an ability to preserve the integrity of biological samples could be needed, particularly if the sample is collected under extreme environmental conditions and then subjected to variable temperature conditions and/or lengthy transportation to an appropriate facility for analysis. Thus, the ability to store biological samples for extended time periods without the need for time-consuming, impractical, inconvenient and/or costly preservation methods, particularly those that require refrigeration, would be highly advantageous.

Accordingly, there is clearly a need in the art for compositions and methods for storing biological samples without dehydration for extended time periods (e.g., in excess of two weeks, three weeks, one month, six months, nine months, one year, or longer) while maintaining the biological activity, for instance, for samples collected under extreme environmental conditions (e.g., conditions including, but not limited to, extreme temperatures (e.g., sub-zero or tropical), atmospheric conditions such as increased pressure (e.g., undersea) or low gravity (e.g., outer space), UV radiation, humidity, etc., particularly over extended time periods, without complicated preparations and storage conditions. The presently disclosed embodiments address these needs and offer other related advantages.

BRIEF SUMMARY OF THE INVENTION

According to certain herein provided embodiments, there is provided a composition for substantially stable storage of nucleic acid molecules in a biological sample and/or substantially stable storage of protein and/or polypeptide molecules in a biological sample, comprising (a) one or more compounds of formula (I) or formula (II):

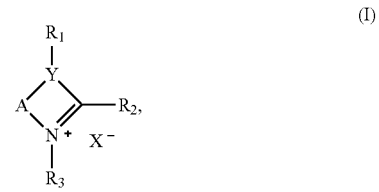

where:
A is —C(R$^4$)=C(R$^4$)— or —C(R$^4$)=C(R$^4$)—C(R$^4$)$_2$—; Y is N, S or O; R$^1$ is, when Y is N, C$_1$-C$_8$alkyl, alkenyl, optionally substituted aralkyl, optionally substituted cycloalkyl, optionally substituted cycloalkylalkyl or optionally substituted heterocyclylalkyl, and when Y is S or O, R$^1$ is absent; R$^2$ is hydrogen, C$_1$-C$_8$alkyl, alkenyl, optionally substituted aralkyl, optionally substituted cycloalkyl, optionally substituted cycloalkylalkyl or optionally substituted heterocyclylalkyl; R$^3$ is C$_1$-C$_{16}$alkyl, optionally substituted aryl or optionally substituted aralkyl; each R$^4$ is independently hydrogen, cyano, nitro, —C(O)OR$^5$, —C(O)N(R$^5$)$_2$, —N(R$^5$)$_2$, halo, haloalkyl, hydroxy, alkyl, alkoxy, haloalkoxy, alkoxyalkyl, alkenyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl or optionally substituted heteroarylalkyl; or two adjacent R$^4$'s, together with the carbons to which they are attached, may form an optionally substituted cycloalkyl, optionally substituted aryl, optionally substituted heterocyclyl or optionally substituted heteroaryl; each R$^5$ is independently hydrogen, alkyl, aryl or aralkyl; and X is a pharmaceutically acceptable anion; or

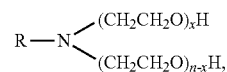

where:
R is R$^1$, R$^2$, R$^3$, R$^4$ or A; A is —C(R$^4$)=C(R$^4$)— or —C(R$^4$)=C(R$^4$)—C(R$^4$)$_2$—; R$^1$ is C$_1$-C$_9$alkyl, alkenyl, optionally substituted aralkyl, optionally substituted cycloalkyl, optionally substituted cycloalkylalkyl or optionally substituted heterocyclylalkyl; R$^2$ is hydrogen, C$_{10}$-C$_{18}$alkyl, alkenyl, optionally substituted aralkyl, optionally substituted cycloalkyl, optionally substituted cycloalkylalkyl or optionally substituted heterocyclylalkyl; R$^3$ is C$_{19}$-C$_{26}$alkyl, optionally substituted aryl or optionally substituted aralkyl; each R$^4$ is independently hydrogen, cyano, nitro, —C(O)OR$^5$, —C(O)N(R$^5$)$_2$, —N(R$^5$)$_2$, halo, haloalkyl, hydroxy, alkyl, alkoxy, haloalkoxy, alkoxyalkyl, alkenyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl or optionally substituted heteroarylalkyl; or two adjacent R$^4$'s, together with the carbons to which they are attached, may form an optionally substituted cycloalkyl, optionally substituted aryl, optionally substituted heterocyclyl or optionally substituted heteroaryl; and each R$^5$ is independently hydrogen, alkyl, aryl or aralkyl; and (b) one, two, or all three of (i) at least one precipitating agent, (ii) at least one lower alcohol, and (iii) at least one chaotrope.

In certain embodiments the composition further comprises one or more of (a) a chelating agent, (b) a reducing agent, (c) a pH buffer, and (d) water. In certain embodiments the pharmaceutically acceptable anion is selected from bromide, chloride, iodide, $C_1$-$C_{12}$alkylsulfonate, hexafluorophosphate, methylsulfate, ethylsulfate, tetrafluoroborate, trifluoromethanesulfonate and bis(trifluoromethylsulfonyl)imide.

In certain of the above described embodiments, in formula (I) A is —C($R^4$)=C($R^4$)—; $R^1$ is $C_1$-$C_8$alkyl; $R^2$ is hydrogen or $C_1$-$C_8$alkyl; and $R^3$ is $C_1$-$C_{16}$alkyl, optionally substituted aryl or optionally substituted aralkyl; each $R^4$ is independently hydrogen, cyano, nitro, —C(O)O$R^5$, —C(O)N($R^5$)$_2$, —N($R^5$)$_2$, halo, haloalkyl, hydroxy, alkyl, alkoxy, haloalkoxy, alkoxyalkyl, alkenyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl or optionally substituted heteroarylalkyl; and each $R^5$ is independently hydrogen, alkyl, aryl or aralkyl. In certain embodiments the compound of formula (I) is selected from: 1-methyl-3-carboxyethyl-imidazolium bromide, 1-hexyl-3-methylimidazolium bromide, 1-octyl-3-methylimidazolium bromide, 1-decyl-3-methylimidazolium bromide, and 1-(2-hydroxyethyl)-3-methylimidazolium bromide.

In certain embodiments the precipitating agent is selected from 5-(4-dimethyl)amino benzylidene rhodanine, sulfosalicylic acid, lithium chloride, and lithium hydroxide. In certain embodiments the lower alcohol is selected from methanol, ethanol (EtOH), n-propanol, isopropanol, n-butanol, and isobutanol (2-methylpropan-1-ol). In certain embodiments the chaoptrope is selected from guanidine hydrochloride, guanidine thiocyanate, potassium thiocyanate, sodium thiocyanate and urea. In certain embodiments the chelating agent is selected from diethylenetriaminepentaacetic acid (DTPA), ethylenediaminetetraacetic acid (EDTA), ethylene glycol tetraacetic acid (EGTA), trans-1,2-diaminocyclohexane-N,N,N',N'-tetraacetic acid (CDTA), 1,2-bis(2-aminophenoxy)ethane-N,N,N',N'-tetraacetic acid (BAPTA), 1,4,7,10-tetraazacyclododecane-1,4,7,10-tetraacetic acid (DOTA), N-(2-hydroxyethyl)ethylenediamine-N,N',N'-triacetic acid, and nitrilotriacetic acid (NTA). In certain embodiments the reducing agent is selected from 2-mercaptoethanol, thiosulfate, TCEP (tris-(2-carboxyethyl) phosphine), dithiothreitol and dithioerythritol. In certain embodiments the pH buffer is selected from citric acid, tartaric acid, malic acid, sulfosalicylic acid, sulfoisophtalic acid, oxalic acid, borate, CAPS (3-(cyclohexylamino)-1-propanesulfonic acid), CAPSO (3-(cyclohexylamino)-2-hydroxy-1-propanesulfonic acid), EPPS (4-(2-hydroxyethyl)-1-piperazinepropanesulfonic acid), HEPES (4-(2-hydroxyethyl)piperazine-1-ethanesulfonic acid), MES (2-(N-morpholino)ethanesulfonic acid), MOPS (3-(N-morpholino)propanesulfonic acid), MOPSO (3-morpholino-2-hydroxypropanesulfonic acid), PIPES (1,4-piperazinediethanesulfonic acid), TAPS (N-[tris(hydroxymethyl)methyl]-3-aminopropanesulfonic acid), TAPSO (2-hydroxy-3-[tris(hydroxymethyl)methylamino]-1-propanesulfonic acid), TES (N-[tris(hydroxymethyl)methyl]-2-aminoethanesulfonic acid), bicine (N,N-Bis(2-hydroxyethyl)glycine), tricine (N-[Tris(hydroxymethyl)methyl]glycine), tris (tris(hydroxymethyl)aminomethane) and bis-tris (2-[Bis(2-hydroxyethyl)amino]-2-(hydroxymethyl)-1,3-propanediol).

In certain embodiments the composition further comprises a surfactant or a detergent, which in certain embodiments is selected from Triton® X-100 4-(1,1,3,3-tetramethylbutyl)phenyl-polyethylene glycol, Nonidet® P40 polyethylene glycol mono(octylphenyl) ether, a Brij® detergent, a Tomamine™ ethoxylated amine detergent, and a Surfonic™ detergent. In certain embodiments the nucleic acid molecules comprise one or more of DNA molecules and RNA molecules. In certain embodiments the biological sample comprises vertebrate blood, which in certain further embodiments is unfractionated. In certain embodiments the biological sample comprises human blood, which in certain further embodiments is unfractionated. In certain embodiments the biological sample is selected from DNA, RNA, blood, buffy coat from blood, urine, feces, serum, serosal fluid, plasma, lymph, cerebrospinal fluid, saliva, mucosal secretion, vaginal fluid, ascites fluid, pleural fluid, pericardial fluid, peritoneal fluid, abdominal fluid, cell culture medium, organ culture medium, buccal cells, bacteria, viruses, yeast cells, plasmid DNA, mRNA, tRNA, rRNA, siRNA, micro RNA, hnRNA, cDNA, a protein, a polypeptide, a lipid, a glycolipid, a glycoprotein, an oligosaccharide, a polysaccharide, a vaccine, a cell, a sorted or selected cell, a tissue, a cell lysate, homogenate or extract, a tissue lysate, homogenate or extract, a blood sample, biopsy specimen, tissue explant, organ culture and a biological fluid.

In certain other embodiments there is provided a substantially stably-stored nucleic acid molecule from a biological sample, comprising the biological sample admixed with any of the above described composition. In certain embodiments there is provided a substantially stably-stored nucleic acid molecule from a vertebrate blood sample, comprising vertebrate blood admixed with any of the above described compositions. In certain embodiments there is provided a substantially stably-stored polypeptide molecule from a vertebrate blood sample, comprising human blood admixed with any of the above described compositions. In certain further embodiments the nucleic acid molecule comprises one or more of a DNA molecule and an RNA molecule.

In certain embodiments the above described composition is capable, following admixture with a first sample of unfractionated human blood to obtain a test mixture and storage of the test mixture without refrigeration for a time period of at least 60 days, of substantially preventing degradation of at least 70% of recoverable DNA from the test mixture, relative to DNA recoverable from a second sample of said unfractionated human blood that is stored at −20° C. during said time period. In certain embodiments the above described composition is capable, following admixture with a first sample of unfractionated human blood to obtain a test mixture and storage of the test mixture without refrigeration for a time period of at least 21 days, of substantially preventing degradation of at least 70% of recoverable RNA from the test mixture, relative to RNA recoverable from a second sample of said unfractionated human blood that is stored at −80° C. during said time period.

Turning to another embodiment there is provided a method for substantially stabilizing one or a plurality of nucleic acid or polypeptide molecules that are present in a biological sample, comprising (a) admixing the biological sample with any of the above described compositions to obtain a mixture; and (b) maintaining the mixture without refrigeration for a time period of at least 7 days, and thereby substantially stabilizing said one or a plurality of nucleic acid or polypeptide molecules that are present in the biological sample, wherein either one, two or all three of: (i) degradation is substantially prevented of at least 70% of recoverable DNA in the mixture, relative to an amount of DNA or polypeptide that is recoverable from the sample when stored for the time period at −20° C. without any of the above described compositions, (ii) degradation is substantially prevented of at least 70% of recoverable RNA in the mixture, relative to an amount of RNA that is recoverable from the sample when stored for the time period at −80° C. without any of the above described compositions, and (iii) degradation is substantially prevented of at least 70% of recoverable polypeptide molecules in the mixture, relative to an amount of polypeptide molecules that is recoverable from the sample when stored for the time period at −20° C. without any of the above described compositions In certain further embodiments the biological sample comprises vertebrate blood, which in certain still further embodiments is unfractionated. In certain other embodiments the biological sample comprises human blood, which in certain further embodiments is unfractionated. In certain other embodiments the biological sample is selected from DNA, RNA, blood, blood buffy coat, urine, feces, serum, serosal fluid, plasma, lymph, cerebrospinal fluid, saliva, mucosal secretion, vaginal fluid, ascites fluid, pleural fluid, pericardial fluid, peritoneal fluid, abdominal fluid, cell culture medium, organ culture medium, buccal cells, bacteria, viruses, yeast cells, plasmid DNA, mRNA, tRNA, rRNA, siRNA, micro RNA, hnRNA, cDNA, a protein, a polypeptide, a lipid, a glycolipid, a glycoprotein, an oligosaccharide, a polysaccharide, a vaccine, a cell, a sorted or selected cell, a tissue, a cell lysate, homogenate or extract, a tissue lysate, homogenate or extract, a blood sample, biopsy specimen, tissue explant, organ culture and a biological fluid. In certain other embodiments the step of maintaining comprises maintaining for a time period of at least 10, 20, 30, 40, 50, 60 or 70 days.

These and other aspects of the present invention will become apparent upon reference to the following detailed description and attached drawings. All references disclosed herein are hereby incorporated by reference in their entirety as if each was incorporated individually.

DETAILED DESCRIPTION

Figure 1:
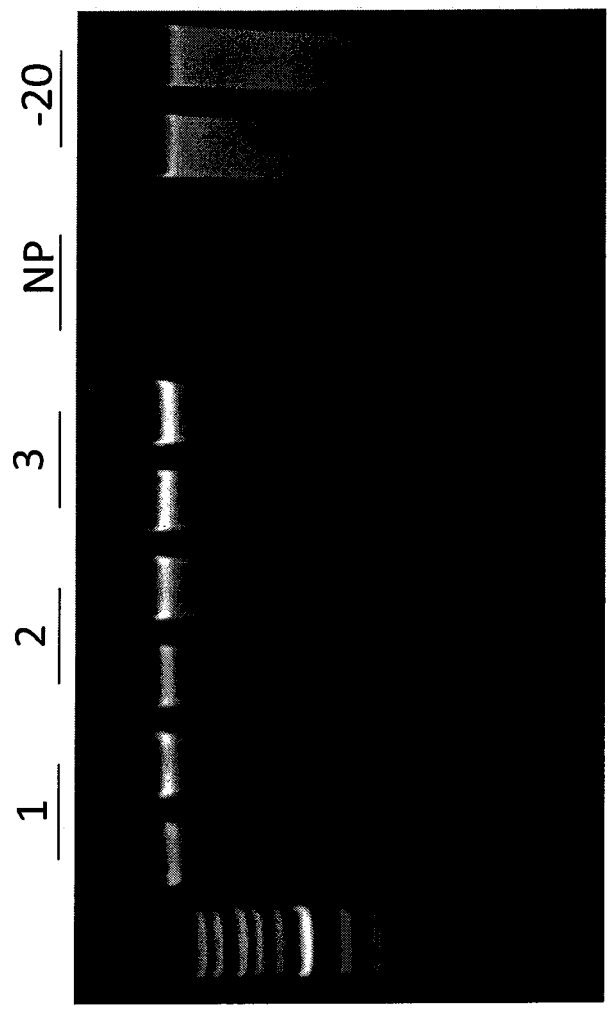
FIG. 1 shows integrity of DNA extracted from human saliva using a Qia Amp™ mini-column (Qiagen, Valencia, Calif.) following storage for 92 days at room temperature following admixture with one of three different formulations each comprising a composition shown in Table 2. NP, unprotected control (room temp.); −20, −20° C. frozen storage control.

The present invention is directed in certain embodiments as described herein to compositions and methods for substantially stable storage of nucleic acid and polypeptide molecules in a biological sample, based on the unexpected discovery that in the presence of (a) certain compositions of formula (I) and/or formula (II) as disclosed herein in greater detail below, and (b) one, two or all three of at least one precipitating agent, at least one lower alcohol and at least one chaotrope as also disclosed in greater detail below; and, in certain further embodiments as elaborated upon below, (c) one or more of a chelating agent, a reducing agent, a pH buffer, and water; a biological sample can be stored in liquid or semi-liquid form at ambient temperature for extended periods of time, such that nucleic acids and/or polypeptides in the sample are substantially protected from degradation that might otherwise occur and substantially all of the biological activity of the sample can be recovered.

Accordingly and as described herein, certain embodiments relate in part to advantages provided by selection of one or more compounds of formula (I) and/or formula (II) and additional components of the composition for substantially stable storage as provided herein, which are compatible with preserving structure and/or activity of nucleic acid molecules and/or polypeptide molecules in a biological sample.

Certain non-limiting embodiments also relate in part to surprising advantages provided upon admixture of a herein described composition for substantially stable storage with particular types of biological samples that contain nucleic acid and/or polypeptide molecules. For instance, upon admixture of saliva or sputum with certain herein described compositions for substantially stable storage, an increase (e.g., in a statistically significant manner relative to an appropriate control, such as an admixture lacking one or more of the composition constituents) in viscosity may be observed which manifests as formation of a viscous liquid, a semi-liquid, gel, suspension, colloid or the like. Such a change in the fluid state of the sample may afford advantageous ease of handling and/or storage, for example, by reducing the potential for loss or contamination of the sample in the course of transporting or archiving the container in which it is being stored, or as another example, by rendering the viscous mixture more amenable to certain processing steps (including automated or semi-automated processing, such as by robotics equipment) that would otherwise be difficult with freely flowing liquid materials.

These and related embodiments permit efficient, convenient and economical storage, transportation, handling and processing of a wide variety of biological samples as provided herein including, but not limited to, polynucleotides, enzymes and other proteins, polypeptides, tissues and cells, without refrigeration or frozen storage. Samples may be stored following admixture of a sample with the herein described composition for substantially stable storage (e.g., contact of the sample with, and mixing in the presence of, the storage composition to afford coating of the sample with the storage composition, which in the case of a substantially liquid sample such as blood will afford a substantially uniform mixture) at ambient temperature.

Following storage, which in preferred embodiments as described herein pertains to storage without refrigeration (e.g., without the need for subjecting the sample-storage composition mixture to significantly reduced temperatures such as lowered sample temperatures that are commonly introduced through the use of refrigerators, freezers or lodging of the sample container in the presence of a coolant or refrigerant such as ice, dry ice or any naturally or artificially chilled medium), the samples may be processed or analyzed for nucleic acid molecules and/or polypeptides contained therein by isolating such biomolecules from other components of the sample while at the same time separating them from the storage composition, which does not compromise the biological activity of the nucleic acid and/or polypeptide molecules. Embodiments provided herein offer advantageously superior recoveries of intact nucleic acid and/or polypeptide molecules from stored biological samples, and may find uses in clinical, healthcare and diagnostic contexts, in biomedical research, biological research and forensic science, and in biological products and other settings where stable sample storage for life sciences may be desired, including in particular situations where refrigeration (including freezing) may be unavailable, unreliable, impractical, expensive, inefficient or otherwise untenable.

According to certain contemplated embodiments there is provided a method for substantially stabilizing one or a plurality of nucleic acid and/or polypeptide molecules that are present in a biological sample, comprising admixing the biological sample with the herein described composition for substantially stable biological sample storage to obtain a mixture; and maintaining the mixture without refrigeration for a time period of at least 7, 8, 9, 10, 11, 12, 13, 14, 15, 16, 17, 18, 19, 20, 21 or more days. Depending on the sample and the type of biomolecule being stabilized, the time period may in certain contemplated embodiments be at least 3, 4, 5, 6, 7, 8, 9, 10, 11, 12, 13, 14, 15, 16, 17, 18, 19, 20, 21, 22, 23, 24, 25, 26 or more weeks, or at least 6, 7, 8, 9, 10, 11, 12, 13, 14, 15, 16, 17, 18 or more months, or at least 1, 2, 3, 4, 5 or more years.

Admixture of the biological sample and the herein described composition for substantially stable biological sample storage may typically be performed using a range of volumetric ratios of the sample to the storage composition, such as a ratio of from about 10 parts sample to one part storage composition (10:1, vol/vol) to about 1 part sample to 10 parts storage composition (1:10, vol/vol), or a ratio therebetween, for instance, 6:1, 5:1, 4:1, 3:1, 2:1, 1:1, 1:2, 1:3, 1:4, 1:5, or 1:6, or any other ratio including intermediate ratios between those just exemplified, which may be determined empirically by the skilled artisan from the disclosure herein, and which may vary as a function of the particular sample and the particular storage composition being employed. Typically, the mixture of sample and storage composition will have a pH between about pH 3 and about pH 10, which may also vary as a function of the particular sample and the particular storage composition being employed, and which may also be determined empirically by the skilled artisan from the disclosure herein. For example, for substantially stable storage of RNA the pH range may be from about pH 3 to about pH 8, preferably in certain embodiments from about pH 3 to about pH 6.5 (e.g., about pH 3.2, 3.5, 3.7, 4.0, 4.2, 4.5, 4.7, 5.0, 5.3, 5.5, 5.8, 6.0, 6.3 or 6.5). For substantially stable storage of DNA the pH range may be from about pH 5 to about pH 10, preferably in certain embodiments from about pH 6 to about pH 9 (e.g., about pH 6.3, 6.5, 6.8, 7.0, 7.4, 7.8, 8.0, 8.2, 8.4, 8.6, 8.8 or 9.0).

Preferably in certain of these and related embodiments, the herein described composition for substantially stable biological sample storage substantially prevents degradation of at least 70% of recoverable DNA, RNA and/or polypeptides in the mixture, relative to an amount of DNA, RNA or polypeptide that is recoverable from the sample when stored for the same time period at −20° C. without the herein described composition for substantially stable biological sample storage. The extended time periods without refrigeration during which the presently disclosed compositions and methods provide stabilization of DNA, RNA and/or polypeptides against degradative effects such as heat, light and/or enzymes (e.g., nucleases, proteases) that may be present in the biological sample are unprecedented, unexpected and advantageous.

For example, in certain embodiments as described herein, storage artifacts may hinder efforts to assess accurately the relative representation in a biological sample of one or more polynucleotides having particular nucleic acid sequences (e.g., mRNA) within a heterogeneous nucleic acid population (e.g., total RNA or total RNA-plus-DNA), due (according to non-limiting theory) to different degradation rates of particular RNA and/or DNA species over time during storage. Consequently, "snapshot" efforts to characterize such a sample at different points in time may lead to dramatically different results, such as disparate quantification values for the relative presence of particular RNA/DNA species over time, leading to erroneous calculation of, e.g., gene expression activity at the time the sample was collected. Improved stabilization as is provided by the herein described embodiments may therefore usefully reduce (e.g., decrease in a statistically significant manner) or substantially eliminate such artifacts, by impairing sample degradation and thus avoiding biases in the composition of the sample that may vary over time.

In other preferred embodiments, the herein described composition for substantially stable biological sample storage substantially prevents degradation of at least 75%, 80%, 85%, 90%, 95% or more of the recoverable DNA, RNA and/or polypeptides in the mixture, relative to an amount of DNA, RNA or polypeptide that is recoverable from the sample when stored for the same time period at −20° C. without the herein described composition for substantially stable biological sample storage. In other preferred embodiments, the herein described composition for substantially stable biological sample storage substantially prevents degradation of at least 75%, 80%, 85%, 90%, 95% or more of the recoverable DNA, RNA and/or polypeptides in the mixture, relative to an amount of DNA, RNA or polypeptide that is recoverable from the sample when stored for the same time period at less than −20° C., −30° C., −40° C., −50° C., −60° C., −70° C., or −80° C. without the herein described composition for substantially stable biological sample storage. Still other embodiments contemplate the herein described storage methods in which the temperature at which the mixture is maintained may vary significantly over time, including variable portions of the time period that may include refrigeration or freezing, such as may occur in the course of certain shipping itineraries.

Composition for Substantially Stable Biological Sample Storage

According to non-limiting theory, a composition for substantially stable storage of nucleic acid and polypeptide molecules in a biological sample, may, as provided herein, comprise one or more compounds of formula (I) and/or formula (II) and one, two or all three of (i) at least one precipitating agent, (ii) at least one lower alcohol, and (iii) at least one chaotrope, and may comprise a molecular structure that, by forming a matrix (e.g., a spatially organized support or scaffold), creates a three dimensional space which allows constituent biological material of the biological sample to associate with the matrix. Further according to non-limiting theory, the composition for substantially stable storage of nucleic acid and polypeptide molecules may also be used in certain contemplated embodiments to spatially organize the introduction of one or more additional agents that may beneficially stabilize, preserve, protect or otherwise contribute to the recovery of nucleic acid and/or protein molecules from the biological sample, such as salts, sugars, inhibitors, buffers and/or other stabilizers. The storage composition also allows inclusion of components (e.g., buffers) for the adjustment of pH and other parameters (e.g., by one or more chelating agents and/or reducing agents) for optimal storage conditions, and may optionally comprise one or a plurality of detectable indicators as provided herein, such as color-based pH indicators, and/or other chemical indicators.

In certain preferred embodiments the stable storage composition comprises one or more compounds of formula (I) and/or formula (II), wherein formula (I) is:

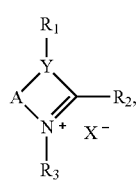
(I)

where:

A is $-C(R^4)=C(R^4)-$ or $-C(R^4)=C(R^4)-C(R^4)_2-$;

Y is N, S or O;

$R^1$ is, when Y is N, $C_1$-$C_8$alkyl, alkenyl, optionally substituted aralkyl, optionally substituted cycloalkyl, optionally substituted cycloalkylalkyl or optionally substituted heterocyclylalkyl, and when Y is S or O, $R^1$ is absent;

$R^2$ is hydrogen, $C_1$-$C_8$alkyl, alkenyl, optionally substituted aralkyl, optionally substituted cycloalkyl, optionally substituted cycloalkylalkyl or optionally substituted heterocyclylalkyl;

$R^3$ is $C_1$-$C_{16}$alkyl, optionally substituted aryl or optionally substituted aralkyl;

each $R^4$ is independently hydrogen, cyano, nitro, $-C(O)OR^5$, $-C(O)N(R^5)_2$, $-N(R^5)_2$, halo, haloalkyl, hydroxy, alkyl, alkoxy, haloalkoxy, alkoxyalkyl, alkenyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl or optionally substituted heteroarylalkyl;

or two adjacent $R^4$'s, together with the carbons to which they are attached, may form an optionally substituted cycloalkyl, optionally substituted aryl, optionally substituted heterocyclyl or optionally substituted heteroaryl;

each $R^5$ is independently hydrogen, alkyl, aryl or aralkyl; and

X is a pharmaceutically acceptable anion; and wherein formula (II) is:

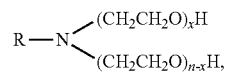
(II)

where:

R is $R^1$, $R^2$, $R^3$, $R^4$ or A;

A is $-C(R^4)=C(R^4)-$ or $-C(R^4)=C(R^4)-C(R^4)_2-$;

$R^1$ is $C_1$-$C_9$alkyl, alkenyl, optionally substituted aralkyl, optionally substituted cycloalkyl, optionally substituted cycloalkylalkyl or optionally substituted heterocyclylalkyl;

$R^2$ is hydrogen, $C_{10}$-$C_{18}$alkyl, alkenyl, optionally substituted aralkyl, optionally substituted cycloalkyl, optionally substituted cycloalkylalkyl or optionally substituted heterocyclylalkyl;

$R^3$ is $C_{19}$-$C_{26}$alkyl, optionally substituted aryl or optionally substituted aralkyl;

each $R^4$ is independently hydrogen, cyano, nitro, $-C(O)OR^5$, $-C(O)N(R^5)_2$, $-N(R^5)_2$, halo, haloalkyl, hydroxy, alkyl, alkoxy, haloalkoxy, alkoxyalkyl, alkenyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl or optionally substituted heteroarylalkyl;

or two adjacent $R^4$'s, together with the carbons to which they are attached, may form an optionally substituted cycloalkyl, optionally substituted aryl, optionally substituted heterocyclyl or optionally substituted heteroaryl; and each $R^5$ is independently hydrogen, alkyl, aryl or aralkyl.

DEFINITIONS

Certain chemical groups named herein may be preceded by a shorthand notation indicating the total number of carbon atoms that are to be found in the indicated chemical group. For example; $C_1$-$C_8$alkyl describes an alkyl group, as defined below, having a total of 1 to 8 carbon atoms. The total number of carbons in the shorthand notation does not include carbons that may exist in substituents of the group described.

In addition to the foregoing, as used in the specification and appended claims, unless specified to the contrary, the following terms have the meaning indicated:

"Alkyl" refers to a straight or branched hydrocarbon chain radical consisting solely of carbon and hydrogen atoms, containing no unsaturation, having from one to 16 carbon atoms, preferably one to eight carbon atoms for $R^1$, $R^2$ and $R^4$ in compounds of formula (I) as set forth herein, or preferably four to sixteen carbon atoms for $R^3$ in compounds of formula (I), and which is attached to the rest of the molecule by a single bond, e.g., methyl, ethyl, n-propyl, 1-methylethyl (iso-propyl), n-butyl, n-pentyl, 1,1-dimethylethyl (t-butyl), 3-methylhexyl, 2-methylhexyl, and the like.

"Alkenyl" refers to a straight or branched hydrocarbon chain radical group consisting solely of carbon and hydrogen atoms, containing at least one double bond, having from two to twelve carbon atoms, preferably two to eight carbon atoms and which is attached to the rest of the molecule by a single bond, e.g., ethenyl, prop-1-enyl, but-1-enyl, pent-1-enyl, penta-1,4-dienyl, and the like.

"Alkylene" or "alkylene chain" refers to a straight or branched divalent hydrocarbon chain linking the rest of the molecule to a radical group, consisting solely of carbon and hydrogen, containing no unsaturation and having from one to twelve carbon atoms, e.g., methylene, ethylene, propylene, n-butylene, and the like. The alkylene chain is attached to the rest of the molecule through a single bond and to the radical group through a single bond. The points of attachment of the alkylene chain to the rest of the molecule and to the radical group can be through one carbon or any two carbons within the chain.

"Alkoxy" refers to a radical of the formula $-OR_a$ where $R_a$ is an alkyl radical as defined above.

"Alkoxyalkyl" refers to a radical of the formula $-R_b-O-R_a$ where $R_b$ is an alkylene chain as defined above and $R_a$ is an alkyl radical as defined above. The oxygen atom may be bonded to any carbon in the alkylene chain and in the alkyl radical.

"Aryl" refers to a hydrocarbon ring system radical comprising hydrogen, 6 to 18 carbon atoms and at least one aromatic ring. For purposes of this invention, the aryl radical may be a monocyclic, bicyclic, tricyclic or tetracyclic ring system, which may included fused or bridged ring systems. Aryl radicals include, but are not limited to, aryl radicals derived from aceanthrylene, acenaphthylene, acephenanthrylene, anthracene, azulene, benzene, chrysene, fluoranthene, fluorene, as-indacene, s-indacene, indane, indene, naphthalene, phenalene, phenanthrene, pleiadene, pyrene, and triphenylene.

"Aralkyl" refers to a radical of the formula —$R_b$—$R_c$ where $R_b$ is an alkylene chain as defined above and $R_c$ is one or more aryl radicals as defined above, for example, benzyl, diphenylmethyl and the like. The aryl part of the aralkyl radical may be optionally substituted as described above for an aryl group.

"Cycloalkyl" refers to a stable non-aromatic monocyclic or polycyclic hydrocarbon radical consisting solely of carbon and hydrogen atoms, which may include fused or bridged ring systems, having from three to fifteen carbon atoms, preferably having from three to ten carbon atoms, and which is saturated or unsaturated and attached to the rest of the molecule by a single bond. Monocyclic radicals include, for example, cyclopropyl, cyclobutyl, cyclopentyl, cyclohexyl, cycloheptyl, and cyclooctyl. Polycyclic radicals include, for example, adamantyl, norbornyl, decalinyl, and the like. Unless otherwise stated specifically in the specification, the term "optionally substituted cycloalkyl" is meant to include cycloalkyl radicals which are optionally substituted by one or more substituents independently selected from the group consisting of alkyl, alkenyl, halo, haloalkyl, haloalkenyl, cyano, nitro, oxo, aryl, aralkyl, cycloalkyl, cycloalkylalkyl, heterocyclyl, heterocyclylalkyl, heteroaryl, heteroarylalkyl, —$R^{15}$—$OR^{14}$, —$R^{15}$—$OC(O)$—$R^{14}$, —$R^{15}$—$N(R^{14})_2$, —$R^{15}$—$C(O)R^{14}$, —$R^{15}$—$C(O)OR^{14}$, —$R^{15}$—$C(O)N(R^{14})_2$, —$R^{15}$—$N(R^{14})C(O)OR^{16}$, —$R^{15}$—$N(R^{14})C(O)R^{16}$, —$R^{15}$—$N(R^{14})S(O)_tR^{16}$ (where t is 1 to 2), —$R^{15}$—$N=C(OR^{14})R^{14}$, —$R^{15}$—$S(O)_tOR^{16}$ (where t is 1 to 2), —$R^{15}$—$S(O)_pR^{16}$ (where p is 0 to 2), and —$R^{15}$—$S(O)_tN(R^{14})_2$ (where t is 1 to 2) where each $R^{14}$ is independently hydrogen, alkyl, haloalkyl, cycloalkyl, cycloalkylalkyl, aryl, aralkyl, heterocyclyl, heterocyclylalkyl, heteroaryl or heteroarylalkyl; each $R^{15}$ is independently a direct bond or a straight or branched alkylene or alkenylene chain; and each $R^{16}$ is alkyl, haloalkyl, cycloalkyl, cycloalkylalkyl, aryl, aralkyl, heterocyclyl, heterocyclylalkyl, heteroaryl or heteroarylalkyl. These optional substituents, including the $R^{14}$ and $R^{16}$ substituents, may be optionally substituted as defined herein.

"Cycloalkylalkyl" refers to a radical of the formula —$R_bR_g$ where $R_b$ is an alkylene chain as defined above and $R_g$ is a cycloalkyl radical as defined above.

"Halo" refers to bromo, chloro, fluoro or iodo.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1-fluoromethyl-2-fluoroethyl, 3-bromo-2-fluoropropyl, 1-bromomethyl-2-bromoethyl, and the like.

"Haloalkoxy" refers to an alkoxy radical, as defined above, that is substituted by one or more halo radicals, as defined above, e.g., trifluoromethoxy, difluoromethoxy, trichloromethoxy, 2,2,2-trifluoroethoxy and the like.

"Heterocyclyl" refers to a stable 3- to 18-membered non-aromatic ring radical which consists of two to twelve carbon atoms and from one to six heteroatoms selected from the group consisting of nitrogen, oxygen and sulfur. Unless stated otherwise specifically in the specification, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be partially or fully saturated. Examples of such heterocyclyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl. Unless stated otherwise specifically in the specification, the term "optionally substituted heterocyclyl" is meant to include heterocyclyl radicals as defined above which are optionally substituted by one or more substituents selected from the group consisting of alkyl, alkenyl, halo, haloalkyl, haloalkenyl, cyano, oxo, thioxo, nitro, aryl, aralkyl, cycloalkyl, cycloalkylalkyl, heterocyclyl, heterocyclylalkyl, heteroaryl, heteroarylalkyl, —$R^{15}$—$OR^{14}$, —$R^{15}$—$OC(O)$—$R^{14}$, —$R^{15}$—$N(R^{14})_2$, —$R^{15}$—$C(O)R^{14}$, —$R^{15}$—$C(O)OR^{14}$, —$R^{15}$—$C(O)N(R^{14})_2$, —$R^{15}$—$N(R^{14})C(O)OR^{16}$, —$R^{15}$—$N(R^{14})C(O)R^{16}$, —$R^{15}$—$N(R^{14})S(O)_tR^{16}$ (where t is 1 to 2), —$R^{15}$—$N=C(OR^{14})R^{14}$, —$R^{15}$—$S(O)_tOR^{16}$ (where t is 1 to 2), —$R^{15}$—$S(O)_pR^{16}$ (where p is 0 to 2), and —$R^{15}$—$S(O)_tN(R^{14})_2$ (where t is 1 to 2) where each $R^{14}$ is independently hydrogen, alkyl, alkenyl, haloalkyl, cycloalkyl, cycloalkylalkyl, aryl, aralkyl, heterocyclyl, heterocyclylalkyl, heteroaryl or heteroarylalkyl; each $R^{15}$ is independently a direct bond or a straight or branched alkylene or alkenylene chain; and each $R^{16}$ is alkyl, alkenyl, haloalkyl, cycloalkyl, cycloalkylalkyl, aryl, aralkyl, heterocyclyl, heterocyclylalkyl, heteroaryl or heteroarylalkyl. These optional substituents, including the $R^{14}$ and $R^{16}$ substituents, may be optionally substituted as defined herein.

"Heterocyclylalkyl" refers to a radical of the formula —$R_bR_h$ where $R_b$ is an alkylene chain as defined above and $R_h$ is a heterocyclyl radical as defined above, and if the heterocyclyl is a nitrogen-containing heterocyclyl, the heterocyclyl may be attached to the alkyl radical at the nitrogen atom. The heterocyclyl part of the heterocyclylalkyl radical may be optionally substituted as defined above for a heterocyclyl group.

"Heteroaryl" refers to a 5- to 14-membered ring system radical comprising hydrogen atoms, one to thirteen carbon atoms, one to six heteroatoms selected from the group consisting of nitrogen, oxygen and sulfur, and at least one aromatic ring. For purposes of this invention, the heteroaryl radical may be a monocyclic, bicyclic, tricyclic or tetracyclic ring system, which may include fused or bridged ring systems; and the nitrogen, carbon or sulfur atoms in the heteroaryl radical may be optionally oxidized; the nitrogen atom may be optionally quaternized. Examples include, but are not limited to, azepinyl, acridinyl, benzimidazolyl, benzthiazolyl, benzindolyl, benzodioxolyl, benzofuranyl, benzooxazolyl, benzothiazolyl, benzothiadiazolyl, benzo[b][1,4]dioxepinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl benzothiophenyl), benzotriazolyl, benzo[4,6]imidazo[1,2-a]pyridinyl, carbazolyl, cinnolinyl, dibenzofuranyl, dibenzothiophenyl, furanyl, furanonyl, isothiazolyl, imidazolyl, indazolyl, indolyl, indazolyl, isoindolyl, indolinyl, isoindolinyl, isoquinolyl, indolizinyl, isoxazolyl, naphthyridinyl, oxadiazolyl, 2-oxoazepinyl, oxazolyl, oxiranyl, 1-oxidopyridinyl, 1-oxidopyrimidinyl, 1-oxidopyrazinyl, 1-oxidopyridazinyl, 1-phenyl-1H-pyrrolyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, pyrrolyl, quinazolinyl, quinoxalinyl, quinolinyl, quinuclidinyl, isoquinolinyl, tetrahydroquinolinyl, thiazolyl, thiadiazolyl, triazolyl, tetrazolyl, triazinyl, and thiophenyl thienyl). Unless stated otherwise specifically in the specification, the term "optionally substituted heteroaryl" is meant to include heteroaryl radicals as defined above which are optionally substituted by one or more substituents selected from the group consisting of alkyl, alkenyl, alkoxy, halo, haloalkyl, haloalkenyl, cyano, oxo, thioxo, nitro, aryl, aralkyl, cycloalkyl, cycloalkylalkyl, heterocyclyl, heterocyclylalkyl, heteroaryl, heteroarylalkyl, $-R^{15}-OR^{14}$, $-R^{15}-OC(O)-R^{14}$, $-R^{15}-N(R^{14})_2$, $-R^{15}-C(O)R^{14}$, $-R^{15}-C(O)OR^{14}$, $-R^{15}-C(O)N(R^{14})_2$, $-R^{15}-N(R^{14})C(O)OR^{16}$, $-R^{15}-N(R^{14})C(O)R^{16}$, $-R^{15}-N(R^{14})S(O)_tR^{16}$ (where t is 1 to 2), $-R^{15}-N=C(OR^{14})R^{14}$, $-R^{15}-S(O)_tOR^{16}$ (where t is 1 to 2), $-R^{15}-S(O)_pR^{16}$ (where p is 0 to 2), and $-R^{15}-S(O)_tN(R^{14})_2$ (where t is 1 to 2) where each $R^{14}$ is independently hydrogen, alkyl, alkenyl, haloalkyl, cycloalkyl, cycloalkylalkyl, aryl, aralkyl, heterocyclyl, heterocyclylalkyl, heteroaryl or heteroarylalkyl; each $R^{15}$ is independently a direct bond or a straight or branched alkylene or alkenylene chain; and each $R^{16}$ is alkyl, alkenyl, haloalkyl, cycloalkyl, cycloalkylalkyl, aryl, aralkyl, heterocyclyl, heterocyclylalkyl, heteroaryl or heteroarylalkyl. These optional substituents, including the $R^{14}$ and $R^{16}$ substituents, may be optionally substituted as defined herein.

"Heteroarylalkyl" refers to a radical of the formula $-R_bR_i$, where $R_b$ is an alkylene chain as defined above and $R_i$ is a heteroaryl radical as defined above. The heteroaryl part of the heteroarylalkyl radical may be optionally substituted as defined above for a heteroaryl group.

As disclosed herein, a composition for substantially stable storage of nucleic acid molecules in a biological sample, may comprise (a) one or more compounds of formula (I); and (b) one, two, or all three of (i) at least one precipitating agent, (ii) at least one lower alcohol, and (iii) at least one chaoptrope.

The pharmaceutically acceptable anion may be any anionic complement to the cationic moiety shown in formula (I), including but not limited to halides, $C_1$-$C_{12}$alkylsulfonate, hexafluorophosphate, methylsulfate, ethylsulfate, tetrafluoroborate, trifluoromethanesulfonate, bis(trifluoromethylsulfonyl)imide, nitrate, phosphate, aryl sulfonate, tetrafluoroborate, trifluoromethanesulfonate, hexafluoroantimonate, hexafluoroarsenate, hexafluorophosphate, tetraphenylborate, or tetra(perfluorophenyl)borate, or any other biocompatible anion that does not interfere with substantial recovery of nucleic acid and/or polypeptide molecules from the stored biological sample.

The pharmaceutically acceptable anion or "anionic moiety" thus includes a pharmaceutically acceptable and chemically stable negatively charged species. It is also preferred that the anionic moiety does not exhibit reactivity towards any other agents comprising the composition for stable storage. Additional examples of pharmaceutically acceptable anionic moieties include, but are not limited to, halogen ions, such as a fluoride ion, chloride ion, bromide ion and iodide ion; anions of inorganic acid salts such as nitrate, perchlorate, sulfate, phosphate, and carbonate; pharmaceutically acceptable anions of lower alkylsulfonic acid salts such as methanesulfonic acid, and ethanesulfonic acid salts; pharmaceutically acceptable anions of arylsulfonic acid salts such as benzenesulfonic acid, 2-naphthalenesulfonic acid and p-toluenesulfonic acid salts; pharmaceutically acceptable anions of organic acid salts such as trichloroacetic acid, trifluoroacetic acid, hydroxyacetic acid, benzoic acid, mandelic acid, butyric acid, propionic acid, formic acid, fumaric acid, succinic acid, citric acid, tartaric acid, oxalic acid, maleic acid, acetic acid, malic acid, lactic acid, and ascorbic acid salts; and pharmaceutically acceptable anions of acidic amino acid salts such as glutamic acid and asparatic acid salts. In the case of certain preferred examples of the compound of formula (I), the halogen anionic moiety precursor may be exchanged for aryl or alkyl sulphonate anionic moieties. Examples include, but are not limited to, benzene sulfonate, p-toluene sulfonate, 2-napthylene sulphonate, methanesulfonate, ethanesulfonate, and propanesulfonate. Those skilled in the art will appreciate that these and other suitable anions may be exchanged with the anionic complement that may be provided with the cationic moiety to obtain the compound of formula (I) as provided herein, having any particular desired anionic, through routine methodologies.

Precipitating agent. According to certain embodiments of the herein described composition for substantially stable storage of nucleic acid and/or polypeptide molecules in a biological sample, a precipitating agent may be included, which refers to compounds that influence the solubility of nucleic acid and/or polypeptide molecules. In some embodiments a precipitating agent is one which has been used in the isolation of nucleic acid molecules, such as an agent that promotes nucleic acid precipitation from biological samples or from extracts of biological samples. Non-limiting examples of precipitating agents include 5-(4-dimethyl) amino benzylidene rhodanine, sulfosalicylic acid, lithium chloride, and lithium hydroxide. Other examples include ammonium sulfate, sodium sulfate, sodium chloride, sodium citrate, dextrans, polyethylene glycol, and salts of polyvalent metal cations such as calcium, magnesium, manganese and iron. Certain embodiments, including but not limited to those presented in Tables 1, 2, 3, 4 and 5, contemplate inclusion of a precipitating agent at a concentration of about 0.05, 0.1, 0.5, 1.0, 1.2, 1.4, 1.6, 1.8, 2.0, 2.2, 2.4, 2.6, 2.8, 3.0, 3.2, 3.4, 3.4, 3.6, 3.8 or 4.0 M, where "about" may be understood to represent quantitative variation that may be more or less than the recited amount by less than 50%, more preferably less than 40%, more preferably less than 30%, and more preferably less than 20%, 15%, 10% or 5%.

Lower alcohol. As described herein, certain preferred embodiments may include at least one lower alcohol in the composition for substantially stable storage of nucleic acid and/or polypeptide molecules in a biological sample. Such alcohols include those based on relatively small straight and branched carbon chains, typically of no more than 8, 7, 6, 5, 4 or 3 carbons. Examples, by way of illustration and not limitation, include methanol, ethanol (EtOH), n-propanol, isopropanol (2-propanol), n-butanol, and isobutanol (2-methylpropan-1-ol); also contemplated is the inclusion as a lower alcohol of ethylene glycol or 2-mercaptoethanol, and it will be appreciated that from the present disclosure the skilled person may select other lower alcohols for use in a stable storage composition, as may vary based on the other components of the composition that are employed, the particular biological sample being stored, whether nucleic acid molecules or polypeptide molecules or both are sought to be recovered, and other factors. Certain embodiments, including but not limited to those presented in Tables 1, 2, 3, 4 and 5, contemplate inclusion of a lower alcohol at a concentration (on a volumetric basis, i.e., vol/vol) of about 5, 6, 7, 8, 9, 10, 11, 12, 13, 14, 15, 16, 17, 18, 19, 20, 21, 22, 23, 24, 25, 26, 27, 28, 29 or 30% (vol/vol), where "about" may be understood to represent quantitative variation that may be more or less than the recited amount by less than 50%, more preferably less than 40%, more preferably less than 30%, and more preferably less than 20%, 15%, 10% or 5%.

Chaotrope. Certain embodiments described herein may include at least one chaotrope in the composition for substantially stable storage of nucleic acid and/or polypeptide molecules in a biological sample. A number of chaotropes or chaotropic agents are known in the art that disrupt the secondary, tertiary and/or quarternary structures of biological macromolecules such as polypeptides, proteins and nucleic acids, including DNA and RNA. Non-limiting examples of such chaotropes as are contemplated for use in certain of the presently disclosed embodiments include guanidine hydrochloride, guanidine thiocyanate, potassium thiocyanate, sodium thiocyanate and urea. Certain contemplated embodiments, including those that may relate to specific types of biological samples, expressly exclude the presence of a chaotrope when a chelating agent is also present, and in particular of a chaotrope at a concentration sufficient to denature a protein, polypeptide or nucleic acid molecule, while certain other contemplated embodiments are not so limited. Certain embodiments, including but not limited to those presented in Tables 1, 2, 3, 4 and 5, contemplate inclusion of a chaotrope at a concentration of about 0.05, 0.1, 0.5, 1.0, 1.2, 1.4, 1.6, 1.8, 2.0, 2.2, 2.4, 2.6, 2.8, 3.0, 3.2, 3.4, 3.4, 3.6, 3.8 or 4.0 M, where "about" may be understood to represent quantitative variation that may be more or less than the recited amount by less than 50%, more preferably less than 40%, more preferably less than 30%, and more preferably less than 20%, 15%, 10% or 5%.

Chelating agents or chelators may, according to certain embodiments, be included in the presently described composition for substantially stable storage of nucleic acid and/or polypeptide molecules in a biological sample, and are known to those familiar with the art for their ability to complex with and hinder the reactivity of metal cations. Exemplary chelating agents include diethylenetriaminepentaacetic acid (DTPA), ethylenediaminetetraacetic acid (EDTA), ethylene glycol tetraacetic acid (EGTA), trans-1, 2-diaminocyclohexane-N,N,N',N'-tetraacetic acid (CDTA), 1,2-bis(2-aminophenoxy)ethane-N,N,N',N'-tetraacetic acid (BAPTA), 1,4,7,10-tetraazacyclododecane-1,4,7,10-tetraacetic acid (DOTA), N-(2-hydroxyethyl)ethylenediamine-N,N',N'-triacetic acid, and nitrilotriacetic acid (NTA).

Reducing agents may, according to certain embodiments, be included in the presently described composition for substantially stable storage of nucleic acid and/or polypeptide molecules in a biological sample, and are known to those familiar with the art. Exemplary reducing agents include 2-mercaptoethanol, thiosulfate, TCEP (tris-(2-carboxyethyl) phosphine), dithiothreitol and dithioerythritol.

According to certain embodiments the herein described composition for substantially stable storage of a nucleic acid and/or polypeptide molecule in a biological sample may include one or more pH buffers, which may be any of a large number of compounds known in the art for their ability to resist changes in the pH of a solution, such as an aqueous solution in which the pH buffer is present. Selection of one or more particular pH buffers for inclusion in a stable storage composition may be done based on the present disclosure and according to routine practices in the art, and may be influenced by a variety of factors including the pH that is desirably to be maintained, the nature of the biological sample, the solvent conditions to be employed, the compound(s) of formula (I) and/or formula (II) to be used, the solubility properties of the compound(s) of formula (I) and/or formula (II) and of one or more of the precipitating agent, the lower alcohol and/or the chaotrope, the inclusion of other components, and other criteria. For example, typically a pH buffer is employed at a pH that is within about 0.1, 0.2, 0.3, 0.4, 0.5, 0.6, 0.7, 0.8, 0.9 or 1.0 pH unit of a proton dissociation constant ($pK_a$) that is a characteristic of the buffer.

Non-limiting examples of pH buffers include citric acid, tartaric acid, malic acid, sulfosalicylic acid, sulfoisophtalic acid, oxalic acid, borate, CAPS (3-(cyclohexylamino)-1-propanesulfonic acid), CAPSO (3-(cyclohexylamino)-2-hydroxy-1-propanesulfonic acid), EPPS (4-(2-hydroxyethyl)-1-piperazinepropanesulfonic acid), HEPES (4-(2-hydroxyethyl)piperazine-1-ethanesulfonic acid), MES (2-(N-morpholino)ethanesulfonic acid), MOPS (3-(N-morpholino)propanesulfonic acid), MOPSO (3-morpholino-2-hydroxypropanesulfonic acid), PIPES (1,4-piperazinediethanesulfonic acid), TAPS (N-[tris(hydroxymethyl)methyl]-3-aminopropanesulfonic acid), TAPSO (2-hydroxy-3-[tris(hydroxymethyl)methylamino]-1-propanesulfonic acid), TES (N-[tris(hydroxymethyl)methyl]-2-aminoethanesulfonic acid), bicine (N,N-Bis(2-hydroxyethyl)glycine), tricine (N-[Tris(hydroxymethyl)methyl]glycine), tris (tris(hydroxymethyl)aminomethane) and bis-tris (2-[Bis(2-hydroxyethyl)amino]-2-(hydroxymethyl)-1,3-propanediol). Certain embodiments contemplated herein, including a number of those set forth in Tables 1, 2, 3, 4 and 5, may feature a formulation having a pH of about 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9 or 9.0, where "about" may be understood to represent quantitative variation that may be more or less than the recited pH value by less than 1, preferably less than 0.5, preferably less than 0.25, and more preferably less than 0.1 pH unit.

The herein described composition for substantially stable storage of a nucleic acid and/or polypeptide molecule in a biological sample may, in certain embodiments, contain a surfactant or a detergent which may, in certain embodiments, be selected from Triton® X-100 4-(1,1,3,3-tetramethylbutyl)phenyl-polyethylene glycol, Nonidet® P40 polyethylene glycol mono(octylphenyl) ether, any of the Brij® family of detergents, any of the Tween® family of surfactants, any of the Tomamine® ethoxylated amine detergents (Air Products and Chemicals, Inc., Carlsbad, Calif.), any of the Surfonic® detergents (Huntsman, The Woodlands, Tex.) which in certain preferred embodiments may be Surfonic® T-15 or Surfonic® T-20, sodium dodecyl sulfate, sodium lauryl sulfate, deoxycholate, octyl-glucopyranoside, betaines, or the like.

Examples of Tomamine® detergents include bis-(2-hydroxyethyl) isodecyloxypropylamine, poly (5) oxyethylene isodecyloxypropylamine, bis-(2-hydroxyethyl) isotridecyloxypropylamine, poly (5) oxyethylene isotridecyloxypropyl amine, bis-(2-hydroxyethyl) linear alkyloxypropylamine, bis (2-hydroxyethyl) soya amine, poly (15) oxyethylene soya amine, bis(2-hydroxyethyl) octadecylamine, poly (5) oxyethylene octadecylamine, poly (8) oxyethylene octadecylamine, poly (10) oxyethylene octadecylamine, poly (15) oxyethylene octadecylamine, bis(2-hydroxyethyl) octadecyloxypropylamine, bis-(2-hydroxyethyl) tallow amine, poly (5) oxyethylene tallow amine, poly (15) oxyethylene tallow amine, poly (3) oxyethylene 1,3 diaminopropane, bis(2-hydroxyethyl) coco amine, bis-(2-hydroxyethyl) isodecyloxypropylamine, poly (5) oxyethylene isodecyloxypropylamine, bis-(2-hydroxyethyl) isotridecyloxypropylamine, poly (5) oxyethylene isotridecyloxypropyl amine, bis-(2-hydroxyethyl) linear alkyloxypropylamine, bis(2-hydroxyethyl) soya amine, poly (15) oxyethylene soya amine, bis(2-hydroxyethyl) octadecylamine, poly (5) oxyethylene octadecylamine, poly (8) oxyethylene octadecylamine, poly (10) oxyethylene octadecylamine, poly (15) oxyethylene octadecylamine, bis(2-hydroxyethyl) octadecyloxypropylamine, bis-(2-hydroxyethyl) tallow amine, poly (5) oxyethylene tallow amine, poly (15) oxyethylene tallow amine, poly (3) oxyethylene 1,3 diaminopropane, and bis(2-hydroxyethyl) coco amine.

Certain contemplated embodiments, including those that may relate to specific types of biological samples, expressly exclude the presence of a denaturing detergent when a chelating agent is also present, and in particular of a detergent of a type and at a concentration sufficient to denature a protein, polypeptide or nucleic acid molecule, while certain other contemplated embodiments are not so limited, where it is to be noted that many detergents and surfactants are non-denaturing for many if not all types of biological samples.

Tables 1-5 show exemplary stable storage compositions. As described herein and in the Examples, certain preferred embodiments contemplate use of these compositions for saliva sample storage, including for recoverable, unrefrigerated storage of DNA, RNA and/or protein from saliva samples. Unless otherwise noted herein, formulations are aqueous solutions and "%" refers to weight as a percentage per unit volume (w/v) with the exception of alcohols (e.g., ethanol, 2-mercaptoethanol) for which "%" refers to volume as a percentage per unit volume (v/v).

TABLE 1

EXEMPLARY COMPOSITIONS FOR STABLE STORAGE OF NUCLEIC ACID AND POLYPEPTIDE MOLECULES IN A BIOLOGICAL SAMPLE

| # | Formulation Composition |
|---|---|
| 1.1 | 3.2M Guanidine hydrochloride, 4% 1-hexyl-3-methylimidazolium bromide, 100 mM Sulfosalicyclic acid, 0.5 mM Yellow #5, 0.2 mM Rifamycin SV, 30% Ethanol (EtOH), pH 8.7. |
| 1.2 | 300 mM MOPS, 4M Guanidine hydrochloride, 1M Thiourea, 4% 1-Octyl-3-methylimidazolium bromide, 10 mM Tris(carboxyethyl)phosphine, 30% Ethanol, pH 7.6 |
| 1.3 | 3.5M LiCl, 300 mM EPPS, 4% 1-Octyl-3-methylimidazolium bromide, 30% Ethanol, 50 mM TCEP-HCl, pH 7.8. |
| 1.4 | 300 mM MOPS, 4M Guanidine hydrochloride, 1% Tomamine E-14-5, 30% Ethanol, pH 7.7. |
| 1.5 | 300 mM MOPS, 4M Guanidine hydrochloride, 1% Surfonic T-15, 30% Ethanol, pH 7.8. |
| 1.6 | 300 mM MOPS, 4M Guanidine hydrochloride, 1% Surfonic T-20, 30% Ethanol, pH 7.8. |
| 1.7 | 300 mM MOPS, 4M Guanidine hydrochloride, 1% Tomamine E-17-5, 30% Ethanol, pH 7.8. |
| 1.8 | 3.5M LiCl, 200 mM Tris, 0.7M Thiourea, 4% 1-Octyl-3-methylimidazolium bromide, 30% Ethanol, 25 mM TCEP-HCl, pH 8.0. |
| 1.9 | 300 mM MOPS, 4M Guanidine hydrochloride, 1% Tomamine E-14-5, 1% 1-Octyl-3-methylimidazolium bromide, 30% ethanol, 10 mM TCEP hydrochloride, pH 8.2. |
| 1.10 | 200 mM MOPS, 4M Guanidine hydrochloride, 1% Tomamine E-14-5, 2% 1-Octyl-3-methylimidazolium bromide, 30% ethanol, 10 mM TCEP hydrochloride, pH 8.3. |
| 1.11 | 300 mM MOPS, 4M Guanidine hydrochloride, 1% Tomamine E-14-5, 4% 1-Octyl-3-methylimidazolium bromide, 30% ethanol, 10 mM TCEP hydrochloride, pH 8.3. |
| 1.12 | 300 mM MOPS, 4M Guanidine hydrochloride, 1% Tomamine E-17-5, 1% 1-Octyl-3-methylimidazolium bromide, 30% ethanol, pH 8.8. |
| 1.13 | 300 mM MOPS, 4M Guanidine hydrochloride, 1% Tomamine E-17-5, 2% 1-Octyl-3-methylimidazolium bromide, 30% ethanol, pH 158.8. |
| 1.14 | 300 mM MOPS, 4M Guanidine hydrochloride, 1% Tomamine E--5, 4% 1-Octyl-3-methylimidazolium bromide, 30% ethanol, pH 8.8. |
| 1.15 | 3.2M Guanidine hydrochloride, 4% 1-hexyl-3-methylimidazolium bromide, 0.5 mM Yellow #5, 0.2 mM Rifamycin SV, 200 mM Bicine, 30% Ethanol, pH 8.8 |
| 1.16 | 3.5M LiCl, 200 mM EPPS, 4% 1-Octyl-3-methylimidazolium bromide, 30% ethanol, 25 mM TCEP hydrochloride, pH 8.6. |
| 1.17 | 3.5M LiCl, 200 mM EPPS, 4% 1-Octyl-3-methylimidazolium bromide, 30% ethanol, 10 mM TCEP hydrochloride, pH 8.6 |
| 1.18 | 3.5M LiCl, 200 mM Tris, 4% 1-Octyl-3-methylimidazolium bromide, 30% ethanol, 25 mM TCEP hydrochloride, pH 8.6. |
| 1.19 | 3.5M LiCl, 200 mM Tris, 4% 1-Octyl-3-methylimidazolium bromide, 30% ethanol, 10 mM TCEP hydrochloride, pH 8.6 |
| 1.20 | 3.5M LiCl, 200 mM Tris, 1% 1-Octyl-3-methylimidazolium bromide, 30% ethanol, 25 mM TCEP hydrochloride, pH 8.6 |
| 1.21 | 3.5M LiCl, 200 mM Tris, 4% 1-Octyl-3-methylimidazolium bromide, 0.7M Urea, 30% ethanol, 25 mM TCEP hydrochloride, pH 8.6 |
| 1.22 | 3.5M LiCl, 200 mM Tris, 4% 1-Octyl-3-methylimidazolium bromide, 0.7M Urea, 30% ethanol, 10 mM TCEP hydrochloride, pH 8 |

TABLE 2

EXEMPLARY COMPOSITIONS FOR STABLE STORAGE OF NUCLEIC ACID AND POLYPEPTIDE MOLECULES IN A BIOLOGICAL SAMPLE (SALIVA)

| # | Chaotrope | Buffer | Alcohol | Polymerase Inhibitor(s) | Additive | pH |
|---|---|---|---|---|---|---|
| 2.1 | 4M Guanidine-HCl | 100 mM Sulfosalicylic acid | 30% EtOH | 0.5 mM Yellow #5 0.2 mM Rifamycin SV | 4% 1-hexyl-3-methylidazolium bromide | 7.5 |
| 2.2 | 4M Guanidine-HCl | 100 mM Sulfosalicylic acid | 30% EtOH | 0.5 mM Yellow #5 | 4% 1-Octyl-3-methylimidazolium | 8.0 |
| 2.3 | 3.2M Guanidine-HCl | 100 mM Sulfosalicylic acid | 30% EtOH | 0.5 mM Yellow #5 0.2 mM Rifamycin S | 4% 1-Hexyl-3-methylimidazolium bromide | 8.7 |

TABLE 3

EXEMPLARY COMPOSITIONS FOR STABLE STORAGE OF NUCLEIC ACID AND POLYPEPTIDE MOLECULES IN A BIOLOGICAL SAMPLE (SALIVA)

| # | Chaotrop/Pptg Agent | Buffer | Alcohol | Reducing Agents | Additional Additive(s) | pH |
|---|---|---|---|---|---|---|
| 3.4 | 4M Guanidine-HCl | 300 mM MOPS | 20% Ethanol | | 4% 1-Hexyl-3-methylimidazolium bromide | 7.6 |
| 3.5 | 4M Guanidine-HCl | 300 mM MOPS | 30% Ethanol | | | 7.6 |
| 3.6 | 4M Guanidine-HCl | 300 mM MOPS | 30% Ethanol | 1M Thiourea & 10 mM TCEP-HCl | 4% 1-Octyl-3-methylimidazolium bromide | 7.6 |
| 3.7 | 3.5M LiCl | 300 mM EPPS | 30% Ethanol | 50 mM TCEP-HCl | 4% 1-Octyl-3-methylimidazolium bromide | 7.8 |
| 3.8 | 4M Guanidine-HCl | 300 mM MOPS | 30% Ethanol | | 1% Tomamine E-14-5 | 7.7 |
| 3.9 | 4M Guanidine-HCl | 300 mM MOPS | 30% Ethanol | | 1% Surfonic T-15 | 7.8 |
| 3.10 | 4M Guanidine-HCl | 300 mM MOPS | 30% Ethanol | | 1% Surfonic T-20 | 7.8 |
| 3.11 | 4M Guanidine-HCl | 300 mM MOPS | 30% Ethanol | | 1% Tomamine E-17.5 | 7.8 |
| 3.12 | 3.5M LiCl | 200 mM Tris | 30% Ethanol | 0.7M Thiourea & 25 mM TCEP-HCl | 4% 1-Octyl-3-methylimidazolium bromide | 8.0 |
| 3.13 | 4M Guanidine-HCl | 300 mM MOPS | 30% Ethanol | 10 mM TCEP-HCl | 1% Tomamine E-14-5 & 1% 1-Octyl-3-methylimidazolium bromide | 8.2 |
| 3.14 | 4M Guanidine-HCl | 200 mM MOPS | 30% Ethanol | 10 mM TCEP-HCl | 1% Tomamine E-14-5 & 2% 1-Octyl-3-methylimidazolium bromide | 8.3 |
| 3.15 | 4M Guanidine-HCl | 300 mM MOPS | 30% Ethanol | 10 mM TCEP-HCl | 1% Tomamine E-14-5 & 4% 1-Octyl-3-methylimidazolium bromide | 8.3 |
| 3.16 | 4M Guanidine-HCl | 300 mM EPPS | 30% Ethanol | | 1% Tomamine E-17-5 & 1% 1-Octyl-3-methylimidazolium bromide | 8.8 |
| 3.17 | 4M Guanidine-HCl | 300 mM MOPS | 30% Ethanol | | 1% Tomamine E-17-5 & 2% 1-Octyl-3-methylimidazolium bromide | 8.8 |
| 3.18 | 4M Guanidine-HCl | 300 mM MOPS | 30% Ethanol | | 1% Tomamine E-17-5 & 2% 1-Octyl-3-methylimidazolium bromide | 8.8 |
| 3.19 | 3.2M Guanidine-HCl | 200 mM Bicine | 30% Ethanol | | a) 4% 1-hexyl-3-methylidazolium bromide b) 0.5 mM Yellow #5 c) 0.2 mM Rifamycin Sv | 8.8 |
| 3.20 | 3.5M LiCl | 200 mM EPPS | 30% Ethanol | 25 mM TCEP-HCl | 4% 1-Octyl-3-methylimidazolium bromide | 8.6 |
| 3.21 | 3.5M LiCl | 200 mM EPPS | 30% Ethanol | 10 mM TCEP-HCl | 4% 1-Octyl-3-methylimidazolium bromide | 8.6 |

TABLE 3-continued

EXEMPLARY COMPOSITIONS FOR STABLE STORAGE OF NUCLEIC ACID AND POLYPEPTIDE MOLECULES IN A BIOLOGICAL SAMPLE (SALIVA)

| # | Chaotrop/Pptg Agent | Buffer | Alcohol | Reducing Agents | Additional Additive(s) | pH |
|---|---|---|---|---|---|---|
| 3.22 | 3.5M LiCl | 200 mM Tris | 30% Ethanol | 25 mM TCEP-HCl | 4% 1-Octyl-3-methylimidazolium bromide | 8.6 |
| 3.23 | 3.5M LiCl | 200 mM Tris | 30% Ethanol | 10 mM TCEP-HCl | 4% 1-Octyl-3-methylimidazolium bromide | 8.6 |
| 3.24 | 3.5M LiCl | 200 mM Tris | 30% Ethanol | 25 mM TCEP-HCl | 1% 1-Octyl-3-methylimidazolium bromide | 8.6 |
| 3.25 | 3.5M LiCl | 200 mM Tris | 30% Ethanol | 25 mM TCEP-HCl | 4% 1-Octyl-3-methylimidazolium bromide 0.7M Urea | 8.6 |
| 3.26 | 3.5M LiCl | 200 mM Tris | 30% Ethanol | 10 mM TCEP-HCl | 4% 1-Octyl-3-methylimidazolium bromide 0.7M Urea | 8.6 |

TABLE 4

EXEMPLARY COMPOSITIONS FOR STABLE STORAGE OF NUCLEIC ACID AND POLYPEPTIDE MOLECULES IN A BIOLOGICAL SAMPLE (SALIVA)

| # | Formulation |
|---|---|
| 4.1 | 300 mM MOPS, 4M Guanidine hydrochloride, 1% Tomamine E-14-5, 1% 1-Octyl-3-methylimidazolium bromide, 30% ethanol, 10 mM TCEP hydrochloride, pH 8.2. |
| 4.2 | 200 mM MOPS, 4M Guanidine hydrochloride, 1% Tomamine E-14-5, 2% 1-Octyl-3-methylimidazolium bromide, 30% ethanol, 10 mM TCEP hydrochloride, pH 8.3. |
| 4.3 | 300 mM MOPS, 4M Guanidine hydrochloride, 1% Tomamine E-14-5, 4% 1-Octyl-3-methylimidazolium bromide, 30% ethanol, 10 mM TCEP hydrochloride, pH 8.3. |
| 4.4 | 300 mM MOPS, 4M Guanidine hydrochloride, 1% Tomamine E-17-5, 1% 1-Octyl-3-methylimidazolium bromide, 30% ethanol, pH 8.8. |
| 4.5 | 300 mM MOPS, 4M Guanidine hydrochloride, 1% Tomamine E-17-5, 2% 1-Octyl-3-methylimidazolium bromide, 30% ethanol, pH 8.8. |
| 4.6 | 300 mM MOPS, 4M Guanidine hydrochloride, 1% Tomamine E-17-5, 4% 1-Octyl-3-methylimidazolium bromide, 30% ethanol, pH 8.8. |
| 4.7 | 3.2M Guanidine hydrochloride, 4% 1-hexyl-3-methylimidazolium bromide, 0.5 mM Yellow #5, 0.2 mM Rifamycin SV, 200 mM EPPS, 30% Ethanol, pH 8.8. |
| 4.8 | 3.2M Guanidine hydrochloride, 4% 1-hexyl-3-methylimidazolium bromide, 0.5 mM Yellow #5, 0.2 mM Rifamycin SV, 200 mM EPPS, 30% Ethanol, pH 8.8. |
| 4.9 | 3.2M Guanidine hydrochloride, 4% 1-hexyl-3-methylimidazolium bromide, 0.5 mM Yellow #5, 0.2 mM Rifamycin SV, 200 mM Bicine, 30% Ethanol, pH 8.8. |
| 4.10 | 3.5M LiCl, 200 mM EPPS, 4% 1-Octyl-3-methylimidazolium bromide, 30% ethanol, 50 mM TCEP hydrochloride, pH 8.6. |
| 4.11 | 3.5M LiCl, 200 mM EPPS, 4% 1-Octyl-3-methylimidazolium bromide, 30% ethanol, 25 mM TCEP hydrochloride, pH 8.6. |
| 4.12 | 3.5M LiCl, 200 mM EPPS, 4% 1-Octyl-3-methylimidazolium bromide, 30% ethanol, 10 mM TCEP hydrochloride, pH 8.6 |
| 4.13 | 3.5M LiCl, 200 mM Tris, 4% 1-Octyl-3-methylimidazolium bromide, 30% ethanol, 25 mM TCEP hydrochloride, pH 8.6. |
| 4.14 | 3.5M LiCl, 200 mM Tris, 4% 1-Octyl-3-methylimidazolium bromide, 30% ethanol, 10 mM TCEP hydrochloride, pH 8.6. |
| 4.15 | 3.5M LiCl, 200 mM Tris, 1% 1-Octyl-3-methylimidazolium bromide, 30% ethanol, 25 mM TCEP hydrochloride, pH 8.6 |
| 4.16 | 4M Guanidine hydrochloride, 200 mM Tris, 4% 1-Hexyl-3-methylimidazolium bromide, 100 mM sodium thiosulfate, 30% ethanol, pH 8.6. |
| 4.17 | 3.5M LiCl, 200 mM Tris, 4% 1-Octyl-3-methylimidazolium bromide, 0.7M Urea, 30% ethanol, 25 mM TCEP hydrochloride, pH 8.6 |
| 4.18 | 3.5M LiCl, 200 mM Tris, 4% 1-Octyl-3-methylimidazolium bromide, 0.7M Urea, 30% ethanol, 10 mM TCEP hydrochloride, pH 8.6 |
| 4.19 | 3.2M Guanidine hydrochloride, 4% 1-hexyl-3-methylimidazolium bromide, 100 mM Sulfosalicyclic acid, 0.5 mM Yellow #5, 0.2 mM Rifamycin SV, 30% Ethanol, pH 8.7. |
| 4.20 | 300 mM MOPS, 4M Guanidine hydrochloride, 1% Tomamine E-14-5, 30% Ethanol, pH 7.7. |
| 4.21 | 3.5M LiCl, 300 mM EPPS, 4% 1-Octyl-3-methylimidazolium bromide, 50 mM TCEP, pH 7.8. |
| 4.22 | 3.0M LiCl, 200 mM EPPS, 4% 1-Octyl-3-methylimidazolium bromide, 30% Ethanol, 25 mM TCEP, pH 8.6. |
| 4.23 | 3.0M LiCl, 200 mM EPPS, 4% 1-Octyl-3-methylimidazolium bromide, 25 mM TCEP, pH 8.6. |

TABLE 5

EXEMPLARY STORAGE COMPOSITIONS

| (A) Compound of Formula (I) | (A) + (B) Precipitating Agent | (A) + (C) Lower Alcohol | (A) + (D) Chaotrope | (A) + (B) + (C) | (A) + (B) + (D) | (A) + (B) + (C) + (D) | (A) + (C) + (D) |
|---|---|---|---|---|---|---|---|
| 1-methyl-3-carboxyethyl-imidazolium bromide | 1-methyl-3-carboxyethyl-imidazolium bromide + 5-(4-dimethyl)amino benzylidene rhodanine | 1-methyl-3-carboxyethyl-imidazolium bromide + methanol | 1-methyl-3-carboxyethyl-imidazolium bromide + guanidine hydrochloride | 1-methyl-3-carboxyethyl-imidazolium bromide + 5-(4-dimethyl)amino benzylidene rhodanine + methanol | 1-methyl-3-carboxyethyl-imidazolium bromide + 5-(4-dimethyl)amino benzylidene rhodanine + guanidine HCl | 1-methyl-3-carboxyethyl-imidazolium bromide + 5-(4-dimethyl)amino benzylidene rhodanine + methanol + guanidine HCl | 1-methyl-3-carboxyethyl-imidazolium bromide + methanol + guanidine HCl |
| 1-hexyl-3-methylimidazolium bromide | 1-hexyl-3-methylimidazolium bromide + 5-(4-dimethyl)amino benzylidene rhodanine | 1-hexyl-3-methylimidazolium bromide + methanol | 1-hexyl-3-methylimidazolium bromide + guanidine hydrochloride | 1-hexyl-3-methylimidazolium bromide + 5-(4-dimethyl)amino benzylidene rhodanine + methanol | 1-hexyl-3-methylimidazolium bromide + 5-(4-dimethyl)amino benzylidene rhodanine + guanidine HCl | 1-hexyl-3-methylimidazolium bromide + 5-(4-dimethyl)amino benzylidene rhodanine + methanol + guanidine HCl | 1-hexyl-3-methylimidazolium bromide + methanol + guanidine HCl |
| 1-decyl-3-methylimidazolium bromide | 1-decyl-3-methylimidazolium bromide + 5-(4-dimethyl)amino benzylidene rhodanine | 1-decyl-3-methylimidazolium bromide + methanol | 1-decyl-3-methylimidazolium bromide + guanidine hydrochloride | 1-decyl-3-methylimidazolium bromide + 5-(4-dimethyl)amino benzylidene rhodanine + methanol | 1-decyl-3-methylimidazolium bromide + 5-(4-dimethyl)amino benzylidene rhodanine + guanidine HCl | 1-decyl-3-methylimidazolium bromide + 5-(4-dimethyl)amino benzylidene rhodanine + methanol + guanidine HCl | 1-decyl-3-methylimidazolium bromide + methanol + guanidine HCl |
| 1-(2-hydroxyethyl)-3-methylimidazolium bromide | 1-(2-hydroxyethyl)-3-methylimidazolium bromide + 5-(4-dimethyl)amino benzylidene rhodanine | 1-(2-hydroxyethyl)-3-methylimidazolium bromide + methanol | 1-(2-hydroxyethyl)-3-methylimidazolium bromide + guanidine hydrochloride | 1-(2-hydroxyethyl)-3-methylimidazolium bromide + 5-(4-dimethyl)amino benzylidene rhodanine + methanol | 1-(2-hydroxyethyl)-3-methylimidazolium bromide + 5-(4-dimethyl)amino benzylidene rhodanine + guanidine HCl | 1-(2-hydroxyethyl)-3-methylimidazolium bromide + 5-(4-dimethyl)amino benzylidene rhodanine + methanol + guanidine HCl | 1-(2-hydroxyethyl)-3-methylimidazolium bromide + methanol + guanidine HCl |
| 1-octyl-3-methylimidazolium bromide | 1-octyl-3-methylimidazolium bromide + 5-(4-dimethyl)amino benzylidene rhodanine | 1-octyl-3-methylimidazolium bromide + methanol | 1-octyl-3-methylimidazolium bromide + guanidine hydrochloride | 1-octyl-3-methylimidazolium bromide + 5-(4-dimethyl)amino benzylidene rhodanine + methanol | 1-octyl-3-methylimidazolium bromide + 5-(4-dimethyl)amino benzylidene rhodanine + guanidine HCl | 1-octyl-3-methylimidazolium bromide + 5-(4-dimethyl)amino benzylidene rhodanine + methanol + guanidine HCl | 1-octyl-3-methylimidazolium bromide + methanol + guanidine HCl |
| 1-methyl-3-carboxyethyl-imidazolium bromide | 1-methyl-3-carboxyethyl-imidazolium bromide + sulfosalicylic acid | 1-methyl-3-carboxyethyl-imidazolium bromide + methanol | 1-methyl-3-carboxyethyl-imidazolium bromide + guanidine hydrochloride | 1-methyl-3-carboxyethyl-imidazolium bromide + sulfosalicylic acid + methanol | 1-methyl-3-carboxyethyl-imidazolium bromide + sulfosalicylic acid + guanidine HCl | 1-methyl-3-carboxyethyl-imidazolium bromide + sulfosalicylic acid + methanol + guanidine HCl | 1-methyl-3-carboxyethyl-imidazolium bromide + methanol + guanidine HCl |

TABLE 5-continued

EXEMPLARY STORAGE COMPOSITIONS

| (A) Compound of Formula (I) | (A) + (B) Precipitating Agent | (A) + (C) Lower Alcohol | (A) + (D) Chaotrope | (A) + (B) + (C) | (A) + (B) + (D) | (A) + (B) + (C) + (D) | (A) + (C) + (D) |
|---|---|---|---|---|---|---|---|
| 1-hexyl-3-methylimidazolium bromide | 1-hexyl-3-methylimidazolium bromide + sulfosalicylic acid | 1-hexyl-3-methylimidazolium bromide + methanol | 1-hexyl-3-methylimidazolium bromide + guanidine hydrochloride | 1-hexyl-3-methylimidazolium bromide + sulfosalicylic acid + methanol | 1-hexyl-3-methylimidazolium bromide + sulfosalicylic acid + guanidine HCl | 1-hexyl-3-methylimidazolium bromide + sulfosalicylic acid + methanol + guanidine HCl | 1-hexyl-3-methylimidazolium bromide + methanol + guanidine HCl |
| 1-decyl-3-methylimidazolium bromide | 1-decyl-3-methylimidazolium bromide + sulfosalicylic acid | 1-decyl-3-methylimidazolium bromide + methanol | 1-decyl-3-methylimidazolium bromide + guanidine hydrochloride | 1-decyl-3-methylimidazolium bromide + sulfosalicylic acid + methanol | 1-decyl-3-methylimidazolium bromide + sulfosalicylic acid + guanidine HCl | 1-decyl-3-methylimidazolium bromide + sulfosalicylic acid + methanol + guanidine HCl | 1-decyl-3-methylimidazolium bromide + methanol + guanidine HCl |
| 1-(2-hydroxyethyl)-3-methylimidazolium bromide | 1-(2-hydroxyethyl)-3-methylimidazolium bromide + sulfosalicylic acid | 1-(2-hydroxyethyl)-3-methylimidazolium bromide + methanol | 1-(2-hydroxyethyl)-3-methylimidazolium bromide + guanidine hydrochloride | 1-(2-hydroxyethyl)-3-methylimidazolium bromide + sulfosalicylic acid + methanol | 1-(2-hydroxyethyl)-3-methylimidazolium bromide + sulfosalicylic acid + guanidine HCl | 1-(2-hydroxyethyl)-3-methylimidazolium bromide + sulfosalicylic acid + methanol + guanidine HCl | 1-(2-hydroxyethyl)-3-methylimidazolium bromide + methanol + guanidine HCl |
| 1-octyl-3-methylimidazolium bromide | 1-octyl-3-methylimidazolium bromide + sulfosalicylic acid | 1-octyl-3-methylimidazolium bromide + methanol | 1-octyl-3-methylimidazolium bromide + guanidine hydrochloride | 1-octyl-3-methylimidazolium bromide + sulfosalicylic acid + methanol | 1-octyl-3-methylimidazolium bromide + sulfosalicylic acid + guanidine HCl | 1-octyl-3-methylimidazolium bromide + sulfosalicylic acid + methanol + guanidine HCl | 1-octyl-3-methylimidazolium bromide + methanol + guanidine HCl |
| 1-methyl-3-carboxyethyl-imidazolium bromide | 1-methyl-3-carboxyethyl-imidazolium bromide + lithium chloride | 1-methyl-3-carboxyethyl-imidazolium bromide + methanol | 1-methyl-3-carboxyethyl-imidazolium bromide + guanidine hydrochloride | 1-methyl-3-carboxyethyl-imidazolium bromide + Lithium chloride + methanol | 1-methyl-3-carboxyethyl-imidazolium bromide + LiCl + guanidine HCl | 1-methyl-3-carboxyethyl-imidazolium bromide + LiCl + methanol + guanidine HCl | 1-methyl-3-carboxyethyl-imidazolium bromide + methanol + guanidine HCl |
| 1-hexyl-3-methylimidazolium bromide | 1-hexyl-3-methylimidazolium bromide + lithium chloride | 1-hexyl-3-methylimidazolium bromide + methanol | 1-hexyl-3-methylimidazolium bromide + guanidine hydrochloride | 1-hexyl-3-methylimidazolium bromide + Lithium chloride + methanol | 1-hexyl-3-methylimidazolium bromide + LiCl + guanidine HCl | 1-hexyl-3-methylimidazolium bromide + LiCl + methanol + guanidine HCl | 1-hexyl-3-methylimidazolium bromide + methanol + guanidine HCl |
| 1-decyl-3-methylimidazolium bromide | 1-decyl-3-methylimidazolium bromide + lithium chloride | 1-decyl-3-methylimidazolium bromide + methanol | 1-decyl-3-methylimidazolium bromide + guanidine hydrochloride | 1-decyl-3-methylimidazolium bromide + Lithium chloride + methanol | 1-decyl-3-methylimidazolium bromide + LiCl + guanidine HCl | 1-decyl-3-methylimidazolium bromide + LiCl + methanol + guanidine HCl | 1-decyl-3-methylimidazolium bromide + methanol + guanidine HCl |
| 1-(2-hydroxyethyl)-3-methylimidazolium bromide | 1-(2-hydroxyethyl)-3-methylimidazolium bromide + lithium chloride | 1-(2-hydroxyethyl)-3-methylimidazolium bromide + methanol | 1-(2-hydroxyethyl)-3-methylimidazolium bromide + guanidine hydrochloride | 1-(2-hydroxyethyl)-3-methylimidazolium bromide + Lithium chloride + methanol | 1-(2-hydroxyethyl)-3-methylimidazolium bromide + LiCl + guanidine HCl | 1-(2-hydroxyethyl)-3-methylimidazolium bromide + LiCl + methanol + guanidine HCl | 1-(2-hydroxyethyl)-3-methylimidazolium bromide + methanol + guanidine HCl |
| 1-octyl-3-methylimidazolium bromide | 1-octyl-3-methylimidazolium bromide + lithium chloride | 1-octyl-3-methylimidazolium bromide + methanol | 1-octyl-3-methylimidazolium bromide + guanidine hydrochloride | 1-octyl-3-methylimidazolium bromide + Lithium chloride + methanol | 1-octyl-3-methylimidazolium bromide + LiCl + guanidine HCl | 1-octyl-3-methylimidazolium bromide + LiCl + methanol + guanidine HCl | 1-octyl-3-methylimidazolium bromide + methanol + guanidine HCl |

TABLE 5-continued

EXEMPLARY STORAGE COMPOSITIONS

| (A) Compound of Formula (I) | (A) + (B) Precipitating Agent | (A) + (C) Lower Alcohol | (A) + (D) Chaotrope | (A) + (B) + (C) | (A) + (B) + (D) | (A) + (B) + (C) + (D) | (A) + (C) + (D) |
|---|---|---|---|---|---|---|---|
| 1-methyl-3-carboxyethyl-imidazolium bromide | 1-methyl-3-carboxyethyl-imidazolium bromide + lithium hydroxide | 1-methyl-3-carboxyethyl-imidazolium bromide + methanol | 1-methyl-3-carboxyethyl-imidazolium bromide + guanidine hydrochloride | 1-methyl-3-carboxyethyl-imidazolium bromide + Lithium hydroxide + methanol | 1-methyl-3-carboxyethyl-imidazolium bromide + LiOH + guanidine HCl | 1-methyl-3-carboxyethyl-imidazolium bromide + LiOH + methanol + guanidine HCl | 1-methyl-3-carboxyethyl-imidazolium bromide + methanol + guanidine HCl |
| 1-hexyl-3-methylimidazolium bromide | 1-hexyl-3-methylimidazolium bromide + lithium hydroxide | 1-hexyl-3-methylimidazolium bromide + methanol | 1-hexyl-3-methylimidazolium bromide + guanidine hydrochloride | 1-hexyl-3-methylimidazolium bromide + Lithium hydroxide + methanol | 1-hexyl-3-methylimidazolium bromide + LiOH + guanidine HCl | 1-hexyl-3-methylimidazolium bromide + LiOH + methanol + guanidine HCl | 1-hexyl-3-methylimidazolium bromide + methanol + guanidine HCl |
| 1-decyl-3-methylimidazolium bromide | 1-decyl-3-methylimidazolium bromide + lithium hydroxide | 1-decyl-3-methylimidazolium bromide + methanol | 1-decyl-3-methylimidazolium bromide + guanidine hydrochloride | 1-decyl-3-methylimidazolium bromide + Lithium hydroxide + methanol | 1-decyl-3-methylimidazolium bromide + LiOH + guanidine HCl | 1-decyl-3-methylimidazolium bromide + LiOH + methanol + guanidine HCl | 1-decyl-3-methylimidazolium bromide + methanol + guanidine HCl |
| 1-(2-hydroxyethyl)-3-methylimidazolium bromide | 1-(2-hydroxyethyl)-3-methylimidazolium bromide + lithium hydroxide | 1-(2-hydroxyethyl)-3-methylimidazolium bromide + methanol | 1-(2-hydroxyethyl)-3-methylimidazolium bromide + guanidine hydrochloride | 1-(2-hydroxyethyl)-3-methylimidazolium bromide + Lithium hydroxide + methanol | 1-(2-hydroxyethyl)-3-methylimidazolium bromide + LiOH + guanidine HCl | 1-(2-hydroxyethyl)-3-methylimidazolium bromide + LiOH + methanol + guanidine HCl | 1-(2-hydroxyethyl)-3-methylimidazolium bromide + methanol + guanidine HCl |
| 1-octyl-3-methylimidazolium bromide | 1-octyl-3-methylimidazolium bromide + lithium hydroxide | 1-octyl-3-methylimidazolium bromide + methanol | 1-octyl-3-methylimidazolium bromide + guanidine hydrochloride | 1-octyl-3-methylimidazolium bromide + Lithium hydroxide + methanol | 1-octyl-3-methylimidazolium bromide + LiOH + guanidine HCl | 1-octyl-3-methylimidazolium bromide + LiOH + methanol + guanidine HCl | 1-octyl-3-methylimidazolium bromide + methanol + guanidine HCl |
| 1-methyl-3-carboxyethyl-imidazolium bromide | 1-methyl-3-carboxyethyl-imidazolium bromide + 5-(4-dimethyl)amino benzylidene rhodanine | 1-methyl-3-carboxyethyl-imidazolium bromide + ethanol | 1-methyl-3-carboxyethyl-imidazolium bromide + guanidine hydrochloride | 1-methyl-3-carboxyethyl-imidazolium bromide + 5-(4-dimethyl)amino benzylidene rhodanine + ethanol | 1-methyl-3-carboxyethyl-imidazolium bromide + 5-(4-dimethyl)amino benzylidene rhodanine + guanidine HCl | 1-methyl-3-carboxyethyl-imidazolium bromide + 5-(4-dimethyl)amino benzylidene rhodanine + ethanol + guanidine HCl | 1-methyl-3-carboxyethyl-imidazolium bromide + ethanol + guanidine HCl |
| 1-hexyl-3-methylimidazolium bromide | 1-hexyl-3-methylimidazolium bromide + 5-(4-dimethyl)amino benzylidene rhodanine | 1-hexyl-3-methylimidazolium bromide + ethanol | 1-hexyl-3-methylimidazolium bromide + guanidine hydrochloride | 1-hexyl-3-methylimidazolium bromide + 5-(4-dimethyl)amino benzylidene rhodanine + ethanol | 1-hexyl-3-methylimidazolium bromide + 5-(4-dimethyl)amino benzylidene rhodanine + guanidine HCl | 1-hexyl-3-methylimidazolium bromide + 5-(4-dimethyl)amino benzylidene rhodanine + ethanol + guanidine HCl | 1-hexyl-3-methylimidazolium bromide + ethanol + guanidine HCl |

TABLE 5-continued

EXEMPLARY STORAGE COMPOSITIONS

| (A) Compound of Formula (I) | (A) + (B) Precipitating Agent | (A) + (C) Lower Alcohol | (A) + (D) Chaotrope | (A) + (B) + (C) | (A) + (B) + (D) | (A) + (B) + (C) + (D) | (A) + (C) + (D) |
|---|---|---|---|---|---|---|---|
| 1-decyl-3-methylimidazolium bromide | 1-decyl-3-methylimidazolium bromide + 5-(4-dimethyl)amino benzylidene rhodanine | 1-decyl-3-methylimidazolium bromide + ethanol | 1-decyl-3-methylimidazolium bromide + guanidine hydrochloride | 1-decyl-3-methylimidazolium bromide + 5-(4-dimethyl)amino benzylidene rhodanine + ethanol | 1-decyl-3-methylimidazolium bromide + 5-(4-dimethyl)amino benzylidene rhodanine + guanidine HCl | 1-decyl-3-methylimidazolium bromide + 5-(4-dimethyl)amino benzylidene rhodanine + ethanol + guanidine HCl | 1-decyl-3-methylimidazolium bromide + ethanol + guanidine HCl |
| 1-(2-hydroxyethyl)-3-methylimidazolium bromide | 1-(2-hydroxyethyl)-3-methylimidazolium bromide + 5-(4-dimethyl)amino benzylidene rhodanine | 1-(2-hydroxyethyl)-3-methylimidazolium bromide + ethanol | 1-(2-hydroxyethyl)-3-methylimidazolium bromide + guanidine hydrochloride | 1-(2-hydroxyethyl)-3-methylimidazolium bromide + 5-(4-dimethyl)amino benzylidene rhodanine + ethanol | 1-(2-hydroxyethyl)-3-methylimidazolium bromide + 5-(4-dimethyl)amino benzylidene rhodanine + guanidine HCl | 1-(2-hydroxyethyl)-3-methylimidazolium bromide + 5-(4-dimethyl)amino benzylidene rhodanine + ethanol + guanidine HCl | 1-(2-hydroxyethyl)-3-methylimidazolium bromide + ethanol + guanidine HCl |
| 1-octyl-3-methylimidazolium bromide | 1-octyl-3-methylimidazolium bromide + 5-(4-dimethyl)amino benzylidene rhodanine | 1-octyl-3-methylimidazolium bromide + ethanol | 1-octyl-3-methylimidazolium bromide + guanidine hydrochloride | 1-octyl-3-methylimidazolium bromide + 5-(4-dimethyl)amino benzylidene rhodanine + ethanol | 1-octyl-3-methylimidazolium bromide + 5-(4-dimethyl)amino benzylidene rhodanine + guanidine HCl | 1-octyl-3-methylimidazolium bromide + 5-(4-dimethyl)amino benzylidene rhodanine + ethanol + guanidine HCl | 1-octyl-3-methylimidazolium bromide + ethanol + guanidine HCl |
| 1-methyl-3-carboxyethyl-imidazolium bromide | 1-methyl-3-carboxyethyl-imidazolium bromide + sulfosalicylic acid | 1-methyl-3-carboxyethyl-imidazolium bromide + ethanol | 1-methyl-3-carboxyethyl-imidazolium bromide + guanidine hydrochloride | 1-methyl-3-carboxyethyl-imidazolium bromide + sulfosalicylic acid + ethanol | 1-methyl-3-carboxyethyl-imidazolium bromide + sulfosalicylic acid + guanidine HCl | 1-methyl-3-carboxyethyl-imidazolium bromide + sulfosalicylic acid + ethanol + guanidine HCl | 1-methyl-3-carboxyethyl-imidazolium bromide + ethanol + guanidine HCl |
| 1-hexyl-3-methylimidazolium bromide | 1-hexyl-3-methylimidazolium bromide + sulfosalicylic acid | 1-hexyl-3-methylimidazolium bromide + ethanol | 1-hexyl-3-methylimidazolium bromide + guanidine hydrochloride | 1-hexyl-3-methylimidazolium bromide + sulfosalicylic acid + ethanol | 1-hexyl-3-methylimidazolium bromide + sulfosalicylic acid + guanidine HCl | 1-hexyl-3-methylimidazolium bromide + sulfosalicylic acid + ethanol + guanidine HCl | 1-hexyl-3-methylimidazolium bromide + ethanol + guanidine HCl |
| 1-decyl-3-methylimidazolium bromide | 1-decyl-3-methylimidazolium bromide + sulfosalicylic acid | 1-decyl-3-methylimidazolium bromide + ethanol | 1-decyl-3-methylimidazolium bromide + guanidine hydrochloride | 1-decyl-3-methylimidazolium bromide + sulfosalicylic acid + ethanol | 1-decyl-3-methylimidazolium bromide + sulfosalicylic acid + guanidine HCl | 1-decyl-3-methylimidazolium bromide + sulfosalicylic acid + ethanol + guanidine HCl | 1-methyl-3-methylimidazolium bromide + ethanol + guanidine HCl |

TABLE 5-continued

EXEMPLARY STORAGE COMPOSITIONS

| (A) Compound of Formula (I) | (A) + (B) Precipitating Agent | (A) + (C) Lower Alcohol | (A) + (D) Chaotrope | (A) + (B) + (C) | (A) + (B) + (D) | (A) + (B) + (C) + (D) | (A) + (C) + (D) |
|---|---|---|---|---|---|---|---|
| 1-(2-hydroxyethyl)-3-methylimidazolium bromide | 1-(2-hydroxyethyl)-3-methylimidazolium bromide + sulfosalicylic acid | 1-(2-hydroxyethyl)-3-methylimidazolium bromide + ethanol | 1-(2-hydroxyethyl)-3-methylimidazolium bromide + guanidine hydrochloride | 1-(2-hydroxyethyl)-3-methylimidazolium bromide + sulfosalicylic acid + ethanol | 1-(2-hydroxyethyl)-3-methylimidazolium bromide + sulfosalicylic acid + guanidine HCl | 1-(2-hydroxyethyl)-3-methylimidazolium bromide + sulfosalicylic acid + ethanol + guanidine HCl | 1-(2-hydroxyethyl)-3-methylimidazolium bromide + ethanol + guanidine HCl |
| 1-octyl-3-methylimidazolium bromide | 1-octyl-3-methylimidazolium bromide + sulfosalicylic acid | 1-octyl-3-methylimidazolium bromide + ethanol | 1-octyl-3-methylimidazolium bromide + guanidine hydrochloride | 1-octyl-3-methylimidazolium bromide + sulfosalicylic acid + ethanol | 1-octyl-3-methylimidazolium bromide + sulfosalicylic acid + guanidine HCl | 1-octyl-3-methylimidazolium bromide + sulfosalicylic acid + ethanol + guanidine HCl | 1-octyl-3-methylimidazolium bromide + ethanol + guanidine HCl |
| 1-methyl-3-carboxyethyl-imidazolium bromide | 1-methyl-3-carboxyethyl-imidazolium bromide + lithium chloride | 1-methyl-3-carboxyethyl-imidazolium bromide + ethanol | 1-methyl-3-carboxyethyl-imidazolium bromide + guanidine hydrochloride | 1-methyl-3-carboxyethyl-imidazolium bromide + LiCl + ethanol | 1-methyl-3-carboxyethyl-imidazolium bromide + LiCl + guanidine HCl | 1-methyl-3-carboxyethyl-imidazolium bromide + LiCl + ethanol + guanidine HCl | 1-methyl-3-carboxyethyl-imidazolium bromide + ethanol + guanidine HCl |
| 1-hexyl-3-methylimidazolium bromide | 1-hexyl-3-methylimidazolium bromide + lithium chloride | 1-hexyl-3-methylimidazolium bromide + ethanol | 1-hexyl-3-methylimidazolium bromide + guanidine hydrochloride | 1-hexyl-3-methylimidazolium bromide + LiCl + ethanol | 1-hexyl-3-methylimidazolium bromide + LiCl + guanidine HCl | 1-hexyl-3-methylimidazolium bromide + LiCl + ethanol + guanidine HCl | 1-hexyl-3-methylimidazolium bromide + ethanol + guanidine HCl |
| 1-decyl-3-methylimidazolium bromide | 1-decyl-3-methylimidazolium bromide + lithium chloride | 1-decyl-3-methylimidazolium bromide + ethanol | 1-decyl-3-methylimidazolium bromide + guanidine hydrochloride | 1-decyl-3-methylimidazolium bromide + LiCl + ethanol | 1-decyl-3-methylimidazolium bromide + LiCl + guanidine HCl | 1-decyl-3-methylimidazolium bromide + LiCl + ethanol + guanidine HCl | 1-decyl-3-methylimidazolium bromide + ethanol + guanidine HCl |
| 1-(2-hydroxyethyl)-3-methylimidazolium bromide | 1-(2-hydroxyethyl)-3-methylimidazolium bromide + lithium chloride | 1-(2-hydroxyethyl)-3-methylimidazolium bromide + ethanol | 1-(2-hydroxyethyl)-3-methylimidazolium bromide + guanidine hydrochloride | 1-(2-hydroxyethyl)-3-methylimidazolium bromide + LiCl + ethanol | 1-(2-hydroxyethyl)-3-methylimidazolium bromide + LiCl + guanidine HCl | 1-(2-hydroxyethyl)-3-methylimidazolium bromide + LiCl + ethanol + guanidine HCl | 1-(2-hydroxyethyl)-3-methylimidazolium bromide + ethanol + guanidine HCl |
| 1-octyl-3-methylimidazolium bromide | 1-octyl-3-methylimidazolium bromide + lithium chloride | 1-octyl-3-methylimidazolium bromide + ethanol | 1-octyl-3-methylimidazolium bromide + guanidine hydrochloride | 1-octyl-3-methylimidazolium bromide + LiCl + ethanol | 1-octyl-3-methylimidazolium bromide + LiCl + guanidine HCl | 1-octyl-3-methylimidazolium bromide + LiCl + ethanol + guanidine HCl | 1-octyl-3-methylimidazolium bromide + ethanol + guanidine HCl |
| 1-methyl-3-carboxyethyl-imidazolium bromide | 1-methyl-3-carboxyethyl-imidazolium bromide + lithium hydroxide | 1-methyl-3-carboxyethyl-imidazolium bromide + ethanol | 1-methyl-3-carboxyethyl-imidazolium bromide + guanidine hydrochloride | 1-methyl-3-carboxyethyl-imidazolium bromide + LiOH + ethanol | 1-methyl-3-carboxyethyl-imidazolium bromide + LiOH + guanidine HCl | 1-methyl-3-carboxyethyl-imidazolium bromide + LiOH + ethanol + guanidine HCl | 1-methyl-3-carboxyethyl-imidazolium bromide + ethanol + guanidine HCl |

TABLE 5-continued

EXEMPLARY STORAGE COMPOSITIONS

| (A) Compound of Formula (I) | (A) + (B) Precipitating Agent | (A) + (C) Lower Alcohol | (A) + (D) Chaotrope | (A) + (B) + (C) | (A) + (B) + (D) | (A) + (B) + (C) + (D) | (A) + (C) + (D) |
|---|---|---|---|---|---|---|---|
| 1-hexyl-3-methylimidazolium bromide | 1-hexyl-3-methylimidazolium bromide + lithium hydroxide | 1-hexyl-3-methylimidazolium bromide + ethanol | 1-hexyl-3-methylimidazolium bromide + guanidine hydrochloride | 1-hexyl-3-methylimidazolium bromide + LiOH + ethanol | 1-hexyl-3-methylimidazolium bromide + LiOH + guanidine HCl | 1-hexyl-3-methylimidazolium bromide + LiOH + ethanol + guanidine HCl | 1-hexyl-3-methylimidazolium bromide + ethanol + guanidine HCl |
| 1-decyl-3-methylimidazolium bromide | 1-decyl-3-methylimidazolium bromide + lithium hydroxide | 1-decyl-3-methylimidazolium bromide + ethanol | 1-decyl-3-methylimidazolium bromide + guanidine hydrochloride | 1-decyl-3-methylimidazolium bromide + LiOH + ethanol | 1-decyl-3-methylimidazolium bromide + LiOH + guanidine HCl | 1-decyl-3-methylimidazolium bromide + LiOH + ethanol + guanidine HCl | 1-decyl-3-methylimidazolium bromide + ethanol + guanidine HCl |
| 1-(2-hydroxyethyl)-3-methylimidazolium bromide | 1-(2-hydroxyethyl)-3-methylimidazolium bromide + lithium hydroxide | 1-(2-hydroxyethyl)-3-methylimidazolium bromide + ethanol | 1-(2-hydroxyethyl)-3-methylimidazolium bromide + guanidine hydrochloride | 1-(2-hydroxyethyl)-3-methylimidazolium bromide + LiOH + ethanol | 1-(2-hydroxyethyl)-3-methylimidazolium bromide + LiOH + guanidine HCl | 1-(2-hydroxyethyl)-3-methylimidazolium bromide + LiOH + ethanol + guanidine HCl | 1-(2-hydroxyethyl)-3-methylimidazolium bromide + ethanol + guanidine HCl |
| 1-octyl-3-methylimidazolium bromide | 1-octyl-3-methylimidazolium bromide + lithium hydroxide | 1-octyl-3-methylimidazolium bromide + ethanol | 1-octyl-3-methylimidazolium bromide + guanidine hydrochloride | 1-octyl-3-methylimidazolium bromide + LiOH + ethanol | 1-octyl-3-methylimidazolium bromide + LiOH + guanidine HCl | 1-octyl-3-methylimidazolium bromide + LiOH + ethanol + guanidine HCl | 1-octyl-3-methylimidazolium bromide + ethanol + guanidine HCl |
| 1-methyl-3-carboxyethyl-imidazolium bromide + 5-(4-dimethyl)amino benzylidene rhodanine | 1-methyl-3-carboxyethyl-imidazolium bromide + 5-(4-dimethyl)amino benzylidene rhodanine | 1-methyl-3-carboxyethyl-imidazolium bromide + n-propanol | 1-methyl-3-carboxyethyl-imidazolium bromide + guanidine hydrochloride | 1-methyl-3-carboxyethyl-imidazolium bromide + 5-(4-dimethyl)amino benzylidene rhodanine + n-propanol | 1-methyl-3-carboxyethyl-imidazolium bromide + 5-(4-dimethyl)amino benzylidene rhodanine + guanidine HCl | 1-methyl-3-carboxyethyl-imidazolium bromide + 5-(4-dimethyl)amino benzylidene rhodanine + n-propanol + guanidine HCl | 1-methyl-3-carboxyethyl-imidazolium bromide + n-propanol + guanidine HCl |
| 1-hexyl-3-methylimidazolium bromide + 5-(4-dimethyl)amino benzylidene rhodanine | 1-hexyl-3-methylimidazolium bromide + 5-(4-dimethyl)amino benzylidene rhodanine | 1-hexyl-3-methylimidazolium bromide + n-propanol | 1-hexyl-3-methylimidazolium bromide + guanidine hydrochloride | 1-hexyl-3-methylimidazolium bromide + 5-(4-dimethyl)amino benzylidene rhodanine + n-propanol | 1-hexyl-3-methylimidazolium bromide + 5-(4-dimethyl)amino benzylidene rhodanine + guanidine HCl | 1-hexyl-3-methylimidazolium bromide + 5-(4-dimethyl)amino benzylidene rhodanine + n-propanol + guanidine HCl | 1-hexyl-3-methylimidazolium bromide + n-propanol + guanidine HCl |
| 1-decyl-3-methylimidazolium bromide + 5-(4-dimethyl)amino benzylidene rhodanine | 1-decyl-3-methylimidazolium bromide + 5-(4-dimethyl)amino benzylidene rhodanine | 1-decyl-3-methylimidazolium bromide + n-propanol | 1-decyl-3-methylimidazolium bromide + guanidine hydrochloride | 1-decyl-3-methylimidazolium bromide + 5-(4-dimethyl)amino benzylidene rhodanine + n-propanol | 1-decyl-3-methylimidazolium bromide + 5-(4-dimethyl)amino benzylidene rhodanine + guanidine HCl | 1-decyl-3-methylimidazolium bromide + 5-(4-dimethyl)amino benzylidene rhodanine + n-propanol + guanidine HCl | 1-decyl-3-methylimidazolium bromide + n-propanol + guanidine HCl |

TABLE 5-continued

EXEMPLARY STORAGE COMPOSITIONS

| (A) Compound of Formula (I) | (A) + (B) Precipitating Agent | (A) + (C) Lower Alcohol | (A) + (D) Chaotrope | (A) + (B) + (C) | (A) + (B) + (D) | (A) + (B) + (C) + (D) | (A) + (C) + (D) |
|---|---|---|---|---|---|---|---|
| 1-(2-hydroxyethyl)-3-methylimidazolium bromide | 1-(2-hydroxyethyl)-3-methylimidazolium bromide + 5-(4-dimethyl)amino benzylidene rhodanine | 1-(2-hydroxyethyl)-3-methylimidazolium bromide + n-propanol | 1-(2-hydroxyethyl)-3-methylimidazolium bromide + guanidine hydrochloride | 1-(2-hydroxyethyl)-3-methylimidazolium bromide + 5-(4-dimethyl)amino benzylidene rhodanine + n-propanol | 1-(2-hydroxyethyl)-3-methylimidazolium bromide + 5-(4-dimethyl)amino benzylidene rhodanine + guanidine HCl | 1-(2-hydroxyethyl)-3-methylimidazolium bromide + 5-(4-dimethyl)amino benzylidene rhodanine + n-propanol + guanidine HCl | 1-(2-hydroxyethyl)-3-methylimidazolium bromide + n-propanol + guanidine HCl |
| 1-octyl-3-methylimidazolium bromide | 1-octyl-3-methylimidazolium bromide + 5-(4-dimethyl)amino benzylidene rhodanine | 1-octyl-3-methylimidazolium bromide + n-propanol | 1-octyl-3-methylimidazolium bromide + guanidine hydrochloride | 1-octyl-3-methylimidazolium bromide + 5-(4-dimethyl)amino benzylidene rhodanine + n-propanol | 1-octyl-3-methylimidazolium bromide + 5-(4-dimethyl)amino benzylidene rhodanine + guanidine HCl | 1-octyl-3-methylimidazolium bromide + 5-(4-dimethyl)amino benzylidene rhodanine + n-propanol + guanidine HCl | 1-octyl-3-methylimidazolium bromide + n-propanol + guanidine HCl |
| 1-methyl-3-carboxyethyl-imidazolium bromide | 1-methyl-3-carboxyethyl-imidazolium bromide + sulfosalicylic acid | 1-methyl-3-carboxyethyl-imidazolium bromide + n-propanol | 1-methyl-3-carboxyethyl-imidazolium bromide + guanidine hydrochloride | 1-methyl-3-carboxyethyl-imidazolium bromide + sulfosalicylic acid + n-propanol | 1-methyl-3-carboxyethyl-imidazolium bromide + sulfosalicylic acid + guanidine HCl | 1-methyl-3-carboxyethyl-imidazolium bromide + sulfosalicylic acid + n-propanol + guanidine HCl | 1-methyl-3-carboxyethyl-imidazolium bromide + n-propanol + guanidine HCl |
| 1-hexyl-3-methylimidazolium bromide | 1-hexyl-3-methylimidazolium bromide + sulfosalicylic acid | 1-hexyl-3-methylimidazolium bromide + n-propanol | 1-hexyl-3-methylimidazolium bromide + guanidine hydrochloride | 1-hexyl-3-methylimidazolium bromide + sulfosalicylic acid + n-propanol | 1-hexyl-3-methylimidazolium bromide + sulfosalicylic acid + guanidine HCl | 1-hexyl-3-methylimidazolium bromide + sulfosalicylic acid + n-propanol + guanidine HCl | 1-hexyl-3-methylimidazolium bromide + n-propanol + guanidine HCl |
| 1-decyl-3-methylimidazolium bromide | 1-decyl-3-methylimidazolium bromide + sulfosalicylic acid | 1-decyl-3-methylimidazolium bromide + n-propanol | 1-decyl-3-methylimidazolium bromide + guanidine hydrochloride | 1-decyl-3-methylimidazolium bromide + sulfosalicylic acid + n-propanol | 1-decyl-3-methylimidazolium bromide + sulfosalicylic acid + guanidine HCl | 1-decyl-3-methylimidazolium bromide + sulfosalicylic acid + n-propanol + guanidine HCl | 1-decyl-3-methylimidazolium bromide + n-propanol + guanidine HCl |
| 1-(2-hydroxyethyl)-3-methylimidazolium bromide | 1-(2-hydroxyethyl)-3-methylimidazolium bromide + sulfosalicylic acid | 1-(2-hydroxyethyl)-3-methylimidazolium bromide + n-propanol | 1-(2-hydroxyethyl)-3-methylimidazolium bromide + guanidine hydrochloride | 1-(2-hydroxyethyl)-3-methylimidazolium bromide + sulfosalicylic acid + n-propanol | 1-(2-hydroxyethyl)-3-methylimidazolium bromide + sulfosalicylic acid + guanidine HCl | 1-(2-hydroxyethyl)-3-methylimidazolium bromide + sulfosalicylic acid + n-propanol + guanidine HCl | 1-(2-hydroxyethyl)-3-methylimidazolium bromide + n-propanol + guanidine HCl |
| 1-octyl-3-methylimidazolium bromide | 1-octyl-3-methylimidazolium bromide + sulfosalicylic acid | 1-octyl-3-methylimidazolium bromide + n-propanol | 1-octyl-3-methylimidazolium bromide + guanidine hydrochloride | 1-octyl-3-methylimidazolium bromide + sulfosalicylic acid + n-propanol | 1-octyl-3-methylimidazolium bromide + sulfosalicylic acid + guanidine HCl | 1-octyl-3-methylimidazolium bromide + sulfosalicylic acid + n-propanol + guanidine HCl | 1-octyl-3-methylimidazolium bromide + n-propanol + guanidine HCl |

TABLE 5-continued

EXEMPLARY STORAGE COMPOSITIONS

| (A) Compound of Formula (I) | (A) + (B) Precipitating Agent | (A) + (C) Lower Alcohol | (A) + (D) Chaotrope | (A) + (B) + (C) | (A) + (B) + (D) | (A) + (B) + (C) + (D) | (A) + (C) + (D) |
|---|---|---|---|---|---|---|---|
| 1-methyl-3-carboxyethyl-imidazolium bromide | 1-methyl-3-carboxyethyl-imidazolium bromide + lithium chloride | 1-methyl-3-carboxyethyl-imidazolium bromide + n-propanol | 1-methyl-3-carboxyethyl-imidazolium bromide + guanidine hydrochloride | 1-methyl-3-carboxyethyl-imidazolium bromide + LiCl + n-propanol | 1-methyl-3-carboxyethyl-imidazolium bromide + LiCl + guanidine HCl | 1-methyl-3-carboxyethyl-imidazolium bromide + LiCl + n-propanol + guanidine HCl | 1-methyl-3-carboxyethyl-imidazolium bromide + n-propanol + guanidine HCl |
| 1-hexyl-3-methylimidazolium bromide | 1-hexyl-3-methylimidazolium bromide + lithium chloride | 1-hexyl-3-methylimidazolium bromide + n-propanol | 1-hexyl-3-methylimidazolium bromide + guanidine hydrochloride | 1-hexyl-3-methylimidazolium bromide + LiCl + n-propanol | 1-hexyl-3-methylimidazolium bromide + LiCl + guanidine HCl | 1-hexyl-3-methylimidazolium bromide + LiCl + n-propanol + guanidine HCl | 1-hexyl-3-methylimidazolium bromide + n-propanol + guanidine HCl |
| 1-decyl-3-methylimidazolium bromide | 1-decyl-3-methylimidazolium bromide + lithium chloride | 1-decyl-3-methylimidazolium bromide + n-propanol | 1-decyl-3-methylimidazolium bromide + guanidine hydrochloride | 1-decyl-3-methylimidazolium bromide + LiCl + n-propanol | 1-decyl-3-methylimidazolium bromide + LiCl + guanidine HCl | 1-decyl-3-methylimidazolium bromide + LiCl + n-propanol + guanidine HCl | 1-decyl-3-methylimidazolium bromide + n-propanol + guanidine HCl |
| 1-(2-hydroxyethyl)-3-methylimidazolium bromide | 1-(2-hydroxyethyl)-3-methylimidazolium bromide + lithium chloride | 1-(2-hydroxyethyl)-3-methylimidazolium bromide + n-propanol | 1-(2-hydroxyethyl)-3-methylimidazolium bromide + guanidine hydrochloride | 1-(2-hydroxyethyl)-3-methylimidazolium bromide + LiCl + n-propanol | 1-(2-hydroxyethyl)-3-methylimidazolium bromide + LiCl + guanidine HCl | 1-(2-hydroxyethyl)-3-methylimidazolium bromide + LiCl + n-propanol + guanidine HCl | 1-(2-hydroxyethyl)-3-methylimidazolium bromide + n-propanol + guanidine HCl |
| 1-octyl-3-methylimidazolium bromide | 1-octyl-3-methylimidazolium bromide + lithium chloride | 1-octyl-3-methylimidazolium bromide + n-propanol | 1-octyl-3-methylimidazolium bromide + guanidine hydrochloride | 1-octyl-3-methylimidazolium bromide + LiCl + n-propanol | 1-octyl-3-methylimidazolium bromide + LiOH + guanidine HCl | 1-octyl-3-methylimidazolium bromide + LiOH + n-propanol + guanidine HCl | 1-octyl-3-methylimidazolium bromide + n-propanol + guanidine HCl |
| 1-methyl-3-carboxyethyl-imidazolium bromide | 1-methyl-3-carboxyethyl-imidazolium bromide + lithium hydroxide | 1-methyl-3-carboxyethyl-imidazolium bromide + n-propanol | 1-methyl-3-carboxyethyl-imidazolium bromide + guanidine hydrochloride | 1-methyl-3-carboxyethyl-imidazolium bromide + LiOH + n-propanol | 1-methyl-3-carboxyethyl-imidazolium bromide + LiOH + guanidine HCl | 1-methyl-3-carboxyethyl-imidazolium bromide + LiOH + n-propanol + guanidine HCl | 1-methyl-3-carboxyethyl-imidazolium bromide + n-propanol + guanidine HCl |
| 1-hexyl-3-methylimidazolium bromide | 1-hexyl-3-methylimidazolium bromide + lithium hydroxide | 1-hexyl-3-methylimidazolium bromide + n-propanol | 1-hexyl-3-methylimidazolium bromide + guanidine hydrochloride | 1-hexyl-3-methylimidazolium bromide + LiOH + n-propanol | 1-hexyl-3-methylimidazolium bromide + LiOH + guanidine HCl | 1-hexyl-3-methylimidazolium bromide + LiOH + n-propanol + guanidine HCl | 1-hexyl-3-methylimidazolium bromide + n-propanol + guanidine HCl |
| 1-decyl-3-methylimidazolium bromide | 1-decyl-3-methylimidazolium bromide + lithium hydroxide | 1-decyl-3-methylimidazolium bromide + n-propanol | 1-decyl-3-methylimidazolium bromide + guanidine hydrochloride | 1-decyl-3-methylimidazolium bromide + LiOH + n-propanol | 1-decyl-3-methylimidazolium bromide + LiOH + guanidine HCl | 1-decyl-3-methylimidazolium bromide + LiOH + n-propanol + guanidine HCl | 1-decyl-3-methylimidazolium bromide + n-propanol + guanidine HCl |
| 1-(2-hydroxyethyl)-3-methylimidazolium bromide | 1-(2-hydroxyethyl)-3-methylimidazolium bromide + lithium hydroxide | 1-(2-hydroxyethyl)-3-methylimidazolium bromide + n-propanol | 1-(2-hydroxyethyl)-3-methylimidazolium bromide + guanidine hydrochloride | 1-(2-hydroxyethyl)-3-methylimidazolium bromide + LiOH + n-propanol | 1-(2-hydroxyethyl)-3-methylimidazolium bromide + LiOH + guanidine HCl | 1-(2-hydroxyethyl)-3-methylimidazolium bromide + LiOH + n-propanol + guanidine HCl | 1-(2-hydroxyethyl)-3-methylimidazolium bromide + n-propanol + guanidine HCl |

TABLE 5-continued

EXEMPLARY STORAGE COMPOSITIONS

| (A) Compound of Formula (I) | (A) + (B) Precipitating Agent | (A) + (C) Lower Alcohol | (A) + (D) Chaotrope | (A) + (B) + (C) | (A) + (B) + (D) | (A) + (B) + (C) + (D) | (A) + (C) + (D) |
|---|---|---|---|---|---|---|---|
| 1-octyl-3-methylimidazolium bromide | 1-octyl-3-methylimidazolium bromide + lithium hydroxide | 1-octyl-3-methylimidazolium bromide + n-propanol | 1-octyl-3-methylimidazolium bromide + guanidine hydrochloride | 1-octyl-3-methylimidazolium bromide + LiOH + n-propanol | 1-octyl-3-methylimidazolium bromide + LiOH + guanidine HCl | 1-octyl-3-methylimidazolium bromide + LiOH + guanidine HCl | 1-octyl-3-methylimidazolium bromide + n-propanol + guanidine HCl |
| 1-methyl-3-carboxyethyl-imidazolium bromide | 1-methyl-3-carboxyethyl-imidazolium bromide + 5-(4-dimethyl)amino benzylidene rhodanine | 1-methyl-3-carboxyethyl-imidazolium bromide + Isopropanol | 1-methyl-3-carboxyethyl-imidazolium bromide + guanidine hydrochloride | 1-methyl-3-carboxyethyl-imidazolium bromide + 5-(4-dimethyl)amino benzylidene rhodanine + isopropanol | 1-methyl-3-carboxyethyl-imidazolium bromide + 5-(4-dimethyl)amino benzylidene rhodanine + guanidine HCl | 1-methyl-3-carboxyethyl-imidazolium bromide + 5-(4-dimethyl)amino benzylidene rhodanine + isopropanol + guanidine HCl | 1-methyl-3-carboxyethyl-imidazolium bromide + isopropanol + guanidine HCl |
| 1-hexyl-3-methylimidazolium bromide | 1-hexyl-3-methylimidazolium bromide + 5-(4-dimethyl)amino benzylidene rhodanine | 1-hexyl-3-methylimidazolium bromide + Isopropanol | 1-hexyl-3-methylimidazolium bromide + guanidine hydrochloride | 1-hexyl-3-methylimidazolium bromide + 5-(4-dimethyl)amino benzylidene rhodanine + isopropanol | 1-hexyl-3-methylimidazolium bromide + 5-(4-dimethyl)amino benzylidene rhodanine + guanidine HCl | 1-hexyl-3-methylimidazolium bromide + 5-(4-dimethyl)amino benzylidene rhodanine + isopropanol + guanidine HCl | 1-hexyl-3-methylimidazolium bromide + isopropanol + guanidine HCl |
| 1-decyl-3-methylimidazolium bromide | 1-decyl-3-methylimidazolium bromide + 5-(4-dimethyl)amino benzylidene rhodanine | 1-decyl-3-methylimidazolium bromide + Isopropanol | 1-decyl-3-methylimidazolium bromide + guanidine hydrochloride | 1-decyl-3-methylimidazolium bromide + 5-(4-dimethyl)amino benzylidene rhodanine + isopropanol | 1-decyl-3-methylimidazolium bromide + 5-(4-dimethyl)amino benzylidene rhodanine + guanidine HCl | 1-decyl-3-methylimidazolium bromide + 5-(4-dimethyl)amino benzylidene rhodanine + isopropanol + guanidine HCl | 1-decyl-3-methylimidazolium bromide + isopropanol + guanidine HCl |
| 1-(2-hydroxyethyl)-3-methylimidazolium bromide | 1-(2-hydroxyethyl)-3-methylimidazolium bromide + 5-(4-dimethyl)amino benzylidene rhodanine | 1-(2-hydroxyethyl)-3-methylimidazolium bromide + Isopropanol | 1-(2-hydroxyethyl)-3-methylimidazolium bromide + guanidine hydrochloride | 1-(2-hydroxyethyl)-3-methylimidazolium bromide + 5-(4-dimethyl)amino benzylidene rhodanine + isopropanol | 1-(2-hydroxyethyl)-3-methylimidazolium bromide + 5-(4-dimethyl)amino benzylidene rhodanine + guanidine HCl | 1-(2-hydroxyethyl)-3-methylimidazolium bromide + 5-(4-dimethyl)amino benzylidene rhodanine + isopropanol + guanidine HCl | 1-(2-hydroxyethyl)-3-methylimidazolium bromide + isopropanol + guanidine HCl |
| 1-octyl-3-methylimidazolium bromide | 1-octyl-3-methylimidazolium bromide + 5-(4-dimethyl)amino benzylidene rhodanine | 1-octyl-3-methylimidazolium bromide + Isopropanol | 1-octyl-3-methylimidazolium bromide + guanidine hydrochloride | 1-octyl-3-methylimidazolium bromide + 5-(4-dimethyl)amino benzylidene rhodanine + isopropanol | 1-octyl-3-methylimidazolium bromide + 5-(4-dimethyl)amino benzylidene rhodanine + guanidine HCl | 1-octyl-3-methylimidazolium bromide + 5-(4-dimethyl)amino benzylidene rhodanine + isopropanol + guanidine HCl | 1-octyl-3-methylimidazolium bromide + isopropanol + guanidine HCl |

TABLE 5-continued

EXEMPLARY STORAGE COMPOSITIONS

| (A) Compound of Formula (I) | (A) + (B) Precipitating Agent | (A) + (C) Lower Alcohol | (A) + (D) Chaotrope | (A) + (B) + (C) | (A) + (B) + (D) | (A) + (B) + (C) + (D) | (A) + (C) + (D) |
|---|---|---|---|---|---|---|---|
| 1-methyl-3-carboxyethyl-imidazolium bromide | 1-methyl-3-carboxyethyl-imidazolium bromide + sulfosalicylic acid | 1-methyl-3-carboxyethyl-imidazolium bromide + Isopropanol | 1-methyl-3-carboxyethyl-imidazolium bromide + guanidine hydrochloride | 1-methyl-3-carboxyethyl-imidazolium bromide + sulfosalicyclic acid + isopropanol | 1-methyl-3-carboxyethyl-imidazolium bromide + sulfosalicyclic acid + guanidine HCl | 1-methyl-3-carboxyethyl-imidazolium bromide + sulfosalicyclic acid + isopropanol + guanidine HCl | 1-methyl-3-carboxyethyl-imidazolium bromide + isopropanol + guanidine HCl |
| 1-hexyl-3-methylimidazolium bromide | 1-hexyl-3-methylimidazolium bromide + sulfosalicylic acid | 1-hexyl-3-methylimidazolium bromide + Isopropanol | 1-hexyl-3-methylimidazolium bromide + guanidine hydrochloride | 1-hexyl-3-methylimidazolium bromide + sulfosalicyclic acid + isopropanol | 1-hexyl-3-methylimidazolium bromide + sulfosalicyclic acid + guanidine HCl | 1-hexyl-3-methylimidazolium bromide + sulfosalicyclic acid + isopropanol + guanidine HCl | 1-hexyl-3-methylimidazolium bromide + isopropanol + guanidine HCl |
| 1-decyl-3-methylimidazolium bromide | 1-decyl-3-methylimidazolium bromide + sulfosalicylic acid | 1-decyl-3-methylimidazolium bromide + Isopropanol | 1-decyl-3-methylimidazolium bromide + guanidine hydrochloride | 1-decyl-3-methylimidazolium bromide + sulfosalicyclic acid + isopropanol | 1-decyl-3-methylimidazolium bromide + sulfosalicyclic acid + guanidine HCl | 1-decyl-3-methylimidazolium bromide + sulfosalicyclic acid + isopropanol + guanidine HCl | 1-decyl-3-methylimidazolium bromide + isopropanol + guanidine HCl |
| 1-(2-hydroxyethyl)-3-methylimidazolium bromide | 1-(2-hydroxyethyl)-3-methylimidazolium bromide + sulfosalicylic acid | 1-(2-hydroxyethyl)-3-methylimidazolium bromide + Isopropanol | 1-(2-hydroxyethyl)-3-methylimidazolium bromide + guanidine hydrochloride | 1-(2-hydroxyethyl)-3-methylimidazolium bromide + sulfosalicyclic acid + isopropanol | 1-(2-hydroxyethyl)-3-methylimidazolium bromide + sulfosalicyclic acid + guanidine HCl | 1-(2-hydroxyethyl)-3-methylimidazolium bromide + sulfosalicyclic acid + isopropanol + guanidine HCl | 1-(2-hydroxyethyl)-3-methylimidazolium bromide + isopropanol + guanidine HCl |
| 1-octyl-3-methylimidazolium bromide | 1-octyl-3-methylimidazolium bromide + sulfosalicylic acid | 1-octyl-3-methylimidazolium bromide + Isopropanol | 1-octyl-3-methylimidazolium bromide + guanidine hydrochloride | 1-octyl-3-methylimidazolium bromide + sulfosalicyclic acid + isopropanol | 1-octyl-3-methylimidazolium bromide + sulfosalicyclic acid + guanidine HCl | 1-octyl-3-methylimidazolium bromide + sulfosalicyclic acid + isopropanol + guanidine HCl | 1-octyl-3-methylimidazolium bromide + isopropanol + guanidine HCl |
| 1-methyl-3-carboxyethyl-imidazolium bromide | 1-methyl-3-carboxyethyl-imidazolium bromide + lithium chloride | 1-methyl-3-carboxyethyl-imidazolium bromide + Isopropanol | 1-methyl-3-carboxyethyl-imidazolium bromide + guanidine hydrochloride | 1-methyl-3-carboxyethyl-imidazolium bromide + LiCl + isopropanol | 1-methyl-3-carboxyethyl-imidazolium bromide + LiCl + guanidine HCl | 1-methyl-3-carboxyethyl-imidazolium bromide + LiCl + isopropanol + guanidine HCl | 1-methyl-3-carboxyethyl-imidazolium bromide + isopropanol + guanidine HCl |
| 1-hexyl-3-methylimidazolium bromide | 1-hexyl-3-methylimidazolium bromide + lithium chloride | 1-hexyl-3-methylimidazolium bromide + Isopropanol | 1-hexyl-3-methylimidazolium bromide + guanidine hydrochloride | 1-hexyl-3-methylimidazolium bromide + LiCl + isopropanol | 1-hexyl-3-methylimidazolium bromide + LiCl + guanidine HCl | 1-hexyl-3-methylimidazolium bromide + LiCl + isopropanol + guanidine HCl | 1-hexyl-3-methylimidazolium bromide + isopropanol + guanidine HCl |
| 1-decyl-3-methylimidazolium bromide | 1-decyl-3-methylimidazolium bromide + lithium chloride | 1-decyl-3-methylimidazolium bromide + Isopropanol | 1-decyl-3-methylimidazolium bromide + guanidine hydrochloride | 1-decyl-3-methylimidazolium bromide + LiCl + isopropanol | 1-decyl-3-methylimidazolium bromide + LiCl + guanidine HCl | 1-decyl-3-methylimidazolium bromide + LiCl + isopropanol + guanidine HCl | 1-decyl-3-methylimidazolium bromide + isopropanol + guanidine HCl |

TABLE 5-continued

EXEMPLARY STORAGE COMPOSITIONS

| (A) Compound of Formula (I) | (A) + (B) Precipitating Agent | (A) + (C) Lower Alcohol | (A) + (D) Chaotrope | (A) + (B) + (C) | (A) + (B) + (D) | (A) + (B) + (C) + (D) | (A) + (C) + (D) |
|---|---|---|---|---|---|---|---|
| 1-(2-hydroxyethyl)-3-methylimidazolium bromide | 1-(2-hydroxyethyl)-3-methylimidazolium bromide + lithium chloride | 1-(2-hydroxyethyl)-3-methylimidazolium bromide + Isopropanol | 1-(2-hydroxyethyl)-3-methylimidazolium bromide + guanidine hydrochloride | 1-(2-hydroxyethyl)-3-methylimidazolium bromide + LiCl + isopropanol | 1-(2-hydroxyethyl)-3-methylimidazolium bromide + LiCl + guanidine HCl | 1-(2-hydroxyethyl)-3-methylimidazolium bromide + LiCl + isopropanol + guanidine HCl | 1-(2-hydroxyethyl)-3-methylimidazolium bromide + isopropanol + guanidine HCl |
| 1-octyl-3-methylimidazolium bromide | 1-octyl-3-methylimidazolium bromide + lithium chloride | 1-octyl-3-methylimidazolium bromide + Isopropanol | 1-octyl-3-methylimidazolium bromide + guanidine hydrochloride | 1-octyl-3-methylimidazolium bromide + LiCl + isopropanol | 1-octyl-3-methylimidazolium bromide + LiCl + guanidine HCl | 1-octyl-3-methylimidazolium bromide + LiCl + isopropanol + guanidine HCl | 1-octyl-3-methylimidazolium bromide + isopropanol + guanidine HCl |
| 1-methyl-3-carboxyethyl-imidazolium bromide | 1-methyl-3-carboxyethyl-imidazolium bromide + lithium hydroxide | 1-methyl-3-carboxyethyl-imidazolium bromide + Isopropanol | 1-methyl-3-carboxyethyl-imidazolium bromide + guanidine hydrochloride | 1-methyl-3-carboxyethyl-imidazolium bromide + LiOH + isopropanol | 1-methyl-3-carboxyethyl-imidazolium bromide + LiOH + guanidine HCl | 1-methyl-3-carboxyethyl-imidazolium bromide + LiOH + isopropanol + guanidine HCl | 1-methyl-3-carboxyethyl-imidazolium bromide + isopropanol + guanidine HCl |
| 1-hexyl-3-methylimidazolium bromide | 1-hexyl-3-methylimidazolium bromide + lithium hydroxide | 1-hexyl-3-methylimidazolium bromide + Isopropanol | 1-hexyl-3-methylimidazolium bromide + guanidine hydrochloride | 1-hexyl-3-methylimidazolium bromide + LiOH + isopropanol | 1-hexyl-3-methylimidazolium bromide + LiOH + guanidine HCl | 1-hexyl-3-methylimidazolium bromide + LiOH + isopropanol + guanidine HCl | 1-hexyl-3-methylimidazolium bromide + isopropanol + guanidine HCl |
| 1-decyl-3-methylimidazolium bromide | 1-decyl-3-methylimidazolium bromide + lithium hydroxide | 1-decyl-3-methylimidazolium bromide + Isopropanol | 1-decyl-3-methylimidazolium bromide + guanidine hydrochloride | 1-decyl-3-methylimidazolium bromide + LiOH + isopropanol | 1-decyl-3-methylimidazolium bromide + LiOH + guanidine HCl | 1-decyl-3-methylimidazolium bromide + LiOH + isopropanol + guanidine HCl | 1-decyl-3-methylimidazolium bromide + isopropanol + guanidine HCl |
| 1-(2-hydroxyethyl)-3-methylimidazolium bromide | 1-octyl-3-methylimidazolium bromide + lithium hydroxide | 1-octyl-3-methylimidazolium bromide + Isopropanol | 1-octyl-3-methylimidazolium bromide + guanidine hydrochloride | 1-octyl-3-methylimidazolium bromide + LiOH + isopropanol | 1-octyl-3-methylimidazolium bromide + LiOH + guanidine HCl | 1-octyl-3-methylimidazolium bromide + LiOH + isopropanol + guanidine HCl | 1-octyl-3-methylimidazolium bromide + isopropanol + guanidine HCl |
| 1-methyl-3-carboxyethyl-imidazolium bromide | 1-methyl-3-carboxyethyl-imidazolium bromide + 5-(4-dimethyl)amino benzylidene rhodanine | 1-methyl-3-carboxyethyl-imidazolium bromide + n-butanol | 1-methyl-3-carboxyethyl-imidazolium bromide + 5-(4-dimethyl)amino benzylidene rhodanine + n-butanol | 1-methyl-3-carboxyethyl-imidazolium bromide + 5-(4-dimethyl)amino benzylidene rhodanine + guanidine HCl | 1-methyl-3-carboxyethyl-imidazolium bromide + 5-(4-dimethyl)amino benzylidene rhodanine + n-butanol + guanidine HCl | 1-methyl-3-carboxyethyl-imidazolium bromide + n-butanol + guanidine HCl |

TABLE 5-continued

EXEMPLARY STORAGE COMPOSITIONS

| (A) Compound of Formula (I) | (A) + (B) Precipitating Agent | (A) + (C) Lower Alcohol | (A) + (D) Chaotrope | (A) + (B) + (C) | (A) + (B) + (D) | (A) + (B) + (C) + (D) | (A) + (C) + (D) |
|---|---|---|---|---|---|---|---|
| 1-hexyl-3-methylimidazolium bromide | 1-hexyl-3-methylimidazolium bromide + 5-(4-dimethyl)amino benzylidene rhodanine | 1-hexyl-3-methylimidazolium bromide + n-butanol | 1-hexyl-3-methylimidazolium bromide + guanidine hydrochloride | 1-hexyl-3-methylimidazolium bromide + 5-(4-dimethyl)amino benzylidene rhodanine + n-butanol | 1-hexyl-3-methylimidazolium bromide + 5-(4-dimethyl)amino benzylidene rhodanine + guanidine HCl | 1-hexyl-3-methylimidazolium bromide + 5-(4-dimethyl)amino benzylidene rhodanine + n-butanol + guanidine HCl | 1-hexyl-3-methylimidazolium bromide + n-butanol + guanidine HCl |
| 1-decyl-3-methylimidazolium bromide | 1-decyl-3-methylimidazolium bromide + 5-(4-dimethyl)amino benzylidene rhodanine | 1-decyl-3-methylimidazolium bromide + n-butanol | 1-decyl-3-methylimidazolium bromide + guanidine hydrochloride | 1-decyl-3-methylimidazolium bromide + 5-(4-dimethyl)amino benzylidene rhodanine + n-butanol | 1-decyl-3-methylimidazolium bromide + 5-(4-dimethyl)amino benzylidene rhodanine + guanidine HCl | 1-decyl-3-methylimidazolium bromide + 5-(4-dimethyl)amino benzylidene rhodanine + n-butanol + guanidine HCl | 1-decyl-3-methylimidazolium bromide + n-butanol + guanidine HCl |
| 1-(2-hydroxyethyl)-3-methylimidazolium bromide | 1-(2-hydroxyethyl)-3-methylimidazolium bromide + 5-(4-dimethyl)amino benzylidene rhodanine | 1-(2-hydroxyethyl)-3-methylimidazolium bromide + n-butanol | 1-(2-hydroxyethyl)-3-methylimidazolium bromide + guanidine hydrochloride | 1-(2-hydroxyethyl)-3-methylimidazolium bromide + 5-(4-dimethyl)amino benzylidene rhodanine + n-butanol | 1-(2-hydroxyethyl)-3-methylimidazolium bromide + 5-(4-dimethyl)amino benzylidene rhodanine + guanidine HCl | 1-(2-hydroxyethyl)-3-methylimidazolium bromide + 5-(4-dimethyl)amino benzylidene rhodanine + n-butanol + guanidine HCl | 1-(2-hydroxyethyl)-3-methylimidazolium bromide + n-butanol + guanidine HCl |
| 1-octyl-3-methylimidazolium bromide | 1-octyl-3-methylimidazolium bromide + 5-(4-dimethyl)amino benzylidene rhodanine | 1-octyl-3-methylimidazolium bromide + n-butanol | 1-octyl-3-methylimidazolium bromide + guanidine hydrochloride | 1-octyl-3-methylimidazolium bromide + 5-(4-dimethyl)amino benzylidene rhodanine + n-butanol | 1-octyl-3-methylimidazolium bromide + 5-(4-dimethyl)amino benzylidene rhodanine + guanidine HCl | 1-octyl-3-methylimidazolium bromide + 5-(4-dimethyl)amino benzylidene rhodanine + n-butanol + guanidine HCl | 1-octyl-3-methylimidazolium bromide + n-butanol + guanidine HCl |
| 1-methyl-3-carboxyethyl-imidazolium bromide | 1-methyl-3-carboxyethyl-imidazolium bromide + sulfosalicylic acid | 1-methyl-3-carboxyethyl-imidazolium bromide + n-butanol | 1-methyl-3-carboxyethyl-imidazolium bromide + guanidine hydrochloride | 1-methyl-3-carboxyethyl-imidazolium bromide + sulfosalicylic acid + n-butanol | 1-methyl-3-carboxyethyl-imidazolium bromide + sulfosalicylic acid + guanidine HCl | 1-methyl-3-carboxyethyl-imidazolium bromide + sulfosalicylic acid + n-butanol + guanidine HCl | 1-methyl-3-carboxyethyl-imidazolium bromide + n-butanol + guanidine HCl |
| 1-hexyl-3-methylimidazolium bromide | 1-hexyl-3-methylimidazolium bromide + sulfosalicylic acid | 1-hexyl-3-methylimidazolium bromide + n-butanol | 1-hexyl-3-methylimidazolium bromide + guanidine hydrochloride | 1-hexyl-3-methylimidazolium bromide + sulfosalicylic acid + n-butanol | 1-hexyl-3-methylimidazolium bromide + sulfosalicylic acid + guanidine HCl | 1-hexyl-3-methylimidazolium bromide + sulfosalicylic acid + n-butanol + guanidine HCl | 1-hexyl-3-methylimidazolium bromide + n-butanol + guanidine HCl |

TABLE 5-continued

EXEMPLARY STORAGE COMPOSITIONS

| (A) Compound of Formula (I) | (A) + (B) Precipitating Agent | (A) + (C) Lower Alcohol | (A) + (D) Chaotrope | (A) + (B) + (C) | (A) + (B) + (D) | (A) + (B) + (C) + (D) | (A) + (C) + (D) |
|---|---|---|---|---|---|---|---|
| 1-decyl-3-methylimidazolium bromide | 1-decyl-3-methylimidazolium bromide + sulfosalicylic acid | 1-decyl-3-methylimidazolium bromide + n-butanol | 1-decyl-3-methylimidazolium bromide + guanidine hydrochloride | 1-decyl-3-methylimidazolium bromide + sulfosalicylic acid + n-butanol | 1-decyl-3-methylimidazolium bromide + sulfosalicylic acid + guanidine HCl | 1-decyl-3-methylimidazolium bromide + sulfosalicylic acid + n-butanol + guanidine HCl | 1-decyl-3-methylimidazolium bromide + n-butanol + guanidine HCl |
| 1-(2-hydroxyethyl)-3-methylimidazolium bromide | 1-(2-hydroxyethyl)-3-methylimidazolium bromide + sulfosalicylic acid | 1-(2-hydroxyethyl)-3-methylimidazolium bromide + n-butanol | 1-(2-hydroxyethyl)-3-methylimidazolium bromide + guanidine hydrochloride | 1-(2-hydroxyethyl)-3-methylimidazolium bromide + sulfosalicylic acid + n-butanol | 1-(2-hydroxyethyl)-3-methylimidazolium bromide + sulfosalicylic acid + guanidine HCl | 1-(2-hydroxyethyl)-3-methylimidazolium bromide + sulfosalicylic acid + n-butanol + guanidine HCl | 1-(2-hydroxyethyl)-3-methylimidazolium bromide + n-butanol + guanidine HCl |
| 1-octyl-3-methylimidazolium bromide | 1-octyl-3-methylimidazolium bromide + sulfosalicylic acid | 1-octyl-3-methylimidazolium bromide + n-butanol | 1-octyl-3-methylimidazolium bromide + guanidine hydrochloride | 1-octyl-3-methylimidazolium bromide + sulfosalicylic acid + n-butanol | 1-octyl-3-methylimidazolium bromide + sulfosalicylic acid + guanidine HCl | 1-octyl-3-methylimidazolium bromide + sulfosalicylic acid + n-butanol + guanidine HCl | 1-octyl-3-methylimidazolium bromide + n-butanol + guanidine HCl |
| 1-methyl-3-carboxyethyl-imidazolium bromide | 1-methyl-3-carboxyethyl-imidazolium bromide + lithium chloride | 1-methyl-3-carboxyethyl-imidazolium bromide + n-butanol | 1-methyl-3-carboxyethyl-imidazolium bromide + guanidine hydrochloride | 1-methyl-3-carboxyethyl-imidazolium bromide + LiCl + n-butanol | 1-methyl-3-carboxyethyl-imidazolium bromide + LiCl + guanidine HCl | 1-methyl-3-carboxyethyl-imidazolium bromide + LiCl + n-butanol + guanidine HCl | 1-methyl-3-carboxyethyl-imidazolium bromide + n-butanol + guanidine HCl |
| 1-hexyl-3-methylimidazolium bromide | 1-hexyl-3-methylimidazolium bromide + lithium chloride | 1-hexyl-3-methylimidazolium bromide + n-butanol | 1-hexyl-3-methylimidazolium bromide + guanidine hydrochloride | 1-hexyl-3-methylimidazolium bromide + LiCl + n-butanol | 1-hexyl-3-methylimidazolium bromide + LiCl + guanidine HCl | 1-hexyl-3-methylimidazolium bromide + LiCl + n-butanol + guanidine HCl | 1-hexyl-3-methylimidazolium bromide + n-butanol + guanidine HCl |
| 1-decyl-3-methylimidazolium bromide | 1-decyl-3-methylimidazolium bromide + lithium chloride | 1-decyl-3-methylimidazolium bromide + n-butanol | 1-decyl-3-methylimidazolium bromide + guanidine hydrochloride | 1-decyl-3-methylimidazolium bromide + LiCl + n-butanol | 1-decyl-3-methylimidazolium bromide + LiCl + guanidine HCl | 1-decyl-3-methylimidazolium bromide + LiCl + n-butanol + guanidine HCl | 1-decyl-3-methylimidazolium bromide + n-butanol + guanidine HCl |
| 1-(2-hydroxyethyl)-3-methylimidazolium bromide | 1-(2-hydroxyethyl)-3-methylimidazolium bromide + lithium chloride | 1-(2-hydroxyethyl)-3-methylimidazolium bromide + n-butanol | 1-(2-hydroxyethyl)-3-methylimidazolium bromide + guanidine hydrochloride | 1-(2-hydroxyethyl)-3-methylimidazolium bromide + LiCl + n-butanol | 1-(2-hydroxyethyl)-3-methylimidazolium bromide + LiCl + guanidine HCl | 1-(2-hydroxyethyl)-3-methylimidazolium bromide + LiCl + n-butanol + guanidine HCl | 1-(2-hydroxyethyl)-3-methylimidazolium bromide + n-butanol + guanidine HCl |
| 1-octyl-3-methylimidazolium bromide | 1-octyl-3-methylimidazolium bromide + lithium chloride | 1-octyl-3-methylimidazolium bromide + n-butanol | 1-octyl-3-methylimidazolium bromide + guanidine hydrochloride | 1-octyl-3-methylimidazolium bromide + LiCl + n-butanol | 1-octyl-3-methylimidazolium bromide + LiCl + guanidine HCl | 1-octyl-3-methylimidazolium bromide + LiCl + n-butanol + guanidine HCl | 1-octyl-3-methylimidazolium bromide + n-butanol + guanidine HCl |

TABLE 5-continued

EXEMPLARY STORAGE COMPOSITIONS

| (A) Compound of Formula (I) | (A) + (B) Precipitating Agent | (A) + (C) Lower Alcohol | (A) + (D) Chaotrope | (A) + (B) + (C) | (A) + (B) + (D) | (A) + (B) + (C) + (D) | (A) + (C) + (D) |
|---|---|---|---|---|---|---|---|
| 1-methyl-3-carboxyethyl-imidazolium bromide | 1-methyl-3-carboxyethyl-imidazolium bromide + lithium hydroxide | 1-methyl-3-carboxyethyl-imidazolium bromide + n-butanol | 1-methyl-3-carboxyethyl-imidazolium bromide + guanidine hydrochloride | 1-methyl-3-carboxyethyl-imidazolium bromide + LiOH + n-butanol | 1-methyl-3-carboxyethyl-imidazolium bromide + LiOH + guanidine HCl | 1-methyl-3-carboxyethyl-imidazolium bromide + LiOH + n-butanol + guanidine HCl | 1-methyl-3-carboxyethyl-imidazolium bromide + n-butanol + guanidine HCl |
| 1-hexyl-3-methylimidazolium bromide | 1-hexyl-3-methylimidazolium bromide + lithium hydroxide | 1-hexyl-3-methylimidazolium bromide + n-butanol | 1-hexyl-3-methylimidazolium bromide + guanidine hydrochloride | 1-hexyl-3-methylimidazolium bromide + LiOH + n-butanol | 1-hexyl-3-methylimidazolium bromide + LiOH + guanidine HCl | 1-hexyl-3-methylimidazolium bromide + LiOH + n-butanol + guanidine HCl | 1-hexyl-3-methylimidazolium bromide + n-butanol + guanidine HCl |
| 1-decyl-3-methylimidazolium bromide | 1-decyl-3-methylimidazolium bromide + lithium hydroxide | 1-decyl-3-methylimidazolium bromide + n-butanol | 1-decyl-3-methylimidazolium bromide + guanidine hydrochloride | 1-decyl-3-methylimidazolium bromide + LiOH + n-butanol | 1-decyl-3-methylimidazolium bromide + LiOH + guanidine HCl | 1-decyl-3-methylimidazolium bromide + LiOH + n-butanol + guanidine HCl | 1-decyl-3-methylimidazolium bromide + n-butanol + guanidine HCl |
| 1-(2-hydroxyethyl)-3-methylimidazolium bromide | 1-(2-hydroxyethyl)-3-methylimidazolium bromide + lithium hydroxide | 1-(2-hydroxyethyl)-3-methylimidazolium bromide + n-butanol | 1-(2-hydroxyethyl)-3-methylimidazolium bromide + guanidine hydrochloride | 1-(2-hydroxyethyl)-3-methylimidazolium bromide + LiOH + n-butanol | 1-(2-hydroxyethyl)-3-methylimidazolium bromide + LiOH + guanidine HCl | 1-(2-hydroxyethyl)-3-methylimidazolium bromide + LiOH + n-butanol + guanidine HCl | 1-(2-hydroxyethyl)-3-methylimidazolium bromide + n-butanol + guanidine HCl |
| 1-octyl-3-methylimidazolium bromide | 1-octyl-3-methylimidazolium bromide + lithium hydroxide | 1-octyl-3-methylimidazolium bromide + n-butanol | 1-octyl-3-methylimidazolium bromide + guanidine hydrochloride | 1-octyl-3-methylimidazolium bromide + LiOH + n-butanol | 1-octyl-3-methylimidazolium bromide + LiOH + guanidine HCl | 1-octyl-3-methylimidazolium bromide + LiOH + n-butanol + guanidine HCl | 1-octyl-3-methylimidazolium bromide + n-butanol + guanidine HCl |
| 1-methyl-3-carboxyethyl-imidazolium bromide | 1-methyl-3-carboxyethyl-imidazolium bromide + 5-(4-dimethyl)amino benzylidene rhodanine | 1-methyl-3-carboxyethyl-imidazolium bromide + isobutanol | 1-methyl-3-carboxyethyl-imidazolium bromide + guanidine hydrochloride | 1-methyl-3-carboxyethyl-imidazolium bromide + 5-(4-dimethyl)amino benzylidene rhodanine + isobutanol | 1-methyl-3-carboxyethyl-imidazolium bromide + 5-(4-dimethyl)amino benzylidene rhodanine + guanidine HCl | 1-methyl-3-carboxyethyl-imidazolium bromide + 5-(4-dimethyl)amino benzylidene rhodanine + isobutanol + guanidine HCl | 1-methyl-3-carboxyethyl-imidazolium bromide + isobutanol + guanidine HCl |
| 1-hexyl-3-methylimidazolium bromide | 1-hexyl-3-methylimidazolium bromide + 5-(4-dimethyl)amino benzylidene rhodanine | 1-hexyl-3-methylimidazolium bromide + isobutanol | 1-hexyl-3-methylimidazolium bromide + guanidine hydrochloride | 1-hexyl-3-methylimidazolium bromide + 5-(4-dimethyl)amino benzylidene rhodanine + isobutanol | 1-hexyl-3-methylimidazolium bromide + 5-(4-dimethyl)amino benzylidene rhodanine + guanidine HCl | 1-hexyl-3-methylimidazolium bromide + 5-(4-dimethyl)amino benzylidene rhodanine + isobutanol + guanidine HCl | 1-hexyl-3-methylimidazolium bromide + isobutanol + guanidine HCl |

TABLE 5-continued

EXEMPLARY STORAGE COMPOSITIONS

| (A) Compound of Formula (I) | (A) + (B) Precipitating Agent | (A) + (C) Lower Alcohol | (A) + (D) Chaotrope | (A) + (B) + (C) | (A) + (B) + (D) | (A) + (B) + (C) + (D) | (A) + (C) + (D) |
|---|---|---|---|---|---|---|---|
| 1-decyl-3-methylimidazolium bromide | 1-decyl-3-methylimidazolium bromide + 5-(4-dimethyl)amino benzylidene rhodanine | 1-decyl-3-methylimidazolium bromide + isobutanol | 1-decyl-3-methylimidazolium bromide + guanidine hydrochloride | 1-decyl-3-methylimidazolium bromide + 5-(4-dimethyl)amino benzylidene rhodanine + isobutanol | 1-decyl-3-methylimidazolium bromide + 5-(4-dimethyl)amino benzylidene rhodanine + guanidine HCl | 1-decyl-3-methylimidazolium bromide + 5-(4-dimethyl)amino benzylidene rhodanine + isobutanol + guanidine HCl | 1-decyl-3-methylimidazolium bromide + isobutanol + guanidine HCl |
| 1-(2-hydroxyethyl)-3-methylimidazolium bromide | 1-(2-hydroxyethyl)-3-methylimidazolium bromide + 5-(4-dimethyl)amino benzylidene rhodanine | 1-(2-hydroxyethyl)-3-methylimidazolium bromide + isobutanol | 1-(2-hydroxyethyl)-3-methylimidazolium bromide + guanidine hydrochloride | 1-(2-hydroxyethyl)-3-methylimidazolium bromide + 5-(4-dimethyl)amino benzylidene rhodanine + isobutanol | 1-(2-hydroxyethyl)-3-methylimidazolium bromide + 5-(4-dimethyl)amino benzylidene rhodanine + guanidine HCl | 1-(2-hydroxyethyl)-3-methylimidazolium bromide + 5-(4-dimethyl)amino benzylidene rhodanine + isobutanol + guanidine HCl | 1-(2-hydroxyethyl)-3-methylimidazolium bromide + isobutanol + guanidine HCl |
| 1-octyl-3-methylimidazolium bromide | 1-octyl-3-methylimidazolium bromide + 5-(4-dimethyl)amino benzylidene rhodanine | 1-octyl-3-methylimidazolium bromide + isobutanol | 1-octyl-3-methylimidazolium bromide + guanidine hydrochloride | 1-octyl-3-methylimidazolium bromide + 5-(4-dimethyl)amino benzylidene rhodanine + isobutanol | 1-octyl-3-methylimidazolium bromide + 5-(4-dimethyl)amino benzylidene rhodanine + guanidine HCl | 1-octyl-3-methylimidazolium bromide + 5-(4-dimethyl)amino benzylidene rhodanine + isobutanol + guanidine HCl | 1-octyl-3-methylimidazolium bromide + isobutanol + guanidine HCl |
| 1-methyl-3-carboxyethyl-imidazolium bromide | 1-methyl-3-carboxyethyl-imidazolium bromide + sulfosalicylic acid | 1-methyl-3-carboxyethyl-imidazolium bromide + isobutanol | 1-methyl-3-carboxyethyl-imidazolium bromide + guanidine hydrochloride | 1-methyl-3-carboxyethyl-imidazolium bromide + sulfosalicylic acid + isobutanol | 1-methyl-3-carboxyethyl-imidazolium bromide + sulfosalicylic acid + guanidine HCl | 1-methyl-3-carboxyethyl-imidazolium bromide + sulfosalicylic acid + isobutanol + guanidine HCl | 1-methyl-3-carboxyethyl-imidazolium bromide + isobutanol + guanidine HCl |
| 1-hexyl-3-methylimidazolium bromide | 1-hexyl-3-methylimidazolium bromide + sulfosalicylic acid | 1-hexyl-3-methylimidazolium bromide + isobutanol | 1-hexyl-3-methylimidazolium bromide + guanidine hydrochloride | 1-hexyl-3-methylimidazolium bromide + sulfosalicylic acid + isobutanol | 1-hexyl-3-methylimidazolium bromide + sulfosalicylic acid + guanidine HCl | 1-hexyl-3-methylimidazolium bromide + sulfosalicylic acid + isobutanol + guanidine HCl | 1-hexyl-3-methylimidazolium bromide + isobutanol + guanidine HCl |
| 1-decyl-3-methylimidazolium bromide | 1-decyl-3-methylimidazolium bromide + sulfosalicylic acid | 1-decyl-3-methylimidazolium bromide + isobutanol | 1-decyl-3-methylimidazolium bromide + guanidine hydrochloride | 1-decyl-3-methylimidazolium bromide + sulfosalicylic acid + isobutanol | 1-decyl-3-methylimidazolium bromide + sulfosalicylic acid + guanidine HCl | 1-decyl-3-methylimidazolium bromide + sulfosalicylic acid + isobutanol + guanidine HCl | 1-decyl-3-methylimidazolium bromide + isobutanol + guanidine HCl |

TABLE 5-continued

EXEMPLARY STORAGE COMPOSITIONS

| (A) Compound of Formula (I) | (A) + (B) Precipitating Agent | (A) + (C) Lower Alcohol | (A) + (D) Chaotrope | (A) + (B) + (C) | (A) + (B) + (D) | (A) + (B) + (C) + (D) | (A) + (C) + (D) |
|---|---|---|---|---|---|---|---|
| 1-(2-hydroxyethyl)-3-methylimidazolium bromide | 1-(2-hydroxyethyl)-3-methylimidazolium bromide + sulfosalicylic acid | 1-(2-hydroxyethyl)-3-methylimidazolium bromide + isobutanol | 1-(2-hydroxyethyl)-3-methylimidazolium bromide + guanidine hydrochloride | 1-(2-hydroxyethyl)-3-methylimidazolium bromide + sulfosalicylic acid + isobutanol | 1-(2-hydroxyethyl)-3-methylimidazolium bromide + sulfosalicylic acid + guanidine HCl | 1-(2-hydroxyethyl)-3-methylimidazolium bromide + sulfosalicylic acid + isobutanol + guanidine HCl | 1-(2-hydroxyethyl)-3-methylimidazolium bromide + isobutanol + guanidine HCl |
| 1-octyl-3-methylimidazolium bromide | 1-octyl-3-methylimidazolium bromide + sulfosalicylic acid | 1-octyl-3-methylimidazolium bromide + isobutanol | 1-octyl-3-methylimidazolium bromide + guanidine hydrochloride | 1-octyl-3-methylimidazolium bromide + sulfosalicylic acid + isobutanol | 1-octyl-3-methylimidazolium bromide + sulfosalicylic acid + guanidine HCl | 1-octyl-3-methylimidazolium bromide + sulfosalicylic acid + isobutanol + guanidine HCl | 1-octyl-3-methylimidazolium bromide + isobutanol + guanidine HCl |
| 1-methyl-3-carboxyethyl-imidazolium bromide | 1-methyl-3-carboxyethyl-imidazolium bromide + lithium chloride | 1-methyl-3-carboxyethyl-imidazolium bromide + isobutanol | 1-methyl-3-carboxyethyl-imidazolium bromide + guanidine hydrochloride | 1-methyl-3-carboxyethyl-imidazolium bromide + LiCl + isobutanol | 1-methyl-3-carboxyethyl-imidazolium bromide + LiCl + guanidine HCl | 1-methyl-3-carboxyethyl-imidazolium bromide + LiCl + isobutanol + guanidine HCl | 1-methyl-3-carboxyethyl-imidazolium bromide + isobutanol + guanidine HCl |
| 1-hexyl-3-methylimidazolium bromide | 1-hexyl-3-methylimidazolium bromide + lithium chloride | 1-hexyl-3-methylimidazolium bromide + isobutanol | 1-hexyl-3-methylimidazolium bromide + guanidine hydrochloride | 1-hexyl-3-methylimidazolium bromide + LiCl + isobutanol | 1-hexyl-3-methylimidazolium bromide + LiCl + guanidine HCl | 1-hexyl-3-methylimidazolium bromide + LiCl + isobutanol + guanidine HCl | 1-hexyl-3-methylimidazolium bromide + isobutanol + guanidine HCl |
| 1-decyl-3-methylimidazolium bromide | 1-decyl-3-methylimidazolium bromide + lithium chloride | 1-decyl-3-methylimidazolium bromide + isobutanol | 1-decyl-3-methylimidazolium bromide + guanidine hydrochloride | 1-decyl-3-methylimidazolium bromide + LiCl + isobutanol | 1-decyl-3-methylimidazolium bromide + LiCl + guanidine HCl | 1-decyl-3-methylimidazolium bromide + LiCl + isobutanol + guanidine HCl | 1-decyl-3-methylimidazolium bromide + isobutanol + guanidine HCl |
| 1-(2-hydroxyethyl)-3-methylimidazolium bromide | 1-(2-hydroxyethyl)-3-methylimidazolium bromide + lithium chloride | 1-(2-hydroxyethyl)-3-methylimidazolium bromide + isobutanol | 1-(2-hydroxyethyl)-3-methylimidazolium bromide + guanidine hydrochloride | 1-(2-hydroxyethyl)-3-methylimidazolium bromide + LiCl + isobutanol | 1-(2-hydroxyethyl)-3-methylimidazolium bromide + LiCl + guanidine HCl | 1-(2-hydroxyethyl)-3-methylimidazolium bromide + LiCl + isobutanol + guanidine HCl | 1-(2-hydroxyethyl)-3-methylimidazolium bromide + isobutanol + guanidine HCl |
| 1-octyl-3-methylimidazolium bromide | 1-octyl-3-methylimidazolium bromide + lithium chloride | 1-octyl-3-methylimidazolium bromide + isobutanol | 1-octyl-3-methylimidazolium bromide + guanidine hydrochloride | 1-octyl-3-methylimidazolium bromide + LiCl + isobutanol | 1-octyl-3-methylimidazolium bromide + LiCl + guanidine HCl | 1-octyl-3-methylimidazolium bromide + LiCl + isobutanol + guanidine HCl | 1-octyl-3-methylimidazolium bromide + isobutanol + guanidine HCl |
| 1-methyl-3-carboxyethyl-imidazolium bromide | 1-methyl-3-carboxyethyl-imidazolium bromide + lithium hydroxide | 1-methyl-3-carboxyethyl-imidazolium bromide + isobutanol | 1-methyl-3-carboxyethyl-imidazolium bromide + guanidine hydrochloride | 1-methyl-3-carboxyethyl-imidazolium bromide + LiOH + isobutanol | 1-methyl-3-carboxyethyl-imidazolium bromide + LiOH + guanidine HCl | 1-methyl-3-carboxyethyl-imidazolium bromide + LiOH + isobutanol + guanidine HCl | 1-methyl-3-carboxyethyl-imidazolium bromide + isobutanol + guanidine HCl |

TABLE 5-continued

EXEMPLARY STORAGE COMPOSITIONS

| (A) Compound of Formula (I) | (A) + (B) Precipitating Agent | (A) + (C) Lower Alcohol | (A) + (D) Chaotrope | (A) + (B) + (C) | (A) + (B) + (D) | (A) + (B) + (C) + (D) | (A) + (C) + (D) |
|---|---|---|---|---|---|---|---|
| 1-hexyl-3-methylimidazolium bromide | 1-hexyl-3-methylimidazolium bromide + lithium hydroxide | 1-hexyl-3-methylimidazolium bromide + isobutanol | 1-hexyl-3-methylimidazolium bromide + guanidine hydrochloride | 1-hexyl-3-methylimidazolium bromide + LiOH + isobutanol | 1-hexyl-3-methylimidazolium bromide + LiOH + guanidine HCl | 1-hexyl-3-methylimidazolium bromide + LiOH + isobutanol + guanidine HCl | 1-hexyl-3-methylimidazolium bromide + isobutanol + guanidine HCl |
| 1-decyl-3-methylimidazolium bromide | 1-decyl-3-methylimidazolium bromide + lithium hydroxide | 1-decyl-3-methylimidazolium bromide + isobutanol | 1-decyl-3-methylimidazolium bromide + guanidine hydrochloride | 1-decyl-3-methylimidazolium bromide + LiOH + isobutanol | 1-decyl-3-methylimidazolium bromide + LiOH + guanidine HCl | 1-decyl-3-methylimidazolium bromide + LiOH + isobutanol + guanidine HCl | 1-decyl-3-methylimidazolium bromide + isobutanol + guanidine HCl |
| 1-(2-hydroxyethyl)-3-methylimidazolium bromide | 1-(2-hydroxyethyl)-3-methylimidazolium bromide + lithium hydroxide | 1-(2-hydroxyethyl)-3-methylimidazolium bromide + isobutanol | 1-(2-hydroxyethyl)-3-methylimidazolium bromide + guanidine hydrochloride | 1-(2-hydroxyethyl)-3-methylimidazolium bromide + LiOH + isobutanol | 1-(2-hydroxyethyl)-3-methylimidazolium bromide + LiOH + guanidine HCl | 1-(2-hydroxyethyl)-3-methylimidazolium bromide + LiOH + isobutanol + guanidine HCl | 1-(2-hydroxyethyl)-3-methylimidazolium bromide + isobutanol + guanidine HCl |
| 1-octyl-3-methylimidazolium bromide | 1-octyl-3-methylimidazolium bromide + lithium hydroxide | 1-octyl-3-methylimidazolium bromide + isobutanol | 1-octyl-3-methylimidazolium bromide + guanidine hydrochloride | 1-octyl-3-methylimidazolium bromide + LiOH + isobutanol | 1-octyl-3-methylimidazolium bromide + LiOH + guanidine HCl | 1-octyl-3-methylimidazolium bromide + LiOH + isobutanol + guanidine HCl | 1-octyl-3-methylimidazolium bromide + isobutanol + guanidine HCl |
| 1-methyl-3-carboxyethyl-imidazolium bromide | 1-methyl-3-carboxyethyl-imidazolium bromide + 5-(4-dimethyl)amino benzylidene rhodanine | 1-methyl-3-carboxyethyl-imidazolium bromide + methanol | 1-methyl-3-carboxyethyl-imidazolium bromide + guanidine thiocyanate | 1-methyl-3-carboxyethyl-imidazolium bromide + 5-(4-dimethyl)amino benzylidene rhodanine + methanol | 1-methyl-3-carboxyethyl-imidazolium bromide + 5-(4-dimethyl)amino benzylidene rhodanine + guanidine thiocyanate | 1-methyl-3-carboxyethyl-imidazolium bromide + 5-(4-dimethyl)amino benzylidene rhodanine + methanol + guanidine thiocyanate | 1-methyl-3-carboxyethyl-imidazolium bromide + methanol + guanidine thiocyanate |
| 1-hexyl-3-methylimidazolium bromide | 1-hexyl-3-methylimidazolium bromide + 5-(4-dimethyl)amino benzylidene rhodanine | 1-hexyl-3-methylimidazolium bromide + methanol | 1-hexyl-3-methylimidazolium bromide + guanidine thiocyanate | 1-hexyl-3-methylimidazolium bromide + 5-(4-dimethyl)amino benzylidene rhodanine + methanol | 1-hexyl-3-methylimidazolium bromide + 5-(4-dimethyl)amino benzylidene rhodanine + guanidine thiocyanate | 1-hexyl-3-methylimidazolium bromide + 5-(4-dimethyl)amino benzylidene rhodanine + methanol + guanidine thiocyanate | 1-hexyl-3-methylimidazolium bromide + methanol + guanidine thiocyanate |
| 1-decyl-3-methylimidazolium bromide | 1-decyl-3-methylimidazolium bromide + 5-(4-dimethyl)amino benzylidene rhodanine | 1-decyl-3-methylimidazolium bromide + methanol | 1-decyl-3-methylimidazolium bromide + guanidine thiocyanate | 1-decyl-3-methylimidazolium bromide + 5-(4-dimethyl)amino benzylidene rhodanine + methanol | 1-decyl-3-methylimidazolium bromide + 5-(4-dimethyl)amino benzylidene rhodanine + guanidine thiocyanate | 1-decyl-3-methylimidazolium bromide + 5-(4-dimethyl)amino benzylidene rhodanine + methanol + guanidine thiocyanate | 1-decyl-3-methylimidazolium bromide + methanol + guanidine thiocyanate |

TABLE 5-continued

EXEMPLARY STORAGE COMPOSITIONS

| (A) Compound of Formula (I) | (A) + (B) Precipitating Agent | (A) + (C) Lower Alcohol | (A) + (D) Chaotrope | (A) + (B) + (C) | (A) + (B) + (D) | (A) + (B) + (C) + (D) | (A) + (C) + (D) |
|---|---|---|---|---|---|---|---|
| 1-(2-hydroxyethyl)-3-methylimidazolium bromide | 1-(2-hydroxyethyl)-3-methylimidazolium bromide + 5-(4-dimethyl)amino benzylidene rhodanine | 1-(2-hydroxyethyl)-3-methylimidazolium bromide + methanol | 1-(2-hydroxyethyl)-3-methylimidazolium bromide + guanidine thiocyanate | 1-(2-hydroxyethyl)-3-methylimidazolium bromide + 5-(4-dimethyl)amino benzylidene rhodanine + methanol | 1-(2-hydroxyethyl)-3-methylimidazolium bromide + 5-(4-dimethyl)amino benzylidene rhodanine + methanol + guanidine thiocyanate | 1-(2-hydroxyethyl)-3-methylimidazolium bromide + 5-(4-dimethyl)amino benzylidene rhodanine + methanol + guanidine thiocyanate | 1-(2-hydroxyethyl)-3-methylimidazolium bromide + methanol + guanidine thiocyanate |
| 1-octyl-3-methylimidazolium bromide | 1-octyl-3-methylimidazolium bromide + 5-(4-dimethyl)amino benzylidene rhodanine | 1-octyl-3-methylimidazolium bromide + methanol | 1-octyl-3-methylimidazolium bromide + guanidine thiocyanate | 1-octyl-3-methylimidazolium bromide + 5-(4-dimethyl)amino benzylidene rhodanine + methanol | 1-octyl-3-methylimidazolium bromide + 5-(4-dimethyl)amino benzylidene rhodanine + methanol | 1-octyl-3-methylimidazolium bromide + 5-(4-dimethyl)amino benzylidene rhodanine + methanol + guanidine thiocyanate | 1-octyl-3-methylimidazolium bromide + methanol + guanidine thiocyanate |
| 1-methyl-3-carboxyethyl-imidazolium bromide | 1-methyl-3-carboxyethyl-imidazolium bromide + sulfosalicylic acid | 1-methyl-3-carboxyethyl-imidazolium bromide + methanol | 1-methyl-3-carboxyethyl-imidazolium bromide + guanidine thiocyanate | 1-methyl-3-carboxyethyl-imidazolium bromide + sulfosalicylic acid + methanol | 1-methyl-3-carboxyethyl-imidazolium bromide + sulfosalicylic acid + guanidine thiocyanate | 1-methyl-3-carboxyethyl-imidazolium bromide + sulfosalicylic acid + methanol + guanidine thiocyanate | 1-methyl-3-carboxyethyl-imidazolium bromide + methanol + guanidine thiocyanate |
| 1-hexyl-3-methylimidazolium bromide | 1-hexyl-3-methylimidazolium bromide + sulfosalicylic acid | 1-hexyl-3-methylimidazolium bromide + methanol | 1-hexyl-3-methylimidazolium bromide + guanidine thiocyanate | 1-hexyl-3-methylimidazolium bromide + sulfosalicylic acid + methanol | 1-hexyl-3-methylimidazolium bromide + sulfosalicylic acid + guanidine thiocyanate | 1-hexyl-3-methylimidazolium bromide + sulfosalicylic acid + methanol + guanidine thiocyanate | 1-hexyl-3-methylimidazolium bromide + methanol + guanidine thiocyanate |
| 1-decyl-3-methylimidazolium bromide | 1-decyl-3-methylimidazolium bromide + sulfosalicylic acid | 1-decyl-3-methylimidazolium bromide + methanol | 1-decyl-3-methylimidazolium bromide + guanidine thiocyanate | 1-decyl-3-methylimidazolium bromide + sulfosalicylic acid + methanol | 1-decyl-3-methylimidazolium bromide + sulfosalicylic acid + guanidine thiocyanate | 1-decyl-3-methylimidazolium bromide + sulfosalicylic acid + methanol + guanidine thiocyanate | 1-decyl-3-methylimidazolium bromide + methanol + guanidine thiocyanate |
| 1-(2-hydroxyethyl)-3-methylimidazolium bromide | 1-(2-hydroxyethyl)-3-methylimidazolium bromide + sulfosalicylic acid | 1-(2-hydroxyethyl)-3-methylimidazolium bromide + methanol | 1-(2-hydroxyethyl)-3-methylimidazolium bromide + guanidine thiocyanate | 1-(2-hydroxyethyl)-3-methylimidazolium bromide + sulfosalicylic acid + methanol | 1-(2-hydroxyethyl)-3-methylimidazolium bromide + sulfosalicylic acid + guanidine thiocyanate | 1-(2-hydroxyethyl)-3-methylimidazolium bromide + sulfosalicylic acid + methanol + guanidine thiocyanate | 1-(2-hydroxyethyl)-3-methylimidazolium bromide + methanol + guanidine thiocyanate |

TABLE 5-continued

EXEMPLARY STORAGE COMPOSITIONS

| (A) Compound of Formula (I) | (A) + (B) Precipitating Agent | (A) + (C) Lower Alcohol | (A) + (D) Chaotrope | (A) + (B) + (C) | (A) + (B) + (D) | (A) + (B) + (C) + (D) | (A) + (C) + (D) |
|---|---|---|---|---|---|---|---|
| 1-octyl-3-methylimidazolium bromide | 1-octyl-3-methylimidazolium bromide + sulfosalicylic acid | 1-octyl-3-methylimidazolium bromide + methanol | 1-octyl-3-methylimidazolium bromide + guanidine thiocyanate | 1-octyl-3-methylimidazolium bromide + sulfosalicylic acid + methanol | 1-octyl-3-methylimidazolium bromide + sulfosalicylic acid + guanidine thiocyanate | 1-octyl-3-methylimidazolium bromide + sulfosalicylic acid + methanol + guanidine thiocyanate | 1-octyl-3-methylimidazolium bromide + methanol + guanidine thiocyanate |
| 1-methyl-3-carboxyethyl-imidazolium bromide + lithium chloride | 1-methyl-3-carboxyethyl-imidazolium bromide + lithium chloride | 1-methyl-3-carboxyethyl-imidazolium bromide + methanol | 1-methyl-3-carboxyethyl-imidazolium bromide + guanidine thiocyanate | 1-methyl-3-carboxyethyl-imidazolium bromide + Lithium chloride + methanol | 1-methyl-3-carboxyethyl-imidazolium bromide + LiCl + guanidine thiocyanate | 1-methyl-3-carboxyethyl-imidazolium bromide + LiCl + methanol + guanidine thiocyanate | 1-methyl-3-carboxyethyl-imidazolium bromide + methanol + guanidine thiocyanate |
| 1-hexyl-3-methylimidazolium bromide | 1-hexyl-3-methylimidazolium bromide + lithium chloride | 1-hexyl-3-methylimidazolium bromide + methanol | 1-hexyl-3-methylimidazolium bromide + guanidine thiocyanate | 1-hexyl-3-methylimidazolium bromide + Lithium chloride + methanol | 1-hexyl-3-methylimidazolium bromide + LiCl + guanidine thiocyanate | 1-hexyl-3-methylimidazolium bromide + LiCl + methanol + guanidine thiocyanate | 1-hexyl-3-methylimidazolium bromide + methanol + guanidine thiocyanate |
| 1-decyl-3-methylimidazolium bromide | 1-decyl-3-methylimidazolium bromide + lithium chloride | 1-decyl-3-methylimidazolium bromide + methanol | 1-decyl-3-methylimidazolium bromide + guanidine thiocyanate | 1-decyl-3-methylimidazolium bromide + Lithium chloride + methanol | 1-decyl-3-methylimidazolium bromide + LiCl + guanidine thiocyanate | 1-decyl-3-methylimidazolium bromide + LiCl + methanol + guanidine thiocyanate | 1-decyl-3-methylimidazolium bromide + methanol + guanidine thiocyanate |
| 1-(2-hydroxyethyl)-3-methylimidazolium bromide | 1-(2-hydroxyethyl)-3-methylimidazolium bromide + lithium chloride | 1-(2-hydroxyethyl)-3-methylimidazolium bromide + methanol | 1-(2-hydroxyethyl)-3-methylimidazolium bromide + guanidine thiocyanate | 1-(2-hydroxyethyl)-3-methylimidazolium bromide + Lithium chloride + methanol | 1-(2-hydroxyethyl)-3-methylimidazolium bromide + LiCl + guanidine thiocyanate | 1-(2-hydroxyethyl)-3-methylimidazolium bromide + LiCl + methanol + guanidine thiocyanate | 1-(2-hydroxyethyl)-3-methylimidazolium bromide + methanol + guanidine thiocyanate |
| 1-octyl-3-methylimidazolium bromide | 1-octyl-3-methylimidazolium bromide + lithium chloride | 1-octyl-3-methylimidazolium bromide + methanol | 1-octyl-3-methylimidazolium bromide + guanidine thiocyanate | 1-octyl-3-methylimidazolium bromide + Lithium chloride + methanol | 1-octyl-3-methylimidazolium bromide + LiCl + guanidine thiocyanate | 1-octyl-3-methylimidazolium bromide + LiCl + methanol + guanidine thiocyanate | 1-octyl-3-methylimidazolium bromide + methanol + guanidine thiocyanate |
| 1-methyl-3-carboxyethyl-imidazolium bromide | 1-methyl-3-carboxyethyl-imidazolium bromide + lithium hydroxide | 1-methyl-3-carboxyethyl-imidazolium bromide + methanol | 1-methyl-3-carboxyethyl-imidazolium bromide + guanidine thiocyanate | 1-methyl-3-carboxyethyl-imidazolium bromide + Lithium hydroxide + methanol | 1-methyl-3-carboxyethyl-imidazolium bromide + LiOH + guanidine thiocyanate | 1-methyl-3-carboxyethyl-imidazolium bromide + LiOH + methanol + guanidine thiocyanate | 1-methyl-3-carboxyethyl-imidazolium bromide + methanol + guanidine thiocyanate |

TABLE 5-continued

EXEMPLARY STORAGE COMPOSITIONS

| (A) Compound of Formula (I) | (A) + (B) Precipitating Agent | (A) + (C) Lower Alcohol | (A) + (D) Chaotrope | (A) + (B) + (C) | (A) + (B) + (D) | (A) + (B) + (C) + (D) | (A) + (C) + (D) |
|---|---|---|---|---|---|---|---|
| 1-hexyl-3-methylimidazolium bromide | 1-hexyl-3-methylimidazolium bromide + lithium hydroxide | 1-hexyl-3-methylimidazolium bromide + methanol | 1-hexyl-3-methylimidazolium bromide + guanidine thiocyanate | 1-hexyl-3-methylimidazolium bromide + Lithium hydroxide + methanol | 1-hexyl-3-methylimidazolium bromide + LiOH + guanidine thiocyanate | 1-hexyl-3-methylimidazolium bromide + LiOH + methanol + guanidine thiocyanate | 1-hexyl-3-methylimidazolium bromide + methanol + guanidine thiocyanate |
| 1-decyl-3-methylimidazolium bromide | 1-decyl-3-methylimidazolium bromide + lithium hydroxide | 1-decyl-3-methylimidazolium bromide + methanol | 1-decyl-3-methylimidazolium bromide + guanidine thiocyanate | 1-decyl-3-methylimidazolium bromide + Lithium hydroxide + methanol | 1-decyl-3-methylimidazolium bromide + LiOH + guanidine thiocyanate | 1-decyl-3-methylimidazolium bromide + LiOH + methanol + guanidine thiocyanate | 1-decyl-3-methylimidazolium bromide + methanol + guanidine thiocyanate |
| 1-(2-hydroxyethyl)-3-methylimidazolium bromide | 1-(2-hydroxyethyl)-3-methylimidazolium bromide + lithium hydroxide | 1-(2-hydroxyethyl)-3-methylimidazolium bromide + methanol | 1-(2-hydroxyethyl)-3-methylimidazolium bromide + guanidine thiocyanate | 1-(2-hydroxyethyl)-3-methylimidazolium bromide + Lithium hydroxide + methanol | 1-(2-hydroxyethyl)-3-methylimidazolium bromide + LiOH + guanidine thiocyanate | 1-(2-hydroxyethyl)-3-methylimidazolium bromide + LiOH + methanol + guanidine thiocyanate | 1-(2-hydroxyethyl)-3-methylimidazolium bromide + methanol + guanidine thiocyanate |
| 1-octyl-3-methylimidazolium bromide | 1-octyl-3-methylimidazolium bromide + lithium hydroxide | 1-octyl-3-methylimidazolium bromide + methanol | 1-octyl-3-methylimidazolium bromide + guanidine thiocyanate | 1-octyl-3-methylimidazolium bromide + Lithium hydroxide + methanol | 1-octyl-3-methylimidazolium bromide + LiOH + guanidine thiocyanate | 1-octyl-3-methylimidazolium bromide + LiOH + methanol + guanidine thiocyanate | 1-octyl-3-methylimidazolium bromide + methanol + guanidine thiocyanate |
| 1-methyl-3-carboxyethyl-imidazolium bromide | 1-methyl-3-carboxyethyl-imidazolium bromide + 5-(4-dimethyl)amino benzylidene rhodanine | 1-methyl-3-carboxyethyl-imidazolium bromide + ethanol | 1-methyl-3-carboxyethyl-imidazolium bromide + guanidine thiocyanate | 1-methyl-3-carboxyethyl-imidazolium bromide + 5-(4-dimethyl)amino benzylidene rhodanine + ethanol | 1-methyl-3-carboxyethyl-imidazolium bromide + 5-(4-dimethyl)amino benzylidene rhodanine + guanidine thiocyanate | 1-methyl-3-carboxyethyl-imidazolium bromide + 5-(4-dimethyl)amino benzylidene rhodanine + ethanol + guanidine thiocyanate | 1-methyl-3-carboxyethyl-imidazolium bromide + ethanol + guanidine thiocyanate |
| 1-hexyl-3-methylimidazolium bromide | 1-hexyl-3-methylimidazolium bromide + 5-(4-dimethyl)amino benzylidene rhodanine | 1-hexyl-3-methylimidazolium bromide + ethanol | 1-hexyl-3-methylimidazolium bromide + guanidine thiocyanate | 1-hexyl-3-methylimidazolium bromide + 5-(4-dimethyl)amino benzylidene rhodanine + ethanol | 1-hexyl-3-methylimidazolium bromide + 5-(4-dimethyl)amino benzylidene rhodanine + guanidine thiocyanate | 1-hexyl-3-methylimidazolium bromide + 5-(4-dimethyl)amino benzylidene rhodanine + ethanol + guanidine thiocyanate | 1-hexyl-3-methylimidazolium bromide + ethanol + guanidine thiocyanate |

TABLE 5-continued

EXEMPLARY STORAGE COMPOSITIONS

| (A) Compound of Formula (I) | (A) + (B) Precipitating Agent | (A) + (C) Lower Alcohol | (A) + (D) Chaotrope | (A) + (B) + (C) | (A) + (B) + (D) | (A) + (B) + (C) + (D) | (A) + (C) + (D) |
|---|---|---|---|---|---|---|---|
| 1-decyl-3-methylimidazolium bromide | 1-decyl-3-methylimidazolium bromide + 5-(4-dimethyl)amino benzylidene rhodanine | 1-decyl-3-methylimidazolium bromide + ethanol | 1-decyl-3-methylimidazolium bromide + guanidine thiocyanate | 1-decyl-3-methylimidazolium bromide + 5-(4-dimethyl)amino benzylidene rhodanine + ethanol | 1-decyl-3-methylimidazolium bromide + 5-(4-dimethyl)amino benzylidene rhodanine + guanidine thiocyanate | 1-decyl-3-methylimidazolium bromide + 5-(4-dimethyl)amino benzylidene rhodanine + ethanol + guanidine thiocyanate | 1-decyl-3-methylimidazolium bromide + ethanol + guanidine thiocyanate |
| 1-(2-hydroxyethyl)-3-methylimidazolium bromide | 1-(2-hydroxyethyl)-3-methylimidazolium bromide + 5-(4-dimethyl)amino benzylidene rhodanine | 1-(2-hydroxyethyl)-3-methylimidazolium bromide + ethanol | 1-(2-hydroxyethyl)-3-methylimidazolium bromide + guanidine thiocyanate | 1-(2-hydroxyethyl)-3-methylimidazolium bromide + 5-(4-dimethyl)amino benzylidene rhodanine + ethanol | 1-(2-hydroxyethyl)-3-methylimidazolium bromide + 5-(4-dimethyl)amino benzylidene rhodanine + guanidine thiocyanate | 1-(2-hydroxyethyl)-3-methylimidazolium bromide + 5-(4-dimethyl)amino benzylidene rhodanine + ethanol + guanidine thiocyanate | 1-(2-hydroxyethyl)-3-methylimidazolium bromide + ethanol + guanidine thiocyanate |
| 1-octyl-3-methylimidazolium bromide | 1-octyl-3-methylimidazolium bromide + 5-(4-dimethyl)amino benzylidene rhodanine | 1-octyl-3-methylimidazolium bromide + ethanol | 1-octyl-3-methylimidazolium bromide + guanidine thiocyanate | 1-octyl-3-methylimidazolium bromide + 5-(4-dimethyl)amino benzylidene rhodanine + ethanol | 1-octyl-3-methylimidazolium bromide + 5-(4-dimethyl)amino benzylidene rhodanine + guanidine thiocyanate | 1-octyl-3-methylimidazolium bromide + 5-(4-dimethyl)amino benzylidene rhodanine + ethanol + guanidine thiocyanate | 1-octyl-3-methylimidazolium bromide + ethanol + guanidine thiocyanate |
| 1-methyl-3-carboxyethyl-imidazolium bromide | 1-methyl-3-carboxyethyl-imidazolium bromide + sulfosalicylic acid | 1-methyl-3-carboxyethyl-imidazolium bromide + ethanol | 1-methyl-3-carboxyethyl-imidazolium bromide + guanidine thiocyanate | 1-methyl-3-carboxyethyl-imidazolium bromide + sulfosalicylic acid + ethanol | 1-methyl-3-carboxyethyl-imidazolium bromide + sulfosalicylic acid + guanidine thiocyanate | 1-methyl-3-carboxyethyl-imidazolium bromide + sulfosalicylic acid + ethanol + guanidine thiocyanate | 1-methyl-3-carboxyethyl-imidazolium bromide + ethanol + guanidine thiocyanate |
| 1-hexyl-3-methylimidazolium bromide | 1-hexyl-3-methylimidazolium bromide + sulfosalicylic acid | 1-hexyl-3-methylimidazolium bromide + ethanol | 1-hexyl-3-methylimidazolium bromide + guanidine thiocyanate | 1-hexyl-3-methylimidazolium bromide + sulfosalicylic acid + ethanol | 1-hexyl-3-methylimidazolium bromide + sulfosalicylic acid + guanidine thiocyanate | 1-hexyl-3-methylimidazolium bromide + sulfosalicylic acid + ethanol + guanidine thiocyanate | 1-hexyl-3-methylimidazolium bromide + ethanol + guanidine thiocyanate |

TABLE 5-continued

EXEMPLARY STORAGE COMPOSITIONS

| (A) Compound of Formula (I) | (A) + (B) Precipitating Agent | (A) + (C) Lower Alcohol | (A) + (D) Chaotrope | (A) + (B) + (C) | (A) + (B) + (D) | (A) + (B) + (C) + (D) | (A) + (C) + (D) |
|---|---|---|---|---|---|---|---|
| 1-decyl-3-methylimidazolium bromide | 1-decyl-3-methylimidazolium bromide + sulfosalicylic acid | 1-decyl-3-methylimidazolium bromide + ethanol | 1-decyl-3-methylimidazolium bromide + guanidine thiocyanate | 1-decyl-3-methylimidazolium bromide + sulfosalicylic acid + ethanol | 1-decyl-3-methylimidazolium bromide + sulfosalicylic acid + guanidine thiocyanate | 1-decyl-3-methylimidazolium bromide + sulfosalicylic acid + ethanol + guanidine thiocyanate | 1-decyl-3-methylimidazolium bromide + ethanol + guanidine thiocyanate |
| 1-(2-hydroxyethyl)-3-methylimidazolium bromide | 1-(2-hydroxyethyl)-3-methylimidazolium bromide + sulfosalicylic acid | 1-(2-hydroxyethyl)-3-methylimidazolium bromide + ethanol | 1-(2-hydroxyethyl)-3-methylimidazolium bromide + guanidine thiocyanate | 1-(2-hydroxyethyl)-3-methylimidazolium bromide + sulfosalicylic acid + ethanol | 1-(2-hydroxyethyl)-3-methylimidazolium bromide + sulfosalicylic acid + guanidine thiocyanate | 1-(2-hydroxyethyl)-3-methylimidazolium bromide + sulfosalicylic acid + ethanol + guanidine thiocyanate | 1-(2-hydroxyethyl)-3-methylimidazolium bromide + ethanol + guanidine thiocyanate |
| 1-octyl-3-methylimidazolium bromide | 1-octyl-3-methylimidazolium bromide + sulfosalicylic acid | 1-octyl-3-methylimidazolium bromide + ethanol | 1-octyl-3-methylimidazolium bromide + guanidine thiocyanate | 1-octyl-3-methylimidazolium bromide + sulfosalicylic acid + ethanol | 1-octyl-3-methylimidazolium bromide + sulfosalicylic acid + guanidine thiocyanate | 1-octyl-3-methylimidazolium bromide + sulfosalicylic acid + ethanol + guanidine thiocyanate | 1-octyl-3-methylimidazolium bromide + ethanol + guanidine thiocyanate |
| 1-methyl-3-carboxyethyl-imidazolium bromide | 1-methyl-3-carboxyethyl-imidazolium bromide + lithium chloride | 1-methyl-3-carboxyethyl-imidazolium bromide + ethanol | 1-methyl-3-carboxyethyl-imidazolium bromide + guanidine thiocyanate | 1-methyl-3-carboxyethyl-imidazolium bromide + LiCl + ethanol | 1-methyl-3-carboxyethyl-imidazolium bromide + LiCl + guanidine thiocyanate | 1-methyl-3-carboxyethyl-imidazolium bromide + LiCl + ethanol + guanidine thiocyanate | 1-methyl-3-carboxyethyl-imidazolium bromide + ethanol + guanidine thiocyanate |
| 1-hexyl-3-methylimidazolium bromide | 1-hexyl-3-methylimidazolium bromide + lithium chloride | 1-hexyl-3-methylimidazolium bromide + ethanol | 1-hexyl-3-methylimidazolium bromide + guanidine thiocyanate | 1-hexyl-3-methylimidazolium bromide + LiCl + ethanol | 1-hexyl-3-methylimidazolium bromide + LiCl + guanidine thiocyanate | 1-hexyl-3-methylimidazolium bromide + LiCl + ethanol + guanidine thiocyanate | 1-hexyl-3-methylimidazolium bromide + ethanol + guanidine thiocyanate |
| 1-decyl-3-methylimidazolium bromide | 1-decyl-3-methylimidazolium bromide + lithium chloride | 1-decyl-3-methylimidazolium bromide + ethanol | 1-decyl-3-methylimidazolium bromide + guanidine thiocyanate | 1-decyl-3-methylimidazolium bromide + LiCl + ethanol | 1-decyl-3-methylimidazolium bromide + LiCl + guanidine thiocyanate | 1-decyl-3-methylimidazolium bromide + LiCl + ethanol + guanidine thiocyanate | 1-decyl-3-methylimidazolium bromide + ethanol + guanidine thiocyanate |
| 1-(2-hydroxyethyl)-3-methylimidazolium bromide | 1-(2-hydroxyethyl)-3-methylimidazolium bromide + lithium chloride | 1-(2-hydroxyethyl)-3-methylimidazolium bromide + ethanol | 1-(2-hydroxyethyl)-3-methylimidazolium bromide + guanidine thiocyanate | 1-(2-hydroxyethyl)-3-methylimidazolium bromide + LiCl + ethanol | 1-(2-hydroxyethyl)-3-methylimidazolium bromide + LiCl + guanidine thiocyanate | 1-(2-hydroxyethyl)-3-methylimidazolium bromide + LiCl + ethanol + guanidine thiocyanate | 1-(2-hydroxyethyl)-3-methylimidazolium bromide + ethanol + guanidine thiocyanate |

TABLE 5-continued

EXEMPLARY STORAGE COMPOSITIONS

| (A) Compound of Formula (I) | (A) + (B) Precipitating Agent | (A) + (C) Lower Alcohol | (A) + (D) Chaotrope | (A) + (B) + (C) | (A) + (B) + (D) | (A) + (B) + (C) + (D) | (A) + (C) + (D) |
|---|---|---|---|---|---|---|---|
| 1-octyl-3-methylimidazolium bromide | 1-octyl-3-methylimidazolium bromide + lithium chloride | 1-octyl-3-methylimidazolium bromide + ethanol | 1-octyl-3-methylimidazolium bromide + guanidine thiocyanate | 1-octyl-3-methylimidazolium bromide + LiCl + ethanol | 1-octyl-3-methylimidazolium bromide + LiCl + guanidine thiocyanate | 1-octyl-3-methylimidazolium bromide + LiCl + ethanol + guanidine thiocyanate | 1-octyl-3-methylimidazolium bromide + ethanol + guanidine thiocyanate |
| 1-methyl-3-carboxyethyl-imidazolium bromide | 1-methyl-3-carboxyethyl-imidazolium bromide + lithium hydroxide | 1-methyl-3-carboxyethyl-imidazolium bromide + ethanol | 1-methyl-3-carboxyethyl-imidazolium bromide + guanidine thiocyanate | 1-methyl-3-carboxyethyl-imidazolium bromide + LiOH + ethanol | 1-methyl-3-carboxyethyl-imidazolium bromide + LiOH + guanidine thiocyanate | 1-methyl-3-carboxyethyl-imidazolium bromide + LiOH + ethanol + guanidine thiocyanate | 1-methyl-3-carboxyethyl-imidazolium bromide + ethanol + guanidine thiocyanate |
| 1-hexyl-3-methylimidazolium bromide | 1-hexyl-3-methylimidazolium bromide + lithium hydroxide | 1-hexyl-3-methylimidazolium bromide + ethanol | 1-hexyl-3-methylimidazolium bromide + guanidine thiocyanate | 1-hexyl-3-methylimidazolium bromide + LiOH + ethanol | 1-hexyl-3-methylimidazolium bromide + LiOH + guanidine thiocyanate | 1-hexyl-3-methylimidazolium bromide + LiOH + ethanol + guanidine thiocyanate | 1-hexyl-3-methylimidazolium bromide + ethanol + guanidine thiocyanate |
| 1-decyl-3-methylimidazolium bromide | 1-decyl-3-methylimidazolium bromide + lithium hydroxide | 1-decyl-3-methylimidazolium bromide + ethanol | 1-decyl-3-methylimidazolium bromide + guanidine thiocyanate | 1-decyl-3-methylimidazolium bromide + LiOH + ethanol | 1-decyl-3-methylimidazolium bromide + LiOH + guanidine thiocyanate | 1-decyl-3-methylimidazolium bromide + LiOH + ethanol + guanidine thiocyanate | 1-decyl-3-methylimidazolium bromide + ethanol + guanidine thiocyanate |
| 1-(2-hydroxyethyl)-3-methylimidazolium bromide | 1-(2-hydroxyethyl)-3-methylimidazolium bromide + lithium hydroxide | 1-(2-hydroxyethyl)-3-methylimidazolium bromide + ethanol | 1-(2-hydroxyethyl)-3-methylimidazolium bromide + guanidine thiocyanate | 1-(2-hydroxyethyl)-3-methylimidazolium bromide + LiOH + ethanol | 1-(2-hydroxyethyl)-3-methylimidazolium bromide + LiOH + guanidine thiocyanate | 1-(2-hydroxyethyl)-3-methylimidazolium bromide + LiOH + ethanol + guanidine thiocyanate | 1-(2-hydroxyethyl)-3-methylimidazolium bromide + ethanol + guanidine thiocyanate |
| 1-octyl-3-methylimidazolium bromide | 1-octyl-3-methylimidazolium bromide + lithium hydroxide | 1-octyl-3-methylimidazolium bromide + ethanol | 1-octyl-3-methylimidazolium bromide + guanidine thiocyanate | 1-octyl-3-methylimidazolium bromide + LiOH + ethanol | 1-octyl-3-methylimidazolium bromide + LiOH + guanidine thiocyanate | 1-octyl-3-methylimidazolium bromide + LiOH + ethanol + guanidine thiocyanate | 1-octyl-3-methylimidazolium bromide + ethanol + guanidine thiocyanate |
| 1-methyl-3-carboxyethyl-imidazolium bromide | 1-methyl-3-carboxyethyl-imidazolium bromide + 5-(4-dimethyl)amino benzylidene rhodanine | 1-methyl-3-carboxyethyl-imidazolium bromide + n-propanol | 1-methyl-3-carboxyethyl-imidazolium bromide + guanidine thiocyanate | 1-methyl-3-carboxyethyl-imidazolium bromide + 5-(4-dimethyl)amino benzylidene rhodanine + n-propanol | 1-methyl-3-carboxyethyl-imidazolium bromide + 5-(4-dimethyl)amino benzylidene rhodanine + guanidine thiocyanate | 1-methyl-3-carboxyethyl-imidazolium bromide + 5-(4-dimethyl)amino benzylidene rhodanine + n-propanol + guanidine thiocyanate | 1-methyl-3-carboxyethyl-imidazolium bromide + n-propanol + guanidine thiocyanate |

TABLE 5-continued

EXEMPLARY STORAGE COMPOSITIONS

| (A) Compound of Formula (I) | (A) + (B) Precipitating Agent | (A) + (C) Lower Alcohol | (A) + (D) Chaotrope | (A) + (B) + (C) | (A) + (B) + (D) | (A) + (B) + (C) + (D) | (A) + (C) + (D) |
|---|---|---|---|---|---|---|---|
| 1-hexyl-3-methylimidazolium bromide | 1-hexyl-3-methylimidazolium bromide + 5-(4-dimethyl)amino benzylidene rhodanine | 1-hexyl-3-methylimidazolium bromide + n-propanol | 1-hexyl-3-methylimidazolium bromide + guanidine thiocyanate | 1-hexyl-3-methylimidazolium bromide + 5-(4-dimethyl)amino benzylidene rhodanine + n-propanol | 1-hexyl-3-methylimidazolium bromide + 5-(4-dimethyl)amino benzylidene rhodanine + guanidine thiocyanate | 1-hexyl-3-methylimidazolium bromide + 5-(4-dimethyl)amino benzylidene rhodanine + n-propanol + guanidine thiocyanate | 1-hexyl-3-methylimidazolium bromide + n-propanol + guanidine thiocyanate |
| 1-decyl-3-methylimidazolium bromide | 1-decyl-3-methylimidazolium bromide + 5-(4-dimethyl)amino benzylidene rhodanine | 1-decyl-3-methylimidazolium bromide + n-propanol | 1-decyl-3-methylimidazolium bromide + guanidine thiocyanate | 1-decyl-3-methylimidazolium bromide + 5-(4-dimethyl)amino benzylidene rhodanine + n-propanol | 1-decyl-3-methylimidazolium bromide + 5-(4-dimethyl)amino benzylidene rhodanine + guanidine thiocyanate | 1-decyl-3-methylimidazolium bromide + 5-(4-dimethyl)amino benzylidene rhodanine + n-propanol + guanidine thiocyanate | 1-decyl-3-methylimidazolium bromide + n-propanol + guanidine thiocyanate |
| 1-(2-hydroxyethyl)-3-methylimidazolium bromide | 1-(2-hydroxyethyl)-3-methylimidazolium bromide + 5-(4-dimethyl)amino benzylidene rhodanine | 1-(2-hydroxyethyl)-3-methylimidazolium bromide + n-propanol | 1-(2-hydroxyethyl)-3-methylimidazolium bromide + guanidine thiocyanate | 1-(2-hydroxyethyl)-3-methylimidazolium bromide + 5-(4-dimethyl)amino benzylidene rhodanine + n-propanol | 1-(2-hydroxyethyl)-3-methylimidazolium bromide + 5-(4-dimethyl)amino benzylidene rhodanine + guanidine thiocyanate | 1-(2-hydroxyethyl)-3-methylimidazolium bromide + 5-(4-dimethyl)amino benzylidene rhodanine + n-propanol + guanidine thiocyanate | 1-(2-hydroxyethyl)-3-methylimidazolium bromide + n-propanol + guanidine thiocyanate |
| 1-octyl-3-methylimidazolium bromide | 1-octyl-3-methylimidazolium bromide + 5-(4-dimethyl)amino benzylidene rhodanine | 1-octyl-3-methylimidazolium bromide + n-propanol | 1-octyl-3-methylimidazolium bromide + guanidine thiocyanate | 1-octyl-3-methylimidazolium bromide + 5-(4-dimethyl)amino benzylidene rhodanine + n-propanol | 1-octyl-3-methylimidazolium bromide + 5-(4-dimethyl)amino benzylidene rhodanine + guanidine thiocyanate | 1-octyl-3-methylimidazolium bromide + 5-(4-dimethyl)amino benzylidene rhodanine + n-propanol + guanidine thiocyanate | 1-octyl-3-methylimidazolium bromide + n-propanol + guanidine thiocyanate |
| 1-methyl-3-carboxyethyl-imidazolium bromide | 1-methyl-3-carboxyethyl-imidazolium bromide + sulfosalicylic acid | 1-methyl-3-carboxyethyl-imidazolium bromide + n-propanol | 1-methyl-3-carboxyethyl-imidazolium bromide + guanidine thiocyanate | 1-methyl-3-carboxyethyl-imidazolium bromide + sulfosalicylic acid + n-propanol | 1-methyl-3-carboxyethyl-imidazolium bromide + sulfosalicylic acid + guanidine thiocyanate | 1-methyl-3-carboxyethyl-imidazolium bromide + sulfosalicylic acid + n-propanol + guanidine thiocyanate | 1-methyl-3-carboxyethyl-imidazolium bromide + n-propanol + guanidine thiocyanate |

TABLE 5-continued

EXEMPLARY STORAGE COMPOSITIONS

| (A) Compound of Formula (I) | (A) + (B) Precipitating Agent | (A) + (C) Lower Alcohol | (A) + (D) Chaotrope | (A) + (B) + (C) | (A) + (B) + (D) | (A) + (B) + (C) + (D) | (A) + (C) + (D) |
|---|---|---|---|---|---|---|---|
| 1-hexyl-3-methylimidazolium bromide | 1-hexyl-3-methylimidazolium bromide + sulfosalicylic acid | 1-hexyl-3-methylimidazolium bromide + n-propanol | 1-hexyl-3-methylimidazolium bromide + guanidine thiocyanate | 1-hexyl-3-methylimidazolium bromide + sulfosalicylic acid + n-propanol | 1-hexyl-3-methylimidazolium bromide + sulfosalicylic acid + guanidine thiocyanate | 1-hexyl-3-methylimidazolium bromide + sulfosalicylic acid + n-propanol + guanidine thiocyanate | 1-hexyl-3-methylimidazolium bromide + n-propanol + guanidine thiocyanate |
| 1-decyl-3-methylimidazolium bromide | 1-decyl-3-methylimidazolium bromide + sulfosalicylic acid | 1-decyl-3-methylimidazolium bromide + n-propanol | 1-decyl-3-methylimidazolium bromide + guanidine thiocyanate | 1-decyl-3-methylimidazolium bromide + sulfosalicylic acid + n-propanol | 1-decyl-3-methylimidazolium bromide + sulfosalicylic acid + guanidine thiocyanate | 1-decyl-3-methylimidazolium bromide + sulfosalicylic acid + n-propanol + guanidine thiocyanate | 1-decyl-3-methylimidazolium bromide + n-propanol + guanidine thiocyanate |
| 1-(2-hydroxyethyl)-3-methylimidazolium bromide | 1-(2-hydroxyethyl)-3-methylimidazolium bromide + sulfosalicylic acid | 1-(2-hydroxyethyl)-3-methylimidazolium bromide + n-propanol | 1-(2-hydroxyethyl)-3-methylimidazolium bromide + guanidine thiocyanate | 1-(2-hydroxyethyl)-3-methylimidazolium bromide + sulfosalicylic acid + n-propanol | 1-(2-hydroxyethyl)-3-methylimidazolium bromide + sulfosalicylic acid + guanidine thiocyanate | 1-(2-hydroxyethyl)-3-methylimidazolium bromide + sulfosalicylic acid + n-propanol + guanidine thiocyanate | 1-(2-hydroxyethyl)-3-methylimidazolium bromide + n-propanol + guanidine thiocyanate |
| 1-octyl-3-methylimidazolium bromide | 1-octyl-3-methylimidazolium bromide + sulfosalicylic acid | 1-octyl-3-methylimidazolium bromide + n-propanol | 1-octyl-3-methylimidazolium bromide + guanidine thiocyanate | 1-octyl-3-methylimidazolium bromide + sulfosalicylic acid + n-propanol | 1-octyl-3-methylimidazolium bromide + sulfosalicylic acid + guanidine thiocyanate | 1-octyl-3-methylimidazolium bromide + sulfosalicylic acid + n-propanol + guanidine thiocyanate | 1-octyl-3-methylimidazolium bromide + n-propanol + guanidine thiocyanate |
| 1-methyl-3-carboxyethyl-imidazolium bromide | 1-methyl-3-carboxyethyl-imidazolium bromide + lithium chloride | 1-methyl-3-carboxyethyl-imidazolium bromide + n-propanol | 1-methyl-3-carboxyethyl-imidazolium bromide + guanidine thiocyanate | 1-methyl-3-carboxyethyl-imidazolium bromide + LiCl + n-propanol | 1-methyl-3-carboxyethyl-imidazolium bromide + LiCl + guanidine thiocyanate | 1-methyl-3-carboxyethyl-imidazolium bromide + LiCl + n-propanol + guanidine thiocyanate | 1-methyl-3-carboxyethyl-imidazolium bromide + n-propanol + guanidine thiocyanate |
| 1-hexyl-3-methylimidazolium bromide | 1-hexyl-3-methylimidazolium bromide + lithium chloride | 1-hexyl-3-methylimidazolium bromide + n-propanol | 1-hexyl-3-methylimidazolium bromide + guanidine thiocyanate | 1-hexyl-3-methylimidazolium bromide + LiCl + n-propanol | 1-hexyl-3-methylimidazolium bromide + LiCl + guanidine thiocyanate | 1-hexyl-3-methylimidazolium bromide + LiCl + n-propanol + guanidine thiocyanate | 1-hexyl-3-methylimidazolium bromide + n-propanol + guanidine thiocyanate |
| 1-decyl-3-methylimidazolium bromide | 1-decyl-3-methylimidazolium bromide + lithium chloride | 1-decyl-3-methylimidazolium bromide + n-propanol | 1-decyl-3-methylimidazolium bromide + guanidine thiocyanate | 1-decyl-3-methylimidazolium bromide + LiCl + n-propanol | 1-decyl-3-methylimidazolium bromide + LiCl + guanidine thiocyanate | 1-decyl-3-methylimidazolium bromide + LiCl + n-propanol + guanidine thiocyanate | 1-decyl-3-methylimidazolium bromide + n-propanol + guanidine thiocyanate |

TABLE 5-continued

EXEMPLARY STORAGE COMPOSITIONS

| (A) Compound of Formula (I) | (A) + (B) Precipitating Agent | (A) + (C) Lower Alcohol | (A) + (D) Chaotrope | (A) + (B) + (C) | (A) + (B) + (D) | (A) + (B) + (C) + (D) | (A) + (C) + (D) |
|---|---|---|---|---|---|---|---|
| 1-(2-hydroxyethyl)-3-methylimidazolium bromide | 1-(2-hydroxyethyl)-3-methylimidazolium bromide + lithium chloride | 1-(2-hydroxyethyl)-3-methylimidazolium bromide + n-propanol | 1-(2-hydroxyethyl)-3-methylimidazolium bromide + guanidine thiocyanate | 1-(2-hydroxyethyl)-3-methylimidazolium bromide + LiCl + n-propanol | 1-(2-hydroxyethyl)-3-methylimidazolium bromide + LiCl + guanidine thiocyanate | 1-(2-hydroxyethyl)-3-methylimidazolium bromide + LiCl + n-propanol + guanidine thiocyanate | 1-(2-hydroxyethyl)-3-methylimidazolium bromide + n-propanol + guanidine thiocyanate |
| 1-octyl-3-methylimidazolium bromide | 1-octyl-3-methylimidazolium bromide + lithium chloride | 1-octyl-3-methylimidazolium bromide + n-propanol | 1-octyl-3-methylimidazolium bromide + guanidine thiocyanate | 1-octyl-3-methylimidazolium bromide + LiCl + n-propanol | 1-octyl-3-methylimidazolium bromide + LiCl + guanidine thiocyanate | 1-octyl-3-methylimidazolium bromide + LiCl + n-propanol + guanidine thiocyanate | 1-octyl-3-methylimidazolium bromide + n-propanol + guanidine thiocyanate |
| 1-methyl-3-carboxyethyl-imidazolium bromide | 1-methyl-3-carboxyethyl-imidazolium bromide + lithium hydroxide | 1-methyl-3-carboxyethyl-imidazolium bromide + n-propanol | 1-methyl-3-carboxyethyl-imidazolium bromide + guanidine thiocyanate | 1-methyl-3-carboxyethyl-imidazolium bromide + LiOH + n-propanol | 1-methyl-3-carboxyethyl-imidazolium bromide + LiOH + guanidine thiocyanate | 1-methyl-3-carboxyethyl-imidazolium bromide + LiOH + n-propanol + guanidine thiocyanate | 1-methyl-3-carboxyethyl-imidazolium bromide + n-propanol + guanidine thiocyanate |
| 1-hexyl-3-methylimidazolium bromide | 1-hexyl-3-methylimidazolium bromide + lithium hydroxide | 1-hexyl-3-methylimidazolium bromide + n-propanol | 1-hexyl-3-methylimidazolium bromide + guanidine thiocyanate | 1-hexyl-3-methylimidazolium bromide + LiOH + n-propanol | 1-hexyl-3-methylimidazolium bromide + LiOH + guanidine thiocyanate | 1-hexyl-3-methylimidazolium bromide + LiOH + n-propanol + guanidine thiocyanate | 1-hexyl-3-methylimidazolium bromide + n-propanol + guanidine thiocyanate |
| 1-decyl-3-methylimidazolium bromide | 1-decyl-3-methylimidazolium bromide + lithium hydroxide | 1-decyl-3-methylimidazolium bromide + n-propanol | 1-decyl-3-methylimidazolium bromide + guanidine thiocyanate | 1-decyl-3-methylimidazolium bromide + LiOH + n-propanol | 1-decyl-3-methylimidazolium bromide + LiOH + guanidine thiocyanate | 1-decyl-3-methylimidazolium bromide + LiOH + n-propanol + guanidine thiocyanate | 1-decyl-3-methylimidazolium bromide + n-propanol + guanidine thiocyanate |
| 1-(2-hydroxyethyl)-3-methylimidazolium bromide | 1-(2-hydroxyethyl)-3-methylimidazolium bromide + lithium hydroxide | 1-(2-hydroxyethyl)-3-methylimidazolium bromide + n-propanol | 1-(2-hydroxyethyl)-3-methylimidazolium bromide + guanidine thiocyanate | 1-(2-hydroxyethyl)-3-methylimidazolium bromide + LiOH + n-propanol | 1-(2-hydroxyethyl)-3-methylimidazolium bromide + LiOH + guanidine thiocyanate | 1-(2-hydroxyethyl)-3-methylimidazolium bromide + LiOH + n-propanol + guanidine thiocyanate | 1-(2-hydroxyethyl)-3-methylimidazolium bromide + n-propanol + guanidine thiocyanate |
| 1-octyl-3-methylimidazolium bromide | 1-octyl-3-methylimidazolium bromide + lithium hydroxide | 1-octyl-3-methylimidazolium bromide + n-propanol | 1-octyl-3-methylimidazolium bromide + guanidine thiocyanate | 1-octyl-3-methylimidazolium bromide + LiOH + n-propanol | 1-octyl-3-methylimidazolium bromide + LiOH + guanidine thiocyanate | 1-octyl-3-methylimidazolium bromide + LiOH + n-propanol + guanidine thiocyanate | 1-octyl-3-methylimidazolium bromide + n-propanol + guanidine thiocyanate |

TABLE 5-continued

EXEMPLARY STORAGE COMPOSITIONS

| (A) Compound of Formula (I) | (A) + (B) Precipitating Agent | (A) + (C) Lower Alcohol | (A) + (D) Chaotrope | (A) + (B) + (C) | (A) + (B) + (D) | (A) + (B) + (C) + (D) | (A) + (C) + (D) |
|---|---|---|---|---|---|---|---|
| 1-methyl-3-carboxyethyl-imidazolium bromide | 1-methyl-3-carboxyethyl-imidazolium bromide + 5-(4-dimethyl)amino benzylidene rhodanine | 1-methyl-3-carboxyethyl-imidazolium bromide + Isopropanol | 1-methyl-3-carboxyethyl-imidazolium bromide + guanidine thiocyanate | 1-methyl-3-carboxyethyl-imidazolium bromide + 5-(4-dimethyl)amino benzylidene rhodanine + isopropanol | 1-methyl-3-carboxyethyl-imidazolium bromide + 5-(4-dimethyl)amino benzylidene rhodanine + guanidine thiocyanate | 1-methyl-3-carboxyethyl-imidazolium bromide + 5-(4-dimethyl)amino benzylidene rhodanine + isopropanol + guanidine thiocyanate | 1-methyl-3-carboxyethyl-imidazolium bromide + isopropanol + guanidine thiocyanate |
| 1-hexyl-3-methylimidazolium bromide | 1-hexyl-3-methylimidazolium bromide + 5-(4-dimethyl)amino benzylidene rhodanine | 1-hexyl-3-methylimidazolium bromide + Isopropanol | 1-hexyl-3-methylimidazolium bromide + guanidine thiocyanate | 1-hexyl-3-methylimidazolium bromide + 5-(4-dimethyl)amino benzylidene rhodanine + isopropanol | 1-hexyl-3-methylimidazolium bromide + 5-(4-dimethyl)amino benzylidene rhodanine + guanidine thiocyanate | 1-hexyl-3-methylimidazolium bromide + 5-(4-dimethyl)amino benzylidene rhodanine + isopropanol + guanidine thiocyanate | 1-hexyl-3-methylimidazolium bromide + isopropanol + guanidine thiocyanate |
| 1-decyl-3-methylimidazolium bromide | 1-decyl-3-methylimidazolium bromide + 5-(4-dimethyl)amino benzylidene rhodanine | 1-decyl-3-methylimidazolium bromide + Isopropanol | 1-decyl-3-methylimidazolium bromide + guanidine thiocyanate | 1-decyl-3-methylimidazolium bromide + 5-(4-dimethyl)amino benzylidene rhodanine + isopropanol | 1-decyl-3-methylimidazolium bromide + 5-(4-dimethyl)amino benzylidene rhodanine + guanidine thiocyanate | 1-decyl-3-methylimidazolium bromide + 5-(4-dimethyl)amino benzylidene rhodanine + isopropanol + guanidine thiocyanate | 1-decyl-3-methylimidazolium bromide + isopropanol + guanidine thiocyanate |
| 1-(2-hydroxyethyl)-3-methylimidazolium bromide | 1-(2-hydroxyethyl)-3-methylimidazolium bromide + 5-(4-dimethyl)amino benzylidene rhodanine | 1-(2-hydroxyethyl)-3-methylimidazolium bromide + Isopropanol | 1-(2-hydroxyethyl)-3-methylimidazolium bromide + guanidine thiocyanate | 1-(2-hydroxyethyl)-3-methylimidazolium bromide + 5-(4-dimethyl)amino benzylidene rhodanine + isopropanol | 1-(2-hydroxyethyl)-3-methylimidazolium bromide + 5-(4-dimethyl)amino benzylidene rhodanine + guanidine thiocyanate | 1-(2-hydroxyethyl)-3-methylimidazolium bromide + 5-(4-dimethyl)amino benzylidene rhodanine + isopropanol + guanidine thiocyanate | 1-(2-hydroxyethyl)-3-methylimidazolium bromide + isopropanol + guanidine thiocyanate |
| 1-octyl-3-methylimidazolium bromide | 1-octyl-3-methylimidazolium bromide + 5-(4-dimethyl)amino benzylidene rhodanine | 1-octyl-3-methylimidazolium bromide + Isopropanol | 1-octyl-3-methylimidazolium bromide + guanidine thiocyanate | 1-octyl-3-methylimidazolium bromide + 5-(4-dimethyl)amino benzylidene rhodanine + isopropanol | 1-octyl-3-methylimidazolium bromide + 5-(4-dimethyl)amino benzylidene rhodanine + guanidine thiocyanate | 1-octyl-3-methylimidazolium bromide + 5-(4-dimethyl)amino benzylidene rhodanine + isopropanol + guanidine thiocyanate | 1-octyl-3-methylimidazolium bromide + isopropanol + guanidine thiocyanate |

TABLE 5-continued

EXEMPLARY STORAGE COMPOSITIONS

| (A) Compound of Formula (I) | (A) + (B) Precipitating Agent | (A) + (C) Lower Alcohol | (A) + (D) Chaotrope | (A) + (B) + (C) | (A) + (B) + (D) | (A) + (B) + (C) + (D) | (A) + (C) + (D) |
|---|---|---|---|---|---|---|---|
| 1-methyl-3-carboxyethyl-imidazolium bromide | 1-methyl-3-carboxyethyl-imidazolium bromide + sulfosalicylic acid | 1-methyl-3-carboxyethyl-imidazolium bromide + Isopropanol | 1-methyl-3-carboxyethyl-imidazolium bromide + guanidine thiocyanate | 1-methyl-3-carboxyethyl-imidazolium bromide + sulfosalicylic acid + isopropanol | 1-methyl-3-carboxyethyl-imidazolium bromide + sulfosalicylic acid + guanidine thiocyanate | 1-methyl-3-carboxyethyl-imidazolium bromide + sulfosalicylic acid + isopropanol + guanidine thiocyanate | 1-methyl-3-carboxyethyl-imidazolium bromide + isopropanol + guanidine thiocyanate |
| 1-hexyl-3-methylimidazolium bromide | 1-hexyl-3-methylimidazolium bromide + sulfosalicylic acid | 1-hexyl-3-methylimidazolium bromide + Isopropanol | 1-hexyl-3-methylimidazolium bromide + guanidine thiocyanate | 1-hexyl-3-methylimidazolium bromide + sulfosalicylic acid + isopropanol | 1-hexyl-3-methylimidazolium bromide + sulfosalicylic acid + guanidine thiocyanate | 1-hexyl-3-methylimidazolium bromide + sulfosalicylic acid + isopropanol + guanidine thiocyanate | 1-hexyl-3-methylimidazolium bromide + isopropanol + guanidine thiocyanate |
| 1-decyl-3-methylimidazolium bromide | 1-decyl-3-methylimidazolium bromide + sulfosalicylic acid | 1-decyl-3-methylimidazolium bromide + Isopropanol | 1-decyl-3-methylimidazolium bromide + guanidine thiocyanate | 1-decyl-3-methylimidazolium bromide + sulfosalicylic acid + isopropanol | 1-decyl-3-methylimidazolium bromide + sulfosalicylic acid + guanidine thiocyanate | 1-decyl-3-methylimidazolium bromide + sulfosalicylic acid + isopropanol + guanidine thiocyanate | 1-decyl-3-methylimidazolium bromide + isopropanol + guanidine thiocyanate |
| 1-(2-hydroxyethyl)-3-methylimidazolium bromide | 1-(2-hydroxyethyl)-3-methylimidazolium bromide + sulfosalicylic acid | 1-(2-hydroxyethyl)-3-methylimidazolium bromide + Isopropanol | 1-(2-hydroxyethyl)-3-methylimidazolium bromide + guanidine thiocyanate | 1-(2-hydroxyethyl)-3-methylimidazolium bromide + sulfosalicylic acid + isopropanol | 1-(2-hydroxyethyl)-3-methylimidazolium bromide + sulfosalicylic acid + guanidine thiocyanate | 1-(2-hydroxyethyl)-3-methylimidazolium bromide + sulfosalicylic acid + isopropanol + guanidine thiocyanate | 1-(2-hydroxyethyl)-3-methylimidazolium bromide + isopropanol + guanidine thiocyanate |
| 1-octyl-3-methylimidazolium bromide | 1-octyl-3-methylimidazolium bromide + sulfosalicylic acid | 1-octyl-3-methylimidazolium bromide + Isopropanol | 1-octyl-3-methylimidazolium bromide + guanidine thiocyanate | 1-octyl-3-methylimidazolium bromide + sulfosalicylic acid + isopropanol | 1-octyl-3-methylimidazolium bromide + sulfosalicylic acid + guanidine thiocyanate | 1-octyl-3-methylimidazolium bromide + sulfosalicylic acid + isopropanol + guanidine thiocyanate | 1-octyl-3-methylimidazolium bromide + isopropanol + guanidine thiocyanate |
| 1-methyl-3-carboxyethyl-imidazolium bromide | 1-methyl-3-carboxyethyl-imidazolium bromide + lithium chloride | 1-methyl-3-carboxyethyl-imidazolium bromide + Isopropanol | 1-methyl-3-carboxyethyl-imidazolium bromide + guanidine thiocyanate | 1-methyl-3-carboxyethyl-imidazolium bromide + LiCl + isopropanol | 1-methyl-3-carboxyethyl-imidazolium bromide + LiCl + guanidine thiocyanate | 1-methyl-3-carboxyethyl-imidazolium bromide + LiCl + isopropanol + guanidine thiocyanate | 1-methyl-3-carboxyethyl-imidazolium bromide + isopropanol + guanidine thiocyanate |

TABLE 5-continued

EXEMPLARY STORAGE COMPOSITIONS

| (A) Compound of Formula (I) | (A) + (B) Precipitating Agent | (A) + (C) Lower Alcohol | (A) + (D) Chaotrope | (A) + (B) + (C) | (A) + (B) + (D) | (A) + (B) + (C) + (D) | (A) + (C) + (D) |
|---|---|---|---|---|---|---|---|
| 1-hexyl-3-methylimidazolium bromide | 1-hexyl-3-methylimidazolium bromide + lithium chloride | 1-hexyl-3-methylimidazolium bromide + Isopropanol | 1-hexyl-3-methylimidazolium bromide + guanidine thiocyanate | 1-hexyl-3-methylimidazolium bromide + LiCl + isopropanol | 1-hexyl-3-methylimidazolium bromide + LiCl + guanidine thiocyanate | 1-hexyl-3-methylimidazolium bromide + LiCl + isopropanol + guanidine thiocyanate | 1-hexyl-3-methylimidazolium bromide + isopropanol + guanidine thiocyanate |
| 1-decyl-3-methylimidazolium bromide | 1-decyl-3-methylimidazolium bromide + lithium chloride | 1-decyl-3-methylimidazolium bromide + Isopropanol | 1-decyl-3-methylimidazolium bromide + guanidine thiocyanate | 1-decyl-3-methylimidazolium bromide + LiCl + isopropanol | 1-decyl-3-methylimidazolium bromide + LiCl + guanidine thiocyanate | 1-decyl-3-methylimidazolium bromide + LiCl + isopropanol + guanidine thiocyanate | 1-decyl-3-methylimidazolium bromide + isopropanol + guanidine thiocyanate |
| 1-(2-hydroxyethyl)-3-methylimidazolium bromide | 1-(2-hydroxyethyl)-3-methylimidazolium bromide + lithium chloride | 1-(2-hydroxyethyl)-3-methylimidazolium bromide + Isopropanol | 1-(2-hydroxyethyl)-3-methylimidazolium bromide + guanidine thiocyanate | 1-(2-hydroxyethyl)-3-methylimidazolium bromide + LiCl + isopropanol | 1-(2-hydroxyethyl)-3-methylimidazolium bromide + LiCl + guanidine thiocyanate | 1-(2-hydroxyethyl)-3-methylimidazolium bromide + LiCl + isopropanol + guanidine thiocyanate | 1-(2-hydroxyethyl)-3-methylimidazolium bromide + isopropanol + guanidine thiocyanate |
| 1-octyl-3-methylimidazolium bromide | 1-octyl-3-methylimidazolium bromide + lithium chloride | 1-octyl-3-methylimidazolium bromide + Isopropanol | 1-octyl-3-methylimidazolium bromide + guanidine thiocyanate | 1-octyl-3-methylimidazolium bromide + LiCl + isopropanol | 1-octyl-3-methylimidazolium bromide + LiCl + guanidine thiocyanate | 1-octyl-3-methylimidazolium bromide + LiCl + isopropanol + guanidine thiocyanate | 1-octyl-3-methylimidazolium bromide + isopropanol + guanidine thiocyanate |
| 1-methyl-3-carboxyethyl-imidazolium bromide | 1-methyl-3-carboxyethyl-imidazolium bromide + lithium hydroxide | 1-methyl-3-carboxyethyl-imidazolium bromide + Isopropanol | 1-methyl-3-carboxyethyl-imidazolium bromide + guanidine thiocyanate | 1-methyl-3-carboxyethyl-imidazolium bromide + LiOH + isopropanol | 1-methyl-3-carboxyethyl-imidazolium bromide + LiOH + guanidine thiocyanate | 1-methyl-3-carboxyethyl-imidazolium bromide + LiOH + isopropanol + guanidine thiocyanate | 1-methyl-3-carboxyethyl-imidazolium bromide + isopropanol + guanidine thiocyanate |
| 1-hexyl-3-methylimidazolium bromide | 1-hexyl-3-methylimidazolium bromide + lithium hydroxide | 1-hexyl-3-methylimidazolium bromide + Isopropanol | 1-hexyl-3-methylimidazolium bromide + guanidine thiocyanate | 1-hexyl-3-methylimidazolium bromide + LiOH + isopropanol | 1-hexyl-3-methylimidazolium bromide + LiOH + guanidine thiocyanate | 1-hexyl-3-methylimidazolium bromide + LiOH + isopropanol + guanidine thiocyanate | 1-hexyl-3-methylimidazolium bromide + isopropanol + guanidine thiocyanate |
| 1-decyl-3-methylimidazolium bromide | 1-decyl-3-methylimidazolium bromide + lithium hydroxide | 1-decyl-3-methylimidazolium bromide + Isopropanol | 1-decyl-3-methylimidazolium bromide + guanidine thiocyanate | 1-decyl-3-methylimidazolium bromide + LiOH + isopropanol | 1-decyl-3-methylimidazolium bromide + LiOH + guanidine thiocyanate | 1-decyl-3-methylimidazolium bromide + LiOH + isopropanol + guanidine thiocyanate | 1-decyl-3-methylimidazolium bromide + isopropanol + guanidine thiocyanate |

TABLE 5-continued

EXEMPLARY STORAGE COMPOSITIONS

| (A) Compound of Formula (I) | (A) + (B) Precipitating Agent | (A) + (C) Lower Alcohol | (A) + (D) Chaotrope | (A) + (B) + (C) | (A) + (B) + (D) | (A) + (B) + (C) + (D) | (A) + (C) + (D) |
|---|---|---|---|---|---|---|---|
| 1-(2-hydroxyethyl)-3-methylimidazolium bromide | 1-(2-hydroxyethyl)-3-methylimidazolium bromide + lithium hydroxide | 1-(2-hydroxyethyl)-3-methylimidazolium bromide + Isopropanol | 1-(2-hydroxyethyl)-3-methylimidazolium bromide + guanidine thiocyanate | 1-(2-hydroxyethyl)-3-methylimidazolium bromide + LiOH + isopropanol | 1-(2-hydroxyethyl)-3-methylimidazolium bromide + LiOH + guanidine thiocyanate | 1-(2-hydroxyethyl)-3-methylimidazolium bromide + LiOH + isopropanol + guanidine thiocyanate | 1-(2-hydroxyethyl)-3-methylimidazolium bromide + isopropanol + guanidine thiocyanate |
| 1-octyl-3-methylimidazolium bromide | 1-octyl-3-methylimidazolium bromide + lithium hydroxide | 1-octyl-3-methylimidazolium bromide + Isopropanol | 1-octyl-3-methylimidazolium bromide + guanidine thiocyanate | 1-octyl-3-methylimidazolium bromide + LiOH + isopropanol | 1-octyl-3-methylimidazolium bromide + LiOH + guanidine thiocyanate | 1-octyl-3-methylimidazolium bromide + LiOH + isopropanol + guanidine thiocyanate | 1-octyl-3-methylimidazolium bromide + isopropanol + guanidine thiocyanate |
| 1-methyl-3-carboxyethyl-imidazolium bromide + 5-(4-dimethyl)amino benzylidene rhodanine | 1-methyl-3-carboxyethyl-imidazolium bromide + 5-(4-dimethyl)amino benzylidene rhodanine | 1-methyl-3-carboxyethyl-imidazolium bromide + n-butanol | 1-methyl-3-carboxyethyl-imidazolium bromide + guanidine thiocyanate | 1-methyl-3-carboxyethyl-imidazolium bromide + 5-(4-dimethyl)amino benzylidene rhodanine + n-butanol | 1-methyl-3-carboxyethyl-imidazolium bromide + 5-(4-dimethyl)amino benzylidene rhodanine + guanidine thiocyanate | 1-methyl-3-carboxyethyl-imidazolium bromide + 5-(4-dimethyl)amino benzylidene rhodanine + n-butanol + guanidine thiocyanate | 1-methyl-3-carboxyethyl-imidazolium bromide + n-butanol + guanidine thiocyanate |
| 1-hexyl-3-methylimidazolium bromide | 1-hexyl-3-methylimidazolium bromide + 5-(4-dimethyl)amino benzylidene rhodanine | 1-hexyl-3-methylimidazolium bromide + n-butanol | 1-hexyl-3-methylimidazolium bromide + guanidine thiocyanate | 1-hexyl-3-methylimidazolium bromide + 5-(4-dimethyl)amino benzylidene rhodanine + n-butanol | 1-hexyl-3-methylimidazolium bromide + 5-(4-dimethyl)amino benzylidene rhodanine + guanidine thiocyanate | 1-hexyl-3-methylimidazolium bromide + 5-(4-dimethyl)amino benzylidene rhodanine + n-butanol + guanidine thiocyanate | 1-hexyl-3-methylimidazolium bromide + n-butanol + guanidine thiocyanate |
| 1-decyl-3-methylimidazolium bromide | 1-decyl-3-methylimidazolium bromide + 5-(4-dimethyl)amino benzylidene rhodanine | 1-decyl-3-methylimidazolium bromide + n-butanol | 1-decyl-3-methylimidazolium bromide + guanidine thiocyanate | 1-decyl-3-methylimidazolium bromide + 5-(4-dimethyl)amino benzylidene rhodanine + n-butanol | 1-decyl-3-methylimidazolium bromide + 5-(4-dimethyl)amino benzylidene rhodanine + guanidine thiocyanate | 1-decyl-3-methylimidazolium bromide + 5-(4-dimethyl)amino benzylidene rhodanine + n-butanol + guanidine thiocyanate | 1-decyl-3-methylimidazolium bromide + n-butanol + guanidine thiocyanate |

TABLE 5-continued

EXEMPLARY STORAGE COMPOSITIONS

| (A) Compound of Formula (I) | (A) + (B) Precipitating Agent | (A) + (C) Lower Alcohol | (A) + (D) Chaotrope | (A) + (B) + (C) | (A) + (B) + (D) | (A) + (B) + (C) + (D) | (A) + (C) + (D) |
|---|---|---|---|---|---|---|---|
| 1-(2-hydroxyethyl)-3-methylimidazolium bromide | 1-(2-hydroxyethyl)-3-methylimidazolium bromide + 5-(4-dimethyl)amino benzylidene rhodanine | 1-(2-hydroxyethyl)-3-methylimidazolium bromide + n-butanol | 1-(2-hydroxyethyl)-3-methylimidazolium bromide + guanidine thiocyanate | 1-(2-hydroxyethyl)-3-methylimidazolium bromide + 5-(4-dimethyl)amino benzylidene rhodanine + n-butanol | 1-(2-hydroxyethyl)-3-methylimidazolium bromide + 5-(4-dimethyl)amino benzylidene rhodanine + guanidine thiocyanate | 1-(2-hydroxyethyl)-3-methylimidazolium bromide + 5-(4-dimethyl)amino benzylidene rhodanine + n-butanol + guanidine thiocyanate | 1-(2-hydroxyethyl)-3-methylimidazolium bromide + n-butanol + guanidine thiocyanate |
| 1-octyl-3-methylimidazolium bromide | 1-octyl-3-methylimidazolium bromide + 5-(4-dimethyl)amino benzylidene rhodanine | 1-octyl-3-methylimidazolium bromide + n-butanol | 1-octyl-3-methylimidazolium bromide + guanidine thiocyanate | 1-octyl-3-methylimidazolium bromide + 5-(4-dimethyl)amino benzylidene rhodanine + n-butanol | 1-octyl-3-methylimidazolium bromide + 5-(4-dimethyl)amino benzylidene rhodanine + guanidine thiocyanate | 1-octyl-3-methylimidazolium bromide + 5-(4-dimethyl)amino benzylidene rhodanine + n-butanol + guanidine thiocyanate | 1-octyl-3-methylimidazolium bromide + n-butanol + guanidine thiocyanate |
| 1-methyl-3-carboxyethyl-imidazolium bromide | 1-methyl-3-carboxyethyl-imidazolium bromide + sulfosalicylic acid | 1-methyl-3-carboxyethyl-imidazolium bromide + n-butanol | 1-methyl-3-carboxyethyl-imidazolium bromide + guanidine thiocyanate | 1-methyl-3-carboxyethyl-imidazolium bromide + sulfosalicylic acid + n-butanol | 1-methyl-3-carboxyethyl-imidazolium bromide + sulfosalicylic acid + guanidine thiocyanate | 1-methyl-3-carboxyethyl-imidazolium bromide + sulfosalicylic acid + n-butanol + guanidine thiocyanate | 1-methyl-3-carboxyethyl-imidazolium bromide + n-butanol + guanidine thiocyanate |
| 1-hexyl-3-methylimidazolium bromide | 1-hexyl-3-methylimidazolium bromide + sulfosalicylic acid | 1-hexyl-3-methylimidazolium bromide + n-butanol | 1-hexyl-3-methylimidazolium bromide + guanidine thiocyanate | 1-hexyl-3-methylimidazolium bromide + sulfosalicylic acid + n-butanol | 1-hexyl-3-methylimidazolium bromide + sulfosalicylic acid + guanidine thiocyanate | 1-hexyl-3-methylimidazolium bromide + sulfosalicylic acid + n-butanol + guanidine thiocyanate | 1-hexyl-3-methylimidazolium bromide + n-butanol + guanidine thiocyanate |
| 1-decyl-3-methylimidazolium bromide | 1-decyl-3-methylimidazolium bromide + sulfosalicylic acid | 1-decyl-3-methylimidazolium bromide + n-butanol | 1-decyl-3-methylimidazolium bromide + guanidine thiocyanate | 1-decyl-3-methylimidazolium bromide + sulfosalicylic acid + n-butanol | 1-decyl-3-methylimidazolium bromide + sulfosalicylic acid + guanidine thiocyanate | 1-decyl-3-methylimidazolium bromide + sulfosalicylic acid + n-butanol + guanidine thiocyanate | 1-decyl-3-methylimidazolium bromide + n-butanol + guanidine thiocyanate |
| 1-(2-hydroxyethyl)-3-methylimidazolium bromide | 1-(2-hydroxyethyl)-3-methylimidazolium bromide + sulfosalicylic acid | 1-(2-hydroxyethyl)-3-methylimidazolium bromide + n-butanol | 1-(2-hydroxyethyl)-3-methylimidazolium bromide + guanidine thiocyanate | 1-(2-hydroxyethyl)-3-methylimidazolium bromide + sulfosalicylic acid + n-butanol | 1-(2-hydroxyethyl)-3-methylimidazolium bromide + sulfosalicylic acid + guanidine thiocyanate | 1-(2-hydroxyethyl)-3-methylimidazolium bromide + sulfosalicylic acid + n-butanol + guanidine thiocyanate | 1-(2-hydroxyethyl)-3-methylimidazolium bromide + n-butanol + guanidine thiocyanate |

TABLE 5-continued

EXEMPLARY STORAGE COMPOSITIONS

| (A) Compound of Formula (I) | (A) + (B) Precipitating Agent | (A) + (C) Lower Alcohol | (A) + (D) Chaotrope | (A) + (B) + (C) | (A) + (B) + (D) | (A) + (B) + (C) + (D) | (A) + (C) + (D) |
|---|---|---|---|---|---|---|---|
| 1-octyl-3-methylimidazolium bromide | 1-octyl-3-methylimidazolium bromide + sulfosalicylic acid | 1-octyl-3-methylimidazolium bromide + n-butanol | 1-octyl-3-methylimidazolium bromide + guanidine thiocyanate | 1-octyl-3-methylimidazolium bromide + sulfosalicylic acid + n-butanol | 1-octyl-3-methylimidazolium bromide + sulfosalicylic acid + guanidine thiocyanate | 1-octyl-3-methylimidazolium bromide + sulfosalicylic acid + n-butanol + guanidine thiocyanate | 1-octyl-3-methylimidazolium bromide + n-butanol + guanidine thiocyanate |
| 1-methyl-3-carboxyethyl-imidazolium bromide | 1-methyl-3-carboxyethyl-imidazolium bromide + lithium chloride | 1-methyl-3-carboxyethyl-imidazolium bromide + n-butanol | 1-methyl-3-carboxyethyl-imidazolium bromide + guanidine thiocyanate | 1-methyl-3-carboxyethyl-imidazolium bromide + LiCl + n-butanol | 1-methyl-3-carboxyethyl-imidazolium bromide + LiCl + guanidine thiocyanate | 1-methyl-3-carboxyethyl-imidazolium bromide + LiCl + n-butanol + guanidine thiocyanate | 1-methyl-3-carboxyethyl-imidazolium bromide + n-butanol + guanidine thiocyanate |
| 1-hexyl-3-methylimidazolium bromide | 1-hexyl-3-methylimidazolium bromide + lithium chloride | 1-hexyl-3-methylimidazolium bromide + n-butanol | 1-hexyl-3-methylimidazolium bromide + guanidine thiocyanate | 1-hexyl-3-methylimidazolium bromide + LiCl + n-butanol | 1-hexyl-3-methylimidazolium bromide + LiCl + guanidine thiocyanate | 1-hexyl-3-methylimidazolium bromide + LiCl + n-butanol + guanidine thiocyanate | 1-hexyl-3-methylimidazolium bromide + n-butanol + guanidine thiocyanate |
| 1-decyl-3-methylimidazolium bromide | 1-decyl-3-methylimidazolium bromide + lithium chloride | 1-decyl-3-methylimidazolium bromide + n-butanol | 1-decyl-3-methylimidazolium bromide + guanidine thiocyanate | 1-decyl-3-methylimidazolium bromide + LiCl + n-butanol | 1-decyl-3-methylimidazolium bromide + LiCl + guanidine thiocyanate | 1-decyl-3-methylimidazolium bromide + LiCl + n-butanol + guanidine thiocyanate | 1-decyl-3-methylimidazolium bromide + n-butanol + guanidine thiocyanate |
| 1-(2-hydroxyethyl)-3-methylimidazolium bromide | 1-(2-hydroxyethyl)-3-methylimidazolium bromide + lithium chloride | 1-(2-hydroxyethyl)-3-methylimidazolium bromide + n-butanol | 1-(2-hydroxyethyl)-3-methylimidazolium bromide + guanidine thiocyanate | 1-(2-hydroxyethyl)-3-methylimidazolium bromide + LiCl + n-butanol | 1-(2-hydroxyethyl)-3-methylimidazolium bromide + LiCl + guanidine thiocyanate | 1-(2-hydroxyethyl)-3-methylimidazolium bromide + LiCl + n-butanol + guanidine thiocyanate | 1-(2-hydroxyethyl)-3-methylimidazolium bromide + n-butanol + guanidine thiocyanate |
| 1-octyl-3-methylimidazolium bromide | 1-octyl-3-methylimidazolium bromide + lithium chloride | 1-octyl-3-methylimidazolium bromide + n-butanol | 1-octyl-3-methylimidazolium bromide + guanidine thiocyanate | 1-octyl-3-methylimidazolium bromide + LiCl + n-butanol | 1-octyl-3-methylimidazolium bromide + LiCl + guanidine thiocyanate | 1-octyl-3-methylimidazolium bromide + LiCl + n-butanol + guanidine thiocyanate | 1-octyl-3-methylimidazolium bromide + n-butanol + guanidine thiocyanate |
| 1-methyl-3-carboxyethyl-imidazolium bromide | 1-methyl-3-carboxyethyl-imidazolium bromide + lithium hydroxide | 1-methyl-3-carboxyethyl-imidazolium bromide + n-butanol | 1-methyl-3-carboxyethyl-imidazolium bromide + guanidine thiocyanate | 1-methyl-3-carboxyethyl-imidazolium bromide + LiOH + n-butanol | 1-methyl-3-carboxyethyl-imidazolium bromide + LiOH + guanidine thiocyanate | 1-methyl-3-carboxyethyl-imidazolium bromide + LiOH + n-butanol + guanidine thiocyanate | 1-methyl-3-carboxyethyl-imidazolium bromide + n-butanol + guanidine thiocyanate |

TABLE 5-continued

EXEMPLARY STORAGE COMPOSITIONS

| (A) Compound of Formula (I) | (A) + (B) Precipitating Agent | (A) + (C) Lower Alcohol | (A) + (D) Chaotrope | (A) + (B) + (C) | (A) + (B) + (D) | (A) + (B) + (C) + (D) | (A) + (C) + (D) |
|---|---|---|---|---|---|---|---|
| 1-hexyl-3-methylimidazolium bromide | 1-hexyl-3-methylimidazolium bromide + lithium hydroxide | 1-hexyl-3-methylimidazolium bromide + n-butanol | 1-hexyl-3-methylimidazolium bromide + guanidine thiocyanate | 1-hexyl-3-methylimidazolium bromide + LiOH + n-butanol | 1-hexyl-3-methylimidazolium bromide + LiOH + guanidine thiocyanate | 1-hexyl-3-methylimidazolium bromide + LiOH + n-butanol + guanidine thiocyanate | 1-hexyl-3-methylimidazolium bromide + n-butanol + guanidine thiocyanate |
| 1-decyl-3-methylimidazolium bromide | 1-decyl-3-methylimidazolium bromide + lithium hydroxide | 1-decyl-3-methylimidazolium bromide + n-butanol | 1-decyl-3-methylimidazolium bromide + guanidine thiocyanate | 1-decyl-3-methylimidazolium bromide + LiOH + n-butanol | 1-decyl-3-methylimidazolium bromide + LiOH + guanidine thiocyanate | 1-decyl-3-methylimidazolium bromide + LiOH + n-butanol + guanidine thiocyanate | 1-decyl-3-methylimidazolium bromide + n-butanol + guanidine thiocyanate |
| 1-(2-hydroxyethyl)-3-methylimidazolium bromide | 1-(2-hydroxyethyl)-3-methylimidazolium bromide + lithium hydroxide | 1-(2-hydroxyethyl)-3-methylimidazolium bromide + n-butanol | 1-(2-hydroxyethyl)-3-methylimidazolium bromide + guanidine thiocyanate | 1-(2-hydroxyethyl)-3-methylimidazolium bromide + LiOH + n-butanol | 1-(2-hydroxyethyl)-3-methylimidazolium bromide + LiOH + guanidine thiocyanate | 1-(2-hydroxyethyl)-3-methylimidazolium bromide + LiOH + n-butanol + guanidine thiocyanate | 1-(2-hydroxyethyl)-3-methylimidazolium bromide + n-butanol + guanidine thiocyanate |
| 1-octyl-3-methylimidazolium bromide | 1-octyl-3-methylimidazolium bromide + lithium hydroxide | 1-octyl-3-methylimidazolium bromide + n-butanol | 1-octyl-3-methylimidazolium bromide + guanidine thiocyanate | 1-octyl-3-methylimidazolium bromide + LiOH + n-butanol | 1-octyl-3-methylimidazolium bromide + LiOH + guanidine thiocyanate | 1-octyl-3-methylimidazolium bromide + LiOH + n-butanol + guanidine thiocyanate | 1-octyl-3-methylimidazolium bromide + n-butanol + guanidine thiocyanate |
| 1-methyl-3-carboxyethyl-imidazolium bromide | 1-methyl-3-carboxyethyl-imidazolium bromide + 5-(4-dimethyl)amino benzylidene rhodanine | 1-methyl-3-carboxyethyl-imidazolium bromide + isobutanol | 1-methyl-3-carboxyethyl-imidazolium bromide + guanidine thiocyanate | 1-methyl-3-carboxyethyl-imidazolium bromide + 5-(4-dimethyl)amino benzylidene rhodanine + isobutanol | 1-methyl-3-carboxyethyl-imidazolium bromide + 5-(4-dimethyl)amino benzylidene rhodanine + guanidine thiocyanate | 1-methyl-3-carboxyethyl-imidazolium bromide + 5-(4-dimethyl)amino benzylidene rhodanine + isobutanol + guanidine thiocyanate | 1-methyl-3-carboxyethyl-imidazolium bromide + isobutanol + guanidine thiocyanate |
| 1-hexyl-3-methylimidazolium bromide | 1-hexyl-3-methylimidazolium bromide + 5-(4-dimethyl)amino benzylidene rhodanine | 1-hexyl-3-methylimidazolium bromide + isobutanol | 1-hexyl-3-methylimidazolium bromide + guanidine thiocyanate | 1-hexyl-3-methylimidazolium bromide + 5-(4-dimethyl)amino benzylidene rhodanine + isobutanol | 1-hexyl-3-methylimidazolium bromide + 5-(4-dimethyl)amino benzylidene rhodanine + guanidine thiocyanate | 1-hexyl-3-methylimidazolium bromide + 5-(4-dimethyl)amino benzylidene rhodanine + isobutanol + guanidine thiocyanate | 1-hexyl-3-methylimidazolium bromide + isobutanol + guanidine thiocyanate |

TABLE 5-continued

EXEMPLARY STORAGE COMPOSITIONS

| (A) Compound of Formula (I) | (A) + (B) Precipitating Agent | (A) + (C) Lower Alcohol | (A) + (D) Chaotrope | (A) + (B) + (C) | (A) + (B) + (D) | (A) + (B) + (C) + (D) | (A) + (C) + (D) |
|---|---|---|---|---|---|---|---|
| 1-decyl-3-methylimidazolium bromide | 1-decyl-3-methylimidazolium bromide + 5-(4-dimethyl)amino benzylidene rhodanine | 1-decyl-3-methylimidazolium bromide + isobutanol | 1-decyl-3-methylimidazolium bromide + guanidine thiocyanate | 1-decyl-3-methylimidazolium bromide + 5-(4-dimethyl)amino benzylidene rhodanine + isobutanol | 1-decyl-3-methylimidazolium bromide + 5-(4-dimethyl)amino benzylidene rhodanine + guanidine thiocyanate | 1-decyl-3-methylimidazolium bromide + 5-(4-dimethyl)amino benzylidene rhodanine + isobutanol + guanidine thiocyanate | 1-decyl-3-methylimidazolium bromide + isobutanol + guanidine thiocyanate |
| 1-(2-hydroxyethyl)-3-methylimidazolium bromide | 1-(2-hydroxyethyl)-3-methylimidazolium bromide + 5-(4-dimethyl)amino benzylidene rhodanine | 1-(2-hydroxyethyl)-3-methylimidazolium bromide + isobutanol | 1-(2-hydroxyethyl)-3-methylimidazolium bromide + guanidine thiocyanate | 1-(2-hydroxyethyl)-3-methylimidazolium bromide + 5-(4-dimethyl)amino benzylidene rhodanine + isobutanol | 1-(2-hydroxyethyl)-3-methylimidazolium bromide + 5-(4-dimethyl)amino benzylidene rhodanine + guanidine thiocyanate | 1-(2-hydroxyethyl)-3-methylimidazolium bromide + 5-(4-dimethyl)amino benzylidene rhodanine + isobutanol + guanidine thiocyanate | 1-(2-hydroxyethyl)-3-methylimidazolium bromide + isobutanol + guanidine thiocyanate |
| 1-octyl-3-methylimidazolium bromide | 1-octyl-3-methylimidazolium bromide + 5-(4-dimethyl)amino benzylidene rhodanine | 1-octyl-3-methylimidazolium bromide + isobutanol | 1-octyl-3-methylimidazolium bromide + guanidine thiocyanate | 1-octyl-3-methylimidazolium bromide + 5-(4-dimethyl)amino benzylidene rhodanine + isobutanol | 1-octyl-3-methylimidazolium bromide + 5-(4-dimethyl)amino benzylidene rhodanine + guanidine thiocyanate | 1-octyl-3-methylimidazolium bromide + 5-(4-dimethyl)amino benzylidene rhodanine + isobutanol + guanidine thiocyanate | 1-octyl-3-methylimidazolium bromide + isobutanol + guanidine thiocyanate |
| 1-methyl-3-carboxyethyl-imidazolium bromide | 1-methyl-3-carboxyethyl-imidazolium bromide + sulfosalicylic acid | 1-methyl-3-carboxyethyl-imidazolium bromide + isobutanol | 1-methyl-3-carboxyethyl-imidazolium bromide + guanidine thiocyanate | 1-methyl-3-carboxyethyl-imidazolium bromide + sulfosalicylic acid + isobutanol | 1-methyl-3-carboxyethyl-imidazolium bromide + sulfosalicylic acid + guanidine thiocyanate | 1-methyl-3-carboxyethyl-imidazolium bromide + sulfosalicylic acid + isobutanol + guanidine thiocyanate | 1-methyl-3-carboxyethyl-imidazolium bromide + isobutanol + guanidine thiocyanate |
| 1-hexyl-3-methylimidazolium bromide | 1-hexyl-3-methylimidazolium bromide + sulfosalicylic acid | 1-hexyl-3-methylimidazolium bromide + isobutanol | 1-hexyl-3-methylimidazolium bromide + guanidine thiocyanate | 1-hexyl-3-methylimidazolium bromide + sulfosalicylic acid + isobutanol | 1-hexyl-3-methylimidazolium bromide + sulfosalicylic acid + guanidine thiocyanate | 1-hexyl-3-methylimidazolium bromide + sulfosalicylic acid + isobutanol + guanidine thiocyanate | 1-hexyl-3-methylimidazolium bromide + isobutanol + guanidine thiocyanate |

TABLE 5-continued

EXEMPLARY STORAGE COMPOSITIONS

| (A) Compound of Formula (I) | (A) + (B) Precipitating Agent | (A) + (C) Lower Alcohol | (A) + (D) Chaotrope | (A) + (B) + (C) | (A) + (B) + (D) | (A) + (B) + (C) + (D) | (A) + (C) + (D) |
|---|---|---|---|---|---|---|---|
| 1-decyl-3-methylimidazolium bromide | 1-decyl-3-methylimidazolium bromide + sulfosalicylic acid | 1-decyl-3-methylimidazolium bromide + isobutanol | 1-decyl-3-methylimidazolium bromide + guanidine thiocyanate | 1-decyl-3-methylimidazolium bromide + sulfosalicylic acid + isobutanol | 1-decyl-3-methylimidazolium bromide + sulfosalicylic acid + guanidine thiocyanate | 1-decyl-3-methylimidazolium bromide + sulfosalicylic acid + isobutanol + guanidine thiocyanate | 1-decyl-3-methylimidazolium bromide + isobutanol + guanidine thiocyanate |
| 1-(2-hydroxyethyl)-3-methylimidazolium bromide | 1-(2-hydroxyethyl)-3-methylimidazolium bromide + sulfosalicylic acid | 1-(2-hydroxyethyl)-3-methylimidazolium bromide + isobutanol | 1-(2-hydroxyethyl)-3-methylimidazolium bromide + guanidine thiocyanate | 1-(2-hydroxyethyl)-3-methylimidazolium bromide + sulfosalicylic acid + isobutanol | 1-(2-hydroxyethyl)-3-methylimidazolium bromide + sulfosalicylic acid + guanidine thiocyanate | 1-(2-hydroxyethyl)-3-methylimidazolium bromide + sulfosalicylic acid + isobutanol + guanidine thiocyanate | 1-(2-hydroxyethyl)-3-methylimidazolium bromide + isobutanol + guanidine thiocyanate |
| 1-octyl-3-methylimidazolium bromide | 1-octyl-3-methylimidazolium bromide + sulfosalicylic acid | 1-octyl-3-methylimidazolium bromide + isobutanol | 1-octyl-3-methylimidazolium bromide + guanidine thiocyanate | 1-octyl-3-methylimidazolium bromide + sulfosalicylic acid + isobutanol | 1-octyl-3-methylimidazolium bromide + sulfosalicylic acid + guanidine thiocyanate | 1-octyl-3-methylimidazolium bromide + sulfosalicylic acid + isobutanol + guanidine thiocyanate | 1-octyl-3-methylimidazolium bromide + isobutanol + guanidine thiocyanate |
| 1-methyl-3-carboxyethyl-imidazolium bromide | 1-methyl-3-carboxyethyl-imidazolium bromide + lithium chloride | 1-methyl-3-carboxyethyl-imidazolium bromide + isobutanol | 1-methyl-3-carboxyethyl-imidazolium bromide + guanidine thiocyanate | 1-methyl-3-carboxyethyl-imidazolium bromide + LiCl + isobutanol | 1-methyl-3-carboxyethyl-imidazolium bromide + LiCl + guanidine thiocyanate | 1-methyl-3-carboxyethyl-imidazolium bromide + LiCl + isobutanol + guanidine thiocyanate | 1-methyl-3-carboxyethyl-imidazolium bromide + isobutanol + guanidine thiocyanate |
| 1-hexyl-3-methylimidazolium bromide | 1-hexyl-3-methylimidazolium bromide + lithium chloride | 1-hexyl-3-methylimidazolium bromide + isobutanol | 1-hexyl-3-methylimidazolium bromide + guanidine thiocyanate | 1-hexyl-3-methylimidazolium bromide + LiCl + isobutanol | 1-hexyl-3-methylimidazolium bromide + LiCl + guanidine thiocyanate | 1-hexyl-3-methylimidazolium bromide + LiCl + isobutanol + guanidine thiocyanate | 1-hexyl-3-methylimidazolium bromide + isobutanol + guanidine thiocyanate |
| 1-decyl-3-methylimidazolium bromide | 1-decyl-3-methylimidazolium bromide + lithium chloride | 1-decyl-3-methylimidazolium bromide + isobutanol | 1-decyl-3-methylimidazolium bromide + guanidine thiocyanate | 1-decyl-3-methylimidazolium bromide + LiCl + isobutanol | 1-decyl-3-methylimidazolium bromide + LiCl + guanidine thiocyanate | 1-decyl-3-methylimidazolium bromide + LiCl + isobutanol + guanidine thiocyanate | 1-decyl-3-methylimidazolium bromide + isobutanol + guanidine thiocyanate |
| 1-(2-hydroxyethyl)-3-methylimidazolium bromide | 1-(2-hydroxyethyl)-3-methylimidazolium bromide + lithium chloride | 1-(2-hydroxyethyl)-3-methylimidazolium bromide + isobutanol | 1-(2-hydroxyethyl)-3-methylimidazolium bromide + guanidine thiocyanate | 1-(2-hydroxyethyl)-3-methylimidazolium bromide + LiCl + isobutanol | 1-(2-hydroxyethyl)-3-methylimidazolium bromide + LiCl + guanidine thiocyanate | 1-(2-hydroxyethyl)-3-methylimidazolium bromide + LiCl + isobutanol + guanidine thiocyanate | 1-(2-hydroxyethyl)-3-methylimidazolium bromide + isobutanol + guanidine thiocyanate |

TABLE 5-continued

EXEMPLARY STORAGE COMPOSITIONS

| (A) Compound of Formula (I) | (A) + (B) Precipitating Agent | (A) + (C) Lower Alcohol | (A) + (D) Chaotrope | (A) + (B) + (C) | (A) + (B) + (D) | (A) + (B) + (C) + (D) | (A) + (C) + (D) |
|---|---|---|---|---|---|---|---|
| 1-octyl-3-methylimidazolium bromide | 1-octyl-3-methylimidazolium bromide + lithium chloride | 1-octyl-3-methylimidazolium bromide + isobutanol | 1-octyl-3-methylimidazolium bromide + guanidine thiocyanate | 1-octyl-3-methylimidazolium bromide + LiCl + isobutanol | 1-octyl-3-methylimidazolium bromide + LiCl + guanidine thiocyanate | 1-octyl-3-methylimidazolium bromide + LiCl + isobutanol + guanidine thiocyanate | 1-octyl-3-methylimidazolium bromide + isobutanol + guanidine thiocyanate |
| 1-methyl-3-carboxyethyl-imidazolium bromide | 1-methyl-3-carboxyethyl-imidazolium bromide + lithium hydroxide | 1-methyl-3-carboxyethyl-imidazolium bromide + isobutanol | 1-methyl-3-carboxyethyl-imidazolium bromide + guanidine thiocyanate | 1-methyl-3-carboxyethyl-imidazolium bromide + LiOH + isobutanol | 1-methyl-3-carboxyethyl-imidazolium bromide + LiOH + guanidine thiocyanate | 1-methyl-3-carboxyethyl-imidazolium bromide + LiOH + isobutanol + guanidine thiocyanate | 1-methyl-3-carboxyethyl-imidazolium bromide + isobutanol + guanidine thiocyanate |
| 1-hexyl-3-methylimidazolium bromide | 1-hexyl-3-methylimidazolium bromide + lithium hydroxide | 1-hexyl-3-methylimidazolium bromide + isobutanol | 1-hexyl-3-methylimidazolium bromide + guanidine thiocyanate | 1-hexyl-3-methylimidazolium bromide + LiOH + isobutanol | 1-hexyl-3-methylimidazolium bromide + LiOH + guanidine thiocyanate | 1-hexyl-3-methylimidazolium bromide + LiOH + isobutanol + guanidine thiocyanate | 1-hexyl-3-methylimidazolium bromide + isobutanol + guanidine thiocyanate |
| 1-decyl-3-methylimidazolium bromide | 1-decyl-3-methylimidazolium bromide + lithium hydroxide | 1-decyl-3-methylimidazolium bromide + isobutanol | 1-decyl-3-methylimidazolium bromide + guanidine thiocyanate | 1-decyl-3-methylimidazolium bromide + LiOH + isobutanol | 1-decyl-3-methylimidazolium bromide + LiOH + guanidine thiocyanate | 1-decyl-3-methylimidazolium bromide + LiOH + isobutanol + guanidine thiocyanate | 1-decyl-3-methylimidazolium bromide + isobutanol + guanidine thiocyanate |
| 1-(2-hydroxyethyl)-3-methylimidazolium bromide | 1-(2-hydroxyethyl)-3-methylimidazolium bromide + lithium hydroxide | 1-(2-hydroxyethyl)-3-methylimidazolium bromide + isobutanol | 1-(2-hydroxyethyl)-3-methylimidazolium bromide + guanidine thiocyanate | 1-(2-hydroxyethyl)-3-methylimidazolium bromide + LiOH + isobutanol | 1-(2-hydroxyethyl)-3-methylimidazolium bromide + LiOH + guanidine thiocyanate | 1-(2-hydroxyethyl)-3-methylimidazolium bromide + LiOH + isobutanol + guanidine thiocyanate | 1-(2-hydroxyethyl)-3-methylimidazolium bromide + isobutanol + guanidine thiocyanate |
| 1-octyl-3-methylimidazolium bromide | 1-octyl-3-methylimidazolium bromide + lithium hydroxide | 1-octyl-3-methylimidazolium bromide + isobutanol | 1-octyl-3-methylimidazolium bromide + potassium thiocyanate | 1-octyl-3-methylimidazolium bromide + LiOH + isobutanol | 1-octyl-3-methylimidazolium bromide + LiOH + potassium thiocyanate | 1-octyl-3-methylimidazolium bromide + LiOH + isobutanol + guanidine thiocyanate | 1-octyl-3-methylimidazolium bromide + isobutanol + guanidine thiocyanate |
| 1-methyl-3-carboxyethyl-imidazolium bromide | 1-methyl-3-carboxyethyl-imidazolium bromide + 5-(4-dimethyl)amino benzylidene rhodanine | 1-methyl-3-carboxyethyl-imidazolium bromide + methanol | 1-methyl-3-carboxyethyl-imidazolium bromide + potassium thiocyanate | 1-methyl-3-carboxyethyl-imidazolium bromide + 5-(4-dimethyl)amino benzylidene rhodanine + methanol | 1-methyl-3-carboxyethyl-imidazolium bromide + 5-(4-dimethyl)amino benzylidene rhodanine + potassium thiocyanate | 1-methyl-3-carboxyethyl-imidazolium bromide + 5-(4-dimethyl)amino benzylidene rhodanine + methanol + potassium thiocyanate | 1-methyl-3-carboxyethyl-imidazolium bromide + methanol + potassium thiocyanate |

TABLE 5-continued

EXEMPLARY STORAGE COMPOSITIONS

| (A) Compound of Formula (I) | (A) + (B) Precipitating Agent | (A) + (C) Lower Alcohol | (A) + (D) Chaotrope | (A) + (B) + (C) | (A) + (B) + (D) | (A) + (B) + (C) + (D) | (A) + (C) + (D) |
|---|---|---|---|---|---|---|---|
| 1-hexyl-3-methylimidazolium bromide | 1-hexyl-3-methylimidazolium bromide + 5-(4-dimethyl)amino benzylidene rhodanine | 1-hexyl-3-methylimidazolium bromide + methanol | 1-hexyl-3-methylimidazolium bromide + potassium thiocyanate | 1-hexyl-3-methylimidazolium bromide + 5-(4-dimethyl)amino benzylidene rhodanine + methanol | 1-hexyl-3-methylimidazolium bromide + 5-(4-dimethyl)amino benzylidene rhodanine + potassium thiocyanate | 1-hexyl-3-methylimidazolium bromide + 5-(4-dimethyl)amino benzylidene rhodanine + methanol + potassium thiocyanate | 1-hexyl-3-methylimidazolium bromide + methanol + potassium thiocyanate |
| 1-decyl-3-methylimidazolium bromide | 1-decyl-3-methylimidazolium bromide + 5-(4-dimethyl)amino benzylidene rhodanine | 1-decyl-3-methylimidazolium bromide + methanol | 1-decyl-3-methylimidazolium bromide + potassium thiocyanate | 1-decyl-3-methylimidazolium bromide + 5-(4-dimethyl)amino benzylidene rhodanine + methanol | 1-decyl-3-methylimidazolium bromide + 5-(4-dimethyl)amino benzylidene rhodanine + potassium thiocyanate | 1-decyl-3-methylimidazolium bromide + 5-(4-dimethyl)amino benzylidene rhodanine + methanol + potassium thiocyanate | 1-decyl-3-methylimidazolium bromide + methanol + potassium thiocyanate |
| 1-(2-hydroxyethyl)-3-methylimidazolium bromide | 1-(2-hydroxyethyl)-3-methylimidazolium bromide + 5-(4-dimethyl)amino benzylidene rhodanine | 1-(2-hydroxyethyl)-3-methylimidazolium bromide + methanol | 1-(2-hydroxyethyl)-3-methylimidazolium bromide + potassium thiocyanate | 1-(2-hydroxyethyl)-3-methylimidazolium bromide + 5-(4-dimethyl)amino benzylidene rhodanine + methanol | 1-(2-hydroxyethyl)-3-methylimidazolium bromide + 5-(4-dimethyl)amino benzylidene rhodanine + potassium thiocyanate | 1-(2-hydroxyethyl)-3-methylimidazolium bromide + 5-(4-dimethyl)amino benzylidene rhodanine + methanol + potassium thiocyanate | 1-(2-hydroxyethyl)-3-methylimidazolium bromide + methanol + potassium thiocyanate |
| 1-octyl-3-methylimidazolium bromide | 1-octyl-3-methylimidazolium bromide + 5-(4-dimethyl)amino benzylidene rhodanine | 1-octyl-3-methylimidazolium bromide + methanol | 1-octyl-3-methylimidazolium bromide + potassium thiocyanate | 1-octyl-3-methylimidazolium bromide + 5-(4-dimethyl)amino benzylidene rhodanine + methanol | 1-octyl-3-methylimidazolium bromide + 5-(4-dimethyl)amino benzylidene rhodanine + potassium thiocyanate | 1-octyl-3-methylimidazolium bromide + 5-(4-dimethyl)amino benzylidene rhodanine + methanol + potassium thiocyanate | 1-octyl-3-methylimidazolium bromide + methanol + potassium thiocyanate |
| 1-methyl-3-carboxyethyl-imidazolium bromide | 1-methyl-3-carboxyethyl-imidazolium bromide + sulfosalicylic acid | 1-methyl-3-carboxyethyl-imidazolium bromide + methanol | 1-methyl-3-carboxyethyl-imidazolium bromide + potassium thiocyanate | 1-methyl-3-carboxyethyl-imidazolium bromide + sulfosalicylic acid + methanol | 1-methyl-3-carboxyethyl-imidazolium bromide + sulfosalicylic acid + potassium thiocyanate | 1-methyl-3-carboxyethyl-imidazolium bromide + sulfosalicylic acid + methanol + potassium thiocyanate | 1-methyl-3-carboxyethyl-imidazolium bromide + methanol + potassium thiocyanate |

TABLE 5-continued

EXEMPLARY STORAGE COMPOSITIONS

| (A) Compound of Formula (I) | (A) + (B) Precipitating Agent | (A) + (C) Lower Alcohol | (A) + (D) Chaotrope | (A) + (B) + (C) | (A) + (B) + (D) | (A) + (B) + (C) + (D) | (A) + (C) + (D) |
|---|---|---|---|---|---|---|---|
| 1-hexyl-3-methylimidazolium bromide | 1-hexyl-3-methylimidazolium bromide + sulfosalicylic acid | 1-hexyl-3-methylimidazolium bromide + methanol | 1-hexyl-3-methylimidazolium bromide + potassium thiocyanate | 1-hexyl-3-methylimidazolium bromide + sulfosalicylic acid + methanol | 1-hexyl-3-methylimidazolium bromide + sulfosalicylic acid + potassium thiocyanate | 1-hexyl-3-methylimidazolium bromide + sulfosalicylic acid + methanol + potassium thiocyanate | 1-hexyl-3-methylimidazolium bromide + methanol + potassium thiocyanate |
| 1-decyl-3-methylimidazolium bromide | 1-decyl-3-methylimidazolium bromide + sulfosalicylic acid | 1-decyl-3-methylimidazolium bromide + methanol | 1-decyl-3-methylimidazolium bromide + potassium thiocyanate | 1-decyl-3-methylimidazolium bromide + sulfosalicylic acid + methanol | 1-decyl-3-methylimidazolium bromide + sulfosalicylic acid + potassium thiocyanate | 1-decyl-3-methylimidazolium bromide + sulfosalicylic acid + methanol + potassium thiocyanate | 1-decyl-3-methylimidazolium bromide + methanol + potassium thiocyanate |
| 1-(2-hydroxyethyl)-3-methylimidazolium bromide | 1-(2-hydroxyethyl)-3-methylimidazolium bromide + sulfosalicylic acid | 1-(2-hydroxyethyl)-3-methylimidazolium bromide + methanol | 1-(2-hydroxyethyl)-3-methylimidazolium bromide + potassium thiocyanate | 1-(2-hydroxyethyl)-3-methylimidazolium bromide + sulfosalicylic acid + methanol | 1-(2-hydroxyethyl)-3-methylimidazolium bromide + sulfosalicylic acid + potassium thiocyanate | 1-(2-hydroxyethyl)-3-methylimidazolium bromide + sulfosalicylic acid + methanol + potassium thiocyanate | 1-(2-hydroxyethyl)-3-methylimidazolium bromide + methanol + potassium thiocyanate |
| 1-octyl-3-methylimidazolium bromide | 1-octyl-3-methylimidazolium bromide + sulfosalicylic acid | 1-octyl-3-methylimidazolium bromide + methanol | 1-octyl-3-methylimidazolium bromide + potassium thiocyanate | 1-octyl-3-methylimidazolium bromide + sulfosalicylic acid + methanol | 1-octyl-3-methylimidazolium bromide + sulfosalicylic acid + potassium thiocyanate | 1-octyl-3-methylimidazolium bromide + sulfosalicylic acid + methanol + potassium thiocyanate | 1-octyl-3-methylimidazolium bromide + methanol + potassium thiocyanate |
| 1-methyl-3-carboxyethyl-imidazolium bromide | 1-methyl-3-carboxyethyl-imidazolium bromide + lithium chloride | 1-methyl-3-carboxyethyl-imidazolium bromide + methanol | 1-methyl-3-carboxyethyl-imidazolium bromide + potassium thiocyanate | 1-methyl-3-carboxyethyl-imidazolium bromide + Lithium chloride + methanol | 1-methyl-3-carboxyethyl-imidazolium bromide + LiCl + potassium thiocyanate | 1-methyl-3-carboxyethyl-imidazolium bromide + LiCl + methanol + potassium thiocyanate | 1-methyl-3-carboxyethyl-imidazolium bromide + methanol + potassium thiocyanate |
| 1-hexyl-3-methylimidazolium bromide | 1-hexyl-3-methylimidazolium bromide + lithium chloride | 1-hexyl-3-methylimidazolium bromide + methanol | 1-hexyl-3-methylimidazolium bromide + potassium thiocyanate | 1-hexyl-3-methylimidazolium bromide + Lithium chloride + methanol | 1-hexyl-3-methylimidazolium bromide + LiCl + potassium thiocyanate | 1-hexyl-3-methylimidazolium bromide + LiCl + methanol + potassium thiocyanate | 1-hexyl-3-methylimidazolium bromide + methanol + potassium thiocyanate |
| 1-decyl-3-methylimidazolium bromide | 1-decyl-3-methylimidazolium bromide + lithium chloride | 1-decyl-3-methylimidazolium bromide + methanol | 1-decyl-3-methylimidazolium bromide + potassium thiocyanate | 1-decyl-3-methylimidazolium bromide + Lithium chloride + methanol | 1-decyl-3-methylimidazolium bromide + LiCl + potassium thiocyanate | 1-decyl-3-methylimidazolium bromide + LiCl + methanol + potassium thiocyanate | 1-decyl-3-methylimidazolium bromide + methanol + potassium thiocyanate |

TABLE 5-continued

EXEMPLARY STORAGE COMPOSITIONS

| (A) Compound of Formula (I) | (A) + (B) Precipitating Agent | (A) + (C) Lower Alcohol | (A) + (D) Chaotrope | (A) + (B) + (C) | (A) + (B) + (D) | (A) + (B) + (C) + (D) | (A) + (C) + (D) |
|---|---|---|---|---|---|---|---|
| 1-(2-hydroxyethyl)-3-methylimidazolium bromide | 1-(2-hydroxyethyl)-3-methylimidazolium bromide + lithium chloride | 1-(2-hydroxyethyl)-3-methylimidazolium bromide + methanol | 1-(2-hydroxyethyl)-3-methylimidazolium bromide + potassium thiocyanate | 1-(2-hydroxyethyl)-3-methylimidazolium bromide + Lithium chloride + methanol | 1-(2-hydroxyethyl)-3-methylimidazolium bromide + LiCl + potassium thiocyanate | 1-(2-hydroxyethyl)-3-methylimidazolium bromide + LiCl + methanol + potassium thiocyanate | 1-(2-hydroxyethyl)-3-methylimidazolium bromide + methanol + potassium thiocyanate |
| 1-octyl-3-methylimidazolium bromide | 1-octyl-3-methylimidazolium bromide + lithium chloride | 1-octyl-3-methylimidazolium bromide + methanol | 1-octyl-3-methylimidazolium bromide + potassium thiocyanate | 1-octyl-3-methylimidazolium bromide + Lithium chloride + methanol | 1-octyl-3-methylimidazolium bromide + LiCl + potassium thiocyanate | 1-octyl-3-methylimidazolium bromide + LiCl + methanol + potassium thiocyanate | 1-octyl-3-methylimidazolium bromide + methanol + potassium thiocyanate |
| 1-methyl-3-carboxyethyl-imidazolium bromide | 1-methyl-3-carboxyethyl-imidazolium bromide + lithium hydroxide | 1-methyl-3-carboxyethyl-imidazolium bromide + methanol | 1-methyl-3-carboxyethyl-imidazolium bromide + potassium thiocyanate | 1-methyl-3-carboxyethyl-imidazolium bromide + Lithium hydroxide + methanol | 1-methyl-3-carboxyethyl-imidazolium bromide + LiOH + potassium thiocyanate | 1-methyl-3-carboxyethyl-imidazolium bromide + LiOH + methanol + potassium thiocyanate | 1-methyl-3-carboxyethyl-imidazolium bromide + methanol + potassium thiocyanate |
| 1-hexyl-3-methylimidazolium bromide | 1-hexyl-3-methylimidazolium bromide + lithium hydroxide | 1-hexyl-3-methylimidazolium bromide + methanol | 1-hexyl-3-methylimidazolium bromide + potassium thiocyanate | 1-hexyl-3-methylimidazolium bromide + Lithium hydroxide + methanol | 1-hexyl-3-methylimidazolium bromide + LiOH + potassium thiocyanate | 1-hexyl-3-methylimidazolium bromide + LiOH + methanol + potassium thiocyanate | 1-hexyl-3-methylimidazolium bromide + methanol + potassium thiocyanate |
| 1-decyl-3-methylimidazolium bromide | 1-decyl-3-methylimidazolium bromide + lithium hydroxide | 1-decyl-3-methylimidazolium bromide + methanol | 1-decyl-3-methylimidazolium bromide + potassium thiocyanate | 1-decyl-3-methylimidazolium bromide + Lithium hydroxide + methanol | 1-decyl-3-methylimidazolium bromide + LiOH + potassium thiocyanate | 1-decyl-3-methylimidazolium bromide + LiOH + methanol + potassium thiocyanate | 1-decyl-3-methylimidazolium bromide + methanol + potassium thiocyanate |
| 1-(2-hydroxyethyl)-3-methylimidazolium bromide | 1-(2-hydroxyethyl)-3-methylimidazolium bromide + lithium hydroxide | 1-(2-hydroxyethyl)-3-methylimidazolium bromide + methanol | 1-(2-hydroxyethyl)-3-methylimidazolium bromide + potassium thiocyanate | 1-(2-hydroxyethyl)-3-methylimidazolium bromide + Lithium hydroxide + methanol | 1-(2-hydroxyethyl)-3-methylimidazolium bromide + LiOH + potassium thiocyanate | 1-(2-hydroxyethyl)-3-methylimidazolium bromide + LiOH + methanol + potassium thiocyanate | 1-(2-hydroxyethyl)-3-methylimidazolium bromide + methanol + potassium thiocyanate |
| 1-octyl-3-methylimidazolium bromide | 1-octyl-3-methylimidazolium bromide + lithium hydroxide | 1-octyl-3-methylimidazolium bromide + methanol | 1-octyl-3-methylimidazolium bromide + potassium thiocyanate | 1-octyl-3-methylimidazolium bromide + Lithium hydroxide + methanol | 1-octyl-3-methylimidazolium bromide + LiOH + potassium thiocyanate | 1-octyl-3-methylimidazolium bromide + LiOH + methanol + potassium thiocyanate | 1-octyl-3-methylimidazolium bromide + methanol + potassium thiocyanate |

TABLE 5-continued

EXEMPLARY STORAGE COMPOSITIONS

| (A) Compound of Formula (I) | (A) + (B) Precipitating Agent | (A) + (C) Lower Alcohol | (A) + (D) Chaotrope | (A) + (B) + (C) | (A) + (B) + (D) | (A) + (B) + (C) + (D) | (A) + (C) + (D) |
|---|---|---|---|---|---|---|---|
| 1-methyl-3-carboxyethyl-imidazolium bromide | 1-methyl-3-carboxyethyl-imidazolium bromide + 5-(4-dimethyl)amino benzylidene rhodanine | 1-methyl-3-carboxyethyl-imidazolium bromide + ethanol | 1-methyl-3-carboxyethyl-imidazolium bromide + potassium thiocyanate | 1-methyl-3-carboxyethyl-imidazolium bromide + 5-(4-dimethyl)amino benzylidene rhodanine + ethanol | 1-methyl-3-carboxyethyl-imidazolium bromide + 5-(4-dimethyl)amino benzylidene rhodanine + potassium thiocyanate | 1-methyl-3-carboxyethyl-imidazolium bromide + 5-(4-dimethyl)amino benzylidene rhodanine + ethanol + potassium thiocyanate | 1-methyl-3-carboxyethyl-imidazolium bromide + ethanol + potassium thiocyanate |
| 1-hexyl-3-methylimidazolium bromide | 1-hexyl-3-methylimidazolium bromide + 5-(4-dimethyl)amino benzylidene rhodanine | 1-hexyl-3-methylimidazolium bromide + ethanol | 1-hexyl-3-methylimidazolium bromide + potassium thiocyanate | 1-hexyl-3-methylimidazolium bromide + 5-(4-dimethyl)amino benzylidene rhodanine + ethanol | 1-hexyl-3-methylimidazolium bromide + 5-(4-dimethyl)amino benzylidene rhodanine + potassium thiocyanate | 1-hexyl-3-methylimidazolium bromide + 5-(4-dimethyl)amino benzylidene rhodanine + ethanol + potassium thiocyanate | 1-hexyl-3-methylimidazolium bromide + ethanol + potassium thiocyanate |
| 1-decyl-3-methylimidazolium bromide | 1-decyl-3-methylimidazolium bromide + 5-(4-dimethyl)amino benzylidene rhodanine | 1-decyl-3-methylimidazolium bromide + ethanol | 1-decyl-3-methylimidazolium bromide + potassium thiocyanate | 1-decyl-3-methylimidazolium bromide + 5-(4-dimethyl)amino benzylidene rhodanine + ethanol | 1-decyl-3-methylimidazolium bromide + 5-(4-dimethyl)amino benzylidene rhodanine + potassium thiocyanate | 1-decyl-3-methylimidazolium bromide + 5-(4-dimethyl)amino benzylidene rhodanine + ethanol + potassium thiocyanate | 1-decyl-3-methylimidazolium bromide + ethanol + potassium thiocyanate |
| 1-(2-hydroxyethyl)-3-methylimidazolium bromide | 1-(2-hydroxyethyl)-3-methylimidazolium bromide + 5-(4-dimethyl)amino benzylidene rhodanine | 1-(2-hydroxyethyl)-3-methylimidazolium bromide + ethanol | 1-(2-hydroxyethyl)-3-methylimidazolium bromide + potassium thiocyanate | 1-(2-hydroxyethyl)-3-methylimidazolium bromide + 5-(4-dimethyl)amino benzylidene rhodanine + ethanol | 1-(2-hydroxyethyl)-3-methylimidazolium bromide + 5-(4-dimethyl)amino benzylidene rhodanine + potassium thiocyanate | 1-(2-hydroxyethyl)-3-methylimidazolium bromide + 5-(4-dimethyl)amino benzylidene rhodanine + ethanol + potassium thiocyanate | 1-(2-hydroxyethyl)-3-methylimidazolium bromide + ethanol + potassium thiocyanate |
| 1-octyl-3-methylimidazolium bromide | 1-octyl-3-methylimidazolium bromide + 5-(4-dimethyl)amino benzylidene rhodanine | 1-octyl-3-methylimidazolium bromide + ethanol | 1-octyl-3-methylimidazolium bromide + potassium thiocyanate | 1-octyl-3-methylimidazolium bromide + 5-(4-dimethyl)amino benzylidene rhodanine + ethanol | 1-octyl-3-methylimidazolium bromide + 5-(4-dimethyl)amino benzylidene rhodanine + potassium thiocyanate | 1-octyl-3-methylimidazolium bromide + 5-(4-dimethyl)amino benzylidene rhodanine + ethanol + potassium thiocyanate | 1-octyl-3-methylimidazolium bromide + ethanol + potassium thiocyanate |

TABLE 5-continued

EXEMPLARY STORAGE COMPOSITIONS

| (A) Compound of Formula (I) | (A) + (B) Precipitating Agent | (A) + (C) Lower Alcohol | (A) + (D) Chaotrope | (A) + (B) + (C) | (A) + (B) + (D) | (A) + (B) + (C) + (D) | (A) + (C) + (D) |
|---|---|---|---|---|---|---|---|
| 1-methyl-3-carboxyethyl-imidazolium bromide | 1-methyl-3-carboxyethyl-imidazolium bromide + sulfosalicylic acid | 1-methyl-3-carboxyethyl-imidazolium bromide + ethanol | 1-methyl-3-carboxyethyl-imidazolium bromide + potassium thiocyanate | 1-methyl-3-carboxyethyl-imidazolium bromide + sulfosalicylic acid + ethanol | 1-methyl-3-carboxyethyl-imidazolium bromide + sulfosalicylic acid + potassium thiocyanate | 1-methyl-3-carboxyethyl-imidazolium bromide + sulfosalicylic acid + ethanol + potassium thiocyanate | 1-methyl-3-carboxyethyl-imidazolium bromide + ethanol + potassium thiocyanate |
| 1-hexyl-3-methylimidazolium bromide | 1-hexyl-3-methylimidazolium bromide + sulfosalicylic acid | 1-hexyl-3-methylimidazolium bromide + ethanol | 1-hexyl-3-methylimidazolium bromide + potassium thiocyanate | 1-hexyl-3-methylimidazolium bromide + sulfosalicylic acid + ethanol | 1-hexyl-3-methylimidazolium bromide + sulfosalicylic acid + potassium thiocyanate | 1-hexyl-3-methylimidazolium bromide + sulfosalicylic acid + ethanol + potassium thiocyanate | 1-hexyl-3-methylimidazolium bromide + ethanol + potassium thiocyanate |
| 1-decyl-3-methylimidazolium bromide | 1-decyl-3-methylimidazolium bromide + sulfosalicylic acid | 1-decyl-3-methylimidazolium bromide + ethanol | 1-decyl-3-methylimidazolium bromide + potassium thiocyanate | 1-decyl-3-methylimidazolium bromide + sulfosalicylic acid + ethanol | 1-decyl-3-methylimidazolium bromide + sulfosalicylic acid + potassium thiocyanate | 1-decyl-3-methylimidazolium bromide + sulfosalicylic acid + ethanol + potassium thiocyanate | 1-decyl-3-methylimidazolium bromide + ethanol + potassium thiocyanate |
| 1-(2-hydroxyethyl)-3-methylimidazolium bromide | 1-(2-hydroxyethyl)-3-methylimidazolium bromide + sulfosalicylic acid | 1-(2-hydroxyethyl)-3-methylimidazolium bromide + ethanol | 1-(2-hydroxyethyl)-3-methylimidazolium bromide + potassium thiocyanate | 1-(2-hydroxyethyl)-3-methylimidazolium bromide + sulfosalicylic acid + ethanol | 1-(2-hydroxyethyl)-3-methylimidazolium bromide + sulfosalicylic acid + potassium thiocyanate | 1-(2-hydroxyethyl)-3-methylimidazolium bromide + sulfosalicylic acid + ethanol + potassium thiocyanate | 1-(2-hydroxyethyl)-3-methylimidazolium bromide + ethanol + potassium thiocyanate |
| 1-octyl-3-methylimidazolium bromide | 1-octyl-3-methylimidazolium bromide + sulfosalicylic acid | 1-octyl-3-methylimidazolium bromide + ethanol | 1-octyl-3-methylimidazolium bromide + potassium thiocyanate | 1-octyl-3-methylimidazolium bromide + sulfosalicylic acid + ethanol | 1-octyl-3-methylimidazolium bromide + sulfosalicylic acid + potassium thiocyanate | 1-octyl-3-methylimidazolium bromide + sulfosalicylic acid + ethanol + potassium thiocyanate | 1-octyl-3-methylimidazolium bromide + ethanol + potassium thiocyanate |
| 1-methyl-3-carboxyethyl-imidazolium bromide | 1-methyl-3-carboxyethyl-imidazolium bromide + lithium chloride | 1-methyl-3-carboxyethyl-imidazolium bromide + ethanol | 1-methyl-3-carboxyethyl-imidazolium bromide + potassium thiocyanate | 1-methyl-3-carboxyethyl-imidazolium bromide + LiCl + ethanol | 1-methyl-3-carboxyethyl-imidazolium bromide + LiCl + potassium thiocyanate | 1-methyl-3-carboxyethyl-imidazolium bromide + LiCl + ethanol + potassium thiocyanate | 1-methyl-3-carboxyethyl-imidazolium bromide + ethanol + potassium thiocyanate |

TABLE 5-continued

EXEMPLARY STORAGE COMPOSITIONS

| (A) Compound of Formula (I) | (A) + (B) Precipitating Agent | (A) + (C) Lower Alcohol | (A) + (D) Chaotrope | (A) + (B) + (C) | (A) + (B) + (D) | (A) + (B) + (C) + (D) | (A) + (C) + (D) |
|---|---|---|---|---|---|---|---|
| 1-hexyl-3-methylimidazolium bromide | 1-hexyl-3-methylimidazolium bromide + lithium chloride | 1-hexyl-3-methylimidazolium bromide + ethanol | 1-hexyl-3-methylimidazolium bromide + potassium thiocyanate | 1-hexyl-3-methylimidazolium bromide + LiCl + ethanol | 1-hexyl-3-methylimidazolium bromide + LiCl + potassium thiocyanate | 1-hexyl-3-methylimidazolium bromide + LiCl + ethanol + potassium thiocyanate | 1-hexyl-3-methylimidazolium bromide + ethanol + potassium thiocyanate |
| 1-decyl-3-methylimidazolium bromide | 1-decyl-3-methylimidazolium bromide + lithium chloride | 1-decyl-3-methylimidazolium bromide + ethanol | 1-decyl-3-methylimidazolium bromide + potassium thiocyanate | 1-decyl-3-methylimidazolium bromide + LiCl + ethanol | 1-decyl-3-methylimidazolium bromide + LiCl + potassium thiocyanate | 1-decyl-3-methylimidazolium bromide + LiCl + ethanol + potassium thiocyanate | 1-decyl-3-methylimidazolium bromide + ethanol + potassium thiocyanate |
| 1-(2-hydroxyethyl)-3-methylimidazolium bromide | 1-(2-hydroxyethyl)-3-methylimidazolium bromide + lithium chloride | 1-(2-hydroxyethyl)-3-methylimidazolium bromide + ethanol | 1-(2-hydroxyethyl)-3-methylimidazolium bromide + potassium thiocyanate | 1-(2-hydroxyethyl)-3-methylimidazolium bromide + LiCl + ethanol | 1-(2-hydroxyethyl)-3-methylimidazolium bromide + LiCl + potassium thiocyanate | 1-(2-hydroxyethyl)-3-methylimidazolium bromide + LiCl + ethanol + potassium thiocyanate | 1-(2-hydroxyethyl)-3-methylimidazolium bromide + ethanol + potassium thiocyanate |
| 1-octyl-3-methylimidazolium bromide | 1-octyl-3-methylimidazolium bromide + lithium chloride | 1-octyl-3-methylimidazolium bromide + ethanol | 1-octyl-3-methylimidazolium bromide + potassium thiocyanate | 1-octyl-3-methylimidazolium bromide + LiCl + ethanol | 1-octyl-3-methylimidazolium bromide + LiCl + potassium thiocyanate | 1-octyl-3-methylimidazolium bromide + LiCl + ethanol + potassium thiocyanate | 1-octyl-3-methylimidazolium bromide + ethanol + potassium thiocyanate |
| 1-methyl-3-carboxyethyl-imidazolium bromide | 1-methyl-3-carboxyethyl-imidazolium bromide + lithium hydroxide | 1-methyl-3-carboxyethyl-imidazolium bromide + ethanol | 1-methyl-3-carboxyethyl-imidazolium bromide + potassium thiocyanate | 1-methyl-3-carboxyethyl-imidazolium bromide + LiOH + ethanol | 1-methyl-3-carboxyethyl-imidazolium bromide + LiOH + potassium thiocyanate | 1-methyl-3-carboxyethyl-imidazolium bromide + LiOH + ethanol + potassium thiocyanate | 1-methyl-3-carboxyethyl-imidazolium bromide + ethanol + potassium thiocyanate |
| 1-hexyl-3-methylimidazolium bromide | 1-hexyl-3-methylimidazolium bromide + lithium hydroxide | 1-hexyl-3-methylimidazolium bromide + ethanol | 1-hexyl-3-methylimidazolium bromide + potassium thiocyanate | 1-hexyl-3-methylimidazolium bromide + LiOH + ethanol | 1-hexyl-3-methylimidazolium bromide + LiOH + potassium thiocyanate | 1-hexyl-3-methylimidazolium bromide + LiOH + ethanol + potassium thiocyanate | 1-hexyl-3-methylimidazolium bromide + ethanol + potassium thiocyanate |
| 1-decyl-3-methylimidazolium bromide | 1-decyl-3-methylimidazolium bromide + lithium hydroxide | 1-decyl-3-methylimidazolium bromide + ethanol | 1-decyl-3-methylimidazolium bromide + potassium thiocyanate | 1-decyl-3-methylimidazolium bromide + LiOH + ethanol | 1-decyl-3-methylimidazolium bromide + LiOH + potassium thiocyanate | 1-decyl-3-methylimidazolium bromide + LiOH + ethanol + potassium thiocyanate | 1-decyl-3-methylimidazolium bromide + ethanol + potassium thiocyanate |

TABLE 5-continued

EXEMPLARY STORAGE COMPOSITIONS

| (A) Compound of Formula (I) | (A) + (B) Precipitating Agent | (A) + (C) Lower Alcohol | (A) + (D) Chaotrope | (A) + (B) + (C) | (A) + (B) + (D) | (A) + (C) + (D) | (A) + (B) + (C) + (D) |
|---|---|---|---|---|---|---|---|
| 1-(2-hydroxyethyl)-3-methylimidazolium bromide | 1-(2-hydroxyethyl)-3-methylimidazolium bromide + lithium hydroxide | 1-(2-hydroxyethyl)-3-methylimidazolium bromide + ethanol | 1-(2-hydroxyethyl)-3-methylimidazolium bromide + potassium thiocyanate | 1-(2-hydroxyethyl)-3-methylimidazolium bromide + LiOH + ethanol | 1-(2-hydroxyethyl)-3-methylimidazolium bromide + LiOH + potassium thiocyanate | 1-(2-hydroxyethyl)-3-methylimidazolium bromide + LiOH + ethanol + potassium thiocyanate | 1-(2-hydroxyethyl)-3-methylimidazolium bromide + ethanol + potassium thiocyanate |
| 1-octyl-3-methylimidazolium bromide | 1-octyl-3-methylimidazolium bromide + lithium hydroxide | 1-octyl-3-methylimidazolium bromide + ethanol | 1-octyl-3-methylimidazolium bromide + potassium thiocyanate | 1-octyl-3-methylimidazolium bromide + LiOH + ethanol | 1-octyl-3-methylimidazolium bromide + LiOH + potassium thiocyanate | 1-octyl-3-methylimidazolium bromide + LiOH + ethanol + potassium thiocyanate | 1-octyl-3-methylimidazolium bromide + ethanol + potassium thiocyanate |
| 1-methyl-3-carboxyethyl-imidazolium bromide | 1-methyl-3-carboxyethyl-imidazolium bromide + 5-(4-dimethyl)amino benzylidene rhodanine | 1-methyl-3-carboxyethyl-imidazolium bromide + n-propanol | 1-methyl-3-carboxyethyl-imidazolium bromide + potassium thiocyanate | 1-methyl-3-carboxyethyl-imidazolium bromide + 5-(4-dimethyl)amino benzylidene rhodanine + n-propanol | 1-methyl-3-carboxyethyl-imidazolium bromide + 5-(4-dimethyl)amino benzylidene rhodanine + potassium thiocyanate | 1-methyl-3-carboxyethyl-imidazolium bromide + 5-(4-dimethyl)amino benzylidene rhodanine + n-propanol + potassium thiocyanate | 1-methyl-3-carboxyethyl-imidazolium bromide + n-propanol + potassium thiocyanate |
| 1-hexyl-3-methylimidazolium bromide | 1-hexyl-3-methylimidazolium bromide + 5-(4-dimethyl)amino benzylidene rhodanine | 1-hexyl-3-methylimidazolium bromide + n-propanol | 1-hexyl-3-methylimidazolium bromide + potassium thiocyanate | 1-hexyl-3-methylimidazolium bromide + 5-(4-dimethyl)amino benzylidene rhodanine + n-propanol | 1-hexyl-3-methylimidazolium bromide + 5-(4-dimethyl)amino benzylidene rhodanine + potassium thiocyanate | 1-hexyl-3-methylimidazolium bromide + 5-(4-dimethyl)amino benzylidene rhodanine + n-propanol + potassium thiocyanate | 1-hexyl-3-methylimidazolium bromide + n-propanol + potassium thiocyanate |
| 1-decyl-3-methylimidazolium bromide | 1-decyl-3-methylimidazolium bromide + 5-(4-dimethyl)amino benzylidene rhodanine | 1-decyl-3-methylimidazolium bromide + n-propanol | 1-decyl-3-methylimidazolium bromide + potassium thiocyanate | 1-decyl-3-methylimidazolium bromide + 5-(4-dimethyl)amino benzylidene rhodanine + n-propanol | 1-decyl-3-methylimidazolium bromide + 5-(4-dimethyl)amino benzylidene rhodanine + potassium thiocyanate | 1-decyl-3-methylimidazolium bromide + 5-(4-dimethyl)amino benzylidene rhodanine + n-propanol + potassium thiocyanate | 1-decyl-3-methylimidazolium bromide + n-propanol + potassium thiocyanate |

TABLE 5-continued

EXEMPLARY STORAGE COMPOSITIONS

| (A) Compound of Formula (I) | (A) + (B) Precipitating Agent | (A) + (C) Lower Alcohol | (A) + (D) Chaotrope | (A) + (B) + (C) | (A) + (B) + (D) | (A) + (B) + (C) + (D) | (A) + (C) + (D) |
|---|---|---|---|---|---|---|---|
| 1-(2-hydroxyethyl)-3-methylimidazolium bromide | 1-(2-hydroxyethyl)-3-methylimidazolium bromide + 5-(4-dimethyl)amino benzylidene rhodanine | 1-(2-hydroxyethyl)-3-methylimidazolium bromide + n-propanol | 1-(2-hydroxyethyl)-3-methylimidazolium bromide + potassium thiocyanate | 1-(2-hydroxyethyl)-3-methylimidazolium bromide + 5-(4-dimethyl)amino benzylidene rhodanine + n-propanol | 1-(2-hydroxyethyl)-3-methylimidazolium bromide + 5-(4-dimethyl)amino benzylidene rhodanine + potassium thiocyanate | 1-(2-hydroxyethyl)-3-methylimidazolium bromide + 5-(4-dimethyl)amino benzylidene rhodanine + n-propanol + potassium thiocyanate | 1-(2-hydroxyethyl)-3-methylimidazolium bromide + n-propanol + potassium thiocyanate |
| 1-octyl-3-methylimidazolium bromide | 1-octyl-3-methylimidazolium bromide + 5-(4-dimethyl)amino benzylidene rhodanine | 1-octyl-3-methylimidazolium bromide + n-propanol | 1-octyl-3-methylimidazolium bromide + potassium thiocyanate | 1-octyl-3-methylimidazolium bromide + 5-(4-dimethyl)amino benzylidene rhodanine + n-propanol | 1-octyl-3-methylimidazolium bromide + 5-(4-dimethyl)amino benzylidene rhodanine + potassium thiocyanate | 1-octyl-3-methylimidazolium bromide + 5-(4-dimethyl)amino benzylidene rhodanine + n-propanol + potassium thiocyanate | 1-octyl-3-methylimidazolium bromide + n-propanol + potassium thiocyanate |
| 1-methyl-3-carboxyethyl-imidazolium bromide | 1-methyl-3-carboxyethyl-imidazolium bromide + sulfosalicylic acid | 1-methyl-3-carboxyethyl-imidazolium bromide + n-propanol | 1-methyl-3-carboxyethyl-imidazolium bromide + potassium thiocyanate | 1-methyl-3-carboxyethyl-imidazolium bromide + sulfosalicylic acid + n-propanol | 1-methyl-3-carboxyethyl-imidazolium bromide + sulfosalicylic acid + potassium thiocyanate | 1-methyl-3-carboxyethyl-imidazolium bromide + sulfosalicylic acid + n-propanol + potassium thiocyanate | 1-methyl-3-carboxyethyl-imidazolium bromide + n-propanol + potassium thiocyanate |
| 1-hexyl-3-methylimidazolium bromide | 1-hexyl-3-methylimidazolium bromide + sulfosalicylic acid | 1-hexyl-3-methylimidazolium bromide + n-propanol | 1-hexyl-3-methylimidazolium bromide + potassium thiocyanate | 1-hexyl-3-methylimidazolium bromide + sulfosalicylic acid + n-propanol | 1-hexyl-3-methylimidazolium bromide + sulfosalicylic acid + potassium thiocyanate | 1-hexyl-3-methylimidazolium bromide + sulfosalicylic acid + n-propanol + potassium thiocyanate | 1-hexyl-3-methylimidazolium bromide + n-propanol + potassium thiocyanate |
| 1-decyl-3-methylimidazolium bromide | 1-decyl-3-methylimidazolium bromide + sulfosalicylic acid | 1-decyl-3-methylimidazolium bromide + n-propanol | 1-decyl-3-methylimidazolium bromide + potassium thiocyanate | 1-decyl-3-methylimidazolium bromide + sulfosalicylic acid + n-propanol | 1-decyl-3-methylimidazolium bromide + sulfosalicylic acid + potassium thiocyanate | 1-decyl-3-methylimidazolium bromide + sulfosalicylic acid + n-propanol + potassium thiocyanate | 1-decyl-3-methylimidazolium bromide + n-propanol + potassium thiocyanate |
| 1-(2-hydroxyethyl)-3-methylimidazolium bromide | 1-(2-hydroxyethyl)-3-methylimidazolium bromide + sulfosalicylic acid | 1-(2-hydroxyethyl)-3-methylimidazolium bromide + n-propanol | 1-(2-hydroxyethyl)-3-methylimidazolium bromide + potassium thiocyanate | 1-(2-hydroxyethyl)-3-methylimidazolium bromide + sulfosalicylic acid + n-propanol | 1-(2-hydroxyethyl)-3-methylimidazolium bromide + sulfosalicylic acid + potassium thiocyanate | 1-(2-hydroxyethyl)-3-methylimidazolium bromide + sulfosalicylic acid + n-propanol + potassium thiocyanate | 1-(2-hydroxyethyl)-3-methylimidazolium bromide + n-propanol + potassium thiocyanate |

TABLE 5-continued

EXEMPLARY STORAGE COMPOSITIONS

| (A) Compound of Formula (I) | (A) + (B) Precipitating Agent | (A) + (C) Lower Alcohol | (A) + (D) Chaotrope | (A) + (B) + (C) | (A) + (B) + (D) | (A) + (B) + (C) + (D) | (A) + (C) + (D) |
|---|---|---|---|---|---|---|---|
| 1-octyl-3-methylimidazolium bromide | 1-octyl-3-methylimidazolium bromide + sulfosalicylic acid | 1-octyl-3-methylimidazolium bromide + n-propanol | 1-octyl-3-methylimidazolium bromide + potassium thiocyanate | 1-octyl-3-methylimidazolium bromide + sulfosalicylic acid + n-propanol | 1-octyl-3-methylimidazolium bromide + sulfosalicylic acid + potassium thiocyanate | 1-octyl-3-methylimidazolium bromide + sulfosalicylic acid + n-propanol + potassium thiocyanate | 1-octyl-3-methylimidazolium bromide + n-propanol + potassium thiocyanate |
| 1-methyl-3-carboxyethyl-imidazolium bromide | 1-methyl-3-carboxyethyl-imidazolium bromide + lithium chloride | 1-methyl-3-carboxyethyl-imidazolium bromide + n-propanol | 1-methyl-3-carboxyethyl-imidazolium bromide + potassium thiocyanate | 1-methyl-3-carboxyethyl-imidazolium bromide + LiCl + n-propanol | 1-methyl-3-carboxyethyl-imidazolium bromide + LiCl + potassium thiocyanate | 1-methyl-3-carboxyethyl-imidazolium bromide + LiCl + n-propanol + potassium thiocyanate | 1-methyl-3-carboxyethyl-imidazolium bromide + n-propanol + potassium thiocyanate |
| 1-hexyl-3-methylimidazolium bromide | 1-hexyl-3-methylimidazolium bromide + lithium chloride | 1-hexyl-3-methylimidazolium bromide + n-propanol | 1-hexyl-3-methylimidazolium bromide + potassium thiocyanate | 1-hexyl-3-methylimidazolium bromide + LiCl + n-propanol | 1-hexyl-3-methylimidazolium bromide + LiCl + potassium thiocyanate | 1-hexyl-3-methylimidazolium bromide + LiCl + n-propanol + potassium thiocyanate | 1-hexyl-3-methylimidazolium bromide + n-propanol + potassium thiocyanate |
| 1-decyl-3-methylimidazolium bromide | 1-decyl-3-methylimidazolium bromide + lithium chloride | 1-decyl-3-methylimidazolium bromide + n-propanol | 1-decyl-3-methylimidazolium bromide + potassium thiocyanate | 1-decyl-3-methylimidazolium bromide + LiCl + n-propanol | 1-decyl-3-methylimidazolium bromide + LiCl + potassium thiocyanate | 1-decyl-3-methylimidazolium bromide + LiCl + n-propanol + potassium thiocyanate | 1-decyl-3-methylimidazolium bromide + n-propanol + potassium thiocyanate |
| 1-(2-hydroxyethyl)-3-methylimidazolium bromide | 1-(2-hydroxyethyl)-3-methylimidazolium bromide + lithium chloride | 1-(2-hydroxyethyl)-3-methylimidazolium bromide + n-propanol | 1-(2-hydroxyethyl)-3-methylimidazolium bromide + potassium thiocyanate | 1-(2-hydroxyethyl)-3-methylimidazolium bromide + LiCl + n-propanol | 1-(2-hydroxyethyl)-3-methylimidazolium bromide + LiCl + potassium thiocyanate | 1-(2-hydroxyethyl)-3-methylimidazolium bromide + LiCl + n-propanol + potassium thiocyanate | 1-(2-hydroxyethyl)-3-methylimidazolium bromide + n-propanol + potassium thiocyanate |
| 1-octyl-3-methylimidazolium bromide | 1-octyl-3-methylimidazolium bromide + lithium chloride | 1-octyl-3-methylimidazolium bromide + n-propanol | 1-octyl-3-methylimidazolium bromide + potassium thiocyanate | 1-octyl-3-methylimidazolium bromide + LiCl + n-propanol | 1-octyl-3-methylimidazolium bromide + LiCl + potassium thiocyanate | 1-octyl-3-methylimidazolium bromide + LiCl + n-propanol + potassium thiocyanate | 1-octyl-3-methylimidazolium bromide + n-propanol + potassium thiocyanate |
| 1-methyl-3-carboxyethyl-imidazolium bromide | 1-methyl-3-carboxyethyl-imidazolium bromide + lithium hydroxide | 1-methyl-3-carboxyethyl-imidazolium bromide + n-propanol | 1-methyl-3-carboxyethyl-imidazolium bromide + potassium thiocyanate | 1-methyl-3-carboxyethyl-imidazolium bromide + LiOH + n-propanol | 1-methyl-3-carboxyethyl-imidazolium bromide + LiOH + potassium thiocyanate | 1-methyl-3-carboxyethyl-imidazolium bromide + LiOH + n-propanol + potassium thiocyanate | 1-methyl-3-carboxyethyl-imidazolium bromide + n-propanol + potassium thiocyanate |

TABLE 5-continued

EXEMPLARY STORAGE COMPOSITIONS

| (A) Compound of Formula (I) | (A) + (B) Precipitating Agent | (A) + (C) Lower Alcohol | (A) + (D) Chaotrope | (A) + (B) + (C) | (A) + (B) + (D) | (A) + (B) + (C) + (D) | (A) + (C) + (D) |
|---|---|---|---|---|---|---|---|
| 1-hexyl-3-methylimidazolium bromide | 1-hexyl-3-methylimidazolium bromide + lithium hydroxide | 1-hexyl-3-methylimidazolium bromide + n-propanol | 1-hexyl-3-methylimidazolium bromide + potassium thiocyanate | 1-hexyl-3-methylimidazolium bromide + LiOH + n-propanol | 1-hexyl-3-methylimidazolium bromide + LiOH + potassium thiocyanate | 1-hexyl-3-methylimidazolium bromide + LiOH + n-propanol + potassium thiocyanate | 1-hexyl-3-methylimidazolium bromide + n-propanol + potassium thiocyanate |
| 1-decyl-3-methylimidazolium bromide | 1-decyl-3-methylimidazolium bromide + lithium hydroxide | 1-decyl-3-methylimidazolium bromide + n-propanol | 1-decyl-3-methylimidazolium bromide + potassium thiocyanate | 1-decyl-3-methylimidazolium bromide + LiOH + n-propanol | 1-decyl-3-methylimidazolium bromide + LiOH + potassium thiocyanate | 1-decyl-3-methylimidazolium bromide + LiOH + n-propanol + potassium thiocyanate | 1-decyl-3-methylimidazolium bromide + n-propanol + potassium thiocyanate |
| 1-(2-hydroxyethyl)-3-methylimidazolium bromide | 1-(2-hydroxyethyl)-3-methylimidazolium bromide + lithium hydroxide | 1-(2-hydroxyethyl)-3-methylimidazolium bromide + n-propanol | 1-(2-hydroxyethyl)-3-methylimidazolium bromide + potassium thiocyanate | 1-(2-hydroxyethyl)-3-methylimidazolium bromide + LiOH + n-propanol | 1-(2-hydroxyethyl)-3-methylimidazolium bromide + LiOH + potassium thiocyanate | 1-(2-hydroxyethyl)-3-methylimidazolium bromide + LiOH + n-propanol + potassium thiocyanate | 1-(2-hydroxyethyl)-3-methylimidazolium bromide + n-propanol + potassium thiocyanate |
| 1-octyl-3-methylimidazolium bromide | 1-octyl-3-methylimidazolium bromide + lithium hydroxide | 1-octyl-3-methylimidazolium bromide + n-propanol | 1-octyl-3-methylimidazolium bromide + potassium thiocyanate | 1-octyl-3-methylimidazolium bromide + LiOH + n-propanol | 1-octyl-3-methylimidazolium bromide + LiOH + potassium thiocyanate | 1-octyl-3-methylimidazolium bromide + LiOH + n-propanol + potassium thiocyanate | 1-octyl-3-methylimidazolium bromide + n-propanol + potassium thiocyanate |
| 1-methyl-3-carboxyethyl-imidazolium bromide + 5-(4-dimethyl)amino benzylidene rhodanine | 1-methyl-3-carboxyethyl-imidazolium bromide + 5-(4-dimethyl)amino benzylidene rhodanine | 1-methyl-3-carboxyethyl-imidazolium bromide + Isopropanol | 1-methyl-3-carboxyethyl-imidazolium bromide + potassium thiocyanate | 1-methyl-3-carboxyethyl-imidazolium bromide + 5-(4-dimethyl)amino benzylidene rhodanine + isopropanol | 1-methyl-3-carboxyethyl-imidazolium bromide + 5-(4-dimethyl)amino benzylidene rhodanine + potassium thiocyanate | 1-methyl-3-carboxyethyl-imidazolium bromide + 5-(4-dimethyl)amino benzylidene rhodanine + isopropanol + potassium thiocyanate | 1-methyl-3-carboxyethyl-imidazolium bromide + isopropanol + potassium thiocyanate |
| 1-hexyl-3-methylimidazolium bromide | 1-hexyl-3-methylimidazolium bromide + 5-(4-dimethyl)amino benzylidene rhodanine | 1-hexyl-3-methylimidazolium bromide + Isopropanol | 1-hexyl-3-methylimidazolium bromide + potassium thiocyanate | 1-hexyl-3-methylimidazolium bromide + 5-(4-dimethyl)amino benzylidene rhodanine + isopropanol | 1-hexyl-3-methylimidazolium bromide + 5-(4-dimethyl)amino benzylidene rhodanine + potassium thiocyanate | 1-hexyl-3-methylimidazolium bromide + 5-(4-dimethyl)amino benzylidene rhodanine + isopropanol + potassium thiocyanate | 1-hexyl-3-methylimidazolium bromide + isopropanol + potassium thiocyanate |

TABLE 5-continued

EXEMPLARY STORAGE COMPOSITIONS

| (A) Compound of Formula (I) | (A) + (B) Precipitating Agent | (A) + (C) Lower Alcohol | (A) + (D) Chaotrope | (A) + (B) + (C) | (A) + (B) + (D) | (A) + (B) + (C) + (D) | (A) + (C) + (D) |
|---|---|---|---|---|---|---|---|
| 1-decyl-3-methylimidazolium bromide | 1-decyl-3-methylimidazolium bromide + 5-(4-dimethyl)amino benzylidene rhodanine | 1-decyl-3-methylimidazolium bromide + Isopropanol | 1-decyl-3-methylimidazolium bromide + potassium thiocyanate | 1-decyl-3-methylimidazolium bromide + 5-(4-dimethyl)amino benzylidene rhodanine + isopropanol | 1-decyl-3-methylimidazolium bromide + 5-(4-dimethyl)amino benzylidene rhodanine + potassium thiocyanate | 1-decyl-3-methylimidazolium bromide + 5-(4-dimethyl)amino benzylidene rhodanine + isopropanol + potassium thiocyanate | 1-decyl-3-methylimidazolium bromide + isopropanol + potassium thiocyanate |
| 1-(2-hydroxyethyl)-3-methylimidazolium bromide | 1-(2-hydroxyethyl)-3-methylimidazolium bromide + 5-(4-dimethyl)amino benzylidene rhodanine | 1-(2-hydroxyethyl)-3-methylimidazolium bromide + Isopropanol | 1-(2-hydroxyethyl)-3-methylimidazolium bromide + potassium thiocyanate | 1-(2-hydroxyethyl)-3-methylimidazolium bromide + 5-(4-dimethyl)amino benzylidene rhodanine + isopropanol | 1-(2-hydroxyethyl)-3-methylimidazolium bromide + 5-(4-dimethyl)amino benzylidene rhodanine + potassium thiocyanate | 1-(2-hydroxyethyl)-3-methylimidazolium bromide + 5-(4-dimethyl)amino benzylidene rhodanine + isopropanol + potassium thiocyanate | 1-(2-hydroxyethyl)-3-methylimidazolium bromide + isopropanol + potassium thiocyanate |
| 1-octyl-3-methylimidazolium bromide | 1-octyl-3-methylimidazolium bromide + 5-(4-dimethyl)amino benzylidene rhodanine | 1-octyl-3-methylimidazolium bromide + Isopropanol | 1-octyl-3-methylimidazolium bromide + potassium thiocyanate | 1-octyl-3-methylimidazolium bromide + 5-(4-dimethyl)amino benzylidene rhodanine + isopropanol | 1-octyl-3-methylimidazolium bromide + 5-(4-dimethyl)amino benzylidene rhodanine + potassium thiocyanate | 1-octyl-3-methylimidazolium bromide + 5-(4-dimethyl)amino benzylidene rhodanine + isopropanol + potassium thiocyanate | 1-octyl-3-methylimidazolium bromide + isopropanol + potassium thiocyanate |
| 1-methyl-3-carboxyethyl-imidazolium bromide | 1-methyl-3-carboxyethyl-imidazolium bromide + sulfosalicylic acid | 1-methyl-3-carboxyethyl-imidazolium bromide + Isopropanol | 1-methyl-3-carboxyethyl-imidazolium bromide + potassium thiocyanate | 1-methyl-3-carboxyethyl-imidazolium bromide + sulfosalicylic acid + isopropanol | 1-methyl-3-carboxyethyl-imidazolium bromide + sulfosalicylic acid + potassium thiocyanate | 1-methyl-3-carboxyethyl-imidazolium bromide + sulfosalicylic acid + isopropanol + potassium thiocyanate | 1-methyl-3-carboxyethyl-imidazolium bromide + isopropanol + potassium thiocyanate |
| 1-hexyl-3-methylimidazolium bromide | 1-hexyl-3-methylimidazolium bromide + sulfosalicylic acid | 1-hexyl-3-methylimidazolium bromide + Isopropanol | 1-hexyl-3-methylimidazolium bromide + potassium thiocyanate | 1-hexyl-3-methylimidazolium bromide + sulfosalicylic acid + isopropanol | 1-hexyl-3-methylimidazolium bromide + sulfosalicylic acid + potassium thiocyanate | 1-hexyl-3-methylimidazolium bromide + sulfosalicylic acid + isopropanol + potassium thiocyanate | 1-hexyl-3-methylimidazolium bromide + isopropanol + potassium thiocyanate |

TABLE 5-continued

EXEMPLARY STORAGE COMPOSITIONS

| (A) Compound of Formula (I) | (A) + (B) Precipitating Agent | (A) + (C) Lower Alcohol | (A) + (D) Chaotrope | (A) + (B) + (C) | (A) + (B) + (D) | (A) + (B) + (C) + (D) | (A) + (C) + (D) |
|---|---|---|---|---|---|---|---|
| 1-decyl-3-methylimidazolium bromide | 1-decyl-3-methylimidazolium bromide + sulfosalicylic acid | 1-decyl-3-methylimidazolium bromide + Isopropanol | 1-decyl-3-methylimidazolium bromide + potassium thiocyanate | 1-decyl-3-methylimidazolium bromide + sulfosalicylic acid + isopropanol | 1-decyl-3-methylimidazolium bromide + sulfosalicylic acid + potassium thiocyanate | 1-decyl-3-methylimidazolium bromide + sulfosalicylic acid + isopropanol + potassium thiocyanate | 1-decyl-3-methylimidazolium bromide + isopropanol + potassium thiocyanate |
| 1-(2-hydroxyethyl)-3-methylimidazolium bromide | 1-(2-hydroxyethyl)-3-methylimidazolium bromide + sulfosalicylic acid | 1-(2-hydroxyethyl)-3-methylimidazolium bromide + Isopropanol | 1-(2-hydroxyethyl)-3-methylimidazolium bromide + potassium thiocyanate | 1-(2-hydroxyethyl)-3-methylimidazolium bromide + sulfosalicylic acid + isopropanol | 1-(2-hydroxyethyl)-3-methylimidazolium bromide + sulfosalicylic acid + potassium thiocyanate | 1-(2-hydroxyethyl)-3-methylimidazolium bromide + sulfosalicylic acid + isopropanol + potassium thiocyanate | 1-(2-hydroxyethyl)-3-methylimidazolium bromide + isopropanol + potassium thiocyanate |
| 1-octyl-3-methylimidazolium bromide | 1-octyl-3-methylimidazolium bromide + sulfosalicylic acid | 1-octyl-3-methylimidazolium bromide + Isopropanol | 1-octyl-3-methylimidazolium bromide + potassium thiocyanate | 1-octyl-3-methylimidazolium bromide + sulfosalicylic acid + isopropanol | 1-octyl-3-methylimidazolium bromide + sulfosalicylic acid + potassium thiocyanate | 1-octyl-3-methylimidazolium bromide + sulfosalicylic acid + isopropanol + potassium thiocyanate | 1-octyl-3-methylimidazolium bromide + isopropanol + potassium thiocyanate |
| 1-methyl-3-carboxyethyl-imidazolium bromide | 1-methyl-3-carboxyethyl-imidazolium bromide + lithium chloride | 1-methyl-3-carboxyethyl-imidazolium bromide + Isopropanol | 1-methyl-3-carboxyethyl-imidazolium bromide + potassium thiocyanate | 1-methyl-3-carboxyethyl-imidazolium bromide + LiCl + isopropanol | 1-methyl-3-carboxyethyl-imidazolium bromide + LiCl + potassium thiocyanate | 1-methyl-3-carboxyethyl-imidazolium bromide + LiCl + isopropanol + potassium thiocyanate | 1-methyl-3-carboxyethyl-imidazolium bromide + isopropanol + potassium thiocyanate |
| 1-hexyl-3-methylimidazolium bromide | 1-hexyl-3-methylimidazolium bromide + lithium chloride | 1-hexyl-3-methylimidazolium bromide + Isopropanol | 1-hexyl-3-methylimidazolium bromide + potassium thiocyanate | 1-hexyl-3-methylimidazolium bromide + LiCl + isopropanol | 1-hexyl-3-methylimidazolium bromide + LiCl + potassium thiocyanate | 1-hexyl-3-methylimidazolium bromide + LiCl + isopropanol + potassium thiocyanate | 1-hexyl-3-methylimidazolium bromide + isopropanol + potassium thiocyanate |
| 1-decyl-3-methylimidazolium bromide | 1-decyl-3-methylimidazolium bromide + lithium chloride | 1-decyl-3-methylimidazolium bromide + Isopropanol | 1-decyl-3-methylimidazolium bromide + potassium thiocyanate | 1-decyl-3-methylimidazolium bromide + LiCl + isopropanol | 1-decyl-3-methylimidazolium bromide + LiCl + potassium thiocyanate | 1-decyl-3-methylimidazolium bromide + LiCl + isopropanol + potassium thiocyanate | 1-decyl-3-methylimidazolium bromide + isopropanol + potassium thiocyanate |
| 1-(2-hydroxyethyl)-3-methylimidazolium bromide | 1-(2-hydroxyethyl)-3-methylimidazolium bromide + lithium chloride | 1-(2-hydroxyethyl)-3-methylimidazolium bromide + Isopropanol | 1-(2-hydroxyethyl)-3-methylimidazolium bromide + potassium thiocyanate | 1-(2-hydroxyethyl)-3-methylimidazolium bromide + LiCl + isopropanol | 1-(2-hydroxyethyl)-3-methylimidazolium bromide + LiCl + potassium thiocyanate | 1-(2-hydroxyethyl)-3-methylimidazolium bromide + LiCl + isopropanol + potassium thiocyanate | 1-(2-hydroxyethyl)-3-methylimidazolium bromide + isopropanol + potassium thiocyanate |

TABLE 5-continued

EXEMPLARY STORAGE COMPOSITIONS

| (A) Compound of Formula (I) | (A) + (B) Precipitating Agent | (A) + (C) Lower Alcohol | (A) + (D) Chaotrope | (A) + (B) + (C) | (A) + (B) + (D) | (A) + (B) + (C) + (D) | (A) + (C) + (D) |
|---|---|---|---|---|---|---|---|
| 1-octyl-3-methylimidazolium bromide | 1-octyl-3-methylimidazolium bromide + lithium chloride | 1-octyl-3-methylimidazolium bromide + Isopropanol | 1-octyl-3-methylimidazolium bromide + potassium thiocyanate | 1-octyl-3-methylimidazolium bromide + LiCl + isopropanol | 1-octyl-3-methylimidazolium bromide + LiCl + potassium thiocyanate | 1-octyl-3-methylimidazolium bromide + LiCl + isopropanol + potassium thiocyanate | 1-octyl-3-methylimidazolium bromide + isopropanol + potassium thiocyanate |
| 1-methyl-3-carboxyethyl-imidazolium bromide | 1-methyl-3-carboxyethyl-imidazolium bromide + lithium hydroxide | 1-methyl-3-carboxyethyl-imidazolium bromide + Isopropanol | 1-methyl-3-carboxyethyl-imidazolium bromide + potassium thiocyanate | 1-methyl-3-carboxyethyl-imidazolium bromide + LiOH + isopropanol | 1-methyl-3-carboxyethyl-imidazolium bromide + LiOH + potassium thiocyanate | 1-methyl-3-carboxyethyl-imidazolium bromide + LiOH + isopropanol + potassium thiocyanate | 1-methyl-3-carboxyethyl-imidazolium bromide + isopropanol + potassium thiocyanate |
| 1-hexyl-3-methylimidazolium bromide | 1-hexyl-3-methylimidazolium bromide + lithium hydroxide | 1-hexyl-3-methylimidazolium bromide + Isopropanol | 1-hexyl-3-methylimidazolium bromide + potassium thiocyanate | 1-hexyl-3-methylimidazolium bromide + LiOH + isopropanol | 1-hexyl-3-methylimidazolium bromide + LiOH + potassium thiocyanate | 1-hexyl-3-methylimidazolium bromide + LiOH + isopropanol + potassium thiocyanate | 1-hexyl-3-methylimidazolium bromide + isopropanol + potassium thiocyanate |
| 1-decyl-3-methylimidazolium bromide | 1-decyl-3-methylimidazolium bromide + lithium hydroxide | 1-decyl-3-methylimidazolium bromide + Isopropanol | 1-decyl-3-methylimidazolium bromide + potassium thiocyanate | 1-decyl-3-methylimidazolium bromide + LiOH + isopropanol | 1-decyl-3-methylimidazolium bromide + LiOH + potassium thiocyanate | 1-decyl-3-methylimidazolium bromide + LiOH + isopropanol + potassium thiocyanate | 1-decyl-3-methylimidazolium bromide + isopropanol + potassium thiocyanate |
| 1-(2-hydroxyethyl)-3-methylimidazolium bromide | 1-(2-hydroxyethyl)-3-methylimidazolium bromide + lithium hydroxide | 1-(2-hydroxyethyl)-3-methylimidazolium bromide + Isopropanol | 1-(2-hydroxyethyl)-3-methylimidazolium bromide + potassium thiocyanate | 1-(2-hydroxyethyl)-3-methylimidazolium bromide + LiOH + isopropanol | 1-(2-hydroxyethyl)-3-methylimidazolium bromide + LiOH + potassium thiocyanate | 1-(2-hydroxyethyl)-3-methylimidazolium bromide + LiOH + isopropanol + potassium thiocyanate | 1-(2-hydroxyethyl)-3-methylimidazolium bromide + isopropanol + potassium thiocyanate |
| 1-octyl-3-methylimidazolium bromide | 1-octyl-3-methylimidazolium bromide + lithium hydroxide | 1-octyl-3-methylimidazolium bromide + Isopropanol | 1-octyl-3-methylimidazolium bromide + potassium thiocyanate | 1-octyl-3-methylimidazolium bromide + LiOH + isopropanol | 1-octyl-3-methylimidazolium bromide + LiOH + potassium thiocyanate | 1-octyl-3-methylimidazolium bromide + LiOH + isopropanol + potassium thiocyanate | 1-octyl-3-methylimidazolium bromide + isopropanol + potassium thiocyanate |
| 1-methyl-3-carboxyethyl-imidazolium bromide + 5-(4-dimethyl)amino benzylidene rhodanine | 1-methyl-3-carboxyethyl-imidazolium bromide + 5-(4-dimethyl)amino benzylidene rhodanine | 1-methyl-3-carboxyethyl-imidazolium bromide + n-butanol | 1-methyl-3-carboxyethyl-imidazolium bromide + potassium thiocyanate | 1-methyl-3-carboxyethyl-imidazolium bromide + 5-(4-dimethyl)amino benzylidene rhodanine + n-butanol | 1-methyl-3-carboxyethyl-imidazolium bromide + 5-(4-dimethyl)amino benzylidene rhodanine + potassium thiocyanate | 1-methyl-3-carboxyethyl-imidazolium bromide + 5-(4-dimethyl)amino benzylidene rhodanine + n-butanol + potassium thiocyanate | 1-methyl-3-carboxyethyl-imidazolium bromide + n-butanol + potassium thiocyanate |

TABLE 5-continued

EXEMPLARY STORAGE COMPOSITIONS

| (A) Compound of Formula (I) | (A) + (B) Precipitating Agent | (A) + (C) Lower Alcohol | (A) + (D) Chaotrope | (A) + (B) + (C) | (A) + (B) + (D) | (A) + (B) + (C) + (D) | (A) + (C) + (D) |
|---|---|---|---|---|---|---|---|
| 1-hexyl-3-methylimidazolium bromide | 1-hexyl-3-methylimidazolium bromide + 5-(4-dimethyl)amino benzylidene rhodanine | 1-hexyl-3-methylimidazolium bromide + n-butanol | 1-hexyl-3-methylimidazolium bromide + potassium thiocyanate | 1-hexyl-3-methylimidazolium bromide + 5-(4-dimethyl)amino benzylidene rhodanine + n-butanol | 1-hexyl-3-methylimidazolium bromide + 5-(4-dimethyl)amino benzylidene rhodanine + potassium thiocyanate | 1-hexyl-3-methylimidazolium bromide + 5-(4-dimethyl)amino benzylidene rhodanine + n-butanol + potassium thiocyanate | 1-hexyl-3-methylimidazolium bromide + n-butanol + potassium thiocyanate |
| 1-decyl-3-methylimidazolium bromide | 1-decyl-3-methylimidazolium bromide + 5-(4-dimethyl)amino benzylidene rhodanine | 1-decyl-3-methylimidazolium bromide + n-butanol | 1-decyl-3-methylimidazolium bromide + potassium thiocyanate | 1-decyl-3-methylimidazolium bromide + 5-(4-dimethyl)amino benzylidene rhodanine + n-butanol | 1-decyl-3-methylimidazolium bromide + 5-(4-dimethyl)amino benzylidene rhodanine + potassium thiocyanate | 1-decyl-3-methylimidazolium bromide + 5-(4-dimethyl)amino benzylidene rhodanine + n-butanol + potassium thiocyanate | 1-decyl-3-methylimidazolium bromide + n-butanol + potassium thiocyanate |
| 1-(2-hydroxyethyl)-3-methylimidazolium bromide | 1-(2-hydroxyethyl)-3-methylimidazolium bromide + 5-(4-dimethyl)amino benzylidene rhodanine | 1-(2-hydroxyethyl)-3-methylimidazolium bromide + n-butanol | 1-(2-hydroxyethyl)-3-methylimidazolium bromide + potassium thiocyanate | 1-(2-hydroxyethyl)-3-methylimidazolium bromide + 5-(4-dimethyl)amino benzylidene rhodanine + n-butanol | 1-(2-hydroxyethyl)-3-methylimidazolium bromide + 5-(4-dimethyl)amino benzylidene rhodanine + potassium thiocyanate | 1-(2-hydroxyethyl)-3-methylimidazolium bromide + 5-(4-dimethyl)amino benzylidene rhodanine + n-butanol + potassium thiocyanate | 1-(2-hydroxyethyl)-3-methylimidazolium bromide + n-butanol + potassium thiocyanate |
| 1-octyl-3-methylimidazolium bromide | 1-octyl-3-methylimidazolium bromide + 5-(4-dimethyl)amino benzylidene rhodanine | 1-octyl-3-methylimidazolium bromide + n-butanol | 1-octyl-3-methylimidazolium bromide + potassium thiocyanate | 1-octyl-3-methylimidazolium bromide + 5-(4-dimethyl)amino benzylidene rhodanine + n-butanol | 1-octyl-3-methylimidazolium bromide + 5-(4-dimethyl)amino benzylidene rhodanine + potassium thiocyanate | 1-octyl-3-methylimidazolium bromide + 5-(4-dimethyl)amino benzylidene rhodanine + n-butanol + potassium thiocyanate | 1-octyl-3-methylimidazolium bromide + n-butanol + potassium thiocyanate |
| 1-methyl-3-carboxyethyl-imidazolium bromide | 1-methyl-3-carboxyethyl-imidazolium bromide + sulfosalicylic acid | 1-methyl-3-carboxyethyl-imidazolium bromide + n-butanol | 1-methyl-3-carboxyethyl-imidazolium bromide + potassium thiocyanate | 1-methyl-3-carboxyethyl-imidazolium bromide + sulfosalicylic acid + n-butanol | 1-methyl-3-carboxyethyl-imidazolium bromide + sulfosalicylic acid + potassium thiocyanate | 1-methyl-3-carboxyethyl-imidazolium bromide + sulfosalicylic acid + n-butanol + potassium thiocyanate | 1-methyl-3-carboxyethyl-imidazolium bromide + n-butanol + potassium thiocyanate |

TABLE 5-continued

EXEMPLARY STORAGE COMPOSITIONS

| (A) Compound of Formula (I) | (A) + (B) Precipitating Agent | (A) + (C) Lower Alcohol | (A) + (D) Chaotrope | (A) + (B) + (C) | (A) + (B) + (D) | (A) + (B) + (C) + (D) | (A) + (C) + (D) |
|---|---|---|---|---|---|---|---|
| 1-hexyl-3-methylimidazolium bromide | 1-hexyl-3-methylimidazolium bromide + sulfosalicylic acid | 1-hexyl-3-methylimidazolium bromide + n-butanol | 1-hexyl-3-methylimidazolium bromide + potassium thiocyanate | 1-hexyl-3-methylimidazolium bromide + sulfosalicylic acid + n-butanol | 1-hexyl-3-methylimidazolium bromide + sulfosalicylic acid + potassium thiocyanate | 1-hexyl-3-methylimidazolium bromide + sulfosalicylic acid + n-butanol + potassium thiocyanate | 1-hexyl-3-methylimidazolium bromide + n-butanol + potassium thiocyanate |
| 1-decyl-3-methylimidazolium bromide | 1-decyl-3-methylimidazolium bromide + sulfosalicylic acid | 1-decyl-3-methylimidazolium bromide + n-butanol | 1-decyl-3-methylimidazolium bromide + potassium thiocyanate | 1-decyl-3-methylimidazolium bromide + sulfosalicylic acid + n-butanol | 1-decyl-3-methylimidazolium bromide + sulfosalicylic acid + potassium thiocyanate | 1-decyl-3-methylimidazolium bromide + sulfosalicylic acid + n-butanol + potassium thiocyanate | 1-decyl-3-methylimidazolium bromide + n-butanol + potassium thiocyanate |
| 1-(2-hydroxyethyl)-3-methylimidazolium bromide | 1-(2-hydroxyethyl)-3-methylimidazolium bromide + sulfosalicylic acid | 1-(2-hydroxyethyl)-3-methylimidazolium bromide + n-butanol | 1-(2-hydroxyethyl)-3-methylimidazolium bromide + potassium thiocyanate | 1-(2-hydroxyethyl)-3-methylimidazolium bromide + sulfosalicylic acid + n-butanol | 1-(2-hydroxyethyl)-3-methylimidazolium bromide + sulfosalicylic acid + potassium thiocyanate | 1-(2-hydroxyethyl)-3-methylimidazolium bromide + sulfosalicylic acid + n-butanol + potassium thiocyanate | 1-(2-hydroxyethyl)-3-methylimidazolium bromide + n-butanol + potassium thiocyanate |
| 1-octyl-3-methylimidazolium bromide | 1-octyl-3-methylimidazolium bromide + sulfosalicylic acid | 1-octyl-3-methylimidazolium bromide + n-butanol | 1-octyl-3-methylimidazolium bromide + potassium thiocyanate | 1-octyl-3-methylimidazolium bromide + sulfosalicylic acid + n-butanol | 1-octyl-3-methylimidazolium bromide + sulfosalicylic acid + potassium thiocyanate | 1-octyl-3-methylimidazolium bromide + sulfosalicylic acid + n-butanol + potassium thiocyanate | 1-octyl-3-methylimidazolium bromide + n-butanol + potassium thiocyanate |
| 1-methyl-3-carboxyethyl-imidazolium bromide | 1-methyl-3-carboxyethyl-imidazolium bromide + lithium chloride | 1-methyl-3-carboxyethyl-imidazolium bromide + n-butanol | 1-methyl-3-carboxyethyl-imidazolium bromide + potassium thiocyanate | 1-methyl-3-carboxyethyl-imidazolium bromide + LiCl + n-butanol | 1-methyl-3-carboxyethyl-imidazolium bromide + LiCl + potassium thiocyanate | 1-methyl-3-carboxyethyl-imidazolium bromide + LiCl + n-butanol + potassium thiocyanate | 1-methyl-3-carboxyethyl-imidazolium bromide + n-butanol + potassium thiocyanate |
| 1-hexyl-3-methylimidazolium bromide | 1-hexyl-3-methylimidazolium bromide + lithium chloride | 1-hexyl-3-methylimidazolium bromide + n-butanol | 1-hexyl-3-methylimidazolium bromide + potassium thiocyanate | 1-hexyl-3-methylimidazolium bromide + LiCl + n-butanol | 1-hexyl-3-methylimidazolium bromide + LiCl + potassium thiocyanate | 1-hexyl-3-methylimidazolium bromide + LiCl + n-butanol + potassium thiocyanate | 1-hexyl-3-methylimidazolium bromide + n-butanol + potassium thiocyanate |
| 1-decyl-3-methylimidazolium bromide | 1-decyl-3-methylimidazolium bromide + lithium chloride | 1-decyl-3-methylimidazolium bromide + n-butanol | 1-decyl-3-methylimidazolium bromide + potassium thiocyanate | 1-decyl-3-methylimidazolium bromide + LiCl + n-butanol | 1-decyl-3-methylimidazolium bromide + LiCl + potassium thiocyanate | 1-decyl-3-methylimidazolium bromide + LiCl + n-butanol + potassium thiocyanate | 1-decyl-3-methylimidazolium bromide + n-butanol + potassium thiocyanate |

TABLE 5-continued

EXEMPLARY STORAGE COMPOSITIONS

| (A) Compound of Formula (I) | (A) + (B) Precipitating Agent | (A) + (C) Lower Alcohol | (A) + (D) Chaotrope | (A) + (B) + (C) | (A) + (B) + (D) | (A) + (B) + (C) + (D) | (A) + (C) + (D) |
|---|---|---|---|---|---|---|---|
| 1-(2-hydroxyethyl)-3-methylimidazolium bromide | 1-(2-hydroxyethyl)-3-methylimidazolium bromide + lithium chloride | 1-(2-hydroxyethyl)-3-methylimidazolium bromide + n-butanol | 1-(2-hydroxyethyl)-3-methylimidazolium bromide + potassium thiocyanate | 1-(2-hydroxyethyl)-3-methylimidazolium bromide + LiCl + n-butanol | 1-(2-hydroxyethyl)-3-methylimidazolium bromide + LiCl + potassium thiocyanate | 1-(2-hydroxyethyl)-3-methylimidazolium bromide + LiCl + n-butanol + potassium thiocyanate | 1-(2-hydroxyethyl)-3-methylimidazolium bromide + n-butanol + potassium thiocyanate |
| 1-octyl-3-methylimidazolium bromide | 1-octyl-3-methylimidazolium bromide + lithium chloride | 1-octyl-3-methylimidazolium bromide + n-butanol | 1-octyl-3-methylimidazolium bromide + potassium thiocyanate | 1-octyl-3-methylimidazolium bromide + LiCl + n-butanol | 1-octyl-3-methylimidazolium bromide + LiCl + potassium thiocyanate | 1-octyl-3-methylimidazolium bromide + LiCl + n-butanol + potassium thiocyanate | 1-octyl-3-methylimidazolium bromide + n-butanol + potassium thiocyanate |
| 1-methyl-3-carboxyethyl-imidazolium bromide | 1-methyl-3-carboxyethyl-imidazolium bromide + lithium hydroxide | 1-methyl-3-carboxyethyl-imidazolium bromide + n-butanol | 1-methyl-3-carboxyethyl-imidazolium bromide + potassium thiocyanate | 1-methyl-3-carboxyethyl-imidazolium bromide + LiOH + n-butanol | 1-methyl-3-carboxyethyl-imidazolium bromide + LiOH + potassium thiocyanate | 1-methyl-3-carboxyethyl-imidazolium bromide + LiOH + n-butanol + potassium thiocyanate | 1-methyl-3-carboxyethyl-imidazolium bromide + n-butanol + potassium thiocyanate |
| 1-hexyl-3-methylimidazolium bromide | 1-hexyl-3-methylimidazolium bromide + lithium hydroxide | 1-hexyl-3-methylimidazolium bromide + n-butanol | 1-hexyl-3-methylimidazolium bromide + potassium thiocyanate | 1-hexyl-3-methylimidazolium bromide + LiOH + n-butanol | 1-hexyl-3-methylimidazolium bromide + LiOH + potassium thiocyanate | 1-hexyl-3-methylimidazolium bromide + LiOH + n-butanol + potassium thiocyanate | 1-hexyl-3-methylimidazolium bromide + n-butanol + potassium thiocyanate |
| 1-decyl-3-methylimidazolium bromide | 1-decyl-3-methylimidazolium bromide + lithium hydroxide | 1-decyl-3-methylimidazolium bromide + n-butanol | 1-decyl-3-methylimidazolium bromide + potassium thiocyanate | 1-decyl-3-methylimidazolium bromide + LiOH + n-butanol | 1-decyl-3-methylimidazolium bromide + LiOH + potassium thiocyanate | 1-decyl-3-methylimidazolium bromide + LiOH + n-butanol + potassium thiocyanate | 1-decyl-3-methylimidazolium bromide + n-butanol + potassium thiocyanate |
| 1-(2-hydroxyethyl)-3-methylimidazolium bromide | 1-(2-hydroxyethyl)-3-methylimidazolium bromide + lithium hydroxide | 1-(2-hydroxyethyl)-3-methylimidazolium bromide + n-butanol | 1-(2-hydroxyethyl)-3-methylimidazolium bromide + potassium thiocyanate | 1-(2-hydroxyethyl)-3-methylimidazolium bromide + LiOH + n-butanol | 1-(2-hydroxyethyl)-3-methylimidazolium bromide + LiOH + potassium thiocyanate | 1-(2-hydroxyethyl)-3-methylimidazolium bromide + LiOH + n-butanol + potassium thiocyanate | 1-(2-hydroxyethyl)-3-methylimidazolium bromide + n-butanol + potassium thiocyanate |
| 1-octyl-3-methylimidazolium bromide | 1-octyl-3-methylimidazolium bromide + lithium hydroxide | 1-octyl-3-methylimidazolium bromide + n-butanol | 1-octyl-3-methylimidazolium bromide + potassium thiocyanate | 1-octyl-3-methylimidazolium bromide + LiOH + n-butanol | 1-octyl-3-methylimidazolium bromide + LiOH + potassium thiocyanate | 1-octyl-3-methylimidazolium bromide + LiOH + n-butanol + potassium thiocyanate | 1-octyl-3-methylimidazolium bromide + n-butanol + potassium thiocyanate |

TABLE 5-continued

EXEMPLARY STORAGE COMPOSITIONS

| (A) Compound of Formula (I) | (A) + (B) Precipitating Agent | (A) + (C) Lower Alcohol | (A) + (D) Chaotrope | (A) + (B) + (C) | (A) + (B) + (D) | (A) + (B) + (C) + (D) | (A) + (C) + (D) |
|---|---|---|---|---|---|---|---|
| 1-methyl-3-carboxyethyl-imidazolium bromide | 1-methyl-3-carboxyethyl-imidazolium bromide + 5-(4-dimethyl)amino benzylidene rhodanine | 1-methyl-3-carboxyethyl-imidazolium bromide + isobutanol | 1-methyl-3-carboxyethyl-imidazolium bromide + potassium thiocyanate | 1-methyl-3-carboxyethyl-imidazolium bromide + 5-(4-dimethyl)amino benzylidene rhodanine + isobutanol | 1-methyl-3-carboxyethyl-imidazolium bromide + 5-(4-dimethyl)amino benzylidene rhodanine + potassium thiocyanate | 1-methyl-3-carboxyethyl-imidazolium bromide + 5-(4-dimethyl)amino benzylidene rhodanine + isobutanol + potassium thiocyanate | 1-methyl-3-carboxyethyl-imidazolium bromide + isobutanol + potassium thiocyanate |
| 1-hexyl-3-methylimidazolium bromide | 1-hexyl-3-methylimidazolium bromide + 5-(4-dimethyl)amino benzylidene rhodanine | 1-hexyl-3-methylimidazolium bromide + isobutanol | 1-hexyl-3-methylimidazolium bromide + potassium thiocyanate | 1-hexyl-3-methylimidazolium bromide + 5-(4-dimethyl)amino benzylidene rhodanine + isobutanol | 1-hexyl-3-methylimidazolium bromide + 5-(4-dimethyl)amino benzylidene rhodanine + potassium thiocyanate | 1-hexyl-3-methylimidazolium bromide + 5-(4-dimethyl)amino benzylidene rhodanine + isobutanol + potassium thiocyanate | 1-hexyl-3-methylimidazolium bromide + isobutanol + potassium thiocyanate |
| 1-decyl-3-methylimidazolium bromide | 1-decyl-3-methylimidazolium bromide + 5-(4-dimethyl)amino benzylidene rhodanine | 1-decyl-3-methylimidazolium bromide + isobutanol | 1-decyl-3-methylimidazolium bromide + potassium thiocyanate | 1-decyl-3-methylimidazolium bromide + 5-(4-dimethyl)amino benzylidene rhodanine + isobutanol | 1-decyl-3-methylimidazolium bromide + 5-(4-dimethyl)amino benzylidene rhodanine + potassium thiocyanate | 1-decyl-3-methylimidazolium bromide + 5-(4-dimethyl)amino benzylidene rhodanine + isobutanol + potassium thiocyanate | 1-decyl-3-methylimidazolium bromide + isobutanol + potassium thiocyanate |
| 1-(2-hydroxyethyl)-3-methylimidazolium bromide | 1-(2-hydroxyethyl)-3-methylimidazolium bromide + 5-(4-dimethyl)amino benzylidene rhodanine | 1-(2-hydroxyethyl)-3-methylimidazolium bromide + isobutanol | 1-(2-hydroxyethyl)-3-methylimidazolium bromide + potassium thiocyanate | 1-(2-hydroxyethyl)-3-methylimidazolium bromide + 5-(4-dimethyl)amino benzylidene rhodanine + isobutanol | 1-(2-hydroxyethyl)-3-methylimidazolium bromide + 5-(4-dimethyl)amino benzylidene rhodanine + potassium thiocyanate | 1-(2-hydroxyethyl)-3-methylimidazolium bromide + 5-(4-dimethyl)amino benzylidene rhodanine + isobutanol + potassium thiocyanate | 1-(2-hydroxyethyl)-3-methylimidazolium bromide + isobutanol + potassium thiocyanate |
| 1-octyl-3-methylimidazolium bromide | 1-octyl-3-methylimidazolium bromide + 5-(4-dimethyl)amino benzylidene rhodanine | 1-octyl-3-methylimidazolium bromide + isobutanol | 1-octyl-3-methylimidazolium bromide + potassium thiocyanate | 1-octyl-3-methylimidazolium bromide + 5-(4-dimethyl)amino benzylidene rhodanine + isobutanol | 1-octyl-3-methylimidazolium bromide + 5-(4-dimethyl)amino benzylidene rhodanine + potassium thiocyanate | 1-octyl-3-methylimidazolium bromide + 5-(4-dimethyl)amino benzylidene rhodanine + isobutanol + potassium thiocyanate | 1-octyl-3-methylimidazolium bromide + isobutanol + potassium thiocyanate |

TABLE 5-continued

EXEMPLARY STORAGE COMPOSITIONS

| (A) Compound of Formula (I) | (A) + (B) Precipitating Agent | (A) + (C) Lower Alcohol | (A) + (D) Chaotrope | (A) + (B) + (C) | (A) + (B) + (D) | (A) + (B) + (C) + (D) | (A) + (C) + (D) |
|---|---|---|---|---|---|---|---|
| 1-methyl-3-carboxyethyl-imidazolium bromide | 1-methyl-3-carboxyethyl-imidazolium bromide + sulfosalicylic acid | 1-methyl-3-carboxyethyl-imidazolium bromide + isobutanol | 1-methyl-3-carboxyethyl-imidazolium bromide + potassium thiocyanate | 1-methyl-3-carboxyethyl-imidazolium bromide + sulfosalicylic acid + isobutanol | 1-methyl-3-carboxyethyl-imidazolium bromide + sulfosalicylic acid + potassium thiocyanate | 1-methyl-3-carboxyethyl-imidazolium bromide + sulfosalicylic acid + isobutanol + potassium thiocyanate | 1-methyl-3-carboxyethyl-imidazolium bromide + isobutanol + potassium thiocyanate |
| 1-hexyl-3-methylimidazolium bromide | 1-hexyl-3-methylimidazolium bromide + sulfosalicylic acid | 1-hexyl-3-methylimidazolium bromide + isobutanol | 1-hexyl-3-methylimidazolium bromide + potassium thiocyanate | 1-hexyl-3-methylimidazolium bromide + sulfosalicylic acid + isobutanol | 1-hexyl-3-methylimidazolium bromide + sulfosalicylic acid + potassium thiocyanate | 1-hexyl-3-methylimidazolium bromide + sulfosalicylic acid + isobutanol + potassium thiocyanate | 1-hexyl-3-methylimidazolium bromide + isobutanol + potassium thiocyanate |
| 1-decyl-3-methylimidazolium bromide | 1-decyl-3-methylimidazolium bromide + sulfosalicylic acid | 1-decyl-3-methylimidazolium bromide + isobutanol | 1-decyl-3-methylimidazolium bromide + potassium thiocyanate | 1-decyl-3-methylimidazolium bromide + sulfosalicylic acid + isobutanol | 1-decyl-3-methylimidazolium bromide + sulfosalicylic acid + potassium thiocyanate | 1-decyl-3-methylimidazolium bromide + sulfosalicylic acid + isobutanol + potassium thiocyanate | 1-decyl-3-methylimidazolium bromide + isobutanol + potassium thiocyanate |
| 1-(2-hydroxyethyl)-3-methylimidazolium bromide | 1-(2-hydroxyethyl)-3-methylimidazolium bromide + sulfosalicylic acid | 1-(2-hydroxyethyl)-3-methylimidazolium bromide + isobutanol | 1-(2-hydroxyethyl)-3-methylimidazolium bromide + potassium thiocyanate | 1-(2-hydroxyethyl)-3-methylimidazolium bromide + sulfosalicylic acid + isobutanol | 1-(2-hydroxyethyl)-3-methylimidazolium bromide + sulfosalicylic acid + potassium thiocyanate | 1-(2-hydroxyethyl)-3-methylimidazolium bromide + sulfosalicylic acid + isobutanol + potassium thiocyanate | 1-(2-hydroxyethyl)-3-methylimidazolium bromide + isobutanol + potassium thiocyanate |
| 1-octyl-3-methylimidazolium bromide | 1-octyl-3-methylimidazolium bromide + sulfosalicylic acid | 1-octyl-3-methylimidazolium bromide + isobutanol | 1-octyl-3-methylimidazolium bromide + potassium thiocyanate | 1-octyl-3-methylimidazolium bromide + sulfosalicylic acid + isobutanol | 1-octyl-3-methylimidazolium bromide + sulfosalicylic acid + potassium thiocyanate | 1-octyl-3-methylimidazolium bromide + sulfosalicylic acid + isobutanol + potassium thiocyanate | 1-octyl-3-methylimidazolium bromide + isobutanol + potassium thiocyanate |
| 1-methyl-3-carboxyethyl-imidazolium bromide | 1-methyl-3-carboxyethyl-imidazolium bromide + lithium chloride | 1-methyl-3-carboxyethyl-imidazolium bromide + isobutanol | 1-methyl-3-carboxyethyl-imidazolium bromide + potassium thiocyanate | 1-methyl-3-carboxyethyl-imidazolium bromide + LiCl + isobutanol | 1-methyl-3-carboxyethyl-imidazolium bromide + LiCl + potassium thiocyanate | 1-methyl-3-carboxyethyl-imidazolium bromide + LiCl + isobutanol + potassium thiocyanate | 1-methyl-3-carboxyethyl-imidazolium bromide + isobutanol + potassium thiocyanate |

TABLE 5-continued

EXEMPLARY STORAGE COMPOSITIONS

| (A) Compound of Formula (I) | (A) + (B) Precipitating Agent | (A) + (C) Lower Alcohol | (A) + (D) Chaotrope | (A) + (B) + (C) | (A) + (B) + (D) | (A) + (B) + (C) + (D) | (A) + (C) + (D) |
|---|---|---|---|---|---|---|---|
| 1-hexyl-3-methylimidazolium bromide | 1-hexyl-3-methylimidazolium bromide + lithium chloride | 1-hexyl-3-methylimidazolium bromide + isobutanol | 1-hexyl-3-methylimidazolium bromide + potassium thiocyanate | 1-hexyl-3-methylimidazolium bromide + LiCl + isobutanol | 1-hexyl-3-methylimidazolium bromide + LiCl + potassium thiocyanate | 1-hexyl-3-methylimidazolium bromide + LiCl + isobutanol + potassium thiocyanate | 1-hexyl-3-methylimidazolium bromide + isobutanol + potassium thiocyanate |
| 1-decyl-3-methylimidazolium bromide | 1-decyl-3-methylimidazolium bromide + lithium chloride | 1-decyl-3-methylimidazolium bromide + isobutanol | 1-decyl-3-methylimidazolium bromide + potassium thiocyanate | 1-decyl-3-methylimidazolium bromide + LiCl + isobutanol | 1-decyl-3-methylimidazolium bromide + LiCl + potassium thiocyanate | 1-decyl-3-methylimidazolium bromide + LiCl + isobutanol + potassium thiocyanate | 1-decyl-3-methylimidazolium bromide + isobutanol + potassium thiocyanate |
| 1-(2-hydroxyethyl)-3-methylimidazolium bromide | 1-(2-hydroxyethyl)-3-methylimidazolium bromide + lithium chloride | 1-(2-hydroxyethyl)-3-methylimidazolium bromide + isobutanol | 1-(2-hydroxyethyl)-3-methylimidazolium bromide + potassium thiocyanate | 1-(2-hydroxyethyl)-3-methylimidazolium bromide + LiCl + isobutanol | 1-(2-hydroxyethyl)-3-methylimidazolium bromide + LiCl + potassium thiocyanate | 1-(2-hydroxyethyl)-3-methylimidazolium bromide + LiCl + isobutanol + potassium thiocyanate | 1-(2-hydroxyethyl)-3-methylimidazolium bromide + isobutanol + potassium thiocyanate |
| 1-octyl-3-methylimidazolium bromide | 1-octyl-3-methylimidazolium bromide + lithium chloride | 1-octyl-3-methylimidazolium bromide + isobutanol | 1-octyl-3-methylimidazolium bromide + potassium thiocyanate | 1-octyl-3-methylimidazolium bromide + LiCl + isobutanol | 1-octyl-3-methylimidazolium bromide + LiCl + potassium thiocyanate | 1-octyl-3-methylimidazolium bromide + LiCl + isobutanol + potassium thiocyanate | 1-octyl-3-methylimidazolium bromide + isobutanol + potassium thiocyanate |
| 1-methyl-3-carboxyethyl-imidazolium bromide | 1-methyl-3-carboxyethyl-imidazolium bromide + lithium hydroxide | 1-methyl-3-carboxyethyl-imidazolium bromide + isobutanol | 1-methyl-3-carboxyethyl-imidazolium bromide + potassium thiocyanate | 1-methyl-3-carboxyethyl-imidazolium bromide + LiOH + isobutanol | 1-methyl-3-carboxyethyl-imidazolium bromide + LiOH + potassium thiocyanate | 1-methyl-3-carboxyethyl-imidazolium bromide + LiOH + isobutanol + potassium thiocyanate | 1-methyl-3-carboxyethyl-imidazolium bromide + isobutanol + potassium thiocyanate |
| 1-hexyl-3-methylimidazolium bromide | 1-hexyl-3-methylimidazolium bromide + lithium hydroxide | 1-hexyl-3-methylimidazolium bromide + isobutanol | 1-hexyl-3-methylimidazolium bromide + potassium thiocyanate | 1-hexyl-3-methylimidazolium bromide + LiOH + isobutanol | 1-hexyl-3-methylimidazolium bromide + LiOH + potassium thiocyanate | 1-hexyl-3-methylimidazolium bromide + LiOH + isobutanol + potassium thiocyanate | 1-hexyl-3-methylimidazolium bromide + isobutanol + potassium thiocyanate |
| 1-decyl-3-methylimidazolium bromide | 1-decyl-3-methylimidazolium bromide + lithium hydroxide | 1-decyl-3-methylimidazolium bromide + isobutanol | 1-decyl-3-methylimidazolium bromide + potassium thiocyanate | 1-decyl-3-methylimidazolium bromide + LiOH + isobutanol | 1-decyl-3-methylimidazolium bromide + LiOH + potassium thiocyanate | 1-decyl-3-methylimidazolium bromide + LiOH + isobutanol + potassium thiocyanate | 1-decyl-3-methylimidazolium bromide + isobutanol + potassium thiocyanate |

TABLE 5-continued

EXEMPLARY STORAGE COMPOSITIONS

| (A) Compound of Formula (I) | (A) + (B) Precipitating Agent | (A) + (C) Lower Alcohol | (A) + (D) Chaotrope | (A) + (B) + (C) | (A) + (B) + (D) | (A) + (B) + (C) + (D) | (A) + (C) + (D) |
|---|---|---|---|---|---|---|---|
| 1-(2-hydroxyethyl)-3-methylimidazolium bromide | 1-(2-hydroxyethyl)-3-methylimidazolium bromide + lithium hydroxide | 1-(2-hydroxyethyl)-3-methylimidazolium bromide + isobutanol | 1-(2-hydroxyethyl)-3-methylimidazolium bromide + potassium thiocyanate | 1-(2-hydroxyethyl)-3-methylimidazolium bromide + LiOH + isobutanol | 1-(2-hydroxyethyl)-3-methylimidazolium bromide + LiOH + potassium thiocyanate | 1-(2-hydroxyethyl)-3-methylimidazolium bromide + LiOH + isobutanol + potassium thiocyanate | 1-(2-hydroxyethyl)-3-methylimidazolium bromide + isobutanol + potassium thiocyanate |
| 1-octyl-3-methylimidazolium bromide | 1-octyl-3-methylimidazolium bromide + lithium hydroxide | 1-octyl-3-methylimidazolium bromide + isobutanol | 1-octyl-3-methylimidazolium bromide + potassium thiocyanate | 1-octyl-3-methylimidazolium bromide + LiOH + isobutanol | 1-octyl-3-methylimidazolium bromide + LiOH + potassium thiocyanate | 1-octyl-3-methylimidazolium bromide + LiOH + isobutanol + potassium thiocyanate | 1-octyl-3-methylimidazolium bromide + isobutanol + potassium thiocyanate |
| 1-methyl-3-carboxyethyl-imidazolium bromide | 1-methyl-3-carboxyethyl-imidazolium bromide + 5-(4-dimethyl)amino benzylidene rhodanine | 1-methyl-3-carboxyethyl-imidazolium bromide + methanol | 1-methyl-3-carboxyethyl-imidazolium bromide + sodium thiocyanate | 1-methyl-3-carboxyethyl-imidazolium bromide + 5-(4-dimethyl)amino benzylidene rhodanine + methanol | 1-methyl-3-carboxyethyl-imidazolium bromide + 5-(4-dimethyl)amino benzylidene rhodanine + sodium thiocyanate | 1-methyl-3-carboxyethyl-imidazolium bromide + 5-(4-dimethyl)amino benzylidene rhodanine + methanol + sodium thiocyanate | 1-methyl-3-carboxyethyl-imidazolium bromide + methanol + sodium thiocyanate |
| 1-hexyl-3-methylimidazolium bromide | 1-hexyl-3-methylimidazolium bromide + 5-(4-dimethyl)amino benzylidene rhodanine | 1-hexyl-3-methylimidazolium bromide + methanol | 1-hexyl-3-methylimidazolium bromide + sodium thiocyanate | 1-hexyl-3-methylimidazolium bromide + 5-(4-dimethyl)amino benzylidene rhodanine + methanol | 1-hexyl-3-methylimidazolium bromide + 5-(4-dimethyl)amino benzylidene rhodanine + sodium thiocyanate | 1-hexyl-3-methylimidazolium bromide + 5-(4-dimethyl)amino benzylidene rhodanine + methanol + sodium thiocyanate | 1-hexyl-3-methylimidazolium bromide + methanol + sodium thiocyanate |
| 1-decyl-3-methylimidazolium bromide | 1-decyl-3-methylimidazolium bromide + 5-(4-dimethyl)amino benzylidene rhodanine | 1-decyl-3-methylimidazolium bromide + methanol | 1-decyl-3-methylimidazolium bromide + sodium thiocyanate | 1-decyl-3-methylimidazolium bromide + 5-(4-dimethyl)amino benzylidene rhodanine + methanol | 1-decyl-3-methylimidazolium bromide + 5-(4-dimethyl)amino benzylidene rhodanine + sodium thiocyanate | 1-decyl-3-methylimidazolium bromide + 5-(4-dimethyl)amino benzylidene rhodanine + methanol + sodium thiocyanate | 1-decyl-3-methylimidazolium bromide + methanol + sodium thiocyanate |

TABLE 5-continued

EXEMPLARY STORAGE COMPOSITIONS

| (A) Compound of Formula (I) | (A) + (B) Precipitating Agent | (A) + (C) Lower Alcohol | (A) + (D) Chaotrope | (A) + (B) + (C) | (A) + (B) + (D) | (A) + (B) + (C) + (D) | (A) + (C) + (D) |
|---|---|---|---|---|---|---|---|
| 1-(2-hydroxyethyl)-3-methylimidazolium bromide | 1-(2-hydroxyethyl)-3-methylimidazolium bromide + 5-(4-dimethyl)amino benzylidene rhodanine | 1-(2-hydroxyethyl)-3-methylimidazolium bromide + methanol | 1-(2-hydroxyethyl)-3-methylimidazolium bromide + sodium thiocyanate | 1-(2-hydroxyethyl)-3-methylimidazolium bromide + 5-(4-dimethyl)amino benzylidene rhodanine + methanol | 1-(2-hydroxyethyl)-3-methylimidazolium bromide + 5-(4-dimethyl)amino benzylidene rhodanine + sodium thiocyanate | 1-(2-hydroxyethyl)-3-methylimidazolium bromide + 5-(4-dimethyl)amino benzylidene rhodanine + methanol + sodium thiocyanate | 1-(2-hydroxyethyl)-3-methylimidazolium bromide + methanol + sodium thiocyanate |
| 1-octyl-3-methylimidazolium bromide | 1-octyl-3-methylimidazolium bromide + 5-(4-dimethyl)amino benzylidene rhodanine | 1-octyl-3-methylimidazolium bromide + methanol | 1-octyl-3-methylimidazolium bromide + sodium thiocyanate | 1-octyl-3-methylimidazolium bromide + 5-(4-dimethyl)amino benzylidene rhodanine + methanol | 1-octyl-3-methylimidazolium bromide + 5-(4-dimethyl)amino benzylidene rhodanine + sodium thiocyanate | 1-octyl-3-methylimidazolium bromide + 5-(4-dimethyl)amino benzylidene rhodanine + methanol + sodium thiocyanate | 1-octyl-3-methylimidazolium bromide + methanol + sodium thiocyanate |
| 1-methyl-3-carboxyethyl-imidazolium bromide | 1-methyl-3-carboxyethyl-imidazolium bromide + sulfosalicylic acid | 1-methyl-3-carboxyethyl-imidazolium bromide + methanol | 1-methyl-3-carboxyethyl-imidazolium bromide + sodium thiocyanate | 1-methyl-3-carboxyethyl-imidazolium bromide + sulfosalicylic acid + methanol | 1-methyl-3-carboxyethyl-imidazolium bromide + sulfosalicylic acid + sodium thiocyanate | 1-methyl-3-carboxyethyl-imidazolium bromide + sulfosalicylic acid + methanol + sodium thiocyanate | 1-methyl-3-carboxyethyl-imidazolium bromide + methanol + sodium thiocyanate |
| 1-hexyl-3-methylimidazolium bromide | 1-hexyl-3-methylimidazolium bromide + sulfosalicylic acid | 1-hexyl-3-methylimidazolium bromide + methanol | 1-hexyl-3-methylimidazolium bromide + sodium thiocyanate | 1-hexyl-3-methylimidazolium bromide + sulfosalicylic acid + methanol | 1-hexyl-3-methylimidazolium bromide + sulfosalicylic acid + sodium thiocyanate | 1-hexyl-3-methylimidazolium bromide + sulfosalicylic acid + methanol + sodium thiocyanate | 1-hexyl-3-methylimidazolium bromide + methanol + sodium thiocyanate |
| 1-decyl-3-methylimidazolium bromide | 1-decyl-3-methylimidazolium bromide + sulfosalicylic acid | 1-decyl-3-methylimidazolium bromide + methanol | 1-decyl-3-methylimidazolium bromide + sodium thiocyanate | 1-decyl-3-methylimidazolium bromide + sulfosalicylic acid + methanol | 1-decyl-3-methylimidazolium bromide + sulfosalicylic acid + sodium thiocyanate | 1-decyl-3-methylimidazolium bromide + sulfosalicylic acid + methanol + sodium thiocyanate | 1-decyl-3-methylimidazolium bromide + methanol + sodium thiocyanate |
| 1-(2-hydroxyethyl)-3-methylimidazolium bromide | 1-(2-hydroxyethyl)-3-methylimidazolium bromide + sulfosalicylic acid | 1-(2-hydroxyethyl)-3-methylimidazolium bromide + methanol | 1-(2-hydroxyethyl)-3-methylimidazolium bromide + sodium thiocyanate | 1-(2-hydroxyethyl)-3-methylimidazolium bromide + sulfosalicylic acid + methanol | 1-(2-hydroxyethyl)-3-methylimidazolium bromide + sulfosalicylic acid + sodium thiocyanate | 1-(2-hydroxyethyl)-3-methylimidazolium bromide + sulfosalicylic acid + methanol + sodium thiocyanate | 1-(2-hydroxyethyl)-3-methylimidazolium bromide + methanol + sodium thiocyanate |

TABLE 5-continued

EXEMPLARY STORAGE COMPOSITIONS

| (A) Compound of Formula (I) | (A) + (B) Precipitating Agent | (A) + (C) Lower Alcohol | (A) + (D) Chaotrope | (A) + (B) + (C) | (A) + (B) + (D) | (A) + (B) + (C) + (D) | (A) + (C) + (D) |
|---|---|---|---|---|---|---|---|
| 1-octyl-3-methylimidazolium bromide | 1-octyl-3-methylimidazolium bromide + sulfosalicylic acid | 1-octyl-3-methylimidazolium bromide + methanol | 1-octyl-3-methylimidazolium bromide + sodium thiocyanate | 1-octyl-3-methylimidazolium bromide + sulfosalicylic acid + methanol | 1-octyl-3-methylimidazolium bromide + sulfosalicylic acid + sodium thiocyanate | 1-octyl-3-methylimidazolium bromide + sulfosalicylic acid + methanol + sodium thiocyanate | 1-octyl-3-methylimidazolium bromide + methanol + sodium thiocyanate |
| 1-methyl-3-carboxyethyl-imidazolium bromide | 1-methyl-3-carboxyethyl-imidazolium bromide + lithium chloride | 1-methyl-3-carboxyethyl-imidazolium bromide + methanol | 1-methyl-3-carboxyethyl-imidazolium bromide + sodium thiocyanate | 1-methyl-3-carboxyethyl-imidazolium bromide + Lithium chloride + methanol | 1-methyl-3-carboxyethyl-imidazolium bromide + LiCl + sodium thiocyanate | 1-methyl-3-carboxyethyl-imidazolium bromide + LiCl + methanol + sodium thiocyanate | 1-methyl-3-carboxyethyl-imidazolium bromide + methanol + sodium thiocyanate |
| 1-hexyl-3-methylimidazolium bromide | 1-hexyl-3-methylimidazolium bromide + lithium chloride | 1-hexyl-3-methylimidazolium bromide + methanol | 1-hexyl-3-methylimidazolium bromide + sodium thiocyanate | 1-hexyl-3-methylimidazolium bromide + Lithium chloride + methanol | 1-hexyl-3-methylimidazolium bromide + LiCl + sodium thiocyanate | 1-hexyl-3-methylimidazolium bromide + LiCl + methanol + sodium thiocyanate | 1-hexyl-3-methylimidazolium bromide + methanol + sodium thiocyanate |
| 1-decyl-3-methylimidazolium bromide | 1-decyl-3-methylimidazolium bromide + lithium chloride | 1-decyl-3-methylimidazolium bromide + methanol | 1-decyl-3-methylimidazolium bromide + sodium thiocyanate | 1-decyl-3-methylimidazolium bromide + Lithium chloride + methanol | 1-decyl-3-methylimidazolium bromide + LiCl + sodium thiocyanate | 1-decyl-3-methylimidazolium bromide + LiCl + methanol + sodium thiocyanate | 1-decyl-3-methylimidazolium bromide + methanol + sodium thiocyanate |
| 1-(2-hydroxyethyl)-3-methylimidazolium bromide | 1-(2-hydroxyethyl)-3-methylimidazolium bromide + lithium chloride | 1-(2-hydroxyethyl)-3-methylimidazolium bromide + methanol | 1-(2-hydroxyethyl)-3-methylimidazolium bromide + sodium thiocyanate | 1-(2-hydroxyethyl)-3-methylimidazolium bromide + Lithium chloride + methanol | 1-(2-hydroxyethyl)-3-methylimidazolium bromide + LiCl + sodium thiocyanate | 1-(2-hydroxyethyl)-3-methylimidazolium bromide + LiCl + methanol + sodium thiocyanate | 1-(2-hydroxyethyl)-3-methylimidazolium bromide + methanol + sodium thiocyanate |
| 1-octyl-3-methylimidazolium bromide | 1-octyl-3-methylimidazolium bromide + lithium chloride | 1-octyl-3-methylimidazolium bromide + methanol | 1-octyl-3-methylimidazolium bromide + sodium thiocyanate | 1-octyl-3-methylimidazolium bromide + Lithium chloride + methanol | 1-octyl-3-methylimidazolium bromide + LiCl + sodium thiocyanate | 1-octyl-3-methylimidazolium bromide + LiCl + methanol + sodium thiocyanate | 1-octyl-3-methylimidazolium bromide + methanol + sodium thiocyanate |
| 1-methyl-3-carboxyethyl-imidazolium bromide | 1-methyl-3-carboxyethyl-imidazolium bromide + lithium hydroxide | 1-methyl-3-carboxyethyl-imidazolium bromide + methanol | 1-methyl-3-carboxyethyl-imidazolium bromide + sodium thiocyanate | 1-methyl-3-carboxyethyl-imidazolium bromide + Lithium hydroxide + methanol | 1-methyl-3-carboxyethyl-imidazolium bromide + LiOH + sodium thiocyanate | 1-methyl-3-carboxyethyl-imidazolium bromide + LiOH + methanol + sodium thiocyanate | 1-methyl-3-carboxyethyl-imidazolium bromide + methanol + sodium thiocyanate |

TABLE 5-continued

EXEMPLARY STORAGE COMPOSITIONS

| (A) Compound of Formula (I) | (A) + (B) Precipitating Agent | (A) + (C) Lower Alcohol | (A) + (D) Chaotrope | (A) + (B) + (C) | (A) + (B) + (D) | (A) + (B) + (C) + (D) | (A) + (C) + (D) |
|---|---|---|---|---|---|---|---|
| 1-hexyl-3-methylimidazolium bromide | 1-hexyl-3-methylimidazolium bromide + lithium hydroxide | 1-hexyl-3-methylimidazolium bromide + methanol | 1-hexyl-3-methylimidazolium bromide + sodium thiocyanate | 1-hexyl-3-methylimidazolium bromide + Lithium hydroxide + methanol | 1-hexyl-3-methylimidazolium bromide + LiOH + sodium thiocyanate | 1-hexyl-3-methylimidazolium bromide + LiOH + methanol + sodium thiocyanate | 1-hexyl-3-methylimidazolium bromide + methanol + sodium thiocyanate |
| 1-decyl-3-methylimidazolium bromide | 1-decyl-3-methylimidazolium bromide + lithium hydroxide | 1-decyl-3-methylimidazolium bromide + methanol | 1-decyl-3-methylimidazolium bromide + sodium thiocyanate | 1-decyl-3-methylimidazolium bromide + Lithium hydroxide + methanol | 1-decyl-3-methylimidazolium bromide + LiOH + sodium thiocyanate | 1-decyl-3-methylimidazolium bromide + LiOH + methanol + sodium thiocyanate | 1-decyl-3-methylimidazolium bromide + methanol + sodium thiocyanate |
| 1-(2-hydroxyethyl)-3-methylimidazolium bromide | 1-(2-hydroxyethyl)-3-methylimidazolium bromide + lithium hydroxide | 1-(2-hydroxyethyl)-3-methylimidazolium bromide + methanol | 1-(2-hydroxyethyl)-3-methylimidazolium bromide + sodium thiocyanate | 1-(2-hydroxyethyl)-3-methylimidazolium bromide + Lithium hydroxide + methanol | 1-(2-hydroxyethyl)-3-methylimidazolium bromide + LiOH + sodium thiocyanate | 1-(2-hydroxyethyl)-3-methylimidazolium bromide + LiOH + methanol + sodium thiocyanate | 1-(2-hydroxyethyl)-3-methylimidazolium bromide + methanol + sodium thiocyanate |
| 1-octyl-3-methylimidazolium bromide | 1-octyl-3-methylimidazolium bromide + lithium hydroxide | 1-octyl-3-methylimidazolium bromide + methanol | 1-octyl-3-methylimidazolium bromide + sodium thiocyanate | 1-octyl-3-methylimidazolium bromide + Lithium hydroxide + methanol | 1-octyl-3-methylimidazolium bromide + LiOH + sodium thiocyanate | 1-octyl-3-methylimidazolium bromide + LiOH + methanol + sodium thiocyanate | 1-octyl-3-methylimidazolium bromide + methanol + sodium thiocyanate |
| 1-methyl-3-carboxyethyl-imidazolium bromide | 1-methyl-3-carboxyethyl-imidazolium bromide + 5-(4-dimethyl)amino benzylidene rhodanine | 1-methyl-3-carboxyethyl-imidazolium bromide + ethanol | 1-methyl-3-carboxyethyl-imidazolium bromide + sodium thiocyanate | 1-methyl-3-carboxyethyl-imidazolium bromide + 5-(4-dimethyl)amino benzylidene rhodanine + ethanol | 1-methyl-3-carboxyethyl-imidazolium bromide + 5-(4-dimethyl)amino benzylidene rhodanine + sodium thiocyanate | 1-methyl-3-carboxyethyl-imidazolium bromide + 5-(4-dimethyl)amino benzylidene rhodanine + ethanol + sodium thiocyanate | 1-methyl-3-carboxyethyl-imidazolium bromide + ethanol + sodium thiocyanate |
| 1-hexyl-3-methylimidazolium bromide | 1-hexyl-3-methylimidazolium bromide + 5-(4-dimethyl)amino benzylidene rhodanine | 1-hexyl-3-methylimidazolium bromide + ethanol | 1-hexyl-3-methylimidazolium bromide + sodium thiocyanate | 1-hexyl-3-methylimidazolium bromide + 5-(4-dimethyl)amino benzylidene rhodanine + ethanol | 1-hexyl-3-methylimidazolium bromide + 5-(4-dimethyl)amino benzylidene rhodanine + sodium thiocyanate | 1-hexyl-3-methylimidazolium bromide + 5-(4-dimethyl)amino benzylidene rhodanine + ethanol + sodium thiocyanate | 1-hexyl-3-methylimidazolium bromide + ethanol + sodium thiocyanate |

TABLE 5-continued

EXEMPLARY STORAGE COMPOSITIONS

| (A) Compound of Formula (I) | (A) + (B) Precipitating Agent | (A) + (C) Lower Alcohol | (A) + (D) Chaotrope | (A) + (B) + (C) | (A) + (B) + (D) | (A) + (B) + (C) + (D) | (A) + (C) + (D) |
|---|---|---|---|---|---|---|---|
| 1-decyl-3-methylimidazolium bromide | 1-decyl-3-methylimidazolium bromide + 5-(4-dimethyl)amino benzylidene rhodanine | 1-decyl-3-methylimidazolium bromide + ethanol | 1-decyl-3-methylimidazolium bromide + sodium thiocyanate | 1-decyl-3-methylimidazolium bromide + 5-(4-dimethyl)amino benzylidene rhodanine + ethanol | 1-decyl-3-methylimidazolium bromide + 5-(4-dimethyl)amino benzylidene rhodanine + sodium thiocyanate | 1-decyl-3-methylimidazolium bromide + 5-(4-dimethyl)amino benzylidene rhodanine + ethanol + sodium thiocyanate | 1-decyl-3-methylimidazolium bromide + ethanol + sodium thiocyanate |
| 1-(2-hydroxyethyl)-3-methylimidazolium bromide | 1-(2-hydroxyethyl)-3-methylimidazolium bromide + 5-(4-dimethyl)amino benzylidene rhodanine | 1-(2-hydroxyethyl)-3-methylimidazolium bromide + ethanol | 1-(2-hydroxyethyl)-3-methylimidazolium bromide + sodium thiocyanate | 1-(2-hydroxyethyl)-3-methylimidazolium bromide + 5-(4-dimethyl)amino benzylidene rhodanine + ethanol | 1-(2-hydroxyethyl)-3-methylimidazolium bromide + 5-(4-dimethyl)amino benzylidene rhodanine + sodium thiocyanate | 1-(2-hydroxyethyl)-3-methylimidazolium bromide + 5-(4-dimethyl)amino benzylidene rhodanine + ethanol + sodium thiocyanate | 1-(2-hydroxyethyl)-3-methylimidazolium bromide + ethanol + sodium thiocyanate |
| 1-octyl-3-methylimidazolium bromide | 1-octyl-3-methylimidazolium bromide + 5-(4-dimethyl)amino benzylidene rhodanine | 1-octyl-3-methylimidazolium bromide + ethanol | 1-octyl-3-methylimidazolium bromide + sodium thiocyanate | 1-octyl-3-methylimidazolium bromide + 5-(4-dimethyl)amino benzylidene rhodanine + ethanol | 1-octyl-3-methylimidazolium bromide + 5-(4-dimethyl)amino benzylidene rhodanine + sodium thiocyanate | 1-octyl-3-methylimidazolium bromide + 5-(4-dimethyl)amino benzylidene rhodanine + ethanol + sodium thiocyanate | 1-octyl-3-methylimidazolium bromide + ethanol + sodium thiocyanate |
| 1-methyl-3-carboxyethyl-imidazolium bromide | 1-methyl-3-carboxyethyl-imidazolium bromide + sulfosalicylic acid | 1-methyl-3-carboxyethyl-imidazolium bromide + ethanol | 1-methyl-3-carboxyethyl-imidazolium bromide + sodium thiocyanate | 1-methyl-3-carboxyethyl-imidazolium bromide + sulfosalicylic acid + ethanol | 1-methyl-3-carboxyethyl-imidazolium bromide + sulfosalicylic acid + sodium thiocyanate | 1-methyl-3-carboxyethyl-imidazolium bromide + sulfosalicylic acid + ethanol + sodium thiocyanate | 1-methyl-3-carboxyethyl-imidazolium bromide + ethanol + sodium thiocyanate |
| 1-hexyl-3-methylimidazolium bromide | 1-hexyl-3-methylimidazolium bromide + sulfosalicylic acid | 1-hexyl-3-methylimidazolium bromide + ethanol | 1-hexyl-3-methylimidazolium bromide + sodium thiocyanate | 1-hexyl-3-methylimidazolium bromide + sulfosalicylic acid + ethanol | 1-hexyl-3-methylimidazolium bromide + sulfosalicylic acid + sodium thiocyanate | 1-hexyl-3-methylimidazolium bromide + sulfosalicylic acid + ethanol + sodium thiocyanate | 1-hexyl-3-methylimidazolium bromide + ethanol + sodium thiocyanate |
| 1-decyl-3-methylimidazolium bromide | 1-decyl-3-methylimidazolium bromide + sulfosalicylic acid | 1-decyl-3-methylimidazolium bromide + ethanol | 1-decyl-3-methylimidazolium bromide + sodium thiocyanate | 1-decyl-3-methylimidazolium bromide + sulfosalicylic acid + ethanol | 1-decyl-3-methylimidazolium bromide + sulfosalicylic acid + sodium thiocyanate | 1-decyl-3-methylimidazolium bromide + sulfosalicylic acid + ethanol + sodium thiocyanate | 1-decyl-3-methylimidazolium bromide + ethanol + sodium thiocyanate |

TABLE 5-continued

EXEMPLARY STORAGE COMPOSITIONS

| (A) Compound of Formula (I) | (A) + (B) Precipitating Agent | (A) + (C) Lower Alcohol | (A) + (D) Chaotrope | (A) + (B) + (C) | (A) + (B) + (D) | (A) + (B) + (C) + (D) | (A) + (C) + (D) |
|---|---|---|---|---|---|---|---|
| 1-(2-hydroxyethyl)-3-methylimidazolium bromide | 1-(2-hydroxyethyl)-3-methylimidazolium bromide + sulfosalicylic acid | 1-(2-hydroxyethyl)-3-methylimidazolium bromide + ethanol | 1-(2-hydroxyethyl)-3-methylimidazolium bromide + sodium thiocyanate | 1-(2-hydroxyethyl)-3-methylimidazolium bromide + sulfosalicylic acid + ethanol | 1-(2-hydroxyethyl)-3-methylimidazolium bromide + sulfosalicylic acid + sodium thiocyanate | 1-(2-hydroxyethyl)-3-methylimidazolium bromide + sulfosalicylic acid + ethanol + sodium thiocyanate | 1-(2-hydroxyethyl)-3-methylimidazolium bromide + ethanol + sodium thiocyanate |
| 1-octyl-3-methylimidazolium bromide | 1-octyl-3-methylimidazolium bromide + sulfosalicylic acid | 1-octyl-3-methylimidazolium bromide + ethanol | 1-octyl-3-methylimidazolium bromide + sodium thiocyanate | 1-octyl-3-methylimidazolium bromide + sulfosalicylic acid + ethanol | 1-octyl-3-methylimidazolium bromide + sulfosalicylic acid + sodium thiocyanate | 1-octyl-3-methylimidazolium bromide + sulfosalicylic acid + ethanol + sodium thiocyanate | 1-octyl-3-methylimidazolium bromide + ethanol + sodium thiocyanate |
| 1-methyl-3-carboxyethyl-imidazolium bromide | 1-methyl-3-carboxyethyl-imidazolium bromide + lithium chloride | 1-methyl-3-carboxyethyl-imidazolium bromide + ethanol | 1-methyl-3-carboxyethyl-imidazolium bromide + sodium thiocyanate | 1-methyl-3-carboxyethyl-imidazolium bromide + LiCl + ethanol | 1-methyl-3-carboxyethyl-imidazolium bromide + LiCl + sodium thiocyanate | 1-methyl-3-carboxyethyl-imidazolium bromide + LiCl + ethanol + sodium thiocyanate | 1-methyl-3-carboxyethyl-imidazolium bromide + ethanol + sodium thiocyanate |
| 1-hexyl-3-methylimidazolium bromide | 1-hexyl-3-methylimidazolium bromide + lithium chloride | 1-hexyl-3-methylimidazolium bromide + ethanol | 1-hexyl-3-methylimidazolium bromide + sodium thiocyanate | 1-hexyl-3-methylimidazolium bromide + LiCl + ethanol | 1-hexyl-3-methylimidazolium bromide + LiCl + sodium thiocyanate | 1-hexyl-3-methylimidazolium bromide + LiCl + ethanol + sodium thiocyanate | 1-hexyl-3-methylimidazolium bromide + ethanol + sodium thiocyanate |
| 1-decyl-3-methylimidazolium bromide | 1-decyl-3-methylimidazolium bromide + lithium chloride | 1-decyl-3-methylimidazolium bromide + ethanol | 1-decyl-3-methylimidazolium bromide + sodium thiocyanate | 1-decyl-3-methylimidazolium bromide + LiCl + ethanol | 1-decyl-3-methylimidazolium bromide + LiCl + sodium thiocyanate | 1-decyl-3-methylimidazolium bromide + LiCl + ethanol + sodium thiocyanate | 1-decyl-3-methylimidazolium bromide + ethanol + sodium thiocyanate |
| 1-(2-hydroxyethyl)-3-methylimidazolium bromide | 1-(2-hydroxyethyl)-3-methylimidazolium bromide + lithium chloride | 1-(2-hydroxyethyl)-3-methylimidazolium bromide + ethanol | 1-(2-hydroxyethyl)-3-methylimidazolium bromide + sodium thiocyanate | 1-(2-hydroxyethyl)-3-methylimidazolium bromide + LiCl + ethanol | 1-(2-hydroxyethyl)-3-methylimidazolium bromide + LiCl + sodium thiocyanate | 1-(2-hydroxyethyl)-3-methylimidazolium bromide + LiCl + ethanol + sodium thiocyanate | 1-(2-hydroxyethyl)-3-methylimidazolium bromide + ethanol + sodium thiocyanate |
| 1-octyl-3-methylimidazolium bromide | 1-octyl-3-methylimidazolium bromide + lithium chloride | 1-octyl-3-methylimidazolium bromide + ethanol | 1-octyl-3-methylimidazolium bromide + sodium thiocyanate | 1-octyl-3-methylimidazolium bromide + LiCl + ethanol | 1-octyl-3-methylimidazolium bromide + LiCl + sodium thiocyanate | 1-octyl-3-methylimidazolium bromide + LiCl + ethanol + sodium thiocyanate | 1-octyl-3-methylimidazolium bromide + ethanol + sodium thiocyanate |

TABLE 5-continued

EXEMPLARY STORAGE COMPOSITIONS

| (A) Compound of Formula (I) | (A) + (B) Precipitating Agent | (A) + (C) Lower Alcohol | (A) + (D) Chaotrope | (A) + (B) + (C) | (A) + (B) + (D) | (A) + (B) + (C) + (D) | (A) + (C) + (D) |
|---|---|---|---|---|---|---|---|
| 1-methyl-3-carboxyethyl-imidazolium bromide | 1-methyl-3-carboxyethyl-imidazolium bromide + lithium hydroxide | 1-methyl-3-carboxyethyl-imidazolium bromide + ethanol | 1-methyl-3-carboxyethyl-imidazolium bromide + sodium thiocyanate | 1-methyl-3-carboxyethyl-imidazolium bromide + LiOH + ethanol | 1-methyl-3-carboxyethyl-imidazolium bromide + LiOH + sodium thiocyanate | 1-methyl-3-carboxyethyl-imidazolium bromide + LiOH + ethanol + sodium thiocyanate | 1-methyl-3-carboxyethyl-imidazolium bromide + ethanol + sodium thiocyanate |
| 1-hexyl-3-methylimidazolium bromide | 1-hexyl-3-methylimidazolium bromide + lithium hydroxide | 1-hexyl-3-methylimidazolium bromide + ethanol | 1-hexyl-3-methylimidazolium bromide + sodium thiocyanate | 1-hexyl-3-methylimidazolium bromide + LiOH + ethanol | 1-hexyl-3-methylimidazolium bromide + LiOH + sodium thiocyanate | 1-hexyl-3-methylimidazolium bromide + LiOH + ethanol + sodium thiocyanate | 1-hexyl-3-methylimidazolium bromide + ethanol + sodium thiocyanate |
| 1-decyl-3-methylimidazolium bromide | 1-decyl-3-methylimidazolium bromide + lithium hydroxide | 1-decyl-3-methylimidazolium bromide + ethanol | 1-decyl-3-methylimidazolium bromide + sodium thiocyanate | 1-decyl-3-methylimidazolium bromide + LiOH + ethanol | 1-decyl-3-methylimidazolium bromide + LiOH + sodium thiocyanate | 1-decyl-3-methylimidazolium bromide + LiOH + ethanol + sodium thiocyanate | 1-decyl-3-methylimidazolium bromide + ethanol + sodium thiocyanate |
| 1-(2-hydroxyethyl)-3-methylimidazolium bromide | 1-(2-hydroxyethyl)-3-methylimidazolium bromide + lithium hydroxide | 1-(2-hydroxyethyl)-3-methylimidazolium bromide + ethanol | 1-(2-hydroxyethyl)-3-methylimidazolium bromide + sodium thiocyanate | 1-(2-hydroxyethyl)-3-methylimidazolium bromide + LiOH + ethanol | 1-(2-hydroxyethyl)-3-methylimidazolium bromide + LiOH + sodium thiocyanate | 1-(2-hydroxyethyl)-3-methylimidazolium bromide + LiOH + ethanol + sodium thiocyanate | 1-(2-hydroxyethyl)-3-methylimidazolium bromide + ethanol + sodium thiocyanate |
| 1-octyl-3-methylimidazolium bromide | 1-octyl-3-methylimidazolium bromide + lithium hydroxide | 1-octyl-3-methylimidazolium bromide + ethanol | 1-octyl-3-methylimidazolium bromide + sodium thiocyanate | 1-octyl-3-methylimidazolium bromide + LiOH + ethanol | 1-octyl-3-methylimidazolium bromide + LiOH + sodium thiocyanate | 1-octyl-3-methylimidazolium bromide + LiOH + ethanol + sodium thiocyanate | 1-octyl-3-methylimidazolium bromide + ethanol + sodium thiocyanate |
| 1-methyl-3-carboxyethyl-imidazolium bromide + 5-(4-dimethyl)amino benzylidene rhodanine | 1-methyl-3-carboxyethyl-imidazolium bromide + n-propanol | 1-methyl-3-carboxyethyl-imidazolium bromide + sodium thiocyanate | 1-methyl-3-carboxyethyl-imidazolium bromide + 5-(4-dimethyl)amino benzylidene rhodanine + n-propanol | 1-methyl-3-carboxyethyl-imidazolium bromide + 5-(4-dimethyl)amino benzylidene rhodanine + sodium thiocyanate | 1-methyl-3-carboxyethyl-imidazolium bromide + 5-(4-dimethyl)amino benzylidene rhodanine + n-propanol + sodium thiocyanate | 1-methyl-3-carboxyethyl-imidazolium bromide + n-propanol + sodium thiocyanate |

TABLE 5-continued

EXEMPLARY STORAGE COMPOSITIONS

| (A) Compound of Formula (I) | (A) + (B) Precipitating Agent | (A) + (C) Lower Alcohol | (A) + (D) Chaotrope | (A) + (B) + (C) | (A) + (B) + (D) | (A) + (B) + (C) + (D) | (A) + (C) + (D) |
|---|---|---|---|---|---|---|---|
| 1-hexyl-3-methylimidazolium bromide | 1-hexyl-3-methylimidazolium bromide + 5-(4-dimethyl)amino benzylidene rhodanine | 1-hexyl-3-methylimidazolium bromide + n-propanol | 1-hexyl-3-methylimidazolium bromide + sodium thiocyanate | 1-hexyl-3-methylimidazolium bromide + 5-(4-dimethyl)amino benzylidene rhodanine + n-propanol | 1-hexyl-3-methylimidazolium bromide + 5-(4-dimethyl)amino benzylidene rhodanine + sodium thiocyanate | 1-hexyl-3-methylimidazolium bromide + 5-(4-dimethyl)amino benzylidene rhodanine + n-propanol + sodium thiocyanate | 1-hexyl-3-methylimidazolium bromide + n-propanol + sodium thiocyanate |
| 1-decyl-3-methylimidazolium bromide | 1-decyl-3-methylimidazolium bromide + 5-(4-dimethyl)amino benzylidene rhodanine | 1-decyl-3-methylimidazolium bromide + n-propanol | 1-decyl-3-methylimidazolium bromide + sodium thiocyanate | 1-decyl-3-methylimidazolium bromide + 5-(4-dimethyl)amino benzylidene rhodanine + n-propanol | 1-decyl-3-methylimidazolium bromide + 5-(4-dimethyl)amino benzylidene rhodanine + sodium thiocyanate | 1-decyl-3-methylimidazolium bromide + 5-(4-dimethyl)amino benzylidene rhodanine + n-propanol + sodium thiocyanate | 1-decyl-3-methylimidazolium bromide + n-propanol + sodium thiocyanate |
| 1-(2-hydroxyethyl)-3-methylimidazolium bromide | 1-(2-hydroxyethyl)-3-methylimidazolium bromide + 5-(4-dimethyl)amino benzylidene rhodanine | 1-(2-hydroxyethyl)-3-methylimidazolium bromide + n-propanol | 1-(2-hydroxyethyl)-3-methylimidazolium bromide + sodium thiocyanate | 1-(2-hydroxyethyl)-3-methylimidazolium bromide + 5-(4-dimethyl)amino benzylidene rhodanine + n-propanol | 1-(2-hydroxyethyl)-3-methylimidazolium bromide + 5-(4-dimethyl)amino benzylidene rhodanine + sodium thiocyanate | 1-(2-hydroxyethyl)-3-methylimidazolium bromide + 5-(4-dimethyl)amino benzylidene rhodanine + n-propanol + sodium thiocyanate | 1-(2-hydroxyethyl)-3-methylimidazolium bromide + n-propanol + sodium thiocyanate |
| 1-octyl-3-methylimidazolium bromide | 1-octyl-3-methylimidazolium bromide + 5-(4-dimethyl)amino benzylidene rhodanine | 1-octyl-3-methylimidazolium bromide + n-propanol | 1-octyl-3-methylimidazolium bromide + sodium thiocyanate | 1-octyl-3-methylimidazolium bromide + 5-(4-dimethyl)amino benzylidene rhodanine + n-propanol | 1-octyl-3-methylimidazolium bromide + 5-(4-dimethyl)amino benzylidene rhodanine + sodium thiocyanate | 1-octyl-3-methylimidazolium bromide + 5-(4-dimethyl)amino benzylidene rhodanine + n-propanol + sodium thiocyanate | 1-octyl-3-methylimidazolium bromide + n-propanol + sodium thiocyanate |
| 1-methyl-3-carboxyethyl-imidazolium bromide | 1-methyl-3-carboxyethyl-imidazolium bromide + sulfosalicylic acid | 1-methyl-3-carboxyethyl-imidazolium bromide + n-propanol | 1-methyl-3-carboxyethyl-imidazolium bromide + sodium thiocyanate | 1-methyl-3-carboxyethyl-imidazolium bromide + sulfosalicylic acid + n-propanol | 1-methyl-3-carboxyethyl-imidazolium bromide + sulfosalicylic acid + sodium thiocyanate | 1-methyl-3-carboxyethyl-imidazolium bromide + sulfosalicylic acid + n-propanol + sodium thiocyanate | 1-methyl-3-carboxyethyl-imidazolium bromide + n-propanol + sodium thiocyanate |

TABLE 5-continued

EXEMPLARY STORAGE COMPOSITIONS

| (A) Compound of Formula (I) | (A) + (B) Precipitating Agent | (A) + (C) Lower Alcohol | (A) + (D) Chaotrope | (A) + (B) + (C) | (A) + (B) + (D) | (A) + (B) + (C) + (D) | (A) + (C) + (D) |
|---|---|---|---|---|---|---|---|
| 1-hexyl-3-methylimidazolium bromide | 1-hexyl-3-methylimidazolium bromide + sulfosalicylic acid | 1-hexyl-3-methylimidazolium bromide + n-propanol | 1-hexyl-3-methylimidazolium bromide + sodium thiocyanate | 1-hexyl-3-methylimidazolium bromide + sulfosalicylic acid + n-propanol | 1-hexyl-3-methylimidazolium bromide + sulfosalicylic acid + sodium thiocyanate | 1-hexyl-3-methylimidazolium bromide + sulfosalicylic acid + n-propanol + sodium thiocyanate | 1-hexyl-3-methylimidazolium bromide + n-propanol + sodium thiocyanate |
| 1-decyl-3-methylimidazolium bromide | 1-decyl-3-methylimidazolium bromide + sulfosalicylic acid | 1-decyl-3-methylimidazolium bromide + n-propanol | 1-decyl-3-methylimidazolium bromide + sodium thiocyanate | 1-decyl-3-methylimidazolium bromide + sulfosalicylic acid + n-propanol | 1-decyl-3-methylimidazolium bromide + sulfosalicylic acid + sodium thiocyanate | 1-decyl-3-methylimidazolium bromide + sulfosalicylic acid + n-propanol + sodium thiocyanate | 1-decyl-3-methylimidazolium bromide + n-propanol + sodium thiocyanate |
| 1-(2-hydroxyethyl)-3-methylimidazolium bromide | 1-(2-hydroxyethyl)-3-methylimidazolium bromide + sulfosalicylic acid | 1-(2-hydroxyethyl)-3-methylimidazolium bromide + n-propanol | 1-(2-hydroxyethyl)-3-methylimidazolium bromide + sodium thiocyanate | 1-(2-hydroxyethyl)-3-methylimidazolium bromide + sulfosalicylic acid + n-propanol | 1-(2-hydroxyethyl)-3-methylimidazolium bromide + sulfosalicylic acid + sodium thiocyanate | 1-(2-hydroxyethyl)-3-methylimidazolium bromide + sulfosalicylic acid + n-propanol + sodium thiocyanate | 1-(2-hydroxyethyl)-3-methylimidazolium bromide + n-propanol + sodium thiocyanate |
| 1-octyl-3-methylimidazolium bromide | 1-octyl-3-methylimidazolium bromide + sulfosalicylic acid | 1-octyl-3-methylimidazolium bromide + n-propanol | 1-octyl-3-methylimidazolium bromide + sodium thiocyanate | 1-octyl-3-methylimidazolium bromide + sulfosalicylic acid + n-propanol | 1-octyl-3-methylimidazolium bromide + sulfosalicylic acid + sodium thiocyanate | 1-octyl-3-methylimidazolium bromide + sulfosalicylic acid + n-propanol + sodium thiocyanate | 1-octyl-3-methylimidazolium bromide + n-propanol + sodium thiocyanate |
| 1-methyl-3-carboxyethyl-imidazolium bromide | 1-methyl-3-carboxyethyl-imidazolium bromide + lithium chloride | 1-methyl-3-carboxyethyl-imidazolium bromide + n-propanol | 1-methyl-3-carboxyethyl-imidazolium bromide + sodium thiocyanate | 1-methyl-3-carboxyethyl-imidazolium bromide + LiCl + n-propanol | 1-methyl-3-carboxyethyl-imidazolium bromide + LiCl + sodium thiocyanate | 1-methyl-3-carboxyethyl-imidazolium bromide + LiCl + n-propanol + sodium thiocyanate | 1-methyl-3-carboxyethyl-imidazolium bromide + n-propanol + sodium thiocyanate |
| 1-hexyl-3-methylimidazolium bromide | 1-hexyl-3-methylimidazolium bromide + lithium chloride | 1-hexyl-3-methylimidazolium bromide + n-propanol | 1-hexyl-3-methylimidazolium bromide + sodium thiocyanate | 1-hexyl-3-methylimidazolium bromide + LiCl + n-propanol | 1-hexyl-3-methylimidazolium bromide + LiCl + sodium thiocyanate | 1-hexyl-3-methylimidazolium bromide + LiCl + n-propanol + sodium thiocyanate | 1-hexyl-3-methylimidazolium bromide + n-propanol + sodium thiocyanate |
| 1-decyl-3-methylimidazolium bromide | 1-decyl-3-methylimidazolium bromide + lithium chloride | 1-decyl-3-methylimidazolium bromide + n-propanol | 1-decyl-3-methylimidazolium bromide + sodium thiocyanate | 1-decyl-3-methylimidazolium bromide + LiCl + n-propanol | 1-decyl-3-methylimidazolium bromide + LiCl + sodium thiocyanate | 1-decyl-3-methylimidazolium bromide + LiCl + n-propanol + sodium thiocyanate | 1-decyl-3-methylimidazolium bromide + n-propanol + sodium thiocyanate |

TABLE 5-continued

EXEMPLARY STORAGE COMPOSITIONS

| (A) Compound of Formula (I) | (A) + (B) Precipitating Agent | (A) + (C) Lower Alcohol | (A) + (D) Chaotrope | (A) + (B) + (C) | (A) + (B) + (D) | (A) + (B) + (C) + (D) | (A) + (C) + (D) |
|---|---|---|---|---|---|---|---|
| 1-(2-hydroxyethyl)-3-methylimidazolium bromide | 1-(2-hydroxyethyl)-3-methylimidazolium bromide + lithium chloride | 1-(2-hydroxyethyl)-3-methylimidazolium bromide + n-propanol | 1-(2-hydroxyethyl)-3-methylimidazolium bromide + sodium thiocyanate | 1-(2-hydroxyethyl)-3-methylimidazolium bromide + LiCl + n-propanol | 1-(2-hydroxyethyl)-3-methylimidazolium bromide + LiCl + sodium thiocyanate | 1-(2-hydroxyethyl)-3-methylimidazolium bromide + LiCl + n-propanol + sodium thiocyanate | 1-(2-hydroxyethyl)-3-methylimidazolium bromide + n-propanol + sodium thiocyanate |
| 1-octyl-3-methylimidazolium bromide | 1-octyl-3-methylimidazolium bromide + lithium chloride | 1-octyl-3-methylimidazolium bromide + n-propanol | 1-octyl-3-methylimidazolium bromide + sodium thiocyanate | 1-octyl-3-methylimidazolium bromide + LiCl + n-propanol | 1-octyl-3-methylimidazolium bromide + LiCl + sodium thiocyanate | 1-octyl-3-methylimidazolium bromide + LiCl + n-propanol + sodium thiocyanate | 1-octyl-3-methylimidazolium bromide + n-propanol + sodium thiocyanate |
| 1-methyl-3-carboxyethyl-imidazolium bromide | 1-methyl-3-carboxyethyl-imidazolium bromide + lithium hydroxide | 1-methyl-3-carboxyethyl-imidazolium bromide + n-propanol | 1-methyl-3-carboxyethyl-imidazolium bromide + sodium thiocyanate | 1-methyl-3-carboxyethyl-imidazolium bromide + LiOH + n-propanol | 1-methyl-3-carboxyethyl-imidazolium bromide + LiOH + sodium thiocyanate | 1-methyl-3-carboxyethyl-imidazolium bromide + LiOH + n-propanol + sodium thiocyanate | 1-methyl-3-carboxyethyl-imidazolium bromide + n-propanol + sodium thiocyanate |
| 1-hexyl-3-methylimidazolium bromide | 1-hexyl-3-methylimidazolium bromide + lithium hydroxide | 1-hexyl-3-methylimidazolium bromide + n-propanol | 1-hexyl-3-methylimidazolium bromide + sodium thiocyanate | 1-hexyl-3-methylimidazolium bromide + LiOH + n-propanol | 1-hexyl-3-methylimidazolium bromide + LiOH + sodium thiocyanate | 1-hexyl-3-methylimidazolium bromide + LiOH + n-propanol + sodium thiocyanate | 1-hexyl-3-methylimidazolium bromide + n-propanol + sodium thiocyanate |
| 1-decyl-3-methylimidazolium bromide | 1-decyl-3-methylimidazolium bromide + lithium hydroxide | 1-decyl-3-methylimidazolium bromide + n-propanol | 1-decyl-3-methylimidazolium bromide + sodium thiocyanate | 1-decyl-3-methylimidazolium bromide + LiOH + n-propanol | 1-decyl-3-methylimidazolium bromide + LiOH + sodium thiocyanate | 1-decyl-3-methylimidazolium bromide + LiOH + n-propanol + sodium thiocyanate | 1-decyl-3-methylimidazolium bromide + n-propanol + sodium thiocyanate |
| 1-(2-hydroxyethyl)-3-methylimidazolium bromide | 1-(2-hydroxyethyl)-3-methylimidazolium bromide + lithium hydroxide | 1-(2-hydroxyethyl)-3-methylimidazolium bromide + n-propanol | 1-(2-hydroxyethyl)-3-methylimidazolium bromide + sodium thiocyanate | 1-(2-hydroxyethyl)-3-methylimidazolium bromide + LiOH + n-propanol | 1-(2-hydroxyethyl)-3-methylimidazolium bromide + LiOH + sodium thiocyanate | 1-(2-hydroxyethyl)-3-methylimidazolium bromide + LiOH + n-propanol + sodium thiocyanate | 1-(2-hydroxyethyl)-3-methylimidazolium bromide + n-propanol + sodium thiocyanate |
| 1-octyl-3-methylimidazolium bromide | 1-octyl-3-methylimidazolium bromide + lithium hydroxide | 1-octyl-3-methylimidazolium bromide + n-propanol | 1-octyl-3-methylimidazolium bromide + sodium thiocyanate | 1-octyl-3-methylimidazolium bromide + LiOH + n-propanol | 1-octyl-3-methylimidazolium bromide + LiOH + sodium thiocyanate | 1-octyl-3-methylimidazolium bromide + LiOH + n-propanol + sodium thiocyanate | 1-octyl-3-methylimidazolium bromide + n-propanol + sodium thiocyanate |

TABLE 5-continued

EXEMPLARY STORAGE COMPOSITIONS

| (A) Compound of Formula (I) | (A) + (B) Precipitating Agent | (A) + (C) Lower Alcohol | (A) + (D) Chaotrope | (A) + (B) + (C) | (A) + (B) + (D) | (A) + (B) + (C) + (D) | (A) + (C) + (D) |
|---|---|---|---|---|---|---|---|
| 1-methyl-3-carboxyethyl-imidazolium bromide | 1-methyl-3-carboxyethyl-imidazolium bromide + 5-(4-dimethyl)amino benzylidene rhodanine | 1-methyl-3-carboxyethyl-imidazolium bromide + Isopropanol | 1-methyl-3-carboxyethyl-imidazolium bromide + sodium thiocyanate | 1-methyl-3-carboxyethyl-imidazolium bromide + 5-(4-dimethyl)amino benzylidene rhodanine + isopropanol | 1-methyl-3-carboxyethyl-imidazolium bromide + 5-(4-dimethyl)amino benzylidene rhodanine + sodium thiocyanate | 1-methyl-3-carboxyethyl-imidazolium bromide + 5-(4-dimethyl)amino benzylidene rhodanine + isopropanol + sodium thiocyanate | 1-methyl-3-carboxyethyl-imidazolium bromide + isopropanol + sodium thiocyanate |
| 1-hexyl-3-methylimidazolium bromide | 1-hexyl-3-methylimidazolium bromide + 5-(4-dimethyl)amino benzylidene rhodanine | 1-hexyl-3-methylimidazolium bromide + Isopropanol | 1-hexyl-3-methylimidazolium bromide + sodium thiocyanate | 1-hexyl-3-methylimidazolium bromide + 5-(4-dimethyl)amino benzylidene rhodanine + isopropanol | 1-hexyl-3-methylimidazolium bromide + 5-(4-dimethyl)amino benzylidene rhodanine + sodium thiocyanate | 1-hexyl-3-methylimidazolium bromide + 5-(4-dimethyl)amino benzylidene rhodanine + isopropanol + sodium thiocyanate | 1-hexyl-3-methylimidazolium bromide + isopropanol + sodium thiocyanate |
| 1-decyl-3-methylimidazolium bromide | 1-decyl-3-methylimidazolium bromide + 5-(4-dimethyl)amino benzylidene rhodanine | 1-decyl-3-methylimidazolium bromide + Isopropanol | 1-decyl-3-methylimidazolium bromide + sodium thiocyanate | 1-decyl-3-methylimidazolium bromide + 5-(4-dimethyl)amino benzylidene rhodanine + isopropanol | 1-decyl-3-methylimidazolium bromide + 5-(4-dimethyl)amino benzylidene rhodanine + sodium thiocyanate | 1-decyl-3-methylimidazolium bromide + 5-(4-dimethyl)amino benzylidene rhodanine + isopropanol + sodium thiocyanate | 1-decyl-3-methylimidazolium bromide + isopropanol + sodium thiocyanate |
| 1-(2-hydroxyethyl)-3-methylimidazolium bromide | 1-(2-hydroxyethyl)-3-methylimidazolium bromide + 5-(4-dimethyl)amino benzylidene rhodanine | 1-(2-hydroxyethyl)-3-methylimidazolium bromide + Isopropanol | 1-(2-hydroxyethyl)-3-methylimidazolium bromide + sodium thiocyanate | 1-(2-hydroxyethyl)-3-methylimidazolium bromide + 5-(4-dimethyl)amino benzylidene rhodanine + isopropanol | 1-(2-hydroxyethyl)-3-methylimidazolium bromide + 5-(4-dimethyl)amino benzylidene rhodanine + sodium thiocyanate | 1-(2-hydroxyethyl)-3-methylimidazolium bromide + 5-(4-dimethyl)amino benzylidene rhodanine + isopropanol + sodium thiocyanate | 1-(2-hydroxyethyl)-3-methylimidazolium bromide + isopropanol + sodium thiocyanate |
| 1-octyl-3-methylimidazolium bromide | 1-octyl-3-methylimidazolium bromide + 5-(4-dimethyl)amino benzylidene rhodanine | 1-octyl-3-methylimidazolium bromide + Isopropanol | 1-octyl-3-methylimidazolium bromide + sodium thiocyanate | 1-octyl-3-methylimidazolium bromide + 5-(4-dimethyl)amino benzylidene rhodanine + isopropanol | 1-octyl-3-methylimidazolium bromide + 5-(4-dimethyl)amino benzylidene rhodanine + sodium thiocyanate | 1-octyl-3-methylimidazolium bromide + 5-(4-dimethyl)amino benzylidene rhodanine + isopropanol + sodium thiocyanate | 1-octyl-3-methylimidazolium bromide + isopropanol + sodium thiocyanate |

TABLE 5-continued

EXEMPLARY STORAGE COMPOSITIONS

| (A) Compound of Formula (I) | (A) + (B) Precipitating Agent | (A) + (C) Lower Alcohol | (A) + (D) Chaotrope | (A) + (B) + (C) | (A) + (B) + (D) | (A) + (B) + (C) + (D) | (A) + (C) + (D) |
|---|---|---|---|---|---|---|---|
| 1-methyl-3-carboxyethyl-imidazolium bromide | 1-methyl-3-carboxyethyl-imidazolium bromide + sulfosalicylic acid | 1-methyl-3-carboxyethyl-imidazolium bromide + Isopropanol | 1-methyl-3-carboxyethyl-imidazolium bromide + sodium thiocyanate | 1-methyl-3-carboxyethyl-imidazolium bromide + sulfosalicylic acid + isopropanol | 1-methyl-3-carboxyethyl-imidazolium bromide + sulfosalicylic acid + sodium thiocyanate | 1-methyl-3-carboxyethyl-imidazolium bromide + sulfosalicylic acid + isopropanol + sodium thiocyanate | 1-methyl-3-carboxyethyl-imidazolium bromide + isopropanol + sodium thiocyanate |
| 1-hexyl-3-methylimidazolium bromide | 1-hexyl-3-methylimidazolium bromide + sulfosalicylic acid | 1-hexyl-3-methylimidazolium bromide + Isopropanol | 1-hexyl-3-methylimidazolium bromide + sodium thiocyanate | 1-hexyl-3-methylimidazolium bromide + sulfosalicylic acid + isopropanol | 1-hexyl-3-methylimidazolium bromide + sulfosalicylic acid + sodium thiocyanate | 1-hexyl-3-methylimidazolium bromide + sulfosalicylic acid + isopropanol + sodium thiocyanate | 1-hexyl-3-methylimidazolium bromide + isopropanol + sodium thiocyanate |
| 1-decyl-3-methylimidazolium bromide | 1-decyl-3-methylimidazolium bromide + sulfosalicylic acid | 1-decyl-3-methylimidazolium bromide + Isopropanol | 1-decyl-3-methylimidazolium bromide + sodium thiocyanate | 1-decyl-3-methylimidazolium bromide + sulfosalicylic acid + isopropanol | 1-decyl-3-methylimidazolium bromide + sulfosalicylic acid + sodium thiocyanate | 1-decyl-3-methylimidazolium bromide + sulfosalicylic acid + isopropanol + sodium thiocyanate | 1-decyl-3-methylimidazolium bromide + isopropanol + sodium thiocyanate |
| 1-(2-hydroxyethyl)-3-methylimidazolium bromide | 1-(2-hydroxyethyl)-3-methylimidazolium bromide + sulfosalicylic acid | 1-(2-hydroxyethyl)-3-methylimidazolium bromide + Isopropanol | 1-(2-hydroxyethyl)-3-methylimidazolium bromide + sodium thiocyanate | 1-(2-hydroxyethyl)-3-methylimidazolium bromide + sulfosalicylic acid + isopropanol | 1-(2-hydroxyethyl)-3-methylimidazolium bromide + sulfosalicylic acid + sodium thiocyanate | 1-(2-hydroxyethyl)-3-methylimidazolium bromide + sulfosalicylic acid + isopropanol + sodium thiocyanate | 1-(2-hydroxyethyl)-3-methylimidazolium bromide + isopropanol + sodium thiocyanate |
| 1-octyl-3-methylimidazolium bromide | 1-octyl-3-methylimidazolium bromide + sulfosalicylic acid | 1-octyl-3-methylimidazolium bromide + Isopropanol | 1-octyl-3-methylimidazolium bromide + sodium thiocyanate | 1-octyl-3-methylimidazolium bromide + sulfosalicylic acid + isopropanol | 1-octyl-3-methylimidazolium bromide + sulfosalicylic acid + sodium thiocyanate | 1-octyl-3-methylimidazolium bromide + sulfosalicylic acid + isopropanol + sodium thiocyanate | 1-octyl-3-methylimidazolium bromide + isopropanol + sodium thiocyanate |
| 1-methyl-3-carboxyethyl-imidazolium bromide | 1-methyl-3-carboxyethyl-imidazolium bromide + lithium chloride | 1-methyl-3-carboxyethyl-imidazolium bromide + Isopropanol | 1-methyl-3-carboxyethyl-imidazolium bromide + sodium thiocyanate | 1-methyl-3-carboxyethyl-imidazolium bromide + LiCl + isopropanol | 1-methyl-3-carboxyethyl-imidazolium bromide + LiCl + sodium thiocyanate | 1-methyl-3-carboxyethyl-imidazolium bromide + LiCl + isopropanol + sodium thiocyanate | 1-methyl-3-carboxyethyl-imidazolium bromide + isopropanol + sodium thiocyanate |

TABLE 5-continued

EXEMPLARY STORAGE COMPOSITIONS

| (A) Compound of Formula (I) | (B) Precipitating Agent | (C) Lower Alcohol | (D) Chaotrope | (A) + (B) | (A) + (C) | (A) + (D) | (A) + (B) + (C) | (A) + (B) + (D) | (A) + (B) + (C) + (D) | (A) + (C) + (D) |
|---|---|---|---|---|---|---|---|---|---|---|
| 1-hexyl-3-methylimidazolium bromide | lithium chloride | Isopropanol | sodium thiocyanate | 1-hexyl-3-methylimidazolium bromide + lithium chloride | 1-hexyl-3-methylimidazolium bromide + Isopropanol | 1-hexyl-3-methylimidazolium bromide + sodium thiocyanate | 1-hexyl-3-methylimidazolium bromide + LiCl + isopropanol | 1-hexyl-3-methylimidazolium bromide + LiCl + sodium thiocyanate | 1-hexyl-3-methylimidazolium bromide + LiCl + isopropanol + sodium thiocyanate | 1-hexyl-3-methylimidazolium bromide + isopropanol + sodium thiocyanate |
| 1-decyl-3-methylimidazolium bromide | lithium chloride | Isopropanol | sodium thiocyanate | 1-decyl-3-methylimidazolium bromide + lithium chloride | 1-decyl-3-methylimidazolium bromide + Isopropanol | 1-decyl-3-methylimidazolium bromide + sodium thiocyanate | 1-decyl-3-methylimidazolium bromide + LiCl + isopropanol | 1-decyl-3-methylimidazolium bromide + LiCl + sodium thiocyanate | 1-decyl-3-methylimidazolium bromide + LiCl + isopropanol + sodium thiocyanate | 1-decyl-3-methylimidazolium bromide + isopropanol + sodium thiocyanate |
| 1-(2-hydroxyethyl)-3-methylimidazolium bromide | lithium chloride | Isopropanol | sodium thiocyanate | 1-(2-hydroxyethyl)-3-methylimidazolium bromide + lithium chloride | 1-(2-hydroxyethyl)-3-methylimidazolium bromide + Isopropanol | 1-(2-hydroxyethyl)-3-methylimidazolium bromide + sodium thiocyanate | 1-(2-hydroxyethyl)-3-methylimidazolium bromide + LiCl + isopropanol | 1-(2-hydroxyethyl)-3-methylimidazolium bromide + LiCl + sodium thiocyanate | 1-(2-hydroxyethyl)-3-methylimidazolium bromide + LiCl + isopropanol + sodium thiocyanate | 1-(2-hydroxyethyl)-3-methylimidazolium bromide + isopropanol + sodium thiocyanate |
| 1-octyl-3-methylimidazolium bromide | lithium chloride | Isopropanol | sodium thiocyanate | 1-octyl-3-methylimidazolium bromide + lithium chloride | 1-octyl-3-methylimidazolium bromide + Isopropanol | 1-octyl-3-methylimidazolium bromide + sodium thiocyanate | 1-octyl-3-methylimidazolium bromide + LiCl + isopropanol | 1-octyl-3-methylimidazolium bromide + LiCl + sodium thiocyanate | 1-octyl-3-methylimidazolium bromide + LiCl + isopropanol + sodium thiocyanate | 1-octyl-3-methylimidazolium bromide + isopropanol + sodium thiocyanate |
| 1-methyl-3-carboxyethyl-imidazolium bromide | lithium hydroxide | Isopropanol | sodium thiocyanate | 1-methyl-3-carboxyethyl-imidazolium bromide + lithium hydroxide | 1-methyl-3-carboxyethyl-imidazolium bromide + Isopropanol | 1-methyl-3-carboxyethyl-imidazolium bromide + sodium thiocyanate | 1-methyl-3-carboxyethyl-imidazolium bromide + LiOH + isopropanol | 1-methyl-3-carboxyethyl-imidazolium bromide + LiOH + sodium thiocyanate | 1-methyl-3-carboxyethyl-imidazolium bromide + LiOH + isopropanol + sodium thiocyanate | 1-methyl-3-carboxyethyl-imidazolium bromide + isopropanol + sodium thiocyanate |
| 1-hexyl-3-methylimidazolium bromide | lithium hydroxide | Isopropanol | sodium thiocyanate | 1-hexyl-3-methylimidazolium bromide + lithium hydroxide | 1-hexyl-3-methylimidazolium bromide + Isopropanol | 1-hexyl-3-methylimidazolium bromide + sodium thiocyanate | 1-hexyl-3-methylimidazolium bromide + LiOH + isopropanol | 1-hexyl-3-methylimidazolium bromide + LiOH + sodium thiocyanate | 1-hexyl-3-methylimidazolium bromide + LiOH + isopropanol + sodium thiocyanate | 1-hexyl-3-methylimidazolium bromide + isopropanol + sodium thiocyanate |
| 1-decyl-3-methylimidazolium bromide | lithium hydroxide | Isopropanol | sodium thiocyanate | 1-decyl-3-methylimidazolium bromide + lithium hydroxide | 1-decyl-3-methylimidazolium bromide + Isopropanol | 1-decyl-3-methylimidazolium bromide + sodium thiocyanate | 1-decyl-3-methylimidazolium bromide + LiOH + isopropanol | 1-decyl-3-methylimidazolium bromide + LiOH + sodium thiocyanate | 1-decyl-3-methylimidazolium bromide + LiOH + isopropanol + sodium thiocyanate | 1-decyl-3-methylimidazolium bromide + isopropanol + sodium thiocyanate |

TABLE 5-continued

EXEMPLARY STORAGE COMPOSITIONS

| (A) Compound of Formula (I) | (A) + (B) Precipitating Agent | (A) + (C) Lower Alcohol | (A) + (D) Chaotrope | (A) + (B) + (C) | (A) + (B) + (D) | (A) + (B) + (C) + (D) | (A) + (C) + (D) |
|---|---|---|---|---|---|---|---|
| 1-(2-hydroxyethyl)-3-methylimidazolium bromide | 1-(2-hydroxyethyl)-3-methylimidazolium bromide + lithium hydroxide | 1-(2-hydroxyethyl)-3-methylimidazolium bromide + Isopropanol | 1-(2-hydroxyethyl)-3-methylimidazolium bromide + sodium thiocyanate | 1-(2-hydroxyethyl)-3-methylimidazolium bromide + LiOH + isopropanol | 1-(2-hydroxyethyl)-3-methylimidazolium bromide + LiOH + sodium thiocyanate | 1-(2-hydroxyethyl)-3-methylimidazolium bromide + LiOH + isopropanol + sodium thiocyanate | 1-(2-hydroxyethyl)-3-methylimidazolium bromide + isopropanol + sodium thiocyanate |
| 1-octyl-3-methylimidazolium bromide | 1-octyl-3-methylimidazolium bromide + lithium hydroxide | 1-octyl-3-methylimidazolium bromide + Isopropanol | 1-octyl-3-methylimidazolium bromide + sodium thiocyanate | 1-octyl-3-methylimidazolium bromide + LiOH + isopropanol | 1-octyl-3-methylimidazolium bromide + LiOH + sodium thiocyanate | 1-octyl-3-methylimidazolium bromide + LiOH + isopropanol + sodium thiocyanate | 1-octyl-3-methylimidazolium bromide + isopropanol + sodium thiocyanate |
| 1-methyl-3-carboxyethyl-imidazolium bromide | 1-methyl-3-carboxyethyl-imidazolium bromide + 5-(4-dimethyl)amino benzylidene rhodanine | 1-methyl-3-carboxyethyl-imidazolium bromide + n-butanol | 1-methyl-3-carboxyethyl-imidazolium bromide + sodium thiocyanate | 1-methyl-3-carboxyethyl-imidazolium bromide + 5-(4-dimethyl)amino benzylidene rhodanine + n-butanol | 1-methyl-3-carboxyethyl-imidazolium bromide + 5-(4-dimethyl)amino benzylidene rhodanine + sodium thiocyanate | 1-methyl-3-carboxyethyl-imidazolium bromide + 5-(4-dimethyl)amino benzylidene rhodanine + n-butanol + sodium thiocyanate | 1-methyl-3-carboxyethyl-imidazolium bromide + n-butanol + sodium thiocyanate |
| 1-hexyl-3-methylimidazolium bromide | 1-hexyl-3-methylimidazolium bromide + 5-(4-dimethyl)amino benzylidene rhodanine | 1-hexyl-3-methylimidazolium bromide + n-butanol | 1-hexyl-3-methylimidazolium bromide + sodium thiocyanate | 1-hexyl-3-methylimidazolium bromide + 5-(4-dimethyl)amino benzylidene rhodanine + n-butanol | 1-hexyl-3-methylimidazolium bromide + 5-(4-dimethyl)amino benzylidene rhodanine + sodium thiocyanate | 1-hexyl-3-methylimidazolium bromide + 5-(4-dimethyl)amino benzylidene rhodanine + n-butanol + sodium thiocyanate | 1-hexyl-3-methylimidazolium bromide + n-butanol + sodium thiocyanate |
| 1-decyl-3-methylimidazolium bromide | 1-decyl-3-methylimidazolium bromide + 5-(4-dimethyl)amino benzylidene rhodanine | 1-decyl-3-methylimidazolium bromide + n-butanol | 1-decyl-3-methylimidazolium bromide + sodium thiocyanate | 1-decyl-3-methylimidazolium bromide + 5-(4-dimethyl)amino benzylidene rhodanine + n-butanol | 1-decyl-3-methylimidazolium bromide + 5-(4-dimethyl)amino benzylidene rhodanine + sodium thiocyanate | 1-decyl-3-methylimidazolium bromide + 5-(4-dimethyl)amino benzylidene rhodanine + n-butanol + sodium thiocyanate | 1-decyl-3-methylimidazolium bromide + n-butanol + sodium thiocyanate |
| 1-(2-hydroxyethyl)-3-methylimidazolium bromide | 1-(2-hydroxyethyl)-3-methylimidazolium bromide + 5-(4-dimethyl)amino benzylidene rhodanine | 1-(2-hydroxyethyl)-3-methylimidazolium bromide + n-butanol | 1-(2-hydroxyethyl)-3-methylimidazolium bromide + sodium thiocyanate | 1-(2-hydroxyethyl)-3-methylimidazolium bromide + 5-(4-dimethyl)amino benzylidene rhodanine + n-butanol | 1-(2-hydroxyethyl)-3-methylimidazolium bromide + 5-(4-dimethyl)amino benzylidene rhodanine + sodium thiocyanate | 1-(2-hydroxyethyl)-3-methylimidazolium bromide + 5-(4-dimethyl)amino benzylidene rhodanine + n-butanol + sodium thiocyanate | 1-(2-hydroxyethyl)-3-methylimidazolium bromide + n-butanol + sodium thiocyanate |

TABLE 5-continued

EXEMPLARY STORAGE COMPOSITIONS

| (A) Compound of Formula (I) | (A) + (B) Precipitating Agent | (A) + (C) Lower Alcohol | (A) + (D) Chaotrope | (A) + (B) + (C) | (A) + (B) + (D) | (A) + (B) + (C) + (D) | (A) + (C) + (D) |
|---|---|---|---|---|---|---|---|
| 1-octyl-3-methylimidazolium bromide | 1-octyl-3-methylimidazolium bromide + 5-(4-dimethyl)amino benzylidene rhodanine | 1-octyl-3-methylimidazolium bromide + n-butanol | 1-octyl-3-methylimidazolium bromide + sodium thiocyanate | 1-octyl-3-methylimidazolium bromide + 5-(4-dimethyl)amino benzylidene rhodanine + n-butanol | 1-octyl-3-methylimidazolium bromide + 5-(4-dimethyl)amino benzylidene rhodanine + sodium thiocyanate | 1-octyl-3-methylimidazolium bromide + 5-(4-dimethyl)amino benzylidene rhodanine + n-butanol + sodium thiocyanate | 1-octyl-3-methylimidazolium bromide + n-butanol + sodium thiocyanate |
| 1-methyl-3-carboxyethyl-imidazolium bromide | 1-methyl-3-carboxyethyl-imidazolium bromide + sulfosalicylic acid | 1-methyl-3-carboxyethyl-imidazolium bromide + n-butanol | 1-methyl-3-carboxyethyl-imidazolium bromide + sodium thiocyanate | 1-methyl-3-carboxyethyl-imidazolium bromide + sulfosalicylic acid + n-butanol | 1-methyl-3-carboxyethyl-imidazolium bromide + sulfosalicylic acid + sodium thiocyanate | 1-methyl-3-carboxyethyl-imidazolium bromide + sulfosalicylic acid + n-butanol + sodium thiocyanate | 1-methyl-3-carboxyethyl-imidazolium bromide + n-butanol + sodium thiocyanate |
| 1-hexyl-3-methylimidazolium bromide | 1-hexyl-3-methylimidazolium bromide + sulfosalicylic acid | 1-hexyl-3-methylimidazolium bromide + n-butanol | 1-hexyl-3-methylimidazolium bromide + sodium thiocyanate | 1-hexyl-3-methylimidazolium bromide + sulfosalicylic acid + n-butanol | 1-hexyl-3-methylimidazolium bromide + sulfosalicylic acid + sodium thiocyanate | 1-hexyl-3-methylimidazolium bromide + sulfosalicylic acid + n-butanol + sodium thiocyanate | 1-hexyl-3-methylimidazolium bromide + n-butanol + sodium thiocyanate |
| 1-decyl-3-methylimidazolium bromide | 1-decyl-3-methylimidazolium bromide + sulfosalicylic acid | 1-decyl-3-methylimidazolium bromide + n-butanol | 1-decyl-3-methylimidazolium bromide + sodium thiocyanate | 1-decyl-3-methylimidazolium bromide + sulfosalicylic acid + n-butanol | 1-decyl-3-methylimidazolium bromide + sulfosalicylic acid + sodium thiocyanate | 1-decyl-3-methylimidazolium bromide + sulfosalicylic acid + n-butanol + sodium thiocyanate | 1-decyl-3-methylimidazolium bromide + n-butanol + sodium thiocyanate |
| 1-(2-hydroxyethyl)-3-methylimidazolium bromide | 1-(2-hydroxyethyl)-3-methylimidazolium bromide + sulfosalicylic acid | 1-(2-hydroxyethyl)-3-methylimidazolium bromide + n-butanol | 1-(2-hydroxyethyl)-3-methylimidazolium bromide + sodium thiocyanate | 1-(2-hydroxyethyl)-3-methylimidazolium bromide + sulfosalicylic acid + n-butanol | 1-(2-hydroxyethyl)-3-methylimidazolium bromide + sulfosalicylic acid + sodium thiocyanate | 1-(2-hydroxyethyl)-3-methylimidazolium bromide + sulfosalicylic acid + n-butanol + sodium thiocyanate | 1-(2-hydroxyethyl)-3-methylimidazolium bromide + n-butanol + sodium thiocyanate |
| 1-octyl-3-methylimidazolium bromide | 1-octyl-3-methylimidazolium bromide + sulfosalicylic acid | 1-octyl-3-methylimidazolium bromide + n-butanol | 1-octyl-3-methylimidazolium bromide + sodium thiocyanate | 1-octyl-3-methylimidazolium bromide + sulfosalicylic acid + n-butanol | 1-octyl-3-methylimidazolium bromide + sulfosalicylic acid + sodium thiocyanate | 1-octyl-3-methylimidazolium bromide + sulfosalicylic acid + n-butanol + sodium thiocyanate | 1-octyl-3-methylimidazolium bromide + n-butanol + sodium thiocyanate |

TABLE 5-continued

EXEMPLARY STORAGE COMPOSITIONS

| (A) Compound of Formula (I) | (A) + (B) Precipitating Agent | (A) + (C) Lower Alcohol | (A) + (D) Chaotrope | (A) + (B) + (C) | (A) + (B) + (D) | (A) + (B) + (C) + (D) | (A) + (C) + (D) |
|---|---|---|---|---|---|---|---|
| 1-methyl-3-carboxyethyl-imidazolium bromide | 1-methyl-3-carboxyethyl-imidazolium bromide + lithium chloride | 1-methyl-3-carboxyethyl-imidazolium bromide + n-butanol | 1-methyl-3-carboxyethyl-imidazolium bromide + sodium thiocyanate | 1-methyl-3-carboxyethyl-imidazolium bromide + LiCl + n-butanol | 1-methyl-3-carboxyethyl-imidazolium bromide + LiCl + sodium thiocyanate | 1-methyl-3-carboxyethyl-imidazolium bromide + LiCl + n-butanol + sodium thiocyanate | 1-methyl-3-carboxyethyl-imidazolium bromide + n-butanol + sodium thiocyanate |
| 1-hexyl-3-methylimidazolium bromide | 1-hexyl-3-methylimidazolium bromide + lithium chloride | 1-hexyl-3-methylimidazolium bromide + n-butanol | 1-hexyl-3-methylimidazolium bromide + sodium thiocyanate | 1-hexyl-3-methylimidazolium bromide + LiCl + n-butanol | 1-hexyl-3-methylimidazolium bromide + LiCl + sodium thiocyanate | 1-hexyl-3-methylimidazolium bromide + LiCl + n-butanol + sodium thiocyanate | 1-hexyl-3-methylimidazolium bromide + n-butanol + sodium thiocyanate |
| 1-decyl-3-methylimidazolium bromide | 1-decyl-3-methylimidazolium bromide + lithium chloride | 1-decyl-3-methylimidazolium bromide + n-butanol | 1-decyl-3-methylimidazolium bromide + sodium thiocyanate | 1-decyl-3-methylimidazolium bromide + LiCl + n-butanol | 1-decyl-3-methylimidazolium bromide + LiCl + sodium thiocyanate | 1-decyl-3-methylimidazolium bromide + LiCl + n-butanol + sodium thiocyanate | 1-decyl-3-methylimidazolium bromide + n-butanol + sodium thiocyanate |
| 1-(2-hydroxyethyl)-3-methylimidazolium bromide | 1-(2-hydroxyethyl)-3-methylimidazolium bromide + lithium chloride | 1-(2-hydroxyethyl)-3-methylimidazolium bromide + n-butanol | 1-(2-hydroxyethyl)-3-methylimidazolium bromide + sodium thiocyanate | 1-(2-hydroxyethyl)-3-methylimidazolium bromide + LiCl + n-butanol | 1-(2-hydroxyethyl)-3-methylimidazolium bromide + LiCl + sodium thiocyanate | 1-(2-hydroxyethyl)-3-methylimidazolium bromide + LiCl + n-butanol + sodium thiocyanate | 1-(2-hydroxyethyl)-3-methylimidazolium bromide + n-butanol + sodium thiocyanate |
| 1-octyl-3-methylimidazolium bromide | 1-octyl-3-methylimidazolium bromide + lithium chloride | 1-octyl-3-methylimidazolium bromide + n-butanol | 1-octyl-3-methylimidazolium bromide + sodium thiocyanate | 1-octyl-3-methylimidazolium bromide + LiCl + n-butanol | 1-octyl-3-methylimidazolium bromide + LiCl + sodium thiocyanate | 1-octyl-3-methylimidazolium bromide + LiCl + n-butanol + sodium thiocyanate | 1-octyl-3-methylimidazolium bromide + n-butanol + sodium thiocyanate |
| 1-methyl-3-carboxyethyl-imidazolium bromide | 1-methyl-3-carboxyethyl-imidazolium bromide + lithium hydroxide | 1-methyl-3-carboxyethyl-imidazolium bromide + n-butanol | 1-methyl-3-carboxyethyl-imidazolium bromide + sodium thiocyanate | 1-methyl-3-carboxyethyl-imidazolium bromide + LiOH + n-butanol | 1-methyl-3-carboxyethyl-imidazolium bromide + LiOH + sodium thiocyanate | 1-methyl-3-carboxyethyl-imidazolium bromide + LiOH + n-butanol + sodium thiocyanate | 1-methyl-3-carboxyethyl-imidazolium bromide + n-butanol + sodium thiocyanate |
| 1-hexyl-3-methylimidazolium bromide | 1-hexyl-3-methylimidazolium bromide + lithium hydroxide | 1-hexyl-3-methylimidazolium bromide + n-butanol | 1-hexyl-3-methylimidazolium bromide + sodium thiocyanate | 1-hexyl-3-methylimidazolium bromide + LiOH + n-butanol | 1-hexyl-3-methylimidazolium bromide + LiOH + sodium thiocyanate | 1-hexyl-3-methylimidazolium bromide + LiOH + n-butanol + sodium thiocyanate | 1-hexyl-3-methylimidazolium bromide + n-butanol + sodium thiocyanate |

TABLE 5-continued

EXEMPLARY STORAGE COMPOSITIONS

| (A) Compound of Formula (I) | (A) + (B) Precipitating Agent | (A) + (C) Lower Alcohol | (A) + (D) Chaotrope | (A) + (B) + (C) | (A) + (B) + (D) | (A) + (B) + (C) + (D) | (A) + (C) + (D) |
|---|---|---|---|---|---|---|---|
| 1-decyl-3-methylimidazolium bromide | 1-decyl-3-methylimidazolium bromide + lithium hydroxide | 1-decyl-3-methylimidazolium bromide + n-butanol | 1-decyl-3-methylimidazolium bromide + sodium thiocyanate | 1-decyl-3-methylimidazolium bromide + LiOH + n-butanol | 1-decyl-3-methylimidazolium bromide + LiOH + sodium thiocyanate | 1-decyl-3-methylimidazolium bromide + LiOH + n-butanol + sodium thiocyanate | 1-decyl-3-methylimidazolium bromide + n-butanol + sodium thiocyanate |
| 1-(2-hydroxyethyl)-3-methylimidazolium bromide | 1-(2-hydroxyethyl)-3-methylimidazolium bromide + lithium hydroxide | 1-(2-hydroxyethyl)-3-methylimidazolium bromide + n-butanol | 1-(2-hydroxyethyl)-3-methylimidazolium bromide + sodium thiocyanate | 1-(2-hydroxyethyl)-3-methylimidazolium bromide + LiOH + n-butanol | 1-(2-hydroxyethyl)-3-methylimidazolium bromide + LiOH + sodium thiocyanate | 1-(2-hydroxyethyl)-3-methylimidazolium bromide + LiOH + n-butanol + sodium thiocyanate | 1-(2-hydroxyethyl)-3-methylimidazolium bromide + n-butanol + sodium thiocyanate |
| 1-octyl-3-methylimidazolium bromide | 1-octyl-3-methylimidazolium bromide + lithium hydroxide | 1-octyl-3-methylimidazolium bromide + n-butanol | 1-octyl-3-methylimidazolium bromide + sodium thiocyanate | 1-octyl-3-methylimidazolium bromide + LiOH + n-butanol | 1-octyl-3-methylimidazolium bromide + LiOH + sodium thiocyanate | 1-octyl-3-methylimidazolium bromide + LiOH + n-butanol + sodium thiocyanate | 1-octyl-3-methylimidazolium bromide + n-butanol + sodium thiocyanate |
| 1-methyl-3-carboxyethyl-imidazolium bromide | 1-methyl-3-carboxyethyl-imidazolium bromide + 5-(4-dimethyl)amino benzylidene rhodanine | 1-methyl-3-carboxyethyl-imidazolium bromide + isobutanol | 1-methyl-3-carboxyethyl-imidazolium bromide + sodium thiocyanate | 1-methyl-3-carboxyethyl-imidazolium bromide + 5-(4-dimethyl)amino benzylidene rhodanine + isobutanol | 1-methyl-3-carboxyethyl-imidazolium bromide + 5-(4-dimethyl)amino benzylidene rhodanine + sodium thiocyanate | 1-methyl-3-carboxyethyl-imidazolium bromide + 5-(4-dimethyl)amino benzylidene rhodanine + isobutanol + sodium thiocyanate | 1-methyl-3-carboxyethyl-imidazolium bromide + isobutanol + sodium thiocyanate |
| 1-hexyl-3-methylimidazolium bromide | 1-hexyl-3-methylimidazolium bromide + 5-(4-dimethyl)amino benzylidene rhodanine | 1-hexyl-3-methylimidazolium bromide + isobutanol | 1-hexyl-3-methylimidazolium bromide + sodium thiocyanate | 1-hexyl-3-methylimidazolium bromide + 5-(4-dimethyl)amino benzylidene rhodanine + isobutanol | 1-hexyl-3-methylimidazolium bromide + 5-(4-dimethyl)amino benzylidene rhodanine + sodium thiocyanate | 1-hexyl-3-methylimidazolium bromide + 5-(4-dimethyl)amino benzylidene rhodanine + isobutanol + sodium thiocyanate | 1-hexyl-3-methylimidazolium bromide + isobutanol + sodium thiocyanate |
| 1-decyl-3-methylimidazolium bromide | 1-decyl-3-methylimidazolium bromide + 5-(4-dimethyl)amino benzylidene rhodanine | 1-decyl-3-methylimidazolium bromide + isobutanol | 1-decyl-3-methylimidazolium bromide + sodium thiocyanate | 1-decyl-3-methylimidazolium bromide + 5-(4-dimethyl)amino benzylidene rhodanine + isobutanol | 1-decyl-3-methylimidazolium bromide + 5-(4-dimethyl)amino benzylidene rhodanine + sodium thiocyanate | 1-decyl-3-methylimidazolium bromide + 5-(4-dimethyl)amino benzylidene rhodanine + isobutanol + sodium thiocyanate | 1-decyl-3-methylimidazolium bromide + isobutanol + sodium thiocyanate |

TABLE 5-continued

EXEMPLARY STORAGE COMPOSITIONS

| (A) Compound of Formula (I) | (A) + (B) Precipitating Agent | (A) + (C) Lower Alcohol | (A) + (D) Chaotrope | (A) + (B) + (C) | (A) + (B) + (D) | (A) + (B) + (C) + (D) | (A) + (C) + (D) |
|---|---|---|---|---|---|---|---|
| 1-(2-hydroxyethyl)-3-methylimidazolium bromide | 1-(2-hydroxyethyl)-3-methylimidazolium bromide + 5-(4-dimethyl)amino benzylidene rhodanine | 1-(2-hydroxyethyl)-3-methylimidazolium bromide + isobutanol | 1-(2-hydroxyethyl)-3-methylimidazolium bromide + sodium thiocyanate | 1-(2-hydroxyethyl)-3-methylimidazolium bromide + 5-(4-dimethyl)amino benzylidene rhodanine + isobutanol | 1-(2-hydroxyethyl)-3-methylimidazolium bromide + 5-(4-dimethyl)amino benzylidene rhodanine + sodium thiocyanate | 1-(2-hydroxyethyl)-3-methylimidazolium bromide + 5-(4-dimethyl)amino benzylidene rhodanine + isobutanol + sodium thiocyanate | 1-(2-hydroxyethyl)-3-methylimidazolium bromide + isobutanol + sodium thiocyanate |
| 1-octyl-3-methylimidazolium bromide | 1-octyl-3-methylimidazolium bromide + 5-(4-dimethyl)amino benzylidene rhodanine | 1-octyl-3-methylimidazolium bromide + isobutanol | 1-octyl-3-methylimidazolium bromide + sodium thiocyanate | 1-octyl-3-methylimidazolium bromide + 5-(4-dimethyl)amino benzylidene rhodanine + isobutanol | 1-octyl-3-methylimidazolium bromide + 5-(4-dimethyl)amino benzylidene rhodanine + sodium thiocyanate | 1-octyl-3-methylimidazolium bromide + 5-(4-dimethyl)amino benzylidene rhodanine + isobutanol + sodium thiocyanate | 1-octyl-3-methylimidazolium bromide + isobutanol + sodium thiocyanate |
| 1-methyl-3-carboxyethyl-imidazolium bromide | 1-methyl-3-carboxyethyl-imidazolium bromide + sulfosalicylic acid | 1-methyl-3-carboxyethyl-imidazolium bromide + isobutanol | 1-methyl-3-carboxyethyl-imidazolium bromide + sodium thiocyanate | 1-methyl-3-carboxyethyl-imidazolium bromide + sulfosalicylic acid + isobutanol | 1-methyl-3-carboxyethyl-imidazolium bromide + sulfosalicylic acid + sodium thiocyanate | 1-methyl-3-carboxyethyl-imidazolium bromide + sulfosalicylic acid + isobutanol + sodium thiocyanate | 1-methyl-3-carboxyethyl-imidazolium bromide + isobutanol + sodium thiocyanate |
| 1-hexyl-3-methylimidazolium bromide | 1-hexyl-3-methylimidazolium bromide + sulfosalicylic acid | 1-hexyl-3-methylimidazolium bromide + isobutanol | 1-hexyl-3-methylimidazolium bromide + sodium thiocyanate | 1-hexyl-3-methylimidazolium bromide + sulfosalicylic acid + isobutanol | 1-hexyl-3-methylimidazolium bromide + sulfosalicylic acid + sodium thiocyanate | 1-hexyl-3-methylimidazolium bromide + sulfosalicylic acid + isobutanol + sodium thiocyanate | 1-hexyl-3-methylimidazolium bromide + isobutanol + sodium thiocyanate |
| 1-decyl-3-methylimidazolium bromide | 1-decyl-3-methylimidazolium bromide + sulfosalicylic acid | 1-decyl-3-methylimidazolium bromide + isobutanol | 1-decyl-3-methylimidazolium bromide + sodium thiocyanate | 1-decyl-3-methylimidazolium bromide + sulfosalicylic acid + isobutanol | 1-decyl-3-methylimidazolium bromide + sulfosalicylic acid + sodium thiocyanate | 1-decyl-3-methylimidazolium bromide + sulfosalicylic acid + isobutanol + sodium thiocyanate | 1-decyl-3-methylimidazolium bromide + isobutanol + sodium thiocyanate |
| 1-(2-hydroxyethyl)-3-methylimidazolium bromide | 1-(2-hydroxyethyl)-3-methylimidazolium bromide + sulfosalicylic acid | 1-(2-hydroxyethyl)-3-methylimidazolium bromide + isobutanol | 1-(2-hydroxyethyl)-3-methylimidazolium bromide + sodium thiocyanate | 1-(2-hydroxyethyl)-3-methylimidazolium bromide + sulfosalicylic acid + isobutanol | 1-(2-hydroxyethyl)-3-methylimidazolium bromide + sulfosalicylic acid + sodium thiocyanate | 1-(2-hydroxyethyl)-3-methylimidazolium bromide + sulfosalicylic acid + isobutanol + sodium thiocyanate | 1-(2-hydroxyethyl)-3-methylimidazolium bromide + isobutanol + sodium thiocyanate |

TABLE 5-continued

EXEMPLARY STORAGE COMPOSITIONS

| (A) Compound of Formula (I) | (A) + (B) Precipitating Agent | (A) + (C) Lower Alcohol | (A) + (D) Chaotrope | (A) + (B) + (C) | (A) + (B) + (D) | (A) + (B) + (C) + (D) | (A) + (C) + (D) |
|---|---|---|---|---|---|---|---|
| 1-octyl-3-methylimidazolium bromide | 1-octyl-3-methylimidazolium bromide + sulfosalicylic acid | 1-octyl-3-methylimidazolium bromide + isobutanol | 1-octyl-3-methylimidazolium bromide + sodium thiocyanate | 1-octyl-3-methylimidazolium bromide + sulfosalicylic acid + isobutanol | 1-octyl-3-methylimidazolium bromide + sulfosalicylic acid + sodium thiocyanate | 1-octyl-3-methylimidazolium bromide + sulfosalicylic acid + isobutanol + sodium thiocyanate | 1-octyl-3-methylimidazolium bromide + isobutanol + sodium thiocyanate |
| 1-methyl-3-carboxyethyl-imidazolium bromide | 1-methyl-3-carboxyethyl-imidazolium bromide + lithium chloride | 1-methyl-3-carboxyethyl-imidazolium bromide + isobutanol | 1-methyl-3-carboxyethyl-imidazolium bromide + sodium thiocyanate | 1-methyl-3-carboxyethyl-imidazolium bromide + LiCl + isobutanol | 1-methyl-3-carboxyethyl-imidazolium bromide + LiCl + sodium thiocyanate | 1-methyl-3-carboxyethyl-imidazolium bromide + LiCl + isobutanol + sodium thiocyanate | 1-methyl-3-carboxyethyl-imidazolium bromide + isobutanol + sodium thiocyanate |
| 1-hexyl-3-methylimidazolium bromide | 1-hexyl-3-methylimidazolium bromide + lithium chloride | 1-hexyl-3-methylimidazolium bromide + isobutanol | 1-hexyl-3-methylimidazolium bromide + sodium thiocyanate | 1-hexyl-3-methylimidazolium bromide + LiCl + isobutanol | 1-hexyl-3-methylimidazolium bromide + LiCl + sodium thiocyanate | 1-hexyl-3-methylimidazolium bromide + LiCl + isobutanol + sodium thiocyanate | 1-hexyl-3-methylimidazolium bromide + isobutanol + sodium thiocyanate |
| 1-decyl-3-methylimidazolium bromide | 1-decyl-3-methylimidazolium bromide + lithium chloride | 1-decyl-3-methylimidazolium bromide + isobutanol | 1-decyl-3-methylimidazolium bromide + sodium thiocyanate | 1-decyl-3-methylimidazolium bromide + LiCl + isobutanol | 1-decyl-3-methylimidazolium bromide + LiCl + sodium thiocyanate | 1-decyl-3-methylimidazolium bromide + LiCl + isobutanol + sodium thiocyanate | 1-decyl-3-methylimidazolium bromide + isobutanol + sodium thiocyanate |
| 1-(2-hydroxyethyl)-3-methylimidazolium bromide | 1-(2-hydroxyethyl)-3-methylimidazolium bromide + lithium chloride | 1-(2-hydroxyethyl)-3-methylimidazolium bromide + isobutanol | 1-(2-hydroxyethyl)-3-methylimidazolium bromide + sodium thiocyanate | 1-(2-hydroxyethyl)-3-methylimidazolium bromide + LiCl + isobutanol | 1-(2-hydroxyethyl)-3-methylimidazolium bromide + LiCl + sodium thiocyanate | 1-(2-hydroxyethyl)-3-methylimidazolium bromide + LiCl + isobutanol + sodium thiocyanate | 1-(2-hydroxyethyl)-3-methylimidazolium bromide + isobutanol + sodium thiocyanate |
| 1-octyl-3-methylimidazolium bromide | 1-octyl-3-methylimidazolium bromide + lithium chloride | 1-octyl-3-methylimidazolium bromide + isobutanol | 1-octyl-3-methylimidazolium bromide + sodium thiocyanate | 1-octyl-3-methylimidazolium bromide + LiCl + isobutanol | 1-octyl-3-methylimidazolium bromide + LiCl + sodium thiocyanate | 1-octyl-3-methylimidazolium bromide + LiCl + isobutanol + sodium thiocyanate | 1-octyl-3-methylimidazolium bromide + isobutanol + sodium thiocyanate |
| 1-methyl-3-carboxyethyl-imidazolium bromide | 1-methyl-3-carboxyethyl-imidazolium bromide + lithium hydroxide | 1-methyl-3-carboxyethyl-imidazolium bromide + isobutanol | 1-methyl-3-carboxyethyl-imidazolium bromide + sodium thiocyanate | 1-methyl-3-carboxyethyl-imidazolium bromide + LiOH + isobutanol | 1-methyl-3-carboxyethyl-imidazolium bromide + LiOH + sodium thiocyanate | 1-methyl-3-carboxyethyl-imidazolium bromide + LiOH + isobutanol + sodium thiocyanate | 1-methyl-3-carboxyethyl-imidazolium bromide + isobutanol + sodium thiocyanate |

TABLE 5-continued

EXEMPLARY STORAGE COMPOSITIONS

| (A) Compound of Formula (I) | (A) + (B) Precipitating Agent | (A) + (C) Lower Alcohol | (A) + (D) Chaotrope | (A) + (B) + (C) | (A) + (B) + (D) | (A) + (B) + (C) + (D) | (A) + (C) + (D) |
|---|---|---|---|---|---|---|---|
| 1-hexyl-3-methylimidazolium bromide | 1-hexyl-3-methylimidazolium bromide + lithium hydroxide | 1-hexyl-3-methylimidazolium bromide + isobutanol | 1-hexyl-3-methylimidazolium bromide + sodium thiocyanate | 1-hexyl-3-methylimidazolium bromide + LiOH + isobutanol | 1-hexyl-3-methylimidazolium bromide + LiOH + sodium thiocyanate | 1-hexyl-3-methylimidazolium bromide + LiOH + isobutanol + sodium thiocyanate | 1-hexyl-3-methylimidazolium bromide + isobutanol + sodium thiocyanate |
| 1-decyl-3-methylimidazolium bromide | 1-decyl-3-methylimidazolium bromide + lithium hydroxide | 1-decyl-3-methylimidazolium bromide + isobutanol | 1-decyl-3-methylimidazolium bromide + sodium thiocyanate | 1-decyl-3-methylimidazolium bromide + LiOH + isobutanol | 1-decyl-3-methylimidazolium bromide + LiOH + sodium thiocyanate | 1-decyl-3-methylimidazolium bromide + LiOH + isobutanol + sodium thiocyanate | 1-decyl-3-methylimidazolium bromide + isobutanol + sodium thiocyanate |
| 1-(2-hydroxyethyl)-3-methylimidazolium bromide | 1-(2-hydroxyethyl)-3-methylimidazolium bromide + lithium hydroxide | 1-(2-hydroxyethyl)-3-methylimidazolium bromide + isobutanol | 1-(2-hydroxyethyl)-3-methylimidazolium bromide + sodium thiocyanate | 1-(2-hydroxyethyl)-3-methylimidazolium bromide + LiOH + isobutanol | 1-(2-hydroxyethyl)-3-methylimidazolium bromide + LiOH + sodium thiocyanate | 1-(2-hydroxyethyl)-3-methylimidazolium bromide + LiOH + isobutanol + sodium thiocyanate | 1-(2-hydroxyethyl)-3-methylimidazolium bromide + isobutanol + sodium thiocyanate |
| 1-octyl-3-methylimidazolium bromide | 1-octyl-3-methylimidazolium bromide + lithium hydroxide | 1-octyl-3-methylimidazolium bromide + isobutanol | 1-octyl-3-methylimidazolium bromide + sodium thiocyanate | 1-octyl-3-methylimidazolium bromide + LiOH + isobutanol | 1-octyl-3-methylimidazolium bromide + LiOH + sodium thiocyanate | 1-octyl-3-methylimidazolium bromide + LiOH + isobutanol + sodium thiocyanate | 1-octyl-3-methylimidazolium bromide + isobutanol + sodium thiocyanate |
| 1-methyl-3-carboxyethyl-imidazolium bromide | 1-methyl-3-carboxyethyl-imidazolium bromide + 5-(4-dimethyl)amino benzylidene rhodanine | 1-methyl-3-carboxyethyl-imidazolium bromide + methanol | 1-methyl-3-carboxyethyl-imidazolium bromide + urea | 1-methyl-3-carboxyethyl-imidazolium bromide + 5-(4-dimethyl)amino benzylidene rhodanine + methanol | 1-methyl-3-carboxyethyl-imidazolium bromide + 5-(4-dimethyl)amino benzylidene rhodanine + urea | 1-methyl-3-carboxyethyl-imidazolium bromide + 5-(4-dimethyl)amino benzylidene rhodanine + methanol + urea | 1-methyl-3-carboxyethyl-imidazolium bromide + methanol + urea |
| 1-hexyl-3-methylimidazolium bromide | 1-hexyl-3-methylimidazolium bromide + 5-(4-dimethyl)amino benzylidene rhodanine | 1-hexyl-3-methylimidazolium bromide + methanol | 1-hexyl-3-methylimidazolium bromide + urea | 1-hexyl-3-methylimidazolium bromide + 5-(4-dimethyl)amino benzylidene rhodanine + methanol | 1-hexyl-3-methylimidazolium bromide + 5-(4-dimethyl)amino benzylidene rhodanine + urea | 1-hexyl-3-methylimidazolium bromide + 5-(4-dimethyl)amino benzylidene rhodanine + methanol + urea | 1-hexyl-3-methylimidazolium bromide + methanol + urea |
| 1-decyl-3-methylimidazolium bromide | 1-decyl-3-methylimidazolium bromide + 5-(4-dimethyl)amino benzylidene rhodanine | 1-decyl-3-methylimidazolium bromide + methanol | 1-decyl-3-methylimidazolium bromide + urea | 1-decyl-3-methylimidazolium bromide + 5-(4-dimethyl)amino benzylidene rhodanine + methanol | 1-decyl-3-methylimidazolium bromide + 5-(4-dimethyl)amino benzylidene rhodanine + urea | 1-decyl-3-methylimidazolium bromide + 5-(4-dimethyl)amino benzylidene rhodanine + methanol + urea | 1-decyl-3-methylimidazolium bromide + methanol + urea |

TABLE 5-continued

EXEMPLARY STORAGE COMPOSITIONS

| (A) Compound of Formula (I) | (A) + (B) Precipitating Agent | (A) + (C) Lower Alcohol | (A) + (D) Chaotrope | (A) + (B) + (C) | (A) + (B) + (D) | (A) + (C) + (D) | (A) + (B) + (C) + (D) | (A) + (C) + (D) |
|---|---|---|---|---|---|---|---|---|
| 1-(2-hydroxyethyl)-3-methylimidazolium bromide | 1-(2-hydroxyethyl)-3-methylimidazolium bromide + 5-(4-dimethyl)amino benzylidene rhodanine | 1-(2-hydroxyethyl)-3-methylimidazolium bromide + methanol | 1-(2-hydroxyethyl)-3-methylimidazolium bromide + urea | 1-(2-hydroxyethyl)-3-methylimidazolium bromide + 5-(4-dimethyl)amino benzylidene rhodanine + methanol | 1-(2-hydroxyethyl)-3-methylimidazolium bromide + 5-(4-dimethyl)amino benzylidene rhodanine + urea | 1-(2-hydroxyethyl)-3-methylimidazolium bromide + methanol + urea | 1-(2-hydroxyethyl)-3-methylimidazolium bromide + 5-(4-dimethyl)amino benzylidene rhodanine + methanol + urea | 1-(2-hydroxyethyl)-3-methylimidazolium bromide + methanol + urea |
| 1-octyl-3-methylimidazolium bromide | 1-octyl-3-methylimidazolium bromide + 5-(4-dimethyl)amino benzylidene rhodanine | 1-octyl-3-methylimidazolium bromide + methanol | 1-octyl-3-methylimidazolium bromide + urea | 1-octyl-3-methylimidazolium bromide + 5-(4-dimethyl)amino benzylidene rhodanine + methanol | 1-octyl-3-methylimidazolium bromide + 5-(4-dimethyl)amino benzylidene rhodanine + urea | 1-octyl-3-methylimidazolium bromide + methanol + urea | 1-octyl-3-methylimidazolium bromide + 5-(4-dimethyl)amino benzylidene rhodanine + methanol + urea | 1-octyl-3-methylimidazolium bromide + methanol + urea |
| 1-methyl-3-carboxyethyl-imidazolium bromide | 1-methyl-3-carboxyethyl-imidazolium bromide + sulfosalicylic acid | 1-methyl-3-carboxyethyl-imidazolium bromide + methanol | 1-methyl-3-carboxyethyl-imidazolium bromide + urea | 1-methyl-3-carboxyethyl-imidazolium bromide + sulfosalicylic acid + methanol | 1-methyl-3-carboxyethyl-imidazolium bromide + sulfosalicylic acid + urea | 1-methyl-3-carboxyethyl-imidazolium bromide + methanol + urea | 1-methyl-3-carboxyethyl-imidazolium bromide + sulfosalicylic acid + methanol + urea | 1-methyl-3-carboxyethyl-imidazolium bromide + methanol + urea |
| 1-hexyl-3-methylimidazolium bromide | 1-hexyl-3-methylimidazolium bromide + sulfosalicylic acid | 1-hexyl-3-methylimidazolium bromide + methanol | 1-hexyl-3-methylimidazolium bromide + urea | 1-hexyl-3-methylimidazolium bromide + sulfosalicylic acid + methanol | 1-hexyl-3-methylimidazolium bromide + sulfosalicylic acid + urea | 1-hexyl-3-methylimidazolium bromide + methanol + urea | 1-hexyl-3-methylimidazolium bromide + sulfosalicylic acid + methanol + urea | 1-hexyl-3-methylimidazolium bromide + methanol + urea |
| 1-decyl-3-methylimidazolium bromide | 1-decyl-3-methylimidazolium bromide + sulfosalicylic acid | 1-decyl-3-methylimidazolium bromide + methanol | 1-decyl-3-methylimidazolium bromide + urea | 1-decyl-3-methylimidazolium bromide + sulfosalicylic acid + methanol | 1-decyl-3-methylimidazolium bromide + sulfosalicylic acid + urea | 1-decyl-3-methylimidazolium bromide + methanol + urea | 1-decyl-3-methylimidazolium bromide + sulfosalicylic acid + methanol + urea | 1-decyl-3-methylimidazolium bromide + methanol + urea |
| 1-(2-hydroxyethyl)-3-methylimidazolium bromide | 1-(2-hydroxyethyl)-3-methylimidazolium bromide + sulfosalicylic acid | 1-(2-hydroxyethyl)-3-methylimidazolium bromide + methanol | 1-(2-hydroxyethyl)-3-methylimidazolium bromide + urea | 1-(2-hydroxyethyl)-3-methylimidazolium bromide + sulfosalicylic acid + methanol | 1-(2-hydroxyethyl)-3-methylimidazolium bromide + sulfosalicylic acid + urea | 1-(2-hydroxyethyl)-3-methylimidazolium bromide + methanol + urea | 1-(2-hydroxyethyl)-3-methylimidazolium bromide + sulfosalicylic acid + methanol + urea | 1-(2-hydroxyethyl)-3-methylimidazolium bromide + methanol + urea |
| 1-octyl-3-methylimidazolium bromide | 1-octyl-3-methylimidazolium bromide + sulfosalicylic acid | 1-octyl-3-methylimidazolium bromide + methanol | 1-octyl-3-methylimidazolium bromide + urea | 1-octyl-3-methylimidazolium bromide + sulfosalicylic acid + methanol | 1-octyl-3-methylimidazolium bromide + sulfosalicylic acid + urea | 1-octyl-3-methylimidazolium bromide + methanol + urea | 1-octyl-3-methylimidazolium bromide + sulfosalicylic acid + methanol + urea | 1-octyl-3-methylimidazolium bromide + methanol + urea |
| 1-methyl-3-carboxyethyl-imidazolium bromide | 1-methyl-3-carboxyethyl-imidazolium bromide + lithium chloride | 1-methyl-3-carboxyethyl-imidazolium bromide + Lithium chloride + methanol | 1-methyl-3-carboxyethyl-imidazolium bromide + urea | 1-methyl-3-carboxyethyl-imidazolium bromide + LiCl + methanol | 1-methyl-3-carboxyethyl-imidazolium bromide + LiCl + urea | 1-methyl-3-carboxyethyl-imidazolium bromide + methanol + urea | 1-methyl-3-carboxyethyl-imidazolium bromide + LiCl + methanol + urea | 1-methyl-3-carboxyethyl-imidazolium bromide + methanol + urea |

TABLE 5-continued

EXEMPLARY STORAGE COMPOSITIONS

| (A) Compound of Formula (I) | (A) + (B) Precipitating Agent | (A) + (C) Lower Alcohol | (A) + (D) Chaotrope | (A) + (B) + (C) | (A) + (B) + (D) | (A) + (B) + (C) + (D) | (A) + (C) + (D) |
|---|---|---|---|---|---|---|---|
| 1-hexyl-3-methylimidazolium bromide | 1-hexyl-3-methylimidazolium bromide + lithium chloride | 1-hexyl-3-methylimidazolium bromide + methanol | 1-hexyl-3-methylimidazolium bromide + urea | 1-hexyl-3-methylimidazolium bromide + Lithium chloride + methanol | 1-hexyl-3-methylimidazolium bromide + LiCl + urea | 1-hexyl-3-methylimidazolium bromide + LiCl + methanol + urea | 1-hexyl-3-methylimidazolium bromide + methanol + urea |
| 1-decyl-3-methylimidazolium bromide | 1-decyl-3-methylimidazolium bromide + lithium chloride | 1-decyl-3-methylimidazolium bromide + methanol | 1-decyl-3-methylimidazolium bromide + urea | 1-decyl-3-methylimidazolium bromide + Lithium chloride + methanol | 1-decyl-3-methylimidazolium bromide + LiCl + urea | 1-decyl-3-methylimidazolium bromide + LiCl + methanol + urea | 1-decyl-3-methylimidazolium bromide + methanol + urea |
| 1-(2-hydroxyethyl)-3-methylimidazolium bromide | 1-(2-hydroxyethyl)-3-methylimidazolium bromide + lithium chloride | 1-(2-hydroxyethyl)-3-methylimidazolium bromide + methanol | 1-(2-hydroxyethyl)-3-methylimidazolium bromide + urea | 1-(2-hydroxyethyl)-3-methylimidazolium bromide + Lithium chloride + methanol | 1-(2-hydroxyethyl)-3-methylimidazolium bromide + LiCl + urea | 1-(2-hydroxyethyl)-3-methylimidazolium bromide + LiCl + methanol + urea | 1-(2-hydroxyethyl)-3-methylimidazolium bromide + methanol + urea |
| 1-octyl-3-methylimidazolium bromide | 1-octyl-3-methylimidazolium bromide + lithium chloride | 1-octyl-3-methylimidazolium bromide + methanol | 1-octyl-3-methylimidazolium bromide + urea | 1-octyl-3-methylimidazolium bromide + Lithium chloride + methanol | 1-octyl-3-methylimidazolium bromide + LiCl + urea | 1-octyl-3-methylimidazolium bromide + LiCl + methanol + urea | 1-octyl-3-methylimidazolium bromide + methanol + urea |
| 1-methyl-3-carboxyethyl-imidazolium bromide | 1-methyl-3-carboxyethyl-imidazolium bromide + lithium hydroxide | 1-methyl-3-carboxyethyl-imidazolium bromide + methanol | 1-methyl-3-carboxyethyl-imidazolium bromide + urea | 1-methyl-3-carboxyethyl-imidazolium bromide + Lithium hydroxide + methanol | 1-methyl-3-carboxyethyl-imidazolium bromide + LiOH + urea | 1-methyl-3-carboxyethyl-imidazolium bromide + LiOH + methanol + urea | 1-methyl-3-carboxyethyl-imidazolium bromide + methanol + urea |
| 1-hexyl-3-methylimidazolium bromide | 1-hexyl-3-methylimidazolium bromide + lithium hydroxide | 1-hexyl-3-methylimidazolium bromide + methanol | 1-hexyl-3-methylimidazolium bromide + urea | 1-hexyl-3-methylimidazolium bromide + Lithium hydroxide + methanol | 1-hexyl-3-methylimidazolium bromide + LiOH + urea | 1-hexyl-3-methylimidazolium bromide + LiOH + methanol + urea | 1-hexyl-3-methylimidazolium bromide + methanol + urea |
| 1-decyl-3-methylimidazolium bromide | 1-decyl-3-methylimidazolium bromide + lithium hydroxide | 1-decyl-3-methylimidazolium bromide + methanol | 1-decyl-3-methylimidazolium bromide + urea | 1-decyl-3-methylimidazolium bromide + Lithium hydroxide + methanol | 1-decyl-3-methylimidazolium bromide + LiOH + urea | 1-decyl-3-methylimidazolium bromide + LiOH + methanol + urea | 1-decyl-3-methylimidazolium bromide + methanol + urea |
| 1-(2-hydroxyethyl)-3-methylimidazolium bromide | 1-(2-hydroxyethyl)-3-methylimidazolium bromide + lithium hydroxide | 1-(2-hydroxyethyl)-3-methylimidazolium bromide + methanol | 1-(2-hydroxyethyl)-3-methylimidazolium bromide + urea | 1-(2-hydroxyethyl)-3-methylimidazolium bromide + Lithium hydroxide + methanol | 1-(2-hydroxyethyl)-3-methylimidazolium bromide + LiOH + urea | 1-(2-hydroxyethyl)-3-methylimidazolium bromide + LiOH + methanol + urea | 1-(2-hydroxyethyl)-3-methylimidazolium bromide + methanol + urea |
| 1-octyl-3-methylimidazolium bromide | 1-octyl-3-methylimidazolium bromide + lithium hydroxide | 1-octyl-3-methylimidazolium bromide + methanol | 1-octyl-3-methylimidazolium bromide + urea | 1-octyl-3-methylimidazolium bromide + Lithium hydroxide + methanol | 1-octyl-3-methylimidazolium bromide + LiOH + urea | 1-octyl-3-methylimidazolium bromide + LiOH + methanol + urea | 1-octyl-3-methylimidazolium bromide + methanol + urea |

TABLE 5-continued

EXEMPLARY STORAGE COMPOSITIONS

| (A) Compound of Formula (I) | (A) + (B) Precipitating Agent | (A) + (C) Lower Alcohol | (A) + (D) Chaotrope | (A) + (B) + (C) | (A) + (B) + (D) | (A) + (B) + (C) + (D) | (A) + (C) + (D) |
|---|---|---|---|---|---|---|---|
| 1-methyl-3-carboxyethyl-imidazolium bromide | 1-methyl-3-carboxyethyl-imidazolium bromide + 5-(4-dimethyl)amino benzylidene rhodanine | 1-methyl-3-carboxyethyl-imidazolium bromide + ethanol | 1-methyl-3-carboxyethyl-imidazolium bromide + urea | 1-methyl-3-carboxyethyl-imidazolium bromide + 5-(4-dimethyl)amino benzylidene rhodanine + ethanol | 1-methyl-3-carboxyethyl-imidazolium bromide + 5-(4-dimethyl)amino benzylidene rhodanine + urea | 1-methyl-3-carboxyethyl-imidazolium bromide + 5-(4-dimethyl)amino benzylidene rhodanine + ethanol + urea | 1-methyl-3-carboxyethyl-imidazolium bromide + ethanol + urea |
| 1-hexyl-3-methylimidazolium bromide | 1-hexyl-3-methylimidazolium bromide + 5-(4-dimethyl)amino benzylidene rhodanine | 1-hexyl-3-methylimidazolium bromide + ethanol | 1-hexyl-3-methylimidazolium bromide + urea | 1-hexyl-3-methylimidazolium bromide + 5-(4-dimethyl)amino benzylidene rhodanine + ethanol | 1-hexyl-3-methylimidazolium bromide + 5-(4-dimethyl)amino benzylidene rhodanine + urea | 1-hexyl-3-methylimidazolium bromide + 5-(4-dimethyl)amino benzylidene rhodanine + ethanol + urea | 1-hexyl-3-methylimidazolium bromide + ethanol + urea |
| 1-decyl-3-methylimidazolium bromide | 1-decyl-3-methylimidazolium bromide + 5-(4-dimethyl)amino benzylidene rhodanine | 1-decyl-3-methylimidazolium bromide + ethanol | 1-decyl-3-methylimidazolium bromide + urea | 1-decyl-3-methylimidazolium bromide + 5-(4-dimethyl)amino benzylidene rhodanine + ethanol | 1-decyl-3-methylimidazolium bromide + 5-(4-dimethyl)amino benzylidene rhodanine + urea | 1-decyl-3-methylimidazolium bromide + 5-(4-dimethyl)amino benzylidene rhodanine + ethanol + urea | 1-decyl-3-methylimidazolium bromide + ethanol + urea |
| 1-(2-hydroxyethyl)-3-methylimidazolium bromide | 1-(2-hydroxyethyl)-3-methylimidazolium bromide + 5-(4-dimethyl)amino benzylidene rhodanine | 1-(2-hydroxyethyl)-3-methylimidazolium bromide + ethanol | 1-(2-hydroxyethyl)-3-methylimidazolium bromide + urea | 1-(2-hydroxyethyl)-3-methylimidazolium bromide + 5-(4-dimethyl)amino benzylidene rhodanine + ethanol | 1-(2-hydroxyethyl)-3-methylimidazolium bromide + 5-(4-dimethyl)amino benzylidene rhodanine + urea | 1-(2-hydroxyethyl)-3-methylimidazolium bromide + 5-(4-dimethyl)amino benzylidene rhodanine + ethanol + urea | 1-(2-hydroxyethyl)-3-methylimidazolium bromide + ethanol + urea |
| 1-octyl-3-methylimidazolium bromide | 1-octyl-3-methylimidazolium bromide + 5-(4-dimethyl)amino benzylidene rhodanine | 1-octyl-3-methylimidazolium bromide + ethanol | 1-octyl-3-methylimidazolium bromide + urea | 1-octyl-3-methylimidazolium bromide + 5-(4-dimethyl)amino benzylidene rhodanine + ethanol | 1-octyl-3-methylimidazolium bromide + 5-(4-dimethyl)amino benzylidene rhodanine + urea | 1-octyl-3-methylimidazolium bromide + 5-(4-dimethyl)amino benzylidene rhodanine + ethanol + urea | 1-octyl-3-methylimidazolium bromide + ethanol + urea |
| 1-methyl-3-carboxyethyl-imidazolium bromide | 1-methyl-3-carboxyethyl-imidazolium bromide + sulfosalicylic acid | 1-methyl-3-carboxyethyl-imidazolium bromide + ethanol | 1-methyl-3-carboxyethyl-imidazolium bromide + urea | 1-methyl-3-carboxyethyl-imidazolium bromide + sulfosalicylic acid + ethanol | 1-methyl-3-carboxyethyl-imidazolium bromide + sulfosalicylic acid + urea | 1-methyl-3-carboxyethyl-imidazolium bromide + sulfosalicylic acid + ethanol + urea | 1-methyl-3-carboxyethyl-imidazolium bromide + ethanol + urea |
| 1-hexyl-3-methylimidazolium bromide | 1-hexyl-3-methylimidazolium bromide + sulfosalicylic acid | 1-hexyl-3-methylimidazolium bromide + ethanol | 1-hexyl-3-methylimidazolium bromide + urea | 1-hexyl-3-methylimidazolium bromide + sulfosalicylic acid + ethanol | 1-hexyl-3-methylimidazolium bromide + sulfosalicylic acid + urea | 1-hexyl-3-methylimidazolium bromide + sulfosalicylic acid + ethanol + urea | 1-hexyl-3-methylimidazolium bromide + ethanol + urea |

TABLE 5-continued

EXEMPLARY STORAGE COMPOSITIONS

| (A) Compound of Formula (I) | (A) + (B) Precipitating Agent | (A) + (C) Lower Alcohol | (A) + (D) Chaotrope | (A) + (B) + (C) | (A) + (B) + (D) | (A) + (B) + (C) + (D) | (A) + (C) + (D) |
|---|---|---|---|---|---|---|---|
| 1-decyl-3-methylimidazolium bromide | 1-decyl-3-methylimidazolium bromide + sulfosalicylic acid | 1-decyl-3-methylimidazolium bromide + ethanol | 1-decyl-3-methylimidazolium bromide + urea | 1-decyl-3-methylimidazolium bromide + sulfosalicylic acid + ethanol | 1-decyl-3-methylimidazolium bromide + sulfosalicylic acid + urea | 1-decyl-3-methylimidazolium bromide + sulfosalicylic acid + ethanol + urea | 1-decyl-3-methylimidazolium bromide + ethanol + urea |
| 1-(2-hydroxyethyl)-3-methylimidazolium bromide | 1-(2-hydroxyethyl)-3-methylimidazolium bromide + sulfosalicylic acid | 1-(2-hydroxyethyl)-3-methylimidazolium bromide + ethanol | 1-(2-hydroxyethyl)-3-methylimidazolium bromide + urea | 1-(2-hydroxyethyl)-3-methylimidazolium bromide + sulfosalicylic acid + ethanol | 1-(2-hydroxyethyl)-3-methylimidazolium bromide + sulfosalicylic acid + urea | 1-(2-hydroxyethyl)-3-methylimidazolium bromide + sulfosalicylic acid + ethanol + urea | 1-(2-hydroxyethyl)-3-methylimidazolium bromide + ethanol + urea |
| 1-octyl-3-methylimidazolium bromide | 1-octyl-3-methylimidazolium bromide + sulfosalicylic acid | 1-octyl-3-methylimidazolium bromide + ethanol | 1-octyl-3-methylimidazolium bromide + urea | 1-octyl-3-methylimidazolium bromide + sulfosalicylic acid + ethanol | 1-octyl-3-methylimidazolium bromide + sulfosalicylic acid + urea | 1-octyl-3-methylimidazolium bromide + sulfosalicylic acid + ethanol + urea | 1-octyl-3-methylimidazolium bromide + ethanol + urea |
| 1-methyl-3-carboxyethyl-imidazolium bromide | 1-methyl-3-carboxyethyl-imidazolium bromide + lithium chloride | 1-methyl-3-carboxyethyl-imidazolium bromide + ethanol | 1-methyl-3-carboxyethyl-imidazolium bromide + urea | 1-methyl-3-carboxyethyl-imidazolium bromide + LiCl + ethanol | 1-methyl-3-carboxyethyl-imidazolium bromide + LiCl + urea | 1-methyl-3-carboxyethyl-imidazolium bromide + LiCl + ethanol + urea | 1-methyl-3-carboxyethyl-imidazolium bromide + ethanol + urea |
| 1-hexyl-3-methylimidazolium bromide | 1-hexyl-3-methylimidazolium bromide + lithium chloride | 1-hexyl-3-methylimidazolium bromide + ethanol | 1-hexyl-3-methylimidazolium bromide + urea | 1-hexyl-3-methylimidazolium bromide + LiCl + ethanol | 1-hexyl-3-methylimidazolium bromide + LiCl + urea | 1-hexyl-3-methylimidazolium bromide + LiCl + ethanol + urea | 1-hexyl-3-methylimidazolium bromide + ethanol + urea |
| 1-decyl-3-methylimidazolium bromide | 1-decyl-3-methylimidazolium bromide + lithium chloride | 1-decyl-3-methylimidazolium bromide + ethanol | 1-decyl-3-methylimidazolium bromide + urea | 1-decyl-3-methylimidazolium bromide + LiCl + ethanol | 1-decyl-3-methylimidazolium bromide + LiCl + urea | 1-decyl-3-methylimidazolium bromide + LiCl + ethanol + urea | 1-decyl-3-methylimidazolium bromide + ethanol + urea |
| 1-(2-hydroxyethyl)-3-methylimidazolium bromide | 1-(2-hydroxyethyl)-3-methylimidazolium bromide + lithium chloride | 1-(2-hydroxyethyl)-3-methylimidazolium bromide + ethanol | 1-(2-hydroxyethyl)-3-methylimidazolium bromide + urea | 1-(2-hydroxyethyl)-3-methylimidazolium bromide + LiCl + ethanol | 1-(2-hydroxyethyl)-3-methylimidazolium bromide + LiCl + urea | 1-(2-hydroxyethyl)-3-methylimidazolium bromide + LiCl + ethanol + urea | 1-(2-hydroxyethyl)-3-methylimidazolium bromide + ethanol + urea |
| 1-octyl-3-methylimidazolium bromide | 1-octyl-3-methylimidazolium bromide + lithium chloride | 1-octyl-3-methylimidazolium bromide + ethanol | 1-octyl-3-methylimidazolium bromide + urea | 1-octyl-3-methylimidazolium bromide + LiCl + ethanol | 1-octyl-3-methylimidazolium bromide + LiCl + urea | 1-octyl-3-methylimidazolium bromide + LiCl + ethanol + urea | 1-octyl-3-methylimidazolium bromide + ethanol + urea |
| 1-methyl-3-carboxyethyl-imidazolium bromide | 1-methyl-3-carboxyethyl-imidazolium bromide + lithium hydroxide | 1-methyl-3-carboxyethyl-imidazolium bromide + ethanol | 1-methyl-3-carboxyethyl-imidazolium bromide + urea | 1-methyl-3-carboxyethyl-imidazolium bromide + LiOH + ethanol | 1-methyl-3-carboxyethyl-imidazolium bromide + LiOH + urea | 1-methyl-3-carboxyethyl-imidazolium bromide + LiOH + ethanol + urea | 1-methyl-3-carboxyethyl-imidazolium bromide + ethanol + urea |
| 1-hexyl-3-methylimidazolium bromide | 1-hexyl-3-methylimidazolium bromide + lithium hydroxide | 1-hexyl-3-methylimidazolium bromide + ethanol | 1-hexyl-3-methylimidazolium bromide + urea | 1-hexyl-3-methylimidazolium bromide + LiOH + ethanol | 1-hexyl-3-methylimidazolium bromide + LiOH + urea | 1-hexyl-3-methylimidazolium bromide + LiOH + ethanol + urea | 1-hexyl-3-methylimidazolium bromide + ethanol + urea |

TABLE 5-continued

EXEMPLARY STORAGE COMPOSITIONS

| (A) Compound of Formula (I) | (A) + (B) Precipitating Agent | (A) + (C) Lower Alcohol | (A) + (D) Chaotrope | (A) + (B) + (C) | (A) + (B) + (D) | (A) + (B) + (C) + (D) | (A) + (C) + (D) |
|---|---|---|---|---|---|---|---|
| 1-decyl-3-methylimidazolium bromide | 1-decyl-3-methylimidazolium bromide + lithium hydroxide | 1-decyl-3-methylimidazolium bromide + ethanol | 1-decyl-3-methylimidazolium bromide + urea | 1-decyl-3-methylimidazolium bromide + LiOH + ethanol | 1-decyl-3-methylimidazolium bromide + LiOH + urea | 1-decyl-3-methylimidazolium bromide + LiOH + ethanol + urea | 1-decyl-3-methylimidazolium bromide + ethanol + urea |
| 1-(2-hydroxyethyl)-3-methylimidazolium bromide | 1-(2-hydroxyethyl)-3-methylimidazolium bromide + lithium hydroxide | 1-(2-hydroxyethyl)-3-methylimidazolium bromide + ethanol | 1-(2-hydroxyethyl)-3-methylimidazolium bromide + urea | 1-(2-hydroxyethyl)-3-methylimidazolium bromide + LiOH + ethanol | 1-(2-hydroxyethyl)-3-methylimidazolium bromide + LiOH + urea | 1-(2-hydroxyethyl)-3-methylimidazolium bromide + LiOH + ethanol + urea | 1-(2-hydroxyethyl)-3-methylimidazolium bromide + ethanol + urea |
| 1-octyl-3-methylimidazolium bromide | 1-octyl-3-methylimidazolium bromide + lithium hydroxide | 1-octyl-3-methylimidazolium bromide + ethanol | 1-octyl-3-methylimidazolium bromide + urea | 1-octyl-3-methylimidazolium bromide + LiOH + ethanol | 1-octyl-3-methylimidazolium bromide + LiOH + urea | 1-octyl-3-methylimidazolium bromide + LiOH + ethanol + urea | 1-octyl-3-methylimidazolium bromide + ethanol + urea |
| 1-methyl-3-carboxyethyl-imidazolium bromide | 1-methyl-3-carboxyethyl-imidazolium bromide + 5-(4-dimethyl)amino benzylidene rhodanine | 1-methyl-3-carboxyethyl-imidazolium bromide + n-propanol | 1-methyl-3-carboxyethyl-imidazolium bromide + urea | 1-methyl-3-carboxyethyl-imidazolium bromide + 5-(4-dimethyl)amino benzylidene rhodanine + n-propanol | 1-methyl-3-carboxyethyl-imidazolium bromide + 5-(4-dimethyl)amino benzylidene rhodanine + urea | 1-methyl-3-carboxyethyl-imidazolium bromide + 5-(4-dimethyl)amino benzylidene rhodanine + n-propanol + urea | 1-methyl-3-carboxyethyl-imidazolium bromide + n-propanol + urea |
| 1-hexyl-3-methylimidazolium bromide | 1-hexyl-3-methylimidazolium bromide + 5-(4-dimethyl)amino benzylidene rhodanine | 1-hexyl-3-methylimidazolium bromide + n-propanol | 1-hexyl-3-methylimidazolium bromide + urea | 1-hexyl-3-methylimidazolium bromide + 5-(4-dimethyl)amino benzylidene rhodanine + n-propanol | 1-hexyl-3-methylimidazolium bromide + 5-(4-dimethyl)amino benzylidene rhodanine + urea | 1-hexyl-3-methylimidazolium bromide + 5-(4-dimethyl)amino benzylidene rhodanine + n-propanol + urea | 1-hexyl-3-methylimidazolium bromide + n-propanol + urea |
| 1-decyl-3-methylimidazolium bromide | 1-decyl-3-methylimidazolium bromide + 5-(4-dimethyl)amino benzylidene rhodanine | 1-decyl-3-methylimidazolium bromide + n-propanol | 1-decyl-3-methylimidazolium bromide + urea | 1-decyl-3-methylimidazolium bromide + 5-(4-dimethyl)amino benzylidene rhodanine + n-propanol | 1-decyl-3-methylimidazolium bromide + 5-(4-dimethyl)amino benzylidene rhodanine + urea | 1-decyl-3-methylimidazolium bromide + 5-(4-dimethyl)amino benzylidene rhodanine + n-propanol + urea | 1-decyl-3-methylimidazolium bromide + n-propanol + urea |
| 1-(2-hydroxyethyl)-3-methylimidazolium bromide | 1-(2-hydroxyethyl)-3-methylimidazolium bromide + 5-(4-dimethyl)amino benzylidene rhodanine | 1-(2-hydroxyethyl)-3-methylimidazolium bromide + n-propanol | 1-(2-hydroxyethyl)-3-methylimidazolium bromide + urea | 1-(2-hydroxyethyl)-3-methylimidazolium bromide + 5-(4-dimethyl)amino benzylidene rhodanine + n-propanol | 1-(2-hydroxyethyl)-3-methylimidazolium bromide + 5-(4-dimethyl)amino benzylidene rhodanine + urea | 1-(2-hydroxyethyl)-3-methylimidazolium bromide + 5-(4-dimethyl)amino benzylidene rhodanine + n-propanol + urea | 1-(2-hydroxyethyl)-3-methylimidazolium bromide + n-propanol + urea |

TABLE 5-continued

EXEMPLARY STORAGE COMPOSITIONS

| (A) Compound of Formula (I) | (A) + (B) Precipitating Agent | (A) + (C) Lower Alcohol | (A) + (D) Chaotrope | (A) + (B) + (C) | (A) + (B) + (D) | (A) + (B) + (C) + (D) | (A) + (C) + (D) |
|---|---|---|---|---|---|---|---|
| 1-octyl-3-methylimidazolium bromide | 1-octyl-3-methylimidazolium bromide + 5-(4-dimethyl)amino benzylidene rhodanine | 1-octyl-3-methylimidazolium bromide + n-propanol | 1-octyl-3-methylimidazolium bromide + urea | 1-octyl-3-methylimidazolium bromide + 5-(4-dimethyl)amino benzylidene rhodanine + n-propanol | 1-octyl-3-methylimidazolium bromide + 5-(4-dimethyl)amino benzylidene rhodanine + urea | 1-octyl-3-methylimidazolium bromide + 5-(4-dimethyl)amino benzylidene rhodanine + n-propanol + urea | 1-octyl-3-methylimidazolium bromide + n-propanol + urea |
| 1-methyl-3-carboxyethyl-imidazolium bromide | 1-methyl-3-carboxyethyl-imidazolium bromide + sulfosalicylic acid | 1-methyl-3-carboxyethyl-imidazolium bromide + n-propanol | 1-methyl-3-carboxyethyl-imidazolium bromide + urea | 1-methyl-3-carboxyethyl-imidazolium bromide + sulfosalicylic acid + n-propanol | 1-methyl-3-carboxyethyl-imidazolium bromide + sulfosalicylic acid + urea | 1-methyl-3-carboxyethyl-imidazolium bromide + sulfosalicylic acid + n-propanol + urea | 1-methyl-3-carboxyethyl-imidazolium bromide + n-propanol + urea |
| 1-hexyl-3-methylimidazolium bromide | 1-hexyl-3-methylimidazolium bromide + sulfosalicylic acid | 1-hexyl-3-methylimidazolium bromide + n-propanol | 1-hexyl-3-methylimidazolium bromide + urea | 1-hexyl-3-methylimidazolium bromide + sulfosalicylic acid + n-propanol | 1-hexyl-3-methylimidazolium bromide + sulfosalicylic acid + urea | 1-hexyl-3-methylimidazolium bromide + sulfosalicylic acid + n-propanol + urea | 1-hexyl-3-methylimidazolium bromide + n-propanol + urea |
| 1-decyl-3-methylimidazolium bromide | 1-decyl-3-methylimidazolium bromide + sulfosalicylic acid | 1-decyl-3-methylimidazolium bromide + n-propanol | 1-decyl-3-methylimidazolium bromide + urea | 1-decyl-3-methylimidazolium bromide + sulfosalicylic acid + n-propanol | 1-decyl-3-methylimidazolium bromide + sulfosalicylic acid + urea | 1-decyl-3-methylimidazolium bromide + sulfosalicylic acid + n-propanol + urea | 1-decyl-3-methylimidazolium bromide + n-propanol + urea |
| 1-(2-hydroxyethyl)-3-methylimidazolium bromide | 1-(2-hydroxyethyl)-3-methylimidazolium bromide + sulfosalicylic acid | 1-(2-hydroxyethyl)-3-methylimidazolium bromide + n-propanol | 1-(2-hydroxyethyl)-3-methylimidazolium bromide + urea | 1-(2-hydroxyethyl)-3-methylimidazolium bromide + sulfosalicylic acid + n-propanol | 1-(2-hydroxyethyl)-3-methylimidazolium bromide + sulfosalicylic acid + urea | 1-(2-hydroxyethyl)-3-methylimidazolium bromide + sulfosalicylic acid + n-propanol + urea | 1-(2-hydroxyethyl)-3-methylimidazolium bromide + n-propanol + urea |
| 1-octyl-3-methylimidazolium bromide | 1-octyl-3-methylimidazolium bromide + sulfosalicylic acid | 1-octyl-3-methylimidazolium bromide + n-propanol | 1-octyl-3-methylimidazolium bromide + urea | 1-octyl-3-methylimidazolium bromide + sulfosalicylic acid + n-propanol | 1-octyl-3-methylimidazolium bromide + sulfosalicylic acid + urea | 1-octyl-3-methylimidazolium bromide + sulfosalicylic acid + n-propanol + urea | 1-octyl-3-methylimidazolium bromide + n-propanol + urea |
| 1-methyl-3-carboxyethyl-imidazolium bromide | 1-methyl-3-carboxyethyl-imidazolium bromide + lithium chloride | 1-methyl-3-carboxyethyl-imidazolium bromide + n-propanol | 1-methyl-3-carboxyethyl-imidazolium bromide + urea | 1-methyl-3-carboxyethyl-imidazolium bromide + LiCl + n-propanol | 1-methyl-3-carboxyethyl-imidazolium bromide + LiCl + urea | 1-methyl-3-carboxyethyl-imidazolium bromide + LiCl + n-propanol + urea | 1-methyl-3-carboxyethyl-imidazolium bromide + n-propanol + urea |
| 1-hexyl-3-methylimidazolium bromide | 1-hexyl-3-methylimidazolium bromide + lithium chloride | 1-hexyl-3-methylimidazolium bromide + n-propanol | 1-hexyl-3-methylimidazolium bromide + urea | 1-hexyl-3-methylimidazolium bromide + LiCl + n-propanol | 1-hexyl-3-methylimidazolium bromide + LiCl + urea | 1-hexyl-3-methylimidazolium bromide + LiCl + n-propanol + urea | 1-hexyl-3-methylimidazolium bromide + n-propanol + urea |

TABLE 5-continued

EXEMPLARY STORAGE COMPOSITIONS

| (A) Compound of Formula (I) | (A) + (B) Precipitating Agent | (A) + (C) Lower Alcohol | (A) + (D) Chaotrope | (A) + (B) + (C) | (A) + (B) + (D) | (A) + (B) + (C) + (D) | (A) + (C) + (D) |
|---|---|---|---|---|---|---|---|
| 1-decyl-3-methylimidazolium bromide | 1-decyl-3-methylimidazolium bromide + lithium chloride | 1-decyl-3-methylimidazolium bromide + n-propanol | 1-decyl-3-methylimidazolium bromide + urea | 1-decyl-3-methylimidazolium bromide + LiCl + n-propanol | 1-decyl-3-methylimidazolium bromide + LiCl + urea | 1-decyl-3-methylimidazolium bromide + LiCl + n-propanol + urea | 1-decyl-3-methylimidazolium bromide + n-propanol + urea |
| 1-(2-hydroxyethyl)-3-methylimidazolium bromide | 1-(2-hydroxyethyl)-3-methylimidazolium bromide + lithium chloride | 1-(2-hydroxyethyl)-3-methylimidazolium bromide + n-propanol | 1-(2-hydroxyethyl)-3-methylimidazolium bromide + urea | 1-(2-hydroxyethyl)-3-methylimidazolium bromide + LiCl + n-propanol | 1-(2-hydroxyethyl)-3-methylimidazolium bromide + LiCl + urea | 1-(2-hydroxyethyl)-3-methylimidazolium bromide + LiCl + n-propanol + urea | 1-(2-hydroxyethyl)-3-methylimidazolium bromide + n-propanol + urea |
| 1-octyl-3-methylimidazolium bromide | 1-octyl-3-methylimidazolium bromide + lithium chloride | 1-octyl-3-methylimidazolium bromide + n-propanol | 1-octyl-3-methylimidazolium bromide + urea | 1-octyl-3-methylimidazolium bromide + LiCl + n-propanol | 1-octyl-3-methylimidazolium bromide + LiCl + urea | 1-octyl-3-methylimidazolium bromide + LiCl + n-propanol + urea | 1-octyl-3-methylimidazolium bromide + n-propanol + urea |
| 1-methyl-3-carboxyethyl-imidazolium bromide | 1-methyl-3-carboxyethyl-imidazolium bromide + lithium hydroxide | 1-methyl-3-carboxyethyl-imidazolium bromide + n-propanol | 1-methyl-3-carboxyethyl-imidazolium bromide + urea | 1-methyl-3-carboxyethyl-imidazolium bromide + LiOH + n-propanol | 1-methyl-3-carboxyethyl-imidazolium bromide + LiOH + urea | 1-methyl-3-carboxyethyl-imidazolium bromide + LiOH + n-propanol + urea | 1-methyl-3-carboxyethyl-imidazolium bromide + n-propanol + urea |
| 1-hexyl-3-methylimidazolium bromide | 1-hexyl-3-methylimidazolium bromide + lithium hydroxide | 1-hexyl-3-methylimidazolium bromide + n-propanol | 1-hexyl-3-methylimidazolium bromide + urea | 1-hexyl-3-methylimidazolium bromide + LiOH + n-propanol | 1-hexyl-3-methylimidazolium bromide + LiOH + urea | 1-hexyl-3-methylimidazolium bromide + LiOH + n-propanol + urea | 1-hexyl-3-methylimidazolium bromide + n-propanol + urea |
| 1-decyl-3-methylimidazolium bromide | 1-decyl-3-methylimidazolium bromide + lithium hydroxide | 1-decyl-3-methylimidazolium bromide + n-propanol | 1-decyl-3-methylimidazolium bromide + urea | 1-decyl-3-methylimidazolium bromide + LiOH + n-propanol | 1-decyl-3-methylimidazolium bromide + LiOH + urea | 1-decyl-3-methylimidazolium bromide + LiOH + n-propanol + urea | 1-decyl-3-methylimidazolium bromide + n-propanol + urea |
| 1-(2-hydroxyethyl)-3-methylimidazolium bromide | 1-(2-hydroxyethyl)-3-methylimidazolium bromide + lithium hydroxide | 1-(2-hydroxyethyl)-3-methylimidazolium bromide + Isopropanol | 1-(2-hydroxyethyl)-3-methylimidazolium bromide + urea | 1-(2-hydroxyethyl)-3-methylimidazolium bromide + LiOH + n-propanol | 1-(2-hydroxyethyl)-3-methylimidazolium bromide + LiOH + urea | 1-(2-hydroxyethyl)-3-methylimidazolium bromide + LiOH + n-propanol + urea | 1-(2-hydroxyethyl)-3-methylimidazolium bromide + isopropanol + urea |
| 1-octyl-3-methylimidazolium bromide | 1-octyl-3-methylimidazolium bromide + lithium hydroxide | 1-octyl-3-methylimidazolium bromide + n-propanol | 1-octyl-3-methylimidazolium bromide + urea | 1-octyl-3-methylimidazolium bromide + LiOH + n-propanol | 1-octyl-3-methylimidazolium bromide + LiOH + urea | 1-octyl-3-methylimidazolium bromide + LiOH + n-propanol + urea | 1-octyl-3-methylimidazolium bromide + n-propanol + urea |
| 1-methyl-3-carboxyethyl-imidazolium bromide | 1-methyl-3-carboxyethyl-imidazolium bromide + 5-(4-dimethyl)amino benzylidene rhodanine | 1-methyl-3-carboxyethyl-imidazolium bromide + Isopropanol | 1-methyl-3-carboxyethyl-imidazolium bromide + urea | 1-methyl-3-carboxyethyl-imidazolium bromide + 5-(4-dimethyl)amino benzylidene rhodanine + isopropanol | 1-methyl-3-carboxyethyl-imidazolium bromide + 5-(4-dimethyl)amino benzylidene rhodanine + urea | 1-methyl-3-carboxyethyl-imidazolium bromide + 5-(4-dimethyl)amino benzylidene rhodanine + isopropanol + urea | 1-methyl-3-carboxyethyl-imidazolium bromide + isopropanol + urea |

TABLE 5-continued

EXEMPLARY STORAGE COMPOSITIONS

| (A) Compound of Formula (I) | (A) + (B) Precipitating Agent | (A) + (C) Lower Alcohol | (A) + (D) Chaotrope | (A) + (B) + (C) | (A) + (B) + (D) | (A) + (B) + (C) + (D) | (A) + (C) + (D) |
|---|---|---|---|---|---|---|---|
| 1-hexyl-3-methylimidazolium bromide | 1-hexyl-3-methylimidazolium bromide + 5-(4-dimethyl)amino benzylidene rhodanine | 1-hexyl-3-methylimidazolium bromide + Isopropanol | 1-hexyl-3-methylimidazolium bromide + urea | 1-hexyl-3-methylimidazolium bromide + 5-(4-dimethyl)amino benzylidene rhodanine + isopropanol | 1-hexyl-3-methylimidazolium bromide + 5-(4-dimethyl)amino benzylidene rhodanine + urea | 1-hexyl-3-methylimidazolium bromide + 5-(4-dimethyl)amino benzylidene rhodanine + isopropanol + urea | 1-hexyl-3-methylimidazolium bromide + isopropanol + urea |
| 1-decyl-3-methylimidazolium bromide | 1-decyl-3-methylimidazolium bromide + 5-(4-dimethyl)amino benzylidene rhodanine | 1-decyl-3-methylimidazolium bromide + Isopropanol | 1-decyl-3-methylimidazolium bromide + urea | 1-decyl-3-methylimidazolium bromide + 5-(4-dimethyl)amino benzylidene rhodanine + isopropanol | 1-decyl-3-methylimidazolium bromide + 5-(4-dimethyl)amino benzylidene rhodanine + urea | 1-decyl-3-methylimidazolium bromide + 5-(4-dimethyl)amino benzylidene rhodanine + isopropanol + urea | 1-decyl-3-methylimidazolium bromide + isopropanol + urea |
| 1-(2-hydroxyethyl)-3-methylimidazolium bromide | 1-(2-hydroxyethyl)-3-methylimidazolium bromide + 5-(4-dimethyl)amino benzylidene rhodanine | 1-(2-hydroxyethyl)-3-methylimidazolium bromide + Isopropanol | 1-(2-hydroxyethyl)-3-methylimidazolium bromide + urea | 1-(2-hydroxyethyl)-3-methylimidazolium bromide + 5-(4-dimethyl)amino benzylidene rhodanine + isopropanol | 1-(2-hydroxyethyl)-3-methylimidazolium bromide + 5-(4-dimethyl)amino benzylidene rhodanine + urea | 1-(2-hydroxyethyl)-3-methylimidazolium bromide + 5-(4-dimethyl)amino benzylidene rhodanine + isopropanol + urea | 1-(2-hydroxyethyl)-3-methylimidazolium bromide + isopropanol + urea |
| 1-octyl-3-methylimidazolium bromide | 1-octyl-3-methylimidazolium bromide + 5-(4-dimethyl)amino benzylidene rhodanine | 1-octyl-3-methylimidazolium bromide + Isopropanol | 1-octyl-3-methylimidazolium bromide + urea | 1-octyl-3-methylimidazolium bromide + 5-(4-dimethyl)amino benzylidene rhodanine + isopropanol | 1-octyl-3-methylimidazolium bromide + 5-(4-dimethyl)amino benzylidene rhodanine + urea | 1-octyl-3-methylimidazolium bromide + 5-(4-dimethyl)amino benzylidene rhodanine + isopropanol + urea | 1-octyl-3-methylimidazolium bromide + isopropanol + urea |
| 1-methyl-3-carboxyethyl-imidazolium bromide | 1-methyl-3-carboxyethyl-imidazolium bromide + sulfosalicylic acid | 1-methyl-3-carboxyethyl-imidazolium bromide + Isopropanol | 1-methyl-3-carboxyethyl-imidazolium bromide + urea | 1-methyl-3-carboxyethyl-imidazolium bromide + sulfosalicylic acid + isopropanol | 1-methyl-3-carboxyethyl-imidazolium bromide + sulfosalicylic acid + urea | 1-methyl-3-carboxyethyl-imidazolium bromide + sulfosalicylic acid + isopropanol + urea | 1-methyl-3-carboxyethyl-imidazolium bromide + isopropanol + urea |
| 1-hexyl-3-methylimidazolium bromide | 1-hexyl-3-methylimidazolium bromide + sulfosalicylic acid | 1-hexyl-3-methylimidazolium bromide + Isopropanol | 1-hexyl-3-methylimidazolium bromide + urea | 1-hexyl-3-methylimidazolium bromide + sulfosalicylic acid + isopropanol | 1-hexyl-3-methylimidazolium bromide + sulfosalicylic acid + urea | 1-hexyl-3-methylimidazolium bromide + sulfosalicylic acid + isopropanol + urea | 1-hexyl-3-methylimidazolium bromide + isopropanol + urea |

TABLE 5-continued

EXEMPLARY STORAGE COMPOSITIONS

| (A) Compound of Formula (I) | (A) + (B) Precipitating Agent | (A) + (C) Lower Alcohol | (A) + (D) Chaotrope | (A) + (B) + (C) | (A) + (B) + (D) | (A) + (B) + (C) + (D) | (A) + (C) + (D) |
|---|---|---|---|---|---|---|---|
| 1-decyl-3-methylimidazolium bromide | 1-decyl-3-methylimidazolium bromide + sulfosalicylic acid | 1-decyl-3-methylimidazolium bromide + Isopropanol | 1-decyl-3-methylimidazolium bromide + urea | 1-decyl-3-methylimidazolium bromide + sulfosalicylic acid + isopropanol | 1-decyl-3-methylimidazolium bromide + sulfosalicylic acid + urea | 1-decyl-3-methylimidazolium bromide + sulfosalicylic acid + isopropanol + urea | 1-decyl-3-methylimidazolium bromide + isopropanol + urea |
| 1-(2-hydroxyethyl)-3-methylimidazolium bromide | 1-(2-hydroxyethyl)-3-methylimidazolium bromide + sulfosalicylic acid | 1-(2-hydroxyethyl)-3-methylimidazolium bromide + Isopropanol | 1-(2-hydroxyethyl)-3-methylimidazolium bromide + urea | 1-(2-hydroxyethyl)-3-methylimidazolium bromide + sulfosalicylic acid + isopropanol | 1-(2-hydroxyethyl)-3-methylimidazolium bromide + sulfosalicylic acid + urea | 1-(2-hydroxyethyl)-3-methylimidazolium bromide + sulfosalicylic acid + isopropanol + urea | 1-(2-hydroxyethyl)-3-methylimidazolium bromide + isopropanol + urea |
| 1-octyl-3-methylimidazolium bromide | 1-octyl-3-methylimidazolium bromide + sulfosalicylic acid | 1-octyl-3-methylimidazolium bromide + Isopropanol | 1-octyl-3-methylimidazolium bromide + urea | 1-octyl-3-methylimidazolium bromide + sulfosalicylic acid + isopropanol | 1-octyl-3-methylimidazolium bromide + sulfosalicylic acid + urea | 1-octyl-3-methylimidazolium bromide + sulfosalicylic acid + isopropanol + urea | 1-octyl-3-methylimidazolium bromide + isopropanol + urea |
| 1-methyl-3-carboxyethyl-imidazolium bromide | 1-methyl-3-carboxyethyl-imidazolium bromide + lithium chloride | 1-methyl-3-carboxyethyl-imidazolium bromide + Isopropanol | 1-methyl-3-carboxyethyl-imidazolium bromide + urea | 1-methyl-3-carboxyethyl-imidazolium bromide + LiCl + isopropanol | 1-methyl-3-carboxyethyl-imidazolium bromide + LiCl + urea | 1-methyl-3-carboxyethyl-imidazolium bromide + LiCl + isopropanol + urea | 1-methyl-3-carboxyethyl-imidazolium bromide + isopropanol + urea |
| 1-hexyl-3-methylimidazolium bromide | 1-hexyl-3-methylimidazolium bromide + lithium chloride | 1-hexyl-3-methylimidazolium bromide + Isopropanol | 1-hexyl-3-methylimidazolium bromide + urea | 1-hexyl-3-methylimidazolium bromide + LiCl + isopropanol | 1-hexyl-3-methylimidazolium bromide + LiCl + urea | 1-hexyl-3-methylimidazolium bromide + LiCl + isopropanol + urea | 1-hexyl-3-methylimidazolium bromide + isopropanol + urea |
| 1-decyl-3-methylimidazolium bromide | 1-decyl-3-methylimidazolium bromide + lithium chloride | 1-decyl-3-methylimidazolium bromide + Isopropanol | 1-decyl-3-methylimidazolium bromide + urea | 1-decyl-3-methylimidazolium bromide + LiCl + isopropanol | 1-decyl-3-methylimidazolium bromide + LiCl + urea | 1-decyl-3-methylimidazolium bromide + LiCl + isopropanol + urea | 1-decyl-3-methylimidazolium bromide + isopropanol + urea |
| 1-(2-hydroxyethyl)-3-methylimidazolium bromide | 1-(2-hydroxyethyl)-3-methylimidazolium bromide + lithium chloride | 1-(2-hydroxyethyl)-3-methylimidazolium bromide + Isopropanol | 1-(2-hydroxyethyl)-3-methylimidazolium bromide + urea | 1-(2-hydroxyethyl)-3-methylimidazolium bromide + LiCl + isopropanol | 1-(2-hydroxyethyl)-3-methylimidazolium bromide + LiCl + urea | 1-(2-hydroxyethyl)-3-methylimidazolium bromide + LiCl + isopropanol + urea | 1-(2-hydroxyethyl)-3-methylimidazolium bromide + isopropanol + urea |
| 1-octyl-3-methylimidazolium bromide | 1-octyl-3-methylimidazolium bromide + lithium chloride | 1-octyl-3-methylimidazolium bromide + Isopropanol | 1-octyl-3-methylimidazolium bromide + urea | 1-octyl-3-methylimidazolium bromide + LiCl + isopropanol | 1-octyl-3-methylimidazolium bromide + LiCl + urea | 1-octyl-3-methylimidazolium bromide + LiCl + isopropanol + urea | 1-octyl-3-methylimidazolium bromide + isopropanol + urea |

TABLE 5-continued

EXEMPLARY STORAGE COMPOSITIONS

| (A) Compound of Formula (I) | (A) + (B) Precipitating Agent | (A) + (C) Lower Alcohol | (A) + (D) Chaotrope | (A) + (B) + (C) | (A) + (B) + (D) | (A) + (B) + (C) + (D) | (A) + (C) + (D) |
|---|---|---|---|---|---|---|---|
| 1-methyl-3-carboxyethyl-imidazolium bromide | 1-methyl-3-carboxyethyl-imidazolium bromide + lithium hydroxide | 1-methyl-3-carboxyethyl-imidazolium bromide + Isopropanol | 1-methyl-3-carboxyethyl-imidazolium bromide + urea | 1-methyl-3-carboxyethyl-imidazolium bromide + LiOH + isopropanol | 1-methyl-3-carboxyethyl-imidazolium bromide + LiOH + urea | 1-methyl-3-carboxyethyl-imidazolium bromide + LiOH + isopropanol + urea | 1-methyl-3-carboxyethyl-imidazolium bromide + isopropanol + urea |
| 1-hexyl-3-methylimidazolium bromide | 1-hexyl-3-methylimidazolium bromide + lithium hydroxide | 1-hexyl-3-methylimidazolium bromide + Isopropanol | 1-hexyl-3-methylimidazolium bromide + urea | 1-hexyl-3-methylimidazolium bromide + LiOH + isopropanol | 1-hexyl-3-methylimidazolium bromide + LiOH + urea | 1-hexyl-3-methylimidazolium bromide + LiOH + isopropanol + urea | 1-hexyl-3-methylimidazolium bromide + isopropanol + urea |
| 1-decyl-3-methylimidazolium bromide | 1-decyl-3-methylimidazolium bromide + lithium hydroxide | 1-decyl-3-methylimidazolium bromide + Isopropanol | 1-decyl-3-methylimidazolium bromide + urea | 1-decyl-3-methylimidazolium bromide + LiOH + isopropanol | 1-decyl-3-methylimidazolium bromide + LiOH + urea | 1-decyl-3-methylimidazolium bromide + LiOH + isopropanol + urea | 1-decyl-3-methylimidazolium bromide + isopropanol + urea |
| 1-(2-hydroxyethyl)-3-methylimidazolium bromide | 1-(2-hydroxyethyl)-3-methylimidazolium bromide + lithium hydroxide | 1-(2-hydroxyethyl)-3-methylimidazolium bromide + Isopropanol | 1-(2-hydroxyethyl)-3-methylimidazolium bromide + urea | 1-(2-hydroxyethyl)-3-methylimidazolium bromide + LiOH + isopropanol | 1-(2-hydroxyethyl)-3-methylimidazolium bromide + LiOH + urea | 1-(2-hydroxyethyl)-3-methylimidazolium bromide + LiOH + isopropanol + urea | 1-(2-hydroxyethyl)-3-methylimidazolium bromide + isopropanol + urea |
| 1-octyl-3-methylimidazolium bromide | 1-octyl-3-methylimidazolium bromide + lithium hydroxide | 1-octyl-3-methylimidazolium bromide + Isopropanol | 1-octyl-3-methylimidazolium bromide + urea | 1-octyl-3-methylimidazolium bromide + LiOH + isopropanol | 1-octyl-3-methylimidazolium bromide + LiOH + urea | 1-octyl-3-methylimidazolium bromide + LiOH + isopropanol + urea | 1-octyl-3-methylimidazolium bromide + isopropanol + urea |
| 1-methyl-3-carboxyethyl-imidazolium bromide | 1-methyl-3-carboxyethyl-imidazolium bromide + 5-(4-dimethyl)amino benzylidene rhodanine | 1-methyl-3-carboxyethyl-imidazolium bromide + n-butanol | 1-methyl-3-carboxyethyl-imidazolium bromide + urea | 1-methyl-3-carboxyethyl-imidazolium bromide + 5-(4-dimethyl)amino benzylidene rhodanine + n-butanol | 1-methyl-3-carboxyethyl-imidazolium bromide + 5-(4-dimethyl)amino benzylidene rhodanine + urea | 1-methyl-3-carboxyethyl-imidazolium bromide + 5-(4-dimethyl)amino benzylidene rhodanine + n-butanol + urea | 1-methyl-3-carboxyethyl-imidazolium bromide + n-butanol + urea |
| 1-hexyl-3-methylimidazolium bromide | 1-hexyl-3-methylimidazolium bromide + 5-(4-dimethyl)amino benzylidene rhodanine | 1-hexyl-3-methylimidazolium bromide + n-butanol | 1-hexyl-3-methylimidazolium bromide + urea | 1-hexyl-3-methylimidazolium bromide + 5-(4-dimethyl)amino benzylidene rhodanine + n-butanol | 1-hexyl-3-methylimidazolium bromide + 5-(4-dimethyl)amino benzylidene rhodanine + urea | 1-hexyl-3-methylimidazolium bromide + 5-(4-dimethyl)amino benzylidene rhodanine + n-butanol + urea | 1-hexyl-3-methylimidazolium bromide + n-butanol + urea |
| 1-decyl-3-methylimidazolium bromide | 1-decyl-3-methylimidazolium bromide + 5-(4-dimethyl)amino benzylidene rhodanine | 1-decyl-3-methylimidazolium bromide + n-butanol | 1-decyl-3-methylimidazolium bromide + urea | 1-decyl-3-methylimidazolium bromide + 5-(4-dimethyl)amino benzylidene rhodanine + n-butanol | 1-decyl-3-methylimidazolium bromide + 5-(4-dimethyl)amino benzylidene rhodanine + urea | 1-decyl-3-methylimidazolium bromide + 5-(4-dimethyl)amino benzylidene rhodanine + n-butanol + urea | 1-decyl-3-methylimidazolium bromide + n-butanol + urea |

TABLE 5-continued

EXEMPLARY STORAGE COMPOSITIONS

| (A) Compound of Formula (I) | (A) + (B) Precipitating Agent | (A) + (C) Lower Alcohol | (A) + (D) Chaotrope | (A) + (B) + (C) | (A) + (B) + (D) | (A) + (B) + (C) + (D) | (A) + (C) + (D) |
|---|---|---|---|---|---|---|---|
| 1-(2-hydroxyethyl)-3-methylimidazolium bromide | 1-(2-hydroxyethyl)-3-methylimidazolium bromide + 5-(4-dimethyl)amino benzylidene rhodanine | 1-(2-hydroxyethyl)-3-methylimidazolium bromide + n-butanol | 1-(2-hydroxyethyl)-3-methylimidazolium bromide + urea | 1-(2-hydroxyethyl)-3-methylimidazolium bromide + 5-(4-dimethyl)amino benzylidene rhodanine + n-butanol | 1-(2-hydroxyethyl)-3-methylimidazolium bromide + 5-(4-dimethyl)amino benzylidene rhodanine + urea | 1-(2-hydroxyethyl)-3-methylimidazolium bromide + 5-(4-dimethyl)amino benzylidene rhodanine + n-butanol + urea | 1-(2-hydroxyethyl)-3-methylimidazolium bromide + n-butanol + urea |
| 1-octyl-3-methylimidazolium bromide | 1-octyl-3-methylimidazolium bromide + 5-(4-dimethyl)amino benzylidene rhodanine | 1-octyl-3-methylimidazolium bromide + n-butanol | 1-octyl-3-methylimidazolium bromide + urea | 1-octyl-3-methylimidazolium bromide + 5-(4-dimethyl)amino benzylidene rhodanine + n-butanol | 1-octyl-3-methylimidazolium bromide + 5-(4-dimethyl)amino benzylidene rhodanine + urea | 1-octyl-3-methylimidazolium bromide + 5-(4-dimethyl)amino benzylidene rhodanine + n-butanol + urea | 1-octyl-3-methylimidazolium bromide + n-butanol + urea |
| 1-methyl-3-carboxyethyl-imidazolium bromide | 1-methyl-3-carboxyethyl-imidazolium bromide + sulfosalicylic acid | 1-methyl-3-carboxyethyl-imidazolium bromide + n-butanol | 1-methyl-3-carboxyethyl-imidazolium bromide + urea | 1-methyl-3-carboxyethyl-imidazolium bromide + sulfosalicylic acid + n-butanol | 1-methyl-3-carboxyethyl-imidazolium bromide + sulfosalicylic acid + urea | 1-methyl-3-carboxyethyl-imidazolium bromide + sulfosalicylic acid + n-butanol + urea | 1-methyl-3-carboxyethyl-imidazolium bromide + n-butanol + urea |
| 1-hexyl-3-methylimidazolium bromide | 1-hexyl-3-methylimidazolium bromide + sulfosalicylic acid | 1-hexyl-3-methylimidazolium bromide + n-butanol | 1-hexyl-3-methylimidazolium bromide + urea | 1-hexyl-3-methylimidazolium bromide + sulfosalicylic acid + n-butanol | 1-hexyl-3-methylimidazolium bromide + sulfosalicylic acid + urea | 1-hexyl-3-methylimidazolium bromide + sulfosalicylic acid + n-butanol + urea | 1-hexyl-3-methylimidazolium bromide + n-butanol + urea |
| 1-decyl-3-methylimidazolium bromide | 1-decyl-3-methylimidazolium bromide + sulfosalicylic acid | 1-decyl-3-methylimidazolium bromide + n-butanol | 1-decyl-3-methylimidazolium bromide + urea | 1-decyl-3-methylimidazolium bromide + sulfosalicylic acid + n-butanol | 1-decyl-3-methylimidazolium bromide + sulfosalicylic acid + urea | 1-decyl-3-methylimidazolium bromide + sulfosalicylic acid + n-butanol + urea | 1-decyl-3-methylimidazolium bromide + n-butanol + urea |
| 1-(2-hydroxyethyl)-3-methylimidazolium bromide | 1-(2-hydroxyethyl)-3-methylimidazolium bromide + sulfosalicylic acid | 1-(2-hydroxyethyl)-3-methylimidazolium bromide + n-butanol | 1-(2-hydroxyethyl)-3-methylimidazolium bromide + urea | 1-(2-hydroxyethyl)-3-methylimidazolium bromide + sulfosalicylic acid + n-butanol | 1-(2-hydroxyethyl)-3-methylimidazolium bromide + sulfosalicylic acid + urea | 1-(2-hydroxyethyl)-3-methylimidazolium bromide + sulfosalicylic acid + n-butanol + urea | 1-(2-hydroxyethyl)-3-methylimidazolium bromide + n-butanol + urea |
| 1-octyl-3-methylimidazolium bromide | 1-octyl-3-methylimidazolium bromide + sulfosalicylic acid | 1-octyl-3-methylimidazolium bromide + n-butanol | 1-octyl-3-methylimidazolium bromide + urea | 1-octyl-3-methylimidazolium bromide + sulfosalicylic acid + n-butanol | 1-octyl-3-methylimidazolium bromide + sulfosalicylic acid + urea | 1-octyl-3-methylimidazolium bromide + sulfosalicylic acid + n-butanol + urea | 1-octyl-3-methylimidazolium bromide + n-butanol + urea |

TABLE 5-continued

EXEMPLARY STORAGE COMPOSITIONS

| (A) Compound of Formula (I) | (A) + (B) Precipitating Agent | (A) + (C) Lower Alcohol | (A) + (D) Chaotrope | (A) + (B) + (C) | (A) + (B) + (D) | (A) + (B) + (C) + (D) | (A) + (C) + (D) |
|---|---|---|---|---|---|---|---|
| 1-methyl-3-carboxyethyl-imidazolium bromide | 1-methyl-3-carboxyethyl-imidazolium bromide + lithium chloride | 1-methyl-3-carboxyethyl-imidazolium bromide + n-butanol | 1-methyl-3-carboxyethyl-imidazolium bromide + urea | 1-methyl-3-carboxyethyl-imidazolium bromide + LiCl + n-butanol | 1-methyl-3-carboxyethyl-imidazolium bromide + LiCl + urea | 1-methyl-3-carboxyethyl-imidazolium bromide + LiCl + n-butanol + urea | 1-methyl-3-carboxyethyl-imidazolium bromide + n-butanol + urea |
| 1-hexyl-3-methylimidazolium bromide | 1-hexyl-3-methylimidazolium bromide + lithium chloride | 1-hexyl-3-methylimidazolium bromide + n-butanol | 1-hexyl-3-methylimidazolium bromide + urea | 1-hexyl-3-methylimidazolium bromide + LiCl + n-butanol | 1-hexyl-3-methylimidazolium bromide + LiCl + urea | 1-hexyl-3-methylimidazolium bromide + LiCl + n-butanol + urea | 1-hexyl-3-methylimidazolium bromide + n-butanol + urea |
| 1-decyl-3-methylimidazolium bromide | 1-decyl-3-methylimidazolium bromide + lithium chloride | 1-decyl-3-methylimidazolium bromide + n-butanol | 1-decyl-3-methylimidazolium bromide + urea | 1-decyl-3-methylimidazolium bromide + LiCl + n-butanol | 1-decyl-3-methylimidazolium bromide + LiCl + urea | 1-decyl-3-methylimidazolium bromide + LiCl + n-butanol + urea | 1-decyl-3-methylimidazolium bromide + n-butanol + urea |
| 1-(2-hydroxyethyl)-3-methylimidazolium bromide | 1-(2-hydroxyethyl)-3-methylimidazolium bromide + lithium chloride | 1-(2-hydroxyethyl)-3-methylimidazolium bromide + n-butanol | 1-(2-hydroxyethyl)-3-methylimidazolium bromide + urea | 1-(2-hydroxyethyl)-3-methylimidazolium bromide + LiCl + n-butanol | 1-(2-hydroxyethyl)-3-methylimidazolium bromide + LiCl + urea | 1-(2-hydroxyethyl)-3-methylimidazolium bromide + LiCl + n-butanol + urea | 1-(2-hydroxyethyl)-3-methylimidazolium bromide + n-butanol + urea |
| 1-octyl-3-methylimidazolium bromide | 1-octyl-3-methylimidazolium bromide + lithium chloride | 1-octyl-3-methylimidazolium bromide + n-butanol | 1-octyl-3-methylimidazolium bromide + urea | 1-octyl-3-methylimidazolium bromide + LiCl + n-butanol | 1-octyl-3-methylimidazolium bromide + LiCl + urea | 1-octyl-3-methylimidazolium bromide + LiCl + n-butanol + urea | 1-octyl-3-methylimidazolium bromide + n-butanol + urea |
| 1-methyl-3-carboxyethyl-imidazolium bromide | 1-methyl-3-carboxyethyl-imidazolium bromide + lithium hydroxide | 1-methyl-3-carboxyethyl-imidazolium bromide + n-butanol | 1-methyl-3-carboxyethyl-imidazolium bromide + urea | 1-methyl-3-carboxyethyl-imidazolium bromide + LiOH + n-butanol | 1-methyl-3-carboxyethyl-imidazolium bromide + LiOH + urea | 1-methyl-3-carboxyethyl-imidazolium bromide + LiOH + n-butanol + urea | 1-methyl-3-carboxyethyl-imidazolium bromide + n-butanol + urea |
| 1-hexyl-3-methylimidazolium bromide | 1-hexyl-3-methylimidazolium bromide + lithium hydroxide | 1-hexyl-3-methylimidazolium bromide + n-butanol | 1-hexyl-3-methylimidazolium bromide + urea | 1-hexyl-3-methylimidazolium bromide + LiOH + n-butanol | 1-hexyl-3-methylimidazolium bromide + LiOH + urea | 1-hexyl-3-methylimidazolium bromide + LiOH + n-butanol + urea | 1-hexyl-3-methylimidazolium bromide + n-butanol + urea |
| 1-decyl-3-methylimidazolium bromide | 1-decyl-3-methylimidazolium bromide + lithium hydroxide | 1-decyl-3-methylimidazolium bromide + n-butanol | 1-decyl-3-methylimidazolium bromide + urea | 1-decyl-3-methylimidazolium bromide + LiOH + n-butanol | 1-decyl-3-methylimidazolium bromide + LiOH + urea | 1-decyl-3-methylimidazolium bromide + LiOH + n-butanol + urea | 1-decyl-3-methylimidazolium bromide + n-butanol + urea |
| 1-(2-hydroxyethyl)-3-methylimidazolium bromide | 1-(2-hydroxyethyl)-3-methylimidazolium bromide + lithium hydroxide | 1-(2-hydroxyethyl)-3-methylimidazolium bromide + n-butanol | 1-(2-hydroxyethyl)-3-methylimidazolium bromide + urea | 1-(2-hydroxyethyl)-3-methylimidazolium bromide + LiOH + n-butanol | 1-(2-hydroxyethyl)-3-methylimidazolium bromide + LiOH + urea | 1-(2-hydroxyethyl)-3-methylimidazolium bromide + LiOH + n-butanol + urea | 1-(2-hydroxyethyl)-3-methylimidazolium bromide + n-butanol + urea |
| 1-octyl-3-methylimidazolium bromide | 1-octyl-3-methylimidazolium bromide + lithium hydroxide | 1-octyl-3-methylimidazolium bromide + n-butanol | 1-octyl-3-methylimidazolium bromide + urea | 1-octyl-3-methylimidazolium bromide + LiOH + n-butanol | 1-octyl-3-methylimidazolium bromide + LiOH + urea | 1-octyl-3-methylimidazolium bromide + LiOH + n-butanol + urea | 1-octyl-3-methylimidazolium bromide + n-butanol + urea |

TABLE 5-continued

EXEMPLARY STORAGE COMPOSITIONS

| (A) Compound of Formula (I) | (A) + (B) Precipitating Agent | (A) + (C) Lower Alcohol | (A) + (D) Chaotrope | (A) + (B) + (C) | (A) + (B) + (D) | (A) + (B) + (C) + (D) | (A) + (C) + (D) |
|---|---|---|---|---|---|---|---|
| 1-methyl-3-carboxyethyl-imidazolium bromide | 1-methyl-3-carboxyethyl-imidazolium bromide + 5-(4-dimethyl)amino benzylidene rhodanine | 1-methyl-3-carboxyethyl-imidazolium bromide + isobutanol | 1-methyl-3-carboxyethyl-imidazolium bromide + urea | 1-methyl-3-carboxyethyl-imidazolium bromide + 5-(4-dimethyl)amino benzylidene rhodanine + isobutanol | 1-methyl-3-carboxyethyl-imidazolium bromide + 5-(4-dimethyl)amino benzylidene rhodanine + urea | 1-methyl-3-carboxyethyl-imidazolium bromide + 5-(4-dimethyl)amino benzylidene rhodanine + isobutanol + urea | 1-methyl-3-carboxyethyl-imidazolium bromide + isobutanol + urea |
| 1-hexyl-3-methylimidazolium bromide | 1-hexyl-3-methylimidazolium bromide + 5-(4-dimethyl)amino benzylidene rhodanine | 1-hexyl-3-methylimidazolium bromide + isobutanol | 1-hexyl-3-methylimidazolium bromide + urea | 1-hexyl-3-methylimidazolium bromide + 5-(4-dimethyl)amino benzylidene rhodanine + isobutanol | 1-hexyl-3-methylimidazolium bromide + 5-(4-dimethyl)amino benzylidene rhodanine + urea | 1-hexyl-3-methylimidazolium bromide + 5-(4-dimethyl)amino benzylidene rhodanine + isobutanol + urea | 1-hexyl-3-methylimidazolium bromide + isobutanol + urea |
| 1-decyl-3-methylimidazolium bromide | 1-decyl-3-methylimidazolium bromide + 5-(4-dimethyl)amino benzylidene rhodanine | 1-decyl-3-methylimidazolium bromide + isobutanol | 1-decyl-3-methylimidazolium bromide + urea | 1-decyl-3-methylimidazolium bromide + 5-(4-dimethyl)amino benzylidene rhodanine + isobutanol | 1-decyl-3-methylimidazolium bromide + 5-(4-dimethyl)amino benzylidene rhodanine + urea | 1-decyl-3-methylimidazolium bromide + 5-(4-dimethyl)amino benzylidene rhodanine + isobutanol + urea | 1-decyl-3-methylimidazolium bromide + isobutanol + urea |
| 1-(2-hydroxyethyl)-3-methylimidazolium bromide | 1-(2-hydroxyethyl)-3-methylimidazolium bromide + 5-(4-dimethyl)amino benzylidene rhodanine | 1-(2-hydroxyethyl)-3-methylimidazolium bromide + isobutanol | 1-(2-hydroxyethyl)-3-methylimidazolium bromide + urea | 1-(2-hydroxyethyl)-3-methylimidazolium bromide + 5-(4-dimethyl)amino benzylidene rhodanine + isobutanol | 1-(2-hydroxyethyl)-3-methylimidazolium bromide + 5-(4-dimethyl)amino benzylidene rhodanine + urea | 1-(2-hydroxyethyl)-3-methylimidazolium bromide + 5-(4-dimethyl)amino benzylidene rhodanine + isobutanol + urea | 1-(2-hydroxyethyl)-3-methylimidazolium bromide + isobutanol + urea |
| 1-octyl-3-methylimidazolium bromide | 1-octyl-3-methylimidazolium bromide + 5-(4-dimethyl)amino benzylidene rhodanine | 1-octyl-3-methylimidazolium bromide + isobutanol | 1-octyl-3-methylimidazolium bromide + urea | 1-octyl-3-methylimidazolium bromide + 5-(4-dimethyl)amino benzylidene rhodanine + isobutanol | 1-octyl-3-methylimidazolium bromide + 5-(4-dimethyl)amino benzylidene rhodanine + urea | 1-octyl-3-methylimidazolium bromide + 5-(4-dimethyl)amino benzylidene rhodanine + isobutanol + urea | 1-octyl-3-methylimidazolium bromide + isobutanol + urea |
| 1-methyl-3-carboxyethyl-imidazolium bromide | 1-methyl-3-carboxyethyl-imidazolium bromide + sulfosalicylic acid | 1-methyl-3-carboxyethyl-imidazolium bromide + isobutanol | 1-methyl-3-carboxyethyl-imidazolium bromide + urea | 1-methyl-3-carboxyethyl-imidazolium bromide + sulfosalicylic acid + isobutanol | 1-methyl-3-carboxyethyl-imidazolium bromide + sulfosalicylic acid + urea | 1-methyl-3-carboxyethyl-imidazolium bromide + sulfosalicylic acid + isobutanol + urea | 1-methyl-3-carboxyethyl-imidazolium bromide + isobutanol + urea |

TABLE 5-continued

EXEMPLARY STORAGE COMPOSITIONS

| (A) Compound of Formula (I) | (A) + (B) Precipitating Agent | (A) + (C) Lower Alcohol | (A) + (D) Chaotrope | (A) + (B) + (C) | (A) + (B) + (D) | (A) + (B) + (C) + (D) | (A) + (C) + (D) |
|---|---|---|---|---|---|---|---|
| 1-hexyl-3-methylimidazolium bromide | 1-hexyl-3-methylimidazolium bromide + sulfosalicylic acid | 1-hexyl-3-methylimidazolium bromide + isobutanol | 1-hexyl-3-methylimidazolium bromide + urea | 1-hexyl-3-methylimidazolium bromide + sulfosalicylic acid + isobutanol | 1-hexyl-3-methylimidazolium bromide + sulfosalicylic acid + urea | 1-hexyl-3-methylimidazolium bromide + sulfosalicylic acid + isobutanol + urea | 1-hexyl-3-methylimidazolium bromide + isobutanol + urea |
| 1-decyl-3-methylimidazolium bromide | 1-decyl-3-methylimidazolium bromide + sulfosalicylic acid | 1-decyl-3-methylimidazolium bromide + isobutanol | 1-decyl-3-methylimidazolium bromide + urea | 1-decyl-3-methylimidazolium bromide + sulfosalicylic acid + isobutanol | 1-decyl-3-methylimidazolium bromide + sulfosalicylic acid + urea | 1-decyl-3-methylimidazolium bromide + sulfosalicylic acid + isobutanol + urea | 1-decyl-3-methylimidazolium bromide + isobutanol + urea |
| 1-(2-hydroxyethyl)-3-methylimidazolium bromide | 1-(2-hydroxyethyl)-3-methylimidazolium bromide + sulfosalicylic acid | 1-(2-hydroxyethyl)-3-methylimidazolium bromide + isobutanol | 1-(2-hydroxyethyl)-3-methylimidazolium bromide + urea | 1-(2-hydroxyethyl)-3-methylimidazolium bromide + sulfosalicylic acid + isobutanol | 1-(2-hydroxyethyl)-3-methylimidazolium bromide + sulfosalicylic acid + urea | 1-(2-hydroxyethyl)-3-methylimidazolium bromide + sulfosalicylic acid + isobutanol + urea | 1-(2-hydroxyethyl)-3-methylimidazolium bromide + isobutanol + urea |
| 1-octyl-3-methylimidazolium bromide | 1-octyl-3-methylimidazolium bromide + sulfosalicylic acid | 1-octyl-3-methylimidazolium bromide + isobutanol | 1-octyl-3-methylimidazolium bromide + urea | 1-octyl-3-methylimidazolium bromide + sulfosalicylic acid + isobutanol | 1-octyl-3-methylimidazolium bromide + sulfosalicylic acid + urea | 1-octyl-3-methylimidazolium bromide + sulfosalicylic acid + isobutanol + urea | 1-octyl-3-methylimidazolium bromide + isobutanol + urea |
| 1-methyl-3-carboxyethyl-imidazolium bromide | 1-methyl-3-carboxyethyl-imidazolium bromide + lithium chloride | 1-methyl-3-carboxyethyl-imidazolium bromide + isobutanol | 1-methyl-3-carboxyethyl-imidazolium bromide + urea | 1-methyl-3-carboxyethyl-imidazolium bromide + LiCl + isobutanol | 1-methyl-3-carboxyethyl-imidazolium bromide + LiCl + urea | 1-methyl-3-carboxyethyl-imidazolium bromide + LiCl + isobutanol + urea | 1-methyl-3-carboxyethyl-imidazolium bromide + isobutanol + urea |
| 1-hexyl-3-methylimidazolium bromide | 1-hexyl-3-methylimidazolium bromide + lithium chloride | 1-hexyl-3-methylimidazolium bromide + isobutanol | 1-hexyl-3-methylimidazolium bromide + urea | 1-hexyl-3-methylimidazolium bromide + LiCl + isobutanol | 1-hexyl-3-methylimidazolium bromide + LiCl + urea | 1-hexyl-3-methylimidazolium bromide + LiCl + isobutanol + urea | 1-hexyl-3-methylimidazolium bromide + isobutanol + urea |
| 1-decyl-3-methylimidazolium bromide | 1-decyl-3-methylimidazolium bromide + lithium chloride | 1-decyl-3-methylimidazolium bromide + isobutanol | 1-decyl-3-methylimidazolium bromide + urea | 1-decyl-3-methylimidazolium bromide + LiCl + isobutanol | 1-decyl-3-methylimidazolium bromide + LiCl + urea | 1-decyl-3-methylimidazolium bromide + LiCl + isobutanol + urea | 1-decyl-3-methylimidazolium bromide + isobutanol + urea |
| 1-(2-hydroxyethyl)-3-methylimidazolium bromide | 1-(2-hydroxyethyl)-3-methylimidazolium bromide + lithium chloride | 1-(2-hydroxyethyl)-3-methylimidazolium bromide + isobutanol | 1-(2-hydroxyethyl)-3-methylimidazolium bromide + urea | 1-(2-hydroxyethyl)-3-methylimidazolium bromide + LiCl + isobutanol | 1-(2-hydroxyethyl)-3-methylimidazolium bromide + LiCl + urea | 1-(2-hydroxyethyl)-3-methylimidazolium bromide + LiCl + isobutanol + urea | 1-(2-hydroxyethyl)-3-methylimidazolium bromide + isobutanol + urea |

TABLE 5-continued

EXEMPLARY STORAGE COMPOSITIONS

| (A) Compound of Formula (I) | (A) + (B) Precipitating Agent | (A) + (C) Lower Alcohol | (A) + (D) Chaotrope | (A) + (B) + (C) | (A) + (B) + (D) | (A) + (B) + (C) + (D) | (A) + (C) + (D) |
|---|---|---|---|---|---|---|---|
| 1-octyl-3-methylimidazolium bromide | 1-octyl-3-methylimidazolium bromide + lithium chloride | 1-octyl-3-methylimidazolium bromide + isobutanol | 1-octyl-3-methylimidazolium bromide + urea | 1-octyl-3-methylimidazolium bromide + LiCl + isobutanol | 1-octyl-3-methylimidazolium bromide + LiCl + urea | 1-octyl-3-methylimidazolium bromide + LiCl + isobutanol + urea | 1-octyl-3-methylimidazolium bromide + isobutanol + urea |
| 1-methyl-3-carboxyethyl-imidazolium bromide | 1-methyl-3-carboxyethyl-imidazolium bromide + lithium hydroxide | 1-methyl-3-carboxyethyl-imidazolium bromide + isobutanol | 1-methyl-3-carboxyethyl-imidazolium bromide + urea | 1-methyl-3-carboxyethyl-imidazolium bromide + LiOH + isobutanol | 1-methyl-3-carboxyethyl-imidazolium bromide + LiOH + urea | 1-methyl-3-carboxyethyl-imidazolium bromide + LiOH + isobutanol + urea | 1-methyl-3-carboxyethyl-imidazolium bromide + isobutanol + urea |
| 1-hexyl-3-methylimidazolium bromide | 1-hexyl-3-methylimidazolium bromide + lithium hydroxide | 1-hexyl-3-methylimidazolium bromide + isobutanol | 1-hexyl-3-methylimidazolium bromide + urea | 1-hexyl-3-methylimidazolium bromide + LiOH + isobutanol | 1-hexyl-3-methylimidazolium bromide + LiOH + urea | 1-hexyl-3-methylimidazolium bromide + LiOH + isobutanol + urea | 1-hexyl-3-methylimidazolium bromide + isobutanol + urea |
| 1-decyl-3-methylimidazolium bromide | 1-decyl-3-methylimidazolium bromide + lithium hydroxide | 1-decyl-3-methylimidazolium bromide + isobutanol | 1-decyl-3-methylimidazolium bromide + urea | 1-decyl-3-methylimidazolium bromide + LiOH + isobutanol | 1-decyl-3-methylimidazolium bromide + LiOH + urea | 1-decyl-3-methylimidazolium bromide + LiOH + isobutanol + urea | 1-decyl-3-methylimidazolium bromide + isobutanol + urea |
| 1-(2-hydroxyethyl)-3-methylimidazolium bromide | 1-(2-hydroxyethyl)-3-methylimidazolium bromide + lithium hydroxide | 1-(2-hydroxyethyl)-3-methylimidazolium bromide + isobutanol | 1-(2-hydroxyethyl)-3-methylimidazolium bromide + urea | 1-(2-hydroxyethyl)-3-methylimidazolium bromide + LiOH + isobutanol | 1-(2-hydroxyethyl)-3-methylimidazolium bromide + LiOH + urea | 1-(2-hydroxyethyl)-3-methylimidazolium bromide + LiOH + isobutanol + urea | 1-(2-hydroxyethyl)-3-methylimidazolium bromide + isobutanol + urea |
| 1-octyl-3-methylimidazolium bromide | 1-octyl-3-methylimidazolium bromide + lithium hydroxide | 1-octyl-3-methylimidazolium bromide + isobutanol | 1-octyl-3-methylimidazolium bromide + urea | 1-octyl-3-methylimidazolium bromide + LiOH + isobutanol | 1-octyl-3-methylimidazolium bromide + LiOH + urea | 1-octyl-3-methylimidazolium bromide + LiOH + isobutanol + urea | 1-octyl-3-methylimidazolium bromide + isobutanol + urea |

The compositions of Tables 1-5 and other invention embodiments as described herein may be used for storage of liquid or non-liquid samples and for storage at ambient temperature, and also may have use for the storage of diverse biological materials and biological samples, such as but not limited to DNA, RNA, proteins and polypeptides, saliva, sputum, blood, buffy coat fraction of blood, peripheral blood mononuclear cells (PBMC) or isolated subsets thereof, other cells of hematopoietic origin such as lymphoid, myeloid, erythroid precursor, bone marrow stromal or other hematopoietic cells, urine, other biological fluids (e.g., serum, serosal fluids, plasma, lymph, cerebrospinal fluid, saliva, mucosal secretions of the secretory tissues and organs, vaginal secretions, ascites fluids, fluids of the pleural, pericardial, peritoneal, abdominal and other body cavities, cell and organ culture medium including cell or organ conditioned medium, lavage fluids and the like, etc.) buccal swabs, bacteria, viruses, engineered viral vectors, yeast cells, vaccines (e.g., natural or synthetic, live or attenuated in the case of intact biological particles such as viral or other microbial vaccines, or extracts of natural, synthetic or artificial materials including products of genetic engineering), cells and tissues, sorted or selected cells, cell or tissue lysates, cell or tissue homogenates or extracts, and the like, or other biological samples.

Certain preferred embodiments of the compositions and methods disclosed herein relate to substantially stable storage of nucleic acid and/or polypeptide molecules in a biological sample that comprises saliva and/or sputum and which may but need not also contain cells such as eptithelial cells (e.g., buccal epithelial cells or nasal or other epithelial cells) or blood cells or other cells that may be present in a saliva or sputum sample, including, for instance, a buccal swab sample that comprises saliva.

Biological samples may therefore also include a blood sample, biopsy specimen, tissue explant, organ culture, biological fluid or any other tissue or cell preparation, or fraction or derivative thereof or isolated therefrom, from a subject or a biological source. The subject or biological source may be a human or non-human animal, including mammals and non-mammals, vertebrates and invertebrates, and may also be any other multicellular organism or single-celled organism such as a eukaryotic (including plants and algae) or prokaryotic organism or archaeon, microorganisms (e.g., bacteria, archaea, fungi, protists, viruses), aquatic plankton, soil, biofilms, microbial mats or clusters, a primary cell culture or culture adapted cell line including but not limited to genetically engineered cell lines that may contain chromosomally integrated or episomal recombinant nucleic acid sequences or artificial chromosomes, immortalized or immortalizable cell lines, somatic cell hybrid cell lines, differentiated or differentiable cell lines, stem cells, germ cells (e.g., sperm, oocytes), transformed cell lines and the like.

The presently used terms "biological sample", "biological molecule" and "biomolecule" encompass any substances and compounds substantially of biological origin that have properties that are relevant within the framework of scientific, diagnostic and/or pharmaceutical applications. Encompassed are not only native molecules, such as those that can be isolated from natural sources, but also forms, fragments and derivatives derived therefrom, as well as recombinant forms and artificial molecules, as long as at least one property of the native molecules is present. Preferred biological samples are those that can be applied for analytical, diagnostic and/or pharmaceutical purposes, such as, but not limited to, nucleic acids and their derivatives (e.g., oligo-nucleotides, DNA, cDNA, PCR products, genomic DNA, plasmids, chromosomes, artificial chromosomes, gene transfer vectors, RNA, mRNA, tRNA, sRNA, miRNA, hnRNA, ribozymes, peptide nucleic acid (PNA)), polypeptides and proteins (e.g., enzymes, receptor proteins, protein complexes, peptide hormones, antibodies, lipoproteins, glycoproteins, inteins, prions), as well as biologically active fragments thereof, carbohydrates and their derivatives (e.g., glycolipids, glycosylated proteins, glycosides, oligosaccharides, mono- and poly-saccharides, and glycosaminoglycans), and lipids and their derivatives (e.g., fats, fatty acids, glycerides, triglycerides, phospholipids, steroids, prostaglandins, and leukotrienes).

It will be clear to one of skill in the art, based on the present disclosure, that the compositions and processes according to embodiments encompassed by the present invention can also be applied to cellular tissues and to complete cells, as well as to portions thereof (e.g., organelles, membranes and membrane fragments, homogenates, extracts, subcellular fractions, lysates, etc.) as long as such derived portions are carriers of the above described biomolecules. For this reason, tissues, cells and portions thereof and the like are basically encompassed by the term "biological sample".

Accordingly, the term "biological sample" may be regarded in its broadest sense, for instance, to refer to a vertebrate or invertebrate cell or tissue, for example in the case of vertebrate cells, to a fish cell (e.g., a zebrafish cell, or a pufferfish cell, etc.), an amphibian cell (e.g., a frog cell), an avian cell, a reptilian cell, a mammalian cell, etc. Examples of mammals include humans or non-human mammals, such as a monkey, ape, cow, sheep, goat, buffalo, antelope, oxen, horse, donkey, mule, deer, elk, caribou, water buffalo, camel, llama, alpaca, rabbit, pig, mouse, rat, guinea pig, hamster, dog, cat, etc. Also envisaged in other embodiments are biological samples that may comprise non-mammalian animals or organs derived therefrom, including, for example, annelids, mollusks, sponges, cnidaria, arthropods, amphibians, fish, birds and reptiles.

In certain other embodiments a biological sample may refer to microorganisms that are derived from aquatic plankton, animal tissues and organs as described above, microbial mats, clusters, sludge, flocs, or biofilms. Microorganisms of the "aquatic" plankton comprises bacterial plankton, archael plankton, viruses and phytoplankton, as well as zooplankton.

According to other embodiments, the term "biological sample" may include a specimen or culture obtained from any source (animal, plant, bacteria, virus, etc.) such as a subject or biological source, as well as from biological and environmental samples. Biological samples may be obtained from any vertebrate or non-vertebrate and may encompass fluids, solids, tissues, and gases. Environmental samples include environmental material such as surface matter, soil, water, biofilms, microbial mats, industrial samples, etc.

As used herein, "soil" is the complex product of geological and biological processes acting on inorganic minerals and biomass deposited on the earth's surface. It contains the majority of biodiversity on earth (Whitman et al., (1998) *Proc. Natl. Acad. Sci. USA*, 95 (12, 6578-83) acting to recycle and biomineralize organic matter, and serves as a substratum to anchor and nourish higher plants.

Biofilms are microbial assemblages on the surface in "aqueous environments" in which microbes are embedded in a hydrated polymeric matrix. This matrix acts like a glue, holding the microbes together, attaching them to the surface and protecting them from detrimental external influences.

They may contain several taxonomically distinct species (e.g., bacteria, fungi, algae, and protozoa), and may form on solid or liquid surfaces of diverse composition, such as metals, glass, plastics, tissue, minerals, and soil particles. Microbial mats and cluster are microbial assemblage/aggregates similar to biofilms in composition, however, not necessarily as firmly attached as solid surfaces.

Certain embodiments relate to a biological sample that may comprise an isolated biomolecule, where the term "isolated" means that the material is removed from its original environment (e.g., the natural environment if it is naturally occurring). For example, a naturally occurring nucleic acid or polypeptide present in an intact cell or in a living animal is not isolated, but the same nucleic acid or polypeptide, separated from some or all of the co-existing materials in the natural system, is isolated. Such nucleic acids could be part of a vector and/or such nucleic acids or polypeptides could be part of a composition, and still be isolated in that such vector or composition is not part of its natural environment.

Certain herein described embodiments relate to stabilization and/or preservation of a biological sample, which involves maintenance, retention or reconstitution of the structural and/or functional integrity of biological samples (including of molecular, multimolecular or oligomeric, organellar, subcellular, cellular, multicellular, or higher organizational levels of biological structure and/or function) and of the biological properties based thereupon. The biological activity of a biological sample that comprises, in a particular embodiment, a macromolecule or biopolymer or the like such as a polypeptide or polynucleotide, may involve, for example, the extensive maintenance of its primary, secondary and/or tertiary structure. The biological activity of a nucleic acid probe comprises, for example, its property of forming in a sequence-specific manner a hybridization complex (e.g., a duplex) with a nucleic acid target which is complementary to the probe. The biological activity of an antibody comprises, for example, a specific binding interaction with its cognate antigen.

As described herein, the biological activity of a substance means any activity which can affect any physical or biochemical properties of a biological system, pathway, molecule, or interaction relating to an organism, including for example but not limited to, viruses, bacteria, bacteriophage, prions, insects, fungi, plants, animals, and humans. Examples of substances with biological activity include, but are not limited to, polynucleotides, peptides, proteins, enzymes, antibodies, small molecules (e.g., a bioactive small molecule), pharmaceutical compositions (e.g., drugs), vaccines, carbohydrates, lipids, steroids, hormones, chemokines, growth factors, cytokines, liposomes, and toxins, liposomes. Persons familiar with the relevant art will recognize appropriate assays and methods for determining the biological activity of substances that affect the physical or biochemical properties of a biological system, for example, one or more biological activities that may include, but are not limited to, gene expression (see, e.g., Asubel, F M et al. (Eds.). 2007. *Current Protocols in Molecular Biology*, Wiley and Sons, Inc. Hoboken, N.J.), receptor-ligand interactions (see for example, Coligan et al. (Eds.). 2007. *Current Protocols in Immunology*, Wiley and Sons, Inc. Hoboken, N.J.), enzymatic activity (see, e.g., Eisenthal and Hanson (Eds.), Enzyme Assays, Second Edition. *Practical Approaches* series, No. 257. 2002, Oxford University Press, Oxford, UK; Kaplan and Colowick (Eds.), *Preparation and Assay of Enzymes, Methods in Enzymology*, (vols. 1, 2 and 6). 1955 and 1961, Academic Press, Ltd., Oxford, UK), cytokine, hormone and bioactive peptide activities and other cell proliferation (e.g., mitogenic) and/or differentiation activities (see for example, Coligan et al. (Eds.). 2007 *Current Protocols in Immunology*, Wiley and Sons, Inc. Hoboken, N.J.), signal transduction (see for example, Bonifacino et al. (Eds.) 2007 *Current Protocols in Cell Biology*, Wiley and Sons, Inc. Hoboken, N.J.) and cell toxicity (e.g., cytotoxicity, excitotoxicity) (see for example, Bus J S et al. (Eds) 2007 *Current Protocols in Toxicology*, Wiley and Sons, Inc. Hoboken, N.J.), apoptosis and necrosis (Green and Reed, 1998 *Science* 281(5381):1309-12; Green D R, 1998 *Nature* December 17: 629; Green D R, 1998 *Cell* 94(6):695-69; Reed, J C (Ed.), 2000 *Apoptosis, Methods in Enzymology* (vol. 322), Academic Press Ltd., Oxford, UK).

In certain embodiments, the invention relates to the long-term storage of biological, chemical and biochemical material under substantially liquid conditions, and in a manner ready for immediate use. As described herein, there are provided embodiments which include (a) the composition for substantially stable storage of nucleic acid and polypeptide molecules in a biological sample as provided herein, comprising one or more compounds of formula (I) and/or formula (II) and one, two, or all three of at least on precipitating agent, at least one lower alcohol, and at least one chaotrope, and (b) preparation and optimization of the stable storage composition with compositions that increase the durability of the long-term storage conditions, including in certain embodiments, e.g., the use of one or more of a chelating agent, a reducing agent, a pH buffer, and water.

These and related embodiments thus provide advantages associated with liquid or semi-liquid storage of biological samples stored without refrigeration, including improved stabilization and preservation of biological activity in biological samples, reduced degradation of biological samples during storage at room temperature in liquid or semi-liquid form (e.g., hydrogel), and simplification of the processes for preparing, shipping and storing biological samples for further use by reducing or eliminating the need for refrigeration. Embodiments as described herein additionally provide superior biological sample recoveries by reducing or eliminating factors that can otherwise reduce sample recovery yields, such as undesirable sample degradation, denaturation and/or sample loss due to adsorption of the sample to sample container surfaces.

As used herein, "hydrogel" is not to be considered as limited to gels which contain water, but extend generally to all hydrophilic gels and gel composites, including those containing organic non-polymeric components in the absence of water. A gel is a state of matter that is intermediate between solids and liquids, and which consists of a solvent inside a three dimensional network.

Liquid Storage of a Biological Sample

Compositions and methods described herein relate to liquid and/or substantially liquid storage of a biological sample, and may include the use of any suitable container. These and related embodiments derive from the observation that stable, long-term liquid storage of biological samples or biological materials may be effected without refrigeration when such samples or materials are stored in a stable storage composition such as those described herein, which include the compound(s) of formula (I) and/or formula (II). According to non-limiting theory, biological materials present in a biological sample may interact with one or more of the components of the herein described composition for substantially stable storage, by specific or non-specific binding or other mechanism of attachment, including those involving formation of non-covalent and/or covalent chemical bonds and or intermolecular associative interactions such as hydrophobic and/or hydrophilic interactions, hydrogen bond formation, electrostatic interactions, and the like. Accordingly, certain of the present invention embodiments provide devices for stable, long-term liquid or semi-liquid storage of biological samples at common indoor ambient room temperatures (e.g., typically 20-27° C. but varying as a function of geography, season and physical plant from about 15-19° C. or about 18-23° C. to about 22-29° C. or about 28-32° C.).

Preferred embodiments involve the use of sample storage devices as described herein that comprise a composition for substantially stable storage of nucleic acid and/or polypeptide molecules in a biological sample that comprises one or more compounds of formula (I) and which is capable of liquid or semi-liquid storage of a biological sample or a biological material without refrigeration, for example, at ambient room temperature. In certain preferred embodiments, there is little or no evaporation of biocompatible solvent (e.g., water) that is allowed to transpire by conditions under which the liquid-storable biological sample is maintained. The samples are preferably stored under liquid or substantially liquid conditions that stabilize the sample, i.e., little or no detectable (e.g., with statistical significance) degradation or undesirable chemical or physical modification of the sample occurs, according to criteria that will vary as a factor of the nature of the sample being stored and that will in any event be familiar to those having skill in the relevant art. As such, it will be appreciated from the present disclosure that according to certain preferred embodiments one or more of the sample, the compound(s) of formula (I) and/or formula (II), and the other herein described components of the stable storage composition will be in fluid contact with one another, e.g., present within a common liquid phase, such as a biocompatible solvent.

Non-limiting examples of sample storage devices may include, bottles, tubes, vials, bags, boxes, racks, multi-well dishes and multi-well plates, which are typically sealed by individual screw caps or snap caps, snap or seal closures, lids, adhesive strips or tape, or multi-cap strips. Other containers and vessels suitable for liquid-storable biological samples as described herein will be known to those familiar with the art, such as for example, specimen collection containers. In certain embodiments, the standard container format for medium to high throughput of sample storage, processing and automation of biological processes is a 96-, 384-, or 1536-well plate or array. Other information regarding biological sample storage devices in general may be found, for example, in US/20050276728 and US/20060099567, including references cited therein.

Certain preferred embodiments provide compositions and methods for storing biological material (e.g., genomic DNA, plasmid DNA, DNA fragments, RNA, oligonucleotides, proteins, polypeptides, peptides, fluorogenic substances, cells, viruses, bacteria, chemical compounds, vaccines, etc.) or other biological samples as provided herein in a mixture that is obtained by admixing the biological sample and the presently described stable storage composition, and that allows complete recovery or substantial recovery (e.g., recovery of at least 50 percent, preferably at least 60 percent, more preferably at least 70 percent, more preferably at least 80 percent, and typically in more preferred embodiments at least 85 percent, more preferably at least 90, 91, 92, 93 or 94 percent, more preferably at least 95 percent, still more preferably greater than 96, 97, 98 or 99 percent) of the sample material. For example, a stable storage composition may be selected based on the properties of one or more of the compound(s) of formula (I) and/or formula (II) and the precipitating agent(s), lower alcohol(s) and/or chatrope(s), and/or other components as described herein (e.g., reducing agent, chelator, pH buffer, detergent or surfactant such as a non-denaturing detergent), and/or of the sample, depending on the particular methodology being employed and in a manner that permits recovery of one or more desired structural or functional properties of the sample (e.g., biological activity). Similarly, as another example, the stable storage composition alone or the mixture obtained by admixing the stable storage composition with the biological sample, may dissociate in an appropriate solvent and may, but need not, become fully solubilized, such that a dispersion, suspension, colloid, gel, hydrogel, sap, slurry, syrup, or the like may be obtained.

In certain preferred embodiments at least one solvent for use in compositions and methods disclosed herein will be aqueous, for example, water or a biocompatible solvent such as a biological fluid, a physiological solution or an aqueous biological buffer solution selected to support a biological structure and/or function of a biomolecule by preserving for that biomolecule a favorable chemical milieu that is conducive to the structure and/or function. Non-limiting examples of such biocompatible solvents include physiological saline (e.g., approximately 145 mM NaCl), Ringer's solution, Hanks' balanced salt solution, Dulbecco's phosphate buffered saline, Erle's balanced salt solution, and other buffers and solutions and the like as will be known to those familiar with the art, including those containing additives as may be desired for particular biomolecules of interest.

According to other embodiments, however, the invention need not be so limited and other solvents may be selected, for instance, based on the solvent polarity/polarizability (SPP) scale value using the system of Catalan et al. (e.g., 1995 *Liebigs Ann.* 241; see also Catalan, 2001 In: *Handbook of Solvents*, Wypych (Ed.), Andrew Publ., NY, and references cited therein), according to which, for example, water has a SPP value of 0.962, toluene a SPP value of 0.655, and 2-propanol a SPP value of 0.848. Methods for determining the SPP value of a solvent based on ultraviolet measurements of the 2-N,N-dimethyl-7-nitrofluorene/2-fluoro-7-nitrofluorene probe/homomorph pair have been described (Catalan et al., 1995). Solvents with desired SPP values (whether as pure single-component solvents or as solvent mixtures of two, three, four or more solvents; for solvent miscibility see, e.g., Godfrey 1972, *Chem. Technol.* 2:359) based on the solubility properties of a particular matrix material can be readily identified by those having familiarity with the art in view of the instant disclosure.

Based on the present disclosure, the skilled person will appreciate that, depending on the physicochemical properties (e.g., molecular mass, hydrophobicity, surface charge distribution, solubility, etc.) of a particular biomolecule of interest (e.g., a nucleic acid molecule such as DNA or RNA, or a polypeptide) that is present in a biological sample to be stored under liquid or semi-liquid conditions as described herein, one or more specific compounds of formula (I) can be identified readily and without undue experimentation, for use according to the present compositions and methods.

As described herein, a composition for substantially stable storage of nucleic acid and polypeptide molecules in a biological sample may, according to certain embodiments (e.g., embodiments as set forth in Tables 1, 2, 3, 4 and 5), be prepared from a solution (e.g., typically an aqueous solution) that comprises from at least about 0.1% to about 10% weight-to-volume of the compound(s) of formula (I) and/or formula (II), which in certain related embodiments may comprise from at least about 0.5% to about 5%, at least about 1% to about 5%, at least about 0.5%, 1.5%, 2%, 2.5%, 3%, 3.5%, 4%, 4.5%, 5%, 5.5%, 6%, 6.5%, 7%, 7.5%, 8%, 8.5%, 9%, 9.5% or 10% weight-to-volume of the compound(s) of formula (I) and/or formula (II), where "about" may be understood to represent quantitative variation that may be more or less than the recited amount by less than 50%, more preferably less than 40%, more preferably less than 30%, and more preferably less than 20%, 15%, 10% or 5%. Similar weight-to-volume ratios and tolerances may pertain for other components in at least some distinct embodiments of the herein described compositions for substantially stable storage of nucleic acid and polypeptide molecules in a biological sample.

According to certain other embodiments, the composition for substantially stable storage of nucleic acid and polypeptide molecules in a biological sample will be identified as having the compatible characteristics for storing a particular type of biological sample in a manner that satisfactorily preserves the desired structural and/or functional properties, said characteristics including the ability to substantially protect nucleic acid and/or polypeptide molecules in a biological sample from degradation during unrefrigerated storage following admixture of the sample with the stable storage composition.

According to non-limiting theory the molecules of the compound(s) of formula (I) and/or formula (II) may be capable of forming at least one hydrogen bond with a component of the biological sample in a manner that is preferential to hydrogen bond formation between the compound(s) of formula (I) and/or formula (II), but these invention embodiments are not so limited so long as the compound(s) of formula (I) and/or formula (II) does not covalently self-assemble. According to non-limiting theory, stabilizing interactions among the biological sample, the compound(s) of formula (I) and/or formula (II) and/or other components of the herein described composition for substantially stable storage of nucleic acid and polypeptide molecules in a biological sample, result from hydrogen-bonding interactions. However, other non-covalent forces may also contribute to the bonding such as, for example, ionic bonds, electrostatic forces, van der Waal's forces, metal coordination, hydrophobic forces and, when the hydrogen-bonding moieties comprise one or more aromatic rings, pi-pi stacking (Russell, J B. 1999. *General Chemistry*. Second Edition. McGraw-Hill, Columbus, Ohio; Lodish et al. (Eds.) 2000. *Molecular Cell Biology*. Fourth Edition. W. H. Freeman).

Also according to non-limiting theory, the compound of formula (I) and/or formula (II) in the herein described composition for substantially stable storage of nucleic acid and polypeptide molecules in a biological sample is capable of non-covalent association with one or more additional components of said stable storage composition, and may also be capable of non-covalent association with one or more molecular species present in the liquid-storable biological sample and having origins in the subject or biological source (e.g., biomolecules such as polypeptides, polynucleotides, naturally occurring oligosaccharides, naturally occurring lipids, and the like). Methodologies and instrumentation for the determination of non-covalent associations between such components will be known to those familiar with the art in view of the present disclosure, and may include techniques such as electrospray ionization mass spectrometry (Loo et al., 1989 *Anal. Biochem*. June; 179(2): 404-412; Di Tullio et al. 2005 *J. Mass Spectrom*. July; 40(7):845-865), diffusion NMR spectroscopy (Cohen et al., 2005 *Angew Chem Int Ed Engl*. January 14; 44(4):520-554), or other approaches by which non-covalent associations between molecular species of interest can be demonstrated readily and without undue experimentation (for example, circular dichroism spectroscopy, scanning probe microscopy, spectrophotometry and spectrofluorometry, and nuclear magnetic resonance of biological macromolecules; see e.g., Schalley C A et al. (Eds.) *Analytical Methods in Supramolecular Chemistry*, 2007, Wiley Publishers, Hoboken, N.J.; Sauvage and Hosseini (Eds.), *Comprehensive Supramolecular Chemistry*, 1996 Elsevier Science, Inc., New York, London, Tokyo; Cragg, P J (Ed.), *A Practical Guide to Supramolecular Chemistry*, 2005 Wiley & Sons, Ltd., West Sussex, UK; James et al. (Eds.), 2001 and 2005, *Nuclear Magnetic Resonance of Macromolecules: Methods in Enzymology* (vols. 338, 399 and 394) Academic Press, Ltd., London, UK).

In certain embodiments and as may be recognized by the skilled artisan in view of the present disclosure, it may be desirable to include in the herein described composition for substantially stable storage of nucleic acid and polypeptide molecules in a biological sample a biological inhibitor or a biochemical inhibitor, which may be a reducing agent, an alkylating agent, an antimicrobial agent, a kinase inhibitor, a phosphatase inhibitor, a caspase inhibitor, a granzyme inhibitor, a cell adhesion inhibitor, a cell division inhibitor, a cell cycle inhibitor, a small molecule inhibitor, a lipid signaling inhibitor and/or a protease inhibitor. Those familiar with the art will be aware of a wide range of readily available inhibitors that may be selected depending on the nature of the biological sample and the particular bioactivity of interest. See, e.g., Calbiochem® Inhibitor SourceBook™ (2004 ($1^{st}$ Ed.) and 2007 ($2^{nd}$ Ed.), EMD Biosciences, La Jolla, Calif.). For antimicrobial agents, see, e.g., Pickering, L K, Ed. 2003 *Red Book: Report of the Committee on Infectious Diseases*, $26^{th}$ edition. Elk Grove Village, Ill., pp. 695-97; American Academy of Pediatrics, 1998, *Pediatrics*, 101 (1), supplement; *Disinfection Sterilization and Preservation*, Seymour S. Block (Ed.), 2001 Lippincott Williams & Wilkins, Philadelphia; *Antimicrobial Inhibitors*, A. I. Laskin and H. A. Lechevalier, (Eds.), 1988 CRC Press, Boca Raton, Fla.; *Principles and Practice of Disinfection, Preservation and Sterilization*, A. D. Russell et al., (Eds.), 1999, Blackwell Science, Malden, Mass.; *Antimicrobial/anti-infective materials*, S. P. Sawan et al., (Eds.), 2000 Technomic Pub. Co., Lancaster, Pa.; *Development of novel antimicrobial agents: emerging strategies*, K. Lohner, (Ed.), 2001 Wymondham, Norfolk, UK; Conte, J. E. *Manual of antibiotics and infectious diseases* ($9^{th}$ Ed.), 2001, Lippincott Williams & Wilkins, Philadelphia.

Biological material provided in or derived from a biological sample may be added to the wells or tubes in combination with the composition for substantially stable storage of nucleic acid and polypeptide molecules in a biological sample in liquid form (e.g., by simultaneously contacting the sample well with the sample and stable storage composition dissolved or dissociated in a solvent, for instance, water). If, following unrefrigerated storage, purification is required of stabilized nucleic acid and/or polypeptide molecules from the mixture obtained by admixing the biological sample and the composition for substantially stable storage of nucleic acid and polypeptide molecules, the nucleic acid(s) and/or polypeptide(s) can be isolated from the sample using techniques well known to those in the art, such as extraction, filtration, centrifugation, ion exchange, size exclusion, chromatography, or phase separation, or other purification methods known to those persons trained in the relevant art.

Detectable Indicator

Detectable indicators include compositions that permit detection (e.g., with statistical significance relative to an appropriate control, as will be know to the skilled artisan) or similar determination of any detectable parameter that directly relates to a condition, process, pathway, induction, activation, inhibition, regulation, dynamic structure, state, contamination, degradation or other activity or functional or structural change in a biological sample, including but not limited to altered enzymatic (including proteolytic and/or nucleolytic), respiratory, metabolic, catabolic, binding, catalytic, allosteric, conformational, or other biochemical or biophysical activity in the biological sample, and also including interactions between intermediates that may be formed as the result of such activities, including metabolites, catabolites, substrates, precursors, cofactors and the like.

A wide variety of detectable indicators are known to the art and can be selected for inclusion in the presently disclosed compositions and methods depending on the particular parameter or parameters that may be of interest for particular biological samples in particular sample storage applications. Non-limiting examples of parameters that may be detected by such detectable indicators include detection of the presence of one or more of an amine, an alcohol, an aldehyde, a thiol, a sulfide, a nitrite, avidin, biotin, an immunoglobulin, an oligosaccharide, a nucleic acid, a polypeptide, an enzyme, a cytoskeletal protein, a reactive oxygen species, a metal ion, pH, $Na^+$, $K^+$, $Cl^-$, a cyanide, a phosphate, selenium, a protease, a nuclease, a kinase, a phosphatase, a glycosidase, and a microbial contaminant, and others.

Examples of a broad range of detectable indicators (including colorimetric indicators) that may be selected for specific purposes are described in Haugland, 2002 *Handbook of Fluorescent Probes and Research Products-Ninth Ed.*, Molecular Probes, Eugene, Oreg.; in Mohr, 1999 *J. Mater. Chem.*, 9: 2259-2264; in Suslick et al., 2004 *Tetrahedron* 60:11133-11138; and in U.S. Pat. No. 6,323,039. (See also, e.g., Fluka Laboratory Products Catalog, 2001 Fluka, Milwaukee, Wis.; and Sigma Life Sciences Research Catalog, 2000, Sigma, St. Louis, Mo.) A detectable indicator may be a fluorescent indicator, a luminescent indicator, a phosphorescent indicator, a radiometric indicator, a dye, an enzyme, a substrate of an enzyme, an energy transfer molecule, or an affinity label. In certain preferred embodiments the detectable indicator may be one or more of phenol red, ethidium bromide, a DNA polymerase, a restriction endonuclease (e.g., a restriction enzyme used as a restriction nuclease such as a site- or sequence-specific restriction endonuclease), cobalt chloride (a moisture indicator that changes from blue color when water is present to pink when dry), Reichardt's dye (Aldrich Chemical) and a fluorogenic protease substrate.

A detectable indicator in certain embodiments may comprise a polynucleotide polymerase and/or a suitable oligonucleotide, either or both of which may be employed as an indicator or, in certain other embodiments, as components of other nucleic acids-based applications of the compositions and methods described herein. For example, one or more oligonucleotides may be included for use as reference controls having use to adjust the amounts of different samples that are used in downstream processing by standardizing their concentrations, or a range of oligonucleotide amounts may be employed to generate a quantitative calibration curve. Polymerases (including DNA polymerases and RNA polymerases) useful in accordance with certain embodiments of the present invention include, but are not limited to, *Thermus thermophilus* (Tth) DNA polymerase, *Thermus aquaticus* (Taq) DNA polymerase, *Thermologa neopolitana* (Tne) DNA polymerase, *Thermotoga maritima* (Tma) DNA polymerase, *Thermococcus litoralis* (Tli or VENT™) DNA polymerase, *Pyrococcus furiosus* (Pfu) DNA polymerase, DEEPVENT™ DNA polymerase, *Pyrococcus woosii* (Pwo) DNA polymerase, *Bacillus sterothermophilus* (Bst) DNA polymerase, *Bacillus caldophilus* (Bca) DNA polymerase, *Sulfolobus acidocaldarius* (Sac) DNA polymerase, *Thermoplasma acidophilum* (Tac) DNA polymerase, *Thermus flavus* (Tfl/Tub) DNA polymerase, *Thermus ruber* (Tru) DNA polymerase, *Thermus brockianus* (DYNAZYME™) DNA polymerase, *Methanobacterium thermoautotrophicum* (Mth) DNA polymerase, mycobacterium DNA polymerase (Mtb, Mlep), and mutants, and variants and derivatives thereof. RNA polymerases such as T3, T5 and SP6 and mutants, variants and derivatives thereof may also be used in accordance with the invention.

Polymerases used in accordance with the invention may be any enzyme that can synthesize a nucleic acid molecule from a nucleic acid template, typically in the 5' to 3' direction. The nucleic acid polymerases used in the present invention may be mesophilic or thermophilic, and are preferably thermophilic. Preferred mesophilic DNA polymerases include T7 DNA polymerase, T5 DNA polymerase, Klenow fragment DNA polymerase, DNA polymerase III and the like. Preferred thermostable DNA polymerases that may be used in the methods of the invention include Taq, Tne, Tma, Pfu, Tfl, Tth, Stoffel fragment, VENT™ and DEEPVENT™ DNA polymerases, and mutants, variants and derivatives thereof (U.S. Pat. No. 5,436,149; U.S. Pat. No. 4,889,818; U.S. Pat. No. 4,965,188; U.S. Pat. No. 5,079,352; U.S. Pat. No. 5,614,365; U.S. Pat. No. 5,374,553; U.S. Pat. No. 5,270,179; U.S. Pat. No. 5,047,342; U.S. Pat. No. 5,512,462; WO 92/06188; WO 92/06200; WO 96/10640; Barnes, W. M., *Gene* 112:29-35 (1992); Lawyer et al., *PCR Meth. Appl.* 2:275-287 (1993); Flaman et al., *Nucl. Acids Res.* 22(15):3259-3260 (1994)).

Other detectable indicators for use in certain embodiments contemplated herein include affinity reagents such as antibodies, lectins, immunoglobulin Fc receptor proteins (e.g., *Staphylococcus aureus* protein A, protein G or other Fc receptors), avidin, biotin, other ligands, receptors or counterreceptors or their analogues or mimetics, and the like. For such affinity methodologies, reagents for immunometric measurements, such as suitably labeled antibodies or lectins, may be prepared including, for example, those labeled with radionuclides, with fluorophores, with affinity tags, with biotin or biotin mimetic sequences or those prepared as antibody-enzyme conjugates (see, e.g., Weir, D. M., *Handbook of Experimental Immunology*, 1986, Blackwell Scientific, Boston; Scouten, W. H., 1987 *Methods in Enzymology* 135:30-65; Harlow and Lane, *Antibodies: A Laboratory Manual*, 1988 Cold Spring Harbor Laboratory, Cold Spring Harbor, N.Y.; Haugland, *Handbook of Fluorescent Probes and Research Products-Ninth Ed.*, 2002 Molecular Probes, Eugene, Oreg.; Scopes, R. K., *Protein Purification: Principles and Practice*, 1987, Springer-Verlag, NY; Hermanson, G. T. et al., *Immobilized Affinity Ligand Techniques*, 1992, Academic Press, Inc., NY; Luo et al., 1998 *J. Biotechnol.* 65:225 and references cited therein).

Certain other embodiments of the present invention relate to compositions and methods for liquid or semi-liquid storage of a biological sample wherein the mixture obtained by admixing the biological sample and the composition for substantially stable storage of nucleic acid and polypeptide molecules contains at least one, and in certain related embodiments two, three, four, five, six, seven, eight, nine, ten or more detectable indicators, each of which comprises a unique and readily identifiable gas chromatography/mass spectrometry (GCMS) tag molecule. Numerous such GCMS tag molecules are known to the art and may be selected for use alone or in combination as detectable identifier moieties, for instance, to encode unique GCMS spectrometric profiles for separate storage mixtures in distinct sample storage containers, such as separate wells of a multi-well storage plate. By way of illustration and not limitation, various different combinations of one, two or more such GCMS tags may be added to individual wells in a manner that permits each well to be identified on the basis of the GCMS "signature" of its contents, thereby permitting any sample that is subsequently removed from a storage device well to be traced back to its well of origin for identification purposes. Examples of GCMS tags include $\alpha,\alpha,\alpha$-trifluorotoluene, $\alpha$-methylstyrene, o-anisidine, any of a number of distinct cocaine analogues or other GCMS tag compounds having readily identifiable GCMS signatures under defined conditions, for instance, as are available from SPEX CertiPrep Inc. (Metuchen, N.J.) or from SigmaAldrich (St. Louis, Mo.), including Supelco® products described in the Supelco® 2005 gas chromatography catalog and available from SigmaAldrich.

The composition for substantially stable storage of nucleic acid and polypeptide molecules in a biological sample may be applied to storage containers for biological samples, for example, by contacting or administering the composition in a solvent to one or a plurality of sample wells of a storage device as described herein. Biological material provided in or derived from a biological sample may also be added to the wells or tubes in combination with the storage composition in liquid (including liquid suspensions) form (e.g., by simultaneously contacting the sample well with the sample and the storage composition dissolved or dissociated in a solvent).

The conditions (e.g., pH, ionic strength, polarity, solubilization capacity) in the composition for substantially stable storage of nucleic acid and polypeptide molecules in a biological sample may be adjusted such that greater than at least 90 percent, preferably greater than 95 percent, more preferably greater than 96, 97, 98 or 99 percent of the biological activity (e.g., enzymatic or affinity activity, or structural integrity or other biological activity as described herein and known to the art) of the biological sample is maintained following unrefrigerated storage of the mixture obtained by admixing the stable storage composition and the biological sample. It will be appreciated, for example, that in addition to the unprecedented advantages provided by the composition for substantially stable storage of nucleic acid and polypeptide molecules in a biological sample as described herein for the first time, buffer conditions and the addition of certain chemicals and enzymes and other reagents may contribute to the stabilization of DNA and RNA (for example, Sambrook, J., Fritsch, E. F. and Maniatis, T. (1989) Molecular Cloning: A Laboratory Manual, Cold Spring Harbor Laboratory Press, New York; Current Protocols, Nucleic Acid Chemistry, Molecular Biology, Wiley and Sons, 2003) and/or proteins, polypeptides, enzymes and/or other biological materials (for example, blood, tissue, bodily fluids) against degradation from enzymes, proteases and environmental factors (see, for example, Current Protocols, Protein Sciences, Cell Biology, Wiley and Sons, 2003). The further inclusion of certain such chemical components to provide beneficial effects on the biological sample are also contemplated and may vary according to particular samples and uses thereof (e.g., Calbiochem® Biochemicals & Immunochemicals Catalog 2004/2005, pp. 68-69 and pages cited therein, EMD Biosciences, La Jolla, Calif.; and suitable solutes such as salts (e.g., KCl, NaCl, $CaCl_2$, $MgCl_2$, etc.) for maintaining, preserving, enhancing, protecting or otherwise promoting one or more biological sample components (e.g., biomolecules), or activity buffers that may be selected and optimized for particular activities of specific biomolecules such as nucleic acid hybridization or activities of enzymes, antibodies or other proteins, or other buffers, for instance, Tris buffer (THAM, Trometanol, 2-amino-2-(hydroxymethyl)-1, 3-propane diol), Tris-EDTA buffer (TE), sodium chloride/sodium citrate buffer (SSC), MOPS/sodium acetate/EDTA buffer (MOPS), ethylenediamine tetraacetic acid (EDTA), sodium acetate buffer at physiological pH, and the like.)

Additional chemical components that may beneficially enhance the recovery of biological activity from a biological sample stored without refrigeration using the herein described stable storage composition may also include but are not limited to solutes that may be included in the biocompatible solvent of which the storage composition is comprised (along with the compound(s) of formula (I) and other components as described herein), where such solutes may provide a desired isotonic, hypertonic or hypotonic environment as may be selected by those familiar with the art, for example an isotonic saline solution to prevent disruption of cellular membranes. Hence, as will be appreciated by those skilled in the art in view of the present disclosure, depending on the particular biological sample to be stored and on the particular biological activity to be recovered from such sample (e.g., DNA, RNA, polypeptide), it may be desirable to formulate the stable storage composition with a biocompatible solvent that is isotonic, hypertonic or hypotonic relative to the sample.

By way of background, osmotic shock results from exposure of cells to solutions of different osmotic pressures, where osmosis involves the net diffusion of water across a selectively permeable membrane that is permeable in both directions to water, but varyingly permeable to solutes, wherein the water diffuses from one solution into another of lower water potential. The osmotic pressure of a solution is the pressure which must be exerted upon it to prevent passage of distilled water into it across a semipermeable membrane (i.e., a membrane that is impermeable to all solutes, but is freely permeable to solvent), and is often measured in Pascals (1 Pa=1 Newton/$m^2$). Conversely, water potential is the net tendency of any system to give up water to its surroundings. As the water potential of pure water at atmospheric pressure is, by definition, zero pressure units, any addition of solute to pure water reduces its water potential and makes its value negative. Thus, water movement is from a system with higher (i.e., less negative) water potential to one with lower (i.e., more negative) water potential.

Hence, according to certain herein disclosed embodiments, a biological sample may comprise a suspension of cells in a hypertonic liquid medium, such as one formulated with a biocompatible solvent having a solute concentration that is higher than that inside the cells present in the liquid solution, thus causing water to diffuse out of the cells. In these and related embodiments a hypertonic liquid matrix is provided having a greater relative solute concentration when compared to the solute concentration of a membrane-bound-aried liquid compartment such as that within the cell (e.g., the cytosol is hypotonic relative to the stable storage composition). Such a hypertonic solution has a lower water potential than a solution that is hypotonic to it and has a correspondingly greater osmotic pressure. Thus, for instance, a hypotonic solution has a solute concentration that is lower than the solute concentration inside cells suspended in that solution, and therefore causes water to diffuse into the cells. A hypotonic solution has a lower relative solute concentration (i.e., higher water potential) than another solution. Certain other embodiments relate to liquid formulations that may be isotonic solutions that have solute concentrations that are equal to intracellular solute concentrations (i.e., as indicated by their osmotic pressure). Separation of isotonic solutions by selectively permeable membranes (e.g., cell membranes) results in no net passage of water in either direction across the cell membrane, since the solutions have the same water potential.

Other chemical components that may be included in stable storage compositions described herein include human placental ribonuclease inhibitor, bovine ribonuclease inhibitor, porcine ribonuclease inhibitor, diethyl pyrocarbonate, formamide, vanadyl-ribonucleoside complexes, macaloid, proteinase K, heparin, hydroxylamine-oxygen-cupric ion, bentonite, ammonium sulfate, or specific inhibiting antibodies.

Accordingly, certain invention embodiments contemplate a composition for substantially stable storage of nucleic acid and polypeptide molecules in a biological sample, comprising one or more compound(s) of formula (I) and additional components as described herein, and a sample treatment composition. The sample treatment composition may comprise an activity buffer as described below, and/or the sample treatment composition may comprise one or more of a cell lysis buffer, a free radical trapping agent, a sample denaturant, and a pathogen-neutralizing agent. As provided by these embodiments, the stable storage composition may thus comprise a set of components prepared to effect a desired treatment on a biological sample when the sample is admixed with the stable storage composition.

An activity buffer may comprise a solvent or solution in liquid form, including a concentrate, which is suitable for a desired use of the biological sample, for example following unrefrigerated storage, such as a functional or structural characterization of one or more components of the sample. Non-limiting examples of such uses may include determining one or more enzyme activities, determining intermolecular binding interactions, detecting the presence of a specific polynucleotide or amino acid sequence or of an immunologically defined epitope or of a defined oligosaccharide structure, detection of particular viruses or of microbial cells or of human or animal cells, determining particular metabolites or catabolites, etc., all of which can be accomplished using conditions that are defined and known to those skilled in the relevant art, including suitable conditions that can be provided through contacting the sample with an appropriate activity buffer.

A cell lysis buffer may be any composition that is selected to lyse (i.e., disrupt a boundary membrane of) a cell or organelle, and many such formulations are known to the art, based on principles of osmotic shock (e.g., hypotonic shock) and/or disruption of a cell membrane such as a plasma membrane through the use of a surfactant such as a detergent (e.g., Triton® X-100 4-(1,1,3,3-tetramethylbutyl)phenyl-polyethylene glycol, Nonidet® P-40 polyethylene glycol mono(octylphenyl) ether, sodium dodecyl sulfate, deoxycholate, octyl-glucopyranoside, betaines, or the like) and/or solute (e.g., urea, guanidine hydrochloride, guanidinium isothiocyanate, high salt concentration) system. Numerous cell lysis buffers are known and can be appropriately selected as a function of the nature of the biological sample and of the biomolecule(s), biological activities or biological structures that are desirably recovered, which may also in some embodiments include the selection of appropriate pH buffers, biological or biochemical inhibitors and detectable indicators.

Sample denaturants similarly may vary as a function of the biological sample and the stable storage composition, but may include an agent that non-covalently alters (e.g., with statistical significance relative to an appropriate control such as an untreated sample) at least one of the three-dimensional conformation, quarternary, tertiary and/or secondary structure, degree of solvation, surface charge profile, surface hydrophobicity profile, or hydrogen bond-forming capability of a biomolecule of interest in the sample. Examples of sample denaturants include chaotropes (e.g., urea, guanidine, thiocyanate salts), denaturing detergents (e.g., sodium dodecyl sulfate), high-salt conditions or other agents or combinations of agents that promote denaturing conditions. As also noted above, certain embodiments are contemplated that expressly exclude, for certain types of samples, the use of a sample denaturant when a chelator is also present, while certain other embodiments may include such components. In certain related embodiments a non-denaturing detergent or surfactant may be present, as in certain other related embodiments may be a non-denaturing concentration of a detergent, surfactant or other additive, which may be determined as a function of the specific conditions that are being employed.

Free radical trapping agents for use in certain embodiments may include any agent that is capable of stably absorbing an unpaired free radical electron from a reactive compound, such as reactive oxygen species (ROS), for example, superoxide, peroxynitrite or hydroxyl radicals, and potentially other reactive species, and antioxidants represent exemplary free radical trapping agents. Accordingly a wide variety of known free radical trapping agents are commercially available and may be selected for inclusion in certain embodiments of the presently disclosed compositions and methods. Examples include ascorbate, beta-carotene, vitamin E, lycopene, tert-nitrosobutane, alpha-phenyl-tert-butylnitrone, 5,5-dimethylpyrroline-N-oxide, and others, as described in, e.g., Halliwell and Gutteridge (*Free Radicals in Biology and Medicine*, 1989 Clarendon Press, Oxford, UK, Chapters 5 and 6); Vanin (1999 *Meth. Enzymol.* 301: 269); Marshall (2001 *Stroke* 32:190); Yang et al. (2000 *Exp. Neurol.* 163:39); Zhao et al. (2001 *Brain Res.* 909:46); and elsewhere.

Certain embodiments contemplate inclusion of a pathogen-neutralizing agent in the presently disclosed compositions and methods, which includes any agent that is capable of completely or partially, but in any event in a manner having statistical significance relative to an appropriate control, neutralizing, impairing, impeding, inhibiting, blocking, preventing, counteracting, reducing, decreasing or otherwise blocking any pathogenic effect of a pathogen such as a bacterium, virus, fungus, parasite, prion, yeast, protozoan, infectious agent or any other microbiological agent that causes a disease or disorder in humans or vertebrate animals. Persons familiar with the relevant art will recognize suitable pathogen-neutralizing agents for use according to the present disclosure. Exemplary agents include sodium azide, borate, sodium hypochlorite, hydrogen peroxide or other oxidizing agents, sodium dichloroisocyanurate, ethanol, isopropanol, antibiotics, fungicides, nucleoside analogues, antiviral compounds, and other microbicides; these or others may be selected according to the properties of the particular biological sample of interest.

Accordingly and in view of the present disclosure, certain preferred embodiments contemplate compositions and methods for the stable unrefrigerated storage for extended time periods of biological samples that contain RNA, whereby substantial recovery of RNA can be achieved following storage (e.g., relative to the recovery that may be achieved following sample storage at −80° C.), wherein the composition comprises any one of formulations 4.11, 4.13, 4.15, 4.19, 4.20, 4.21, 4.22 or 4.23 (see Table 4), and wherein in certain such embodiments the sample comprises saliva (e.g., mammalian saliva, for example, primate saliva such as human saliva) or a fraction or component thereof. Certain other preferred embodiments contemplate compositions and methods for the stable unrefrigerated storage for extended time periods of biological samples that contain DNA, whereby substantial recovery of DNA can be achieved following storage (e.g., relative to the recovery that may be achieved following sample storage at −20° C.), wherein the composition comprises any one of formulations 4.1-4.6, 4.9, 4.11, 4.13, 4.15, 4.19, 4.20, 4.21, 4.22 or 4.23 (see Table 4), and wherein in certain such embodiments the sample comprises saliva (e.g., mammalian saliva, for example, primate saliva such as human saliva) or a fraction or component thereof.

Also provided herein are embodiments directed to kits that comprise the composition for substantially stable storage of nucleic acid and polypeptide molecules in a biological sample as described herein, along with one or more ancillary reagents that may be selected for desired uses. Optionally the kit may also include a box, case, jar, drum, drawer, cabinet, carton, carrier, handle, rack, tray, pan, tank, bag, envelope, sleeve, housing or the like, such as any other suitable container. Ancillary reagents may include one or more solvents or buffers as described herein and known to the art, and may in certain embodiments include an activity buffer.

It is contemplated that the present invention will be of major value in high throughput screening; i.e., in automated testing or screening of a large number of biological samples. It has particular value, for example, in screening synthetic or natural product libraries for active compounds. The apparatus and methods of the present invention are therefore amenable to automated, cost-effective high throughput biological sample testing or drug screening and have immediate application in a broad range of pharmaceutical drug development programs. Typically, and in certain preferred embodiments such as for high throughput drug screening, candidate agents are provided as "libraries" or collections of compounds, compositions or molecules. Such molecules typically include compounds known in the art as "small molecules" and having molecular weights less than $10^5$ daltons, preferably less than $10^4$ daltons and still more preferably less than $10^3$ daltons. Candidate agents further may be provided as members of a combinatorial library, which preferably includes synthetic agents prepared according to a plurality of predetermined chemical reactions performed in a plurality of reaction vessels, which may be provided as wells in a storage device according to the present disclosure. For example, various starting compounds may be prepared employing one or more of solid-phase synthesis, recorded random mix methodologies and recorded reaction split techniques that permit a given constituent to traceably undergo a plurality of permutations and/or combinations of reaction conditions. The resulting products comprise a library that can be screened followed by iterative selection and synthesis procedures, such as a synthetic combinatorial library of peptides (see e.g., PCT/US91/08694 and PCT/US91/04666) or other compositions that may include small molecules as provided herein (see e.g., PCT/US94/08542, EP 0774464, U.S. Pat. No. 5,798,035, U.S. Pat. No. 5,789,172, U.S. Pat. No. 5,751,629).

The following Examples are presented by way of illustration and not limitation.

EXAMPLES

Example 1

Storage of Saliva

This Example describes the preparation and characterization of a liquid-storable biological sample. In this and the following Examples, standard cell and molecular biology techniques were employed, essentially according to known methodologies (e.g., Sambrook, J., Fritsch, E. F. and Maniatis, T. (1989) Molecular Cloning: A Laboratory Manual, Cold Spring Harbor Laboratory Press, New York; Current Protocols, Nucleic Acid Chemistry, Molecular Biology, Wiley and Sons, 2003; Current Protocols, Protein Sciences, Cell Biology, Wiley and Sons, 2003). All reagents in this and the following Examples were from Sigma-Aldrich (St. Louis, Mo.) unless otherwise specified.

Stabilization of DNA in Saliva at Room Temperature for >90 days. Saliva was collected from a human donor and kept on ice during the experimental setup. The tube of saliva was mixed thoroughly and 1 mL aliquots were removed and each was mixed separately with an equal amount of formulations 2.1-2.3 (Table 2) in screw cap vials. Ten aliquots were prepared for each formulation tested as well as 10 unprotected aliquots and 10 frozen controls stored at −20° C. Except for the −20° C. all samples were held at room temperature in a cardboard sample box protected from light. After 92 days duplicate samples were removed and the DNA extracted from a 300 uL aliquot of each tube using the QiaAmp Mini DNA kit from Qiagen (Valencia, Calif.) according to the manufacturer's instructions. Samples were eluted in 100 uL of AE buffer and a 10 uL aliquot from each DNA extract was loaded onto a 0.8% agarose gel and electrophoresed for 40 min at a constant 150 V. The gel was illuminated at 302 nm using a UV light box and the image captured using a Kodak Gel Logic 100 (Kodak, Rochester, N.Y.) imaging system (FIG. 1).

Example 2

Stabilization of DNA in Saliva for 70 Days at Room Temperature

Figure 2:
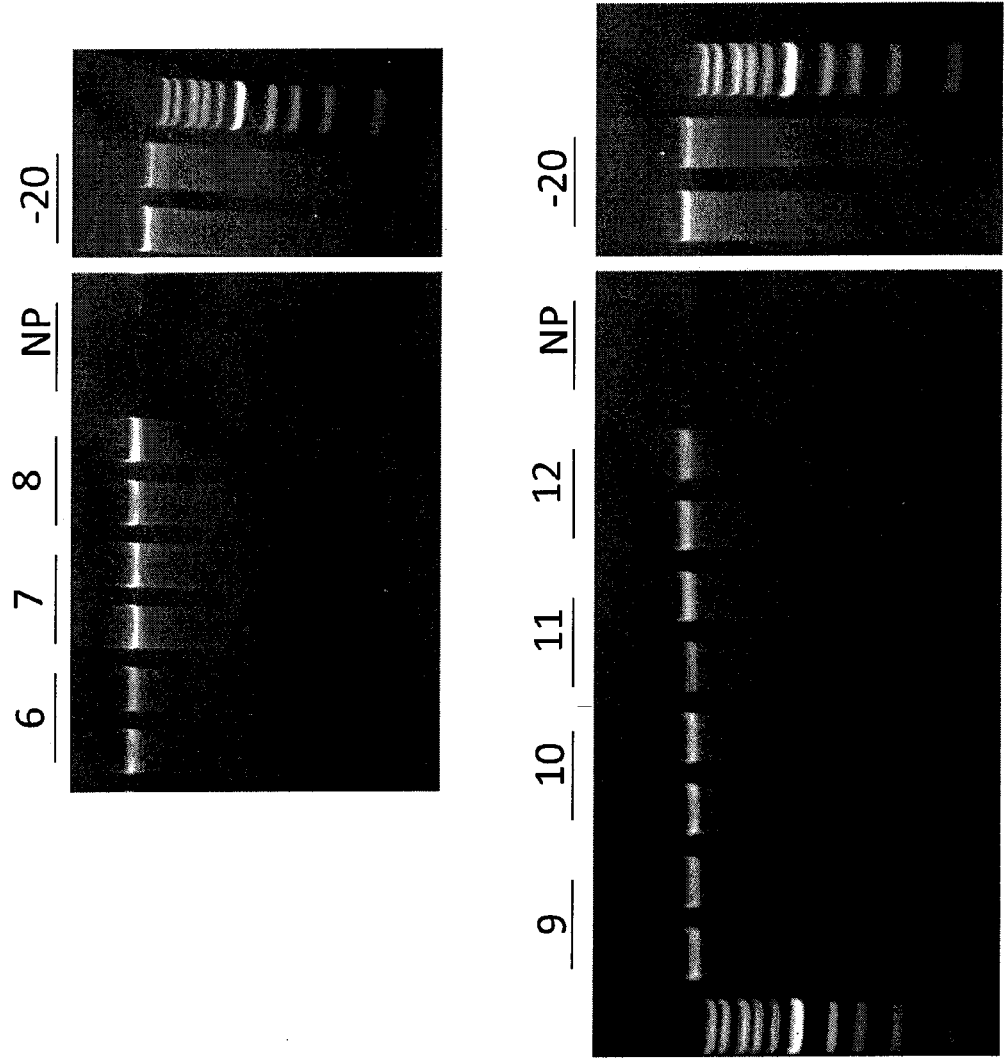
FIG. 2 shows integrity of DNA extracted from human saliva following storage for 70 days at room temperature following admixture with one of the indicated formulations each comprising a composition shown in Table 3. NP, unprotected (no stabilizing formulation added); −20, −20° C. frozen storage (control).

Saliva was collected from a human donor and kept on ice during the experimental setup. The tube of saliva was mixed thoroughly and 200 µL aliquots were removed and mixed with an equal amount of formulations 3.6-3.12 (Table 3) in screw cap polypropylene vials. Ten aliquots were prepared for each formulation tested as well as 10 unprotected aliquots and 10 frozen controls that were stored at −20° C. Except for the −20° C. controls all samples were held at room temperature in a cardboard sample box protected from light. After 70 days duplicate samples were removed and the DNA extracted from a 300 uL aliquot of each tube using the QiaAmp™ Mini DNA kit from Qiagen (Valencia, Calif.). Samples were eluted in 100 uL of AE buffer and a 10 uL aliquot from each DNA extract was loaded onto a 0.8% agarose gel and electrophoresed for 40 min at a constant 150 V. The gel was illuminated at 302 nm using a UV light box and the image captured using a Kodak Gel Logic 100 imaging system (FIG. 2).

Example 3

Stabilization of DNA in Saliva at Room Temperature for 70 Days

Figure 3:
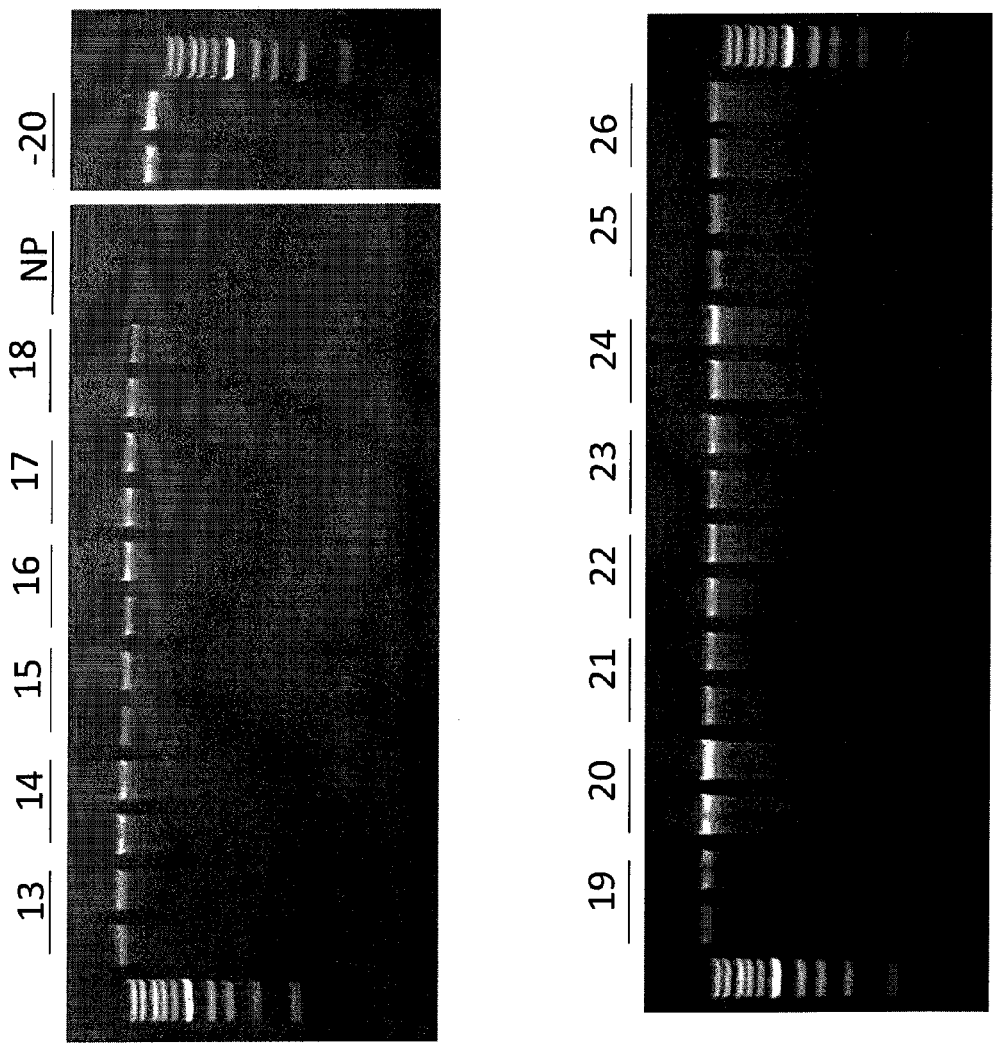
FIG. 3 shows integrity of DNA extracted from human saliva following storage for 40 days at room temperature following admixture with one of the indicated formulations each comprising a composition shown in Table 3. NP, unprotected (no stabilizing formulation added); −20, −20° C. frozen storage (control).

Saliva was collected from a human donor and kept on ice during the experimental setup. The tube of saliva was mixed thoroughly and 200 µL aliquots were removed and mixed with 150 uL of formulations 3.13-3.26 (Table 3) in screw cap polypropylene vials. Ten aliquots were prepared for each formulation and tested as well as 10 unprotected aliquots and 10 frozen controls that were stored at −20° C. Except for the −20° C. controls, all samples were held at room temperature in a cardboard sample box protected from light. After 40 days duplicate samples were removed and the DNA extracted from the sample using the QiaAm™ Mini DNA kit from Qiagen (Valencia, Calif.) according to the manufacturer's instructions. Purified DNA was eluted in 100 µL of AE buffer and a 10 µL aliquot from each DNA extract was loaded onto a 0.8% agarose gel and electrophoresed for 40 min at a constant 150 V. The gel was illuminated at 302 nm using a UV light box and the image captured using a Kodak Gel Logic 100 imaging system (FIG. 3).

Example 4

Syntheses of Exemplary Compounds of Formula (I)

This example describes syntheses of three exemplary compounds of formula (I). All reagents were from Sigma-Aldrich (St. Louis, Mo.) unless otherwise noted.

Synthesis of 1-Hexyl-3-methylimidazolium bromide

A 35 mL glass pressure tube (Ace Glass Cat#8648-07) containing a stir bar was charged with 6.158 g (0.075 moles) of 1-methylimdazole followed by 12.380 g (0.075 moles) of 1-bromohexane. The tube was sealed with a threaded Teflon plug and an O-ring and the tubes were placed in an oil bath on a VWR stirring hot plate. The temperature was raised to 90° C. and maintained at this temperature for 16 hours during which time the solution became viscous and the stir bar had stopped. The tube was removed from the bath and mixed vigorously on a vortexing mixer to completely mix the two layers and the was tube replaced into the oil bath at 90° C. The tube was heated for another hour and then mixed vigorously a second time followed by another hour of heating at 90° C. The cycle was repeated once more until the viscous liquid was homogeneous. The liquid was extracted with equal volumes of ethyl acetate three times followed by rotary evaporation to remove the residual ethyl acetate to give 18.147 g of the 1-hexyl-3-methylimidazolium bromide as a viscous lightly yellow colored oil. Compound is also available from IoLiTec (Heilbronn, Germany).

Synthesis of 1-Octyl-3-methylimidazolium bromide

A 35 mL glass pressure tube (Ace Glass Cat#8648-07) containing a stir bar was charged with 4.105 g (0.050 moles) of 1-methylimdazole followed by 9.656 g (0.050 moles) of 1-bromooctane. The tube was sealed with a threaded Teflon plug and an O-ring and the tubes were placed in an oil bath on a VWR stirring hot plate. The temperature was raised to 90° C. and maintained at this temperature for 16 hours during which time the solution became viscous and the stir bar had stopped. The tube was removed from the bath and mixed vigorously on a vortexing mixer to completely mix the two layers and the tube replaced into the oil bath at 90° C. and the temperature raised to 90° C. The tube was heated for another hour and then mixed vigorously a second time followed by another hour of heating at 90° C. The cycle was repeated once more until the viscous liquid was homogeneous. The liquid was extracted with equal volumes of ethyl acetate three times followed by rotary evaporation to remove the residual ethyl acetate to give 13.239 g of the 1-hexyl-3-methylimidazolium bromide as a viscous lightly yellow colored oil. Compound is also available from IoLiTec (Heilbronn, Germany).

Synthesis of 1-Decyl-3-methylimidazolium bromide

A 35 mL glass pressure tube (Ace Glass Cat#8648-07) containing a stir bar was charged with 4.105 g (0.050 moles) of 1-methylimdazole followed by 11.059 g (0.050 moles) of 1-bromodecane. The tube was sealed with a threaded Teflon plug and an O-ring and the tubes were placed in an oil bath on a VWR stirring hot plate. The temperature was raised to 90° C. and maintained at this temperature for 16 hours during which time the solution became viscous and the stir bar had stopped. The tube was removed from the bath and mixed vigorously on a vortexing mixer to completely mix the two layers and the tube replaced into the oil bath at 90° C. and the temperature raised to 100° C. The tube was heated for another hour and then mixed vigorously a second time followed by another hour of heating at 100° C. The cycle was repeated once more until the viscous liquid was homogeneous. The liquid was extracted with equal volumes of ethyl acetate three times followed by rotary evaporation to remove the residual ethyl acetate to give 14.532 g of the 1-hexyl-3-methylimidazolium bromide as a viscous lightly yellow colored oil. Compound is also available from IoLiTec (Heilbronn, Germany).

Example 5

Stabilization of DNA in Human Saliva Samples Stored for Extended Time Periods without Refrigeration Freshly collected saliva samples (200 µL each) from healthy human volunteers were stored for 39, 40 or 90 days at room temperature, or for 58 or 90 days at 50° C., following admixture of the saliva in 1.5 mL microcentrifuge tubes with 150 µL one of formulations 4.1-4.18 (Table 4). Control samples were stored without any added formulation at the same temperatures and for the same time periods; additional control samples were stored for the comparable time periods at −20° C. Following the storage periods, DNA from the samples was purified using QIAamp™ Mini blood kit (QIAGEN, Valencia, Calif.) and the DNA was eluted in 100 µL of AE buffer, per the supplier's instructions. Ten percent of the eluted volume was loaded onto a 0.8% agarose and resolved by gel electrophoresis (150 V, 30 min in 1×TAE buffer). The gel image was stained with ethidium bromide and analyzed.

Well resolved bands were observed for samples stored using formulations 4.1, 4.3-4.7 and 4.9-4.18, having intensities that were greater than or comparable to those observed for the −20° C. control groups, and which generally were accompanied by fewer discernible degradation products in the form of "smears" than were seen in the −20° C. control. Little or no cleanly resolving DNA was detected in the electrophoretogram lanes to which had been applied samples that had been stored without refrigeration and without any additives or stabilizers. Quantification of recoverable DNA from samples stored in formulation 4.11, 4.13, 4.15 or 4.22 for 90 days at room temperature or at 50° C., using the PicoGreen® reagent (Invitrogen, Carlsbad, Calif.) according to the supplier's recommendations, showed recoveries that were comparable or superior to recoveries from control samples stored at −20° C.

In a separate experiment, the same protocol was used except that test samples from each of four donors were admixed in duplicate with one of formulations 4.19-4.22 (Table 4) and stored for 27 days at 37° C. Again, little or no signal was detected from samples that were stored without refrigeration in the absence of stabilizers, and control samples stored at −20° C. exhibited smearing indicative of DNA degradation. Samples that had been stored in one of formulations 4.19-4.22 exhibited well-defined electrophoretic resolution. Quantification of recoverable DNA, using the PicoGreen® reagent (Invitrogen, Carlsbad, Calif.) according to the supplier's recommendations, showed recoveries of about 10-20 μg/mL from samples stored using 4.19-4.22, which was comparable to recoveries from −20° C. control samples; some variability in recovery between donors was observed.

A gel electrophoretic assay was used to determine whether formulation 4.21 protected DNA from nuclease degradation. Hind III-digested lambda DNA was incubated with exonuclease III for one hour at 37° C. in the presence or absence of formulation 4.21. No exonuclease was added to control reactions that were held on ice for one hour in the absence or presence of formulation 4.21. All reactions were stopped by the addition of gel electrophoresis sample buffer and the initiation of agarose gel electrophoresis. The results showed that in the absence of formulation 4.21, exonuclease III readily digested the lambda DNA at 37° C. and no readily discernible DNA bands appeared in the gel following electrophoresis. By contrast, the electrophoretic profile of the sample exposed to exonuclease III for one hour at 37° C. in the presence of formulation 4.21 was essentially the same as those of the control samples to which no nuclease had been added, suggesting (according to non-limiting theory) that formulation 4.21 inactivated exonuclease III and/or protected DNA from exonuclease degradation.

Unless the context requires otherwise, throughout the present specification and claims, the word "comprise" and variations thereof, such as, "comprises" and "comprising" are to be construed in an open, inclusive sense, that is as "including, but not limited to".

Reference throughout this specification to "one embodiment" or "an embodiment" or "an aspect" means that a particular feature, structure or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

From the foregoing, it will be appreciated that, although specific embodiments of the invention have been described herein for purposes of illustration, various modifications may be made without deviating from the spirit and scope of \the invention. Accordingly, the invention is not limited except as by the appended claims.

What is claimed is:

1. An admixture comprising:
A) a composition for substantially stable storage of nucleic acid and polypeptide molecules in a biological sample at room temperature, comprising:
 (a) a compound selected from the group consisting of:
   1-methyl-3-carboxyethyl-imidazolium bromide,
   1-hexyl-3-methylimidazolium bromide,
   1-octyl-3-methylimidazolium bromide,
   1-decyl-3-methylimidazolium bromide, and
   1-(2-hydroxyethyl)-3-methylimidazolium bromide;
 (b) one, two, or all three of:
   (i) at least one precipitating agent,
   (ii) at least one lower alcohol, and
   (iii) at least one chaotrope;
 (c) one or more of:
   (i) a chelating agent,
   (ii) a reducing agent,
   (iii) a pH buffer, and
   (iv) water; and
 (d) a surfactant or detergent,
 wherein the composition is an aqueous solution and the compound of (a) is present in the composition at a concentration of about 0.1% to about 10% (w/v); and
B) a biological sample comprising saliva or sputum.

2. The admixture of claim 1 wherein the precipitating agent is selected from the group consisting of:
5-(4-dimethyl)amino benzylidene rhodanine,
sulfosalicylic acid,
lithium chloride, and
lithium hydroxide.

3. The admixture of claim 1 wherein the lower alcohol is selected from the group consisting of methanol, ethanol, n-propanol, isopropanol, n-butanol, and isobutanol (2-methylpropan-1-ol).

4. The admixture of claim 1 wherein the chaotrope is selected from the group consisting of:
guanidine hydrochloride, guanidine thiocyanate, potassium thiocyanate, sodium thiocyanate and urea.

5. The admixture of claim 1 wherein the chelating agent is selected from the group consisting of diethylenetriaminepentaacetic acid (DTPA), ethylenediaminetetraacetic acid (EDTA), ethylene glycol tetraacetic acid (EGTA), trans-1, 2-diaminocyclohexane-N,N,N',N'-tetraacetic acid (CDTA), 1,2-bis(2-aminophenoxy)ethane-N,N,N',N'-tetraacetic acid (BAPTA), 1,4,7,10-tetraazacyclododecane-1,4,7,10-tetraacetic acid (DOTA), N-(2-hydroxyethyl)ethylenediamine-N,N',N'-triacetic acid, and nitrilotriacetic acid (NTA).

6. The admixture of claim 1 wherein the reducing agent is selected from the group consisting of 2-mercaptoethanol, thiosulfate, TCEP (tris-(2-carboxyethyl) phosphine), dithiothreitol and dithioerythritol.

7. The admixture of claim 1 wherein the pH buffer is selected from the group consisting of citric acid, tartaric acid, malic acid, sulfosalicylic acid, sulfoisophtalic acid, oxalic acid, borate, CAPS (3-(cyclohexylamino)-1-propanesulfonic acid), CAPSO (3-(cyclohexylamino)-2-hydroxy-1-propanesulfonic acid), EPPS (4-(2-hydroxyethyl)-1-piperazinepropanesulfonic acid), HEPES (4-(2-hydroxyethyl) piperazine-1-ethanesulfonic acid), MES (2-(N-morpholino) ethanesulfonic acid), MOPS (3-(N-morpholino) propanesulfonic acid), MOPSO (3-morpholino-2-hydroxypropanesulfonic acid), PIPES (1,4-piperazinediethanesulfonic acid), TAPS (N-[tris (hydroxymethyl)methyl]-3-aminopropanesulfonic acid), TAPSO (2-hydroxy-3-[tris(hydroxymethyl)methylamino]-1-propanesulfonic acid), TES (N-[tris(hydroxymethyl) methyl]-2-aminoethanesulfonic acid), bicine (N,N-Bis(2-hydroxyethyl)glycine), tricine (N-[Tris(hydroxymethyl) methyl]glycine), tris (tris(hydroxymethyl)aminomethane) and bis-tris (2-[Bis(2-hydroxyethyl)amino]-2-(hydroxymethyl)-1,3-propanediol).

8. The admixture of claim 1 wherein the surfactant or detergent is selected from 4-(1,1,3,3-Tetramethylbutyl)phenyl-polyethylene glycol and octylphenoxypolyethoxyethanol.

9. The admixture of claim 1 wherein the saliva or sputum is unfractionated.

10. The admixture of claim 1 wherein the saliva or sputum is human saliva.

11. The admixture of claim 10 wherein the human saliva is unfractionated.

12. The admixture of claim 1, wherein the surfactant is any of the Tween family of nonionic polyoxyethylene surfactants.

13. An admixture of claim 1, wherein the composition comprises
(a) a compound selected from the group consisting of:
1-methyl-3-carboxyethyl-imidazolium bromide,
1-hexyl-3-methylimidazolium bromide,
1-octyl-3-methylimidazolium bromide,
1-decyl-3-methylimidazolium bromide, and
1-(2-hydroxyethyl)-3-methylimidazolium bromide;
(b) at least one chaotrope;
(c) a pH buffer,
(d) water, and
(e) a surfactant or detergent,
wherein the composition is an aqueous solution and the compound of (a) is present in the composition at a concentration of about 0.1% to about 10% (w/v).

14. The admixture of claim 1 which is capable, upon storage without refrigeration for a time period of at least 60 days, of substantially preventing degradation of at least 70% of recoverable DNA from the admixture, relative to DNA recoverable from a second sample of the biological sample comprising saliva or sputum that is stored at −20° C. during said time period.

15. The admixture of claim 1 which is capable, upon storage without refrigeration for a time period of at least 21 days, of substantially preventing degradation of at least 70% of recoverable RNA from the admixture, relative to RNA recoverable from a second sample of the biological sample comprising saliva or sputum that is stored at −80° C. during said time period.

16. A substantially stably-stored nucleic acid molecule from a biological sample comprising saliva or sputum, comprising the composition of claim 1.

17. A substantially stably-stored polypeptide molecule from a human saliva sample, comprising the composition of claim 1.

18. The substantially stably-stored nucleic acid molecule of claim 16 wherein the nucleic acid molecule comprises one or more of a DNA molecule and an RNA molecule.

19. A method for substantially stabilizing one or a plurality of nucleic acid or polypeptide molecules that are present in a biological sample comprising saliva or sputum, comprising:
(a) admixing the biological sample comprising saliva or sputum with a composition comprising
(A) a compound selected from the group consisting of:
1-methyl-3-carboxyethyl-imidazolium bromide,
1-hexyl-3-methylimidazolium bromide,
1-octyl-3-methylimidazolium bromide,
1-decyl-3-methylimidazolium bromide, and
1-(2-hydroxyethyl)-3-methylimidazolium bromide;
(B) one, two, or all three of:
(i) at least one precipitating agent,
(ii) at least one lower alcohol, and
(iii) at least one chaotrope;
(C) one or more of:
(i) a chelating agent,
(ii) a reducing agent,
(iii) a pH buffer, and
(iv) water; and
(D) a surfactant or detergent,
wherein the composition is an aqueous solution and the compound of (A) is present in the composition at a concentration of about 0.1% to about 10% (w/v), to obtain a mixture; and
(b) maintaining the mixture without refrigeration for a time period of at least 7 days, and thereby substantially stabilizing said one or a plurality of nucleic acid or polypeptide molecules that are present in the biological sample, wherein either one, two or all three of:
(1) degradation is substantially prevented of at least 70% of recoverable DNA in the mixture, relative to an amount of DNA or polypeptide that is recoverable from the sample when stored for the time period at −20° C. without the composition,
(2) degradation is substantially prevented of at least 70% of recoverable RNA in the mixture, relative to an amount of RNA that is recoverable from the sample when stored for the time period at −80° C. without the composition, and
(3) degradation is substantially prevented of at least 70% of recoverable polypeptide molecules in the mixture, relative to an amount of polypeptide molecules that is recoverable from the sample when stored for the time period at −20° C. without the composition.

20. The method of claim 19 wherein the biological sample comprises vertebrate saliva or sputum.

21. The method of claim 20 wherein the vertebrate saliva or sputum is unfractionated.

22. The method of claim 19 wherein the biological sample comprises human saliva.

23. The method of claim 22 wherein the human saliva is unfractionated.

24. The method of claim 19 wherein the step of maintaining comprises maintaining for a time period of at least 10, 20, 30, 40, 50, 60 or 70 days.

\* \* \* \* \*